(12) United States Patent
Cioffi et al.

(10) Patent No.: US 9,045,445 B2
(45) Date of Patent: Jun. 2, 2015

(54) GLYCINE TRANSPORTER-1 INHIBITORS, METHODS OF MAKING THEM, AND USES THEREOF

(75) Inventors: Christopher L. Cioffi, Troy, NY (US); Mark A. Wolf, Denlanson, NY (US); Peter R. Guzzo, Niskayuna, NY (US); Shuang Liu, Schenectady, NY (US); Kashinath Sadalapure, Singapore (SG)

(73) Assignee: Albany Molecular Research, Inc., Albany, NY (US)

( * ) Notice: Subject to any disclaimer, the term of this patent is extended or adjusted under 35 U.S.C. 154(b) by 362 days.

(21) Appl. No.: 13/151,992

(22) Filed: Jun. 2, 2011

(65) Prior Publication Data

US 2011/0312931 A1 Dec. 22, 2011

Related U.S. Application Data

(60) Provisional application No. 61/351,662, filed on Jun. 4, 2010.

(51) Int. Cl.

| | |
|---|---|
| *A61K 31/496* | (2006.01) |
| *C07D 403/12* | (2006.01) |
| *C07D 295/26* | (2006.01) |
| *C07D 205/04* | (2006.01) |
| *C07D 207/48* | (2006.01) |
| *C07D 211/58* | (2006.01) |
| *C07D 213/71* | (2006.01) |
| *C07D 233/84* | (2006.01) |
| *C07D 241/04* | (2006.01) |
| *C07D 249/04* | (2006.01) |
| *C07D 309/14* | (2006.01) |
| *C07D 313/04* | (2006.01) |
| *C07D 405/12* | (2006.01) |
| *C07D 487/08* | (2006.01) |

(52) U.S. Cl.
CPC ............ *C07D 295/26* (2013.01); *C07D 205/04* (2013.01); *C07D 207/48* (2013.01); *C07D 211/58* (2013.01); *C07D 213/71* (2013.01); *C07D 233/84* (2013.01); *C07D 241/04* (2013.01); *C07D 249/04* (2013.01); *C07D 309/14* (2013.01); *C07D 313/04* (2013.01); *C07D 405/12* (2013.01); *C07D 487/08* (2013.01)

(58) Field of Classification Search
CPC ........................... A61K 31/496; C07D 403/12
USPC ............ 544/336, 358, 359, 366; 514/252.12, 514/252.13, 254.01
See application file for complete search history.

(56) References Cited

U.S. PATENT DOCUMENTS

| | | |
|---|---|---|
| 3,145,209 A | 8/1964 | Krapcho |
| 3,975,443 A | 8/1976 | Harper et al. |
| 4,880,802 A | 11/1989 | Schohe et al. |
| 5,032,604 A | 7/1991 | Baldwin et al. |
| 5,464,788 A | 11/1995 | Bock et al. |
| 5,688,806 A | 11/1997 | Desai et al. |
| 5,856,326 A | 1/1999 | Anthony et al. |
| 5,859,012 A | 1/1999 | Dinsmore et al. |
| 5,859,015 A | 1/1999 | Graham et al. |
| 5,885,995 A | 3/1999 | Dinsmore |
| 5,919,785 A | 7/1999 | Dinsmore et al. |
| 5,939,418 A | 8/1999 | Quan et al. |
| 6,060,038 A | 5/2000 | Burns et al. |
| 6,110,924 A | 8/2000 | Bosies et al. |
| 6,162,809 A | 12/2000 | Kohl et al. |
| 6,333,322 B1 | 12/2001 | Miyamoto et al. |
| 6,335,343 B1 | 1/2002 | Lumma, Jr. et al. |
| 6,355,643 B1 | 3/2002 | Lumma et al. |
| 6,376,496 B1 | 4/2002 | Hartman et al. |
| 6,380,193 B1 | 4/2002 | Li et al. |
| 6,403,595 B1 | 6/2002 | Tawada et al. |

(Continued)

FOREIGN PATENT DOCUMENTS

| | | |
|---|---|---|
| DE | 19700431 | 7/1998 |
| DE | 19944066 | 3/2001 |

(Continued)

OTHER PUBLICATIONS

Duan et al., "Discovery of Low Nanomolar Non-hydroxamate Inhibitors of Tumor Necrosis Factor-alpha Converting Enzyme (TACE)," *Bioorg. Med. Chem. Lett.* 17(1) 266-271 (2007).

Briner et al., "Privileged Structure Based Ligands for Melanocortin-4 Receptors Aliphatic Piperazine Derivatives," *Bioorg. Med. Chem. Lett.* 316(13) 3449-3453 (2006).

International Search Report and Written Opinion for PCT/US11/38939 (mailed Sep. 14, 2011).

(Continued)

*Primary Examiner* — Golam M M Shameem
(74) *Attorney, Agent, or Firm* — LeClairRyan, a Professional Corporation

(57) ABSTRACT

The compounds of the present invention are represented by the following formula (I):

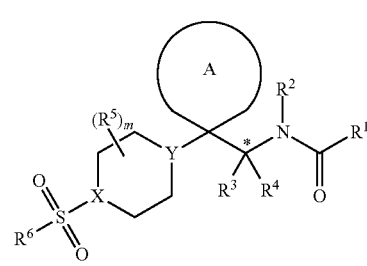

wherein the substituents $R^1$, $R^2$, $R^3$, $R^4$, $(R^5)_m$, $R^6$, A, X, and Y are as defined herein. The compounds are useful in methods of treating a disorder which is created by or is dependent upon inhibiting GlyT-1.

13 Claims, No Drawings

(56) References Cited

U.S. PATENT DOCUMENTS

| | | |
|---|---|---|
| 6,509,338 B1 | 1/2003 | Olson et al. |
| 6,642,228 B1 | 11/2003 | Hayashi et al. |
| 6,653,102 B2 | 11/2003 | Roch et al. |
| 6,861,422 B2 | 3/2005 | Hoffmann et al. |
| 6,900,322 B1 | 5/2005 | Reggelin et al. |
| 6,906,096 B2 | 6/2005 | Alper et al. |
| 6,936,620 B2 | 8/2005 | Duan et al. |
| 6,951,871 B2 | 10/2005 | Aslanian et al. |
| 6,953,792 B2 | 10/2005 | Castro Pineiro et al. |
| 7,105,505 B2 | 9/2006 | Zeng et al. |
| 7,119,203 B2 | 10/2006 | Barta et al. |
| 7,220,529 B2 | 5/2007 | Matsumoto |
| 7,220,735 B2 | 5/2007 | Ting et al. |
| 7,229,996 B2 | 6/2007 | Ma et al. |
| 7,241,798 B2 | 7/2007 | Segelstein et al. |
| 7,279,485 B2 | 10/2007 | Cheng et al. |
| 7,294,624 B2 | 11/2007 | Duan et al. |
| 7,314,879 B2 | 1/2008 | Backer et al. |
| 7,345,043 B2 | 3/2008 | Anandan et al. |
| 7,365,075 B2 | 4/2008 | DeGraffenreid et al. |
| 7,408,066 B2 | 8/2008 | Aslanian et al. |
| 7,427,631 B2 | 9/2008 | Eriksson et al. |
| 7,452,911 B2 | 11/2008 | Stenkamp et al. |
| 7,511,040 B2 | 3/2009 | Belanger et al. |
| 7,547,698 B2 | 6/2009 | Kamboj et al. |
| 7,553,838 B2 | 6/2009 | Fraley et al. |
| 7,572,811 B2 | 8/2009 | Pan et al. |
| 7,625,880 B2 | 12/2009 | Jankowski et al. |
| 7,629,338 B2 | 12/2009 | Wood et al. |
| 7,629,343 B2 | 12/2009 | Watkins et al. |
| 7,632,838 B2 | 12/2009 | Xiang et al. |
| 7,635,698 B2 | 12/2009 | Rosse et al. |
| 7,635,705 B2 | 12/2009 | Aslanian et al. |
| 7,638,531 B2 | 12/2009 | Mutahi et al. |
| 7,718,669 B2 | 5/2010 | Petry et al. |
| 7,728,144 B2 | 6/2010 | Ji et al. |
| 7,737,149 B2 | 6/2010 | Buttar et al. |
| 7,745,642 B2 | 6/2010 | Bradley et al. |
| 7,754,722 B2 | 7/2010 | Magar et al. |
| 7,759,339 B2 | 7/2010 | Aertgeerts et al. |
| 7,767,677 B2 | 8/2010 | Kamboj et al. |
| 7,786,110 B2 * | 8/2010 | Dillon et al. ............... 514/227.8 |
| 7,820,673 B2 | 10/2010 | Kubo et al. |
| 7,834,035 B2 | 11/2010 | Bessis et al. |
| 7,842,696 B2 * | 11/2010 | Bischoff et al. .......... 514/255.01 |
| 7,851,474 B2 | 12/2010 | Xie et al. |
| 7,879,880 B2 | 2/2011 | Solomon et al. |
| 7,880,001 B2 | 2/2011 | Link et al. |
| 7,880,002 B2 | 2/2011 | Carson et al. |
| 7,919,496 B2 | 4/2011 | Kamboj et al. |
| 8,017,612 B2 | 9/2011 | Abe et al. |
| 8,058,269 B2 | 11/2011 | Chen et al. |
| 8,138,333 B2 | 3/2012 | Angbrant et al. |
| 8,193,368 B2 * | 6/2012 | Dillon et al. ................. 548/254 |
| 8,247,563 B2 | 8/2012 | Bhat et al. |
| 2002/0010184 A1 | 1/2002 | Dinsmore et al. |
| 2002/0052380 A1 | 5/2002 | Dinsmore et al. |
| 2002/0082420 A1 | 6/2002 | Himmelsbach et al. |
| 2002/0177601 A1 | 11/2002 | Himmelsbach et al. |
| 2004/0072860 A1 | 4/2004 | Zhu et al. |
| 2004/0110764 A1 | 6/2004 | Stump et al. |
| 2004/0180925 A1 | 9/2004 | Matsuno et al. |
| 2005/0043533 A1 | 2/2005 | Babiak et al. |
| 2005/0124625 A1 | 6/2005 | Salvati et al. |
| 2005/0197336 A1 | 9/2005 | Anandan et al. |
| 2005/0209278 A1 | 9/2005 | McDonald et al. |
| 2005/0250789 A1 | 11/2005 | Burns et al. |
| 2006/0058311 A1 | 3/2006 | Munzert et al. |
| 2006/0074088 A1 | 4/2006 | Munzert et al. |
| 2006/0211707 A1 | 9/2006 | Aissaoui et al. |
| 2006/0241118 A1 | 10/2006 | Owen et al. |
| 2007/0043027 A1 | 2/2007 | Rueckle et al. |
| 2007/0073060 A1 | 3/2007 | Demont et al. |
| 2007/0142369 A1 | 6/2007 | van Heek et al. |
| 2007/0161578 A1 | 7/2007 | Hwa et al. |
| 2007/0197505 A1 | 8/2007 | Morgan et al. |
| 2007/0219217 A1 | 9/2007 | Eriksson et al. |
| 2008/0004259 A1 | 1/2008 | Arrington et al. |
| 2008/0004263 A1 | 1/2008 | Santora et al. |
| 2008/0064706 A1 | 3/2008 | Folmer et al. |
| 2008/0097078 A1 | 4/2008 | Arimoto et al. |
| 2008/0153810 A1 | 6/2008 | Ronsheim et al. |
| 2008/0188659 A1 | 8/2008 | Saiah et al. |
| 2009/0030039 A1 | 1/2009 | Coesemans et al. |
| 2009/0082399 A1 | 3/2009 | Bugada et al. |
| 2009/0099200 A1 | 4/2009 | Li et al. |
| 2009/0105208 A1 | 4/2009 | Gilbert et al. |
| 2009/0105218 A1 | 4/2009 | Ulven et al. |
| 2009/0175788 A1 | 7/2009 | Gentile et al. |
| 2009/0227595 A1 | 9/2009 | Hitchcock et al. |
| 2009/0227629 A1 | 9/2009 | Branch et al. |
| 2009/0269278 A1 | 10/2009 | Burns et al. |
| 2009/0270510 A1 | 10/2009 | Bradley et al. |
| 2009/0286828 A1 | 11/2009 | Bozzoli et al. |
| 2010/0137428 A1 | 6/2010 | Bozzoli et al. |
| 2010/0184996 A1 | 7/2010 | Perboni et al. |
| 2010/0216837 A1 | 8/2010 | Bozzoli et al. |

FOREIGN PATENT DOCUMENTS

| | | |
|---|---|---|
| EP | 0608858 | 8/1994 |
| JP | 2008 013527 | 1/2008 |
| JP | 2008-266236 A | 11/2008 |
| JP | 2009 029730 | 2/2009 |
| KR | 20080045537 | 5/2008 |
| WO | WO 95/02405 | 1/1995 |
| WO | WO 96/26936 | 9/1996 |
| WO | WO 97/36591 | 10/1997 |
| WO | WO 97/36592 | 10/1997 |
| WO | WO 97/36889 | 10/1997 |
| WO | WO 99/48911 | 9/1999 |
| WO | 99/59975 A1 | 11/1999 |
| WO | 00/25770 A1 | 5/2000 |
| WO | WO 00/42852 | 7/2000 |
| WO | WO 00/51611 | 9/2000 |
| WO | WO 00/51614 | 9/2000 |
| WO | WO 00/75135 | 12/2000 |
| WO | WO 01/14331 | 3/2001 |
| WO | WO 01/22963 | 4/2001 |
| WO | WO 01/23390 | 4/2001 |
| WO | 03/031410 A1 | 4/2003 |
| WO | WO 03/091247 | 11/2003 |
| WO | 2004/014294 A2 | 2/2004 |
| WO | WO 2004/010942 | 2/2004 |
| WO | WO 2004/037817 | 5/2004 |
| WO | 2004/058735 A2 | 7/2004 |
| WO | 2004/111014 A1 | 12/2004 |
| WO | 2005/040109 A1 | 5/2005 |
| WO | WO 2005/089502 | 9/2005 |
| WO | 2005/108384 A1 | 11/2005 |
| WO | WO 2006/008644 | 1/2006 |
| WO | WO 2006/024517 | 3/2006 |
| WO | WO 2006/100080 | 9/2006 |
| WO | WO 2006/102423 | 9/2006 |
| WO | 2006/105127 A2 | 10/2006 |
| WO | 2006/133098 A2 | 12/2006 |
| WO | WO 2006/129199 | 12/2006 |
| WO | 2007/039173 A1 | 4/2007 |
| WO | WO 2007/057742 | 5/2007 |
| WO | 2007/081857 A2 | 7/2007 |
| WO | 2007/087220 A2 | 8/2007 |
| WO | 2007/117180 A1 | 10/2007 |
| WO | WO 2007/119833 | 10/2007 |
| WO | 2007/147831 A1 | 12/2007 |
| WO | 2007/147834 A1 | 12/2007 |
| WO | 2007/147836 A1 | 12/2007 |
| WO | 2007/147839 A1 | 12/2007 |
| WO | WO 2007/138999 | 12/2007 |
| WO | WO 2007/139150 | 12/2007 |
| WO | WO 2007/143745 | 12/2007 |
| WO | 2008/002583 A1 | 1/2008 |
| WO | WO 2008/009416 | 1/2008 |
| WO | WO 2008/053157 | 5/2008 |
| WO | WO 2008/066151 | 6/2008 |

(56) References Cited

FOREIGN PATENT DOCUMENTS

| WO | WO 2008/080455 | 7/2008 |
| --- | --- | --- |
| WO | WO 2008/097428 | 8/2008 |
| WO | 2008/110598 A1 | 9/2008 |
| WO | WO 2008/106479 | 9/2008 |
| WO | WO 2008/110611 | 9/2008 |
| WO | 2008/122115 A1 | 10/2008 |
| WO | WO 2008/139161 | 11/2008 |
| WO | WO 2008/145681 | 12/2008 |
| WO | WO 2008/146914 | 12/2008 |
| WO | 2009/013535 A1 | 1/2009 |
| WO | WO 2009/005645 | 1/2009 |
| WO | WO 2009/005671 | 1/2009 |
| WO | 2009/026422 A2 | 2/2009 |
| WO | 2010/001078 A2 | 1/2010 |
| WO | WO 2011/153359 | 12/2011 |

OTHER PUBLICATIONS

Translation of First Office Action for Chinese Patent Application No. 201180038081.9 (Jan. 16, 2014).

Extended European Search Report for European Patent Application No. 11790414.4 (Nov. 21, 2013).

First Examination Report for New Zealand Patent Application No. 604035 (Aug. 2, 2013).

Wolkenberg et al., "Recent Progress in the Discovery of Non-Sarcosine Based GlyT1 Inhibitors," Curr. Topics in Med. Chem., 10:170-186 (2010).

Duan et al., "Non-Hydroxamate 5-Phenylpyrimidine-2,4,6-trione Derivatives as Selective Inhibitors of Tumor Necrosis Factor-Alpha Converting Enzyme," Bioorg. Med. Chem. Lett. 15:2970-2973 (2005).

Search Report and Written Opinion for Singapore 2013000047 dated Jan. 6, 2015.

Examination Report for EP 11790414.4 dated Nov. 26, 2014.

* cited by examiner

GLYCINE TRANSPORTER-1 INHIBITORS, METHODS OF MAKING THEM, AND USES THEREOF

This application claims the benefit of U.S. Provisional Patent Application Ser. No. 61/351,662, filed Jun. 4, 2010, which is hereby incorporated by reference in its entirety.

FIELD OF THE INVENTION

The present invention relates to compounds, compositions, and methods for the treatment of various neurological and psychological disorders, and the use of the compounds in combination therapy. In particular, the present invention relates to such compounds, compositions, and methods, where the compounds are novel glycine transporter-1 (GlyT-1) inhibitors.

BACKGROUND OF THE INVENTION

Schizophrenia is a chronic and devastating mental illness that affects approximately 1% of the world's population (Andreasen, *Brain Res. Rev.*, 31:106 (2000)). Over 2.2 million adults age 18 years and older in the United States are diagnosed with schizophrenia, which is approximately twice the number of people stricken with Alzheimer's disease and virtually six times more than those diagnosed with insulin-dependent diabetes. Men and women are affected equally and the incident rate is nearly the same for all countries and ethnic groups throughout the world, ranking the disease among the top ten causes of disability worldwide (Andreasen, *Brain Res. Rev.*, 31:106 (2000)).

The symptoms of schizophrenia generally appear in late adolescence or early adulthood and can be grouped into three specific categories. These include positive symptoms (auditory and visual hallucinations, disorganized thoughts and speech, delusions and irrational fears), negative symptoms (social withdrawal, adhedonia, blunted affect, lack of energy and catatonia), and cognitive dysfunction (diminished capacity for learning and memory, attention, vigilance and social cognition). Negative symptoms and especially cognitive impairment are considered to be the primary contributors to poor social functioning, the inability to work, lack of independent living skills and poor quality of life for nearly all patients (Andreasen, *Brain Res. Rev.*, 31:106 (2000)).

The N-methyl-D-aspartate (NMDA) glutamate receptor is an ionotropic glutamate receptor involved in fast excitatory neurotransmission, which plays a key role in a variety of CNS functions, most notably long term potentiation (LTP) and neuronal plasticity. A growing body of evidence is emerging that suggests glutamatergic neurotransmission is playing a key role in the etiology of the schizophrenia. The "glutamate hypothesis" originated from the discovery that the non-competitive NMDA receptor antagonists ketamine and phencyclidine (PCP) induce positive, negative, and cognitive symptoms in healthy individuals and exacerbate symptoms in stable patients (Coyle, *Cell. Mol. Neurobiol.*, 26:365 (2006)). These observations suggest that NMDA receptor hypofunction is playing a critical role in schizophrenia (Coyle, *Cell. Mol. Neurobiol.*, 26:365 (2006); Millan, *Psychopharmacology*, 179:30 (2005)). Thus, agents that can enhance receptor function may effectively ameliorate the full symptomology of psychosis. Direct agonism is not a viable approach as it leads to excitotoxicity (M. J. Marino, et. al., *J. Med. Chem.*, 51:1077 (2008)). Consequently, several strategies to indirectly potentiate the receptor and avoid toxic side effects are being investigated (M. J. Marino, et. al., *J. Med. Chem.*, 51:1077 (2008); Hui, et. al., *Recent Pat. CNS Drug Discov.*, 4:220 (2009); Stone, et. al., *CNS Neurol. Diord. Drug Targets*, 6:265 (2007); Gray, et. al., *Mol. Psychiatry*, 12:904 (2007)).

Glycine is an inhibitory neurotransmitter at strychnine-sensitive glycine receptors (GlyA site) and an excitatory neurotransmitter at the glycine modulatory site located on the NR1 subunit of the NMDA receptor (GlyB site). It is an obligatory co-agonist that allows glutamate to bind and stimulate the receptor (Harsing Jr., et. al., *Current Med. Chem.*, 13:1017 (2006)). Thus, a method to potentiate NMDA receptor function would be to increase synaptic glycine concentrations at the GlyB site. Studies show that patients experience improvement of negative symptoms when administered glycine (0.8 g/kg/day) or D-serine (a GlyB site agonist, 0.03 g/kg/day) in conjunction with clozapine (Javitt, *Biol. Psychiatry*, 63:6 (2008). Large doses of these amino acids were required due to poor pharmacokinetics (PK) and CNS-penetrance; however these encouraging results provided an impetus to discover alternative approaches for increasing synaptic glycine levels.

Two high-affinity transporters that regulate synaptic glycine concentrations have been identified: GlyT-1 and GlyT-2 (Harsing Jr., et. al., *Current Med. Chem.*, 13:1017 (2006)). Both share a high level of homology across species and approximate 50% homology with each other. Glycine transporters belong to the $Na^+/Cl^-$ solute carrier 6 (SLC6) family, which includes the dopamine (DA), serotonin (5-HT), norepinephrine (NE), leucine, taurine, proline, and GABA transporters. GlyT-2 is expressed in the brainstem and spinal chord and is co-localized with strychnine-sensitive glycine receptors. GlyT-1 is primarily expressed in neuronal and glial cells of the forebrain and is largely co-localized with NMDA receptors (Harsing Jr., et. al., *Current Med. Chem.*, 13:1017 (2006)). Thus, inhibition of GlyT-1 provides an opportunity to elevate glycine levels within close proximity to the GlyB site.

Knockout studies reveal that complete, homozygous GlyT-1 (−/−) knockout in mice is neonatally lethal, however heterozygous GlyT-1 (+/−) mice survive to adulthood and display enhanced NMDA receptor function in the hippocampus, better memory retention and no disruption in sensory gating when dosed with amphetamine (Gomeza, et. al., *Handb. Exp. Pharmacols.*, 457 (2006)).

A small placebo controlled study was conducted whereby 20 stably treated schizophrenic patients were given sarcosine, a weak but selective GlyT-1 inhibitor, at a dose of 2 g per day. Patients exhibited improvement with negative and cognitive symptoms (Lane, et. al., *Biol. Psychiatry*, 63:9 (2009)).

Some glycine transporter-1 inhibitors are known in the art and have been reported to be efficacious in animal models predictive of antipsychotic activity. A handful of GlyT-1 inhibitors have advanced into Phase I, Phase II, and Phase III clinical studies. However, there is a need for other GlyT-1 inihibitors efficacious in the treatment of neurological and psychological disorders. The present invention is directed to achieving this objective.

SUMMARY OF THE INVENTION

The present invention relates to compounds represented by the formula (I) having the following structure:

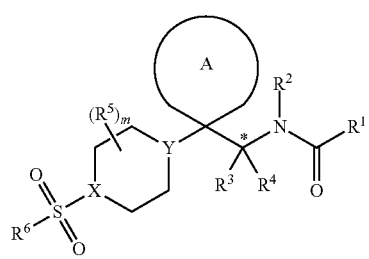

wherein:
R¹ is phenyl, which is independently and optionally substituted from 1 to 5 times with $R^{1a}$;
$R^{1a}$ is selected from the group consisting of:
  (1) hydrogen,
  (2) halogen,
  (3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$ cycloalkylalkyl is optionally substituted from 1 to 11 times with $R^7$,
  (4) aryl or heteroaryl which is independently and optionally substituted from 1 to 7 times with $R^8$,
  (5) —$OR^9$,
  (6) —$SR^{10}$,
  (7) —$S(O)_pR^{10}$,
  (8) —$S(O)NR^{11}R^{12}$,
  (9) —$C(O)_pR^{10}$,
  (10) —$C(O)NR^{11}R^{12}$,
  (11) —CN,
  (12) —$NO_2$,
  (13) —$NR^{11}R^{12}$,
  (14) —$NR^{11}C(O)_pR^{10}$, and
  (15) —$NR^{11}C(S)R^{10}$;
$R^2$ is hydrogen;
$R^3$ and $R^4$ are each independently hydrogen or $C_1$-$C_3$ alkyl, or $R^3$ and $R^4$ together with the carbon atom to which they are attached form a 3-, 4-, 5- or 6-membered cycloalkyl optionally substituted from 1 to 10 times with $R^7$;
$R^5$ is selected from the group consisting of:
  (1) hydrogen,
  (2) $C_1$-$C_6$ alkyl which is optionally substituted from 1 to 11 times with $R^7$,
  (3) gem-dialkyl, and
  (4) gem-dihalo; or
two $R^5$ substituents on the same carbon, together with the carbon atom to which they are attached, may form a 3-, 4-, or 5-membered cycloalkyl optionally substituted from 1 to 10 times with $R^7$; or
two $R^5$ substituents on adjacent carbons of the ring to which they are attached, together may form a 3-, 4-, 5- or 6-membered cycloalkyl optionally substituted from 1 to 10 times with $R^7$;
two non-adjacent carbons of the ring

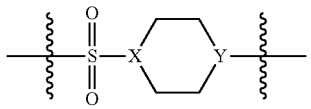

may form a —$CH_2$— or —$CH_2CH_2$-bridge;
$R^6$ is selected from the group consisting of:
  (1) $C_1$-$C_6$ alkyl, $C_3$-$C_7$ cycloalkyl, or $C_4$-$C_7$ cycloalkylalkyl, wherein each of the $C_1$-$C_6$ alkyl, $C_3$-$C_7$ cycloalkyl, and $C_4$-$C_7$ cycloalkylalkyl is optionally substituted from 1 to 11 times with $R^7$,
  (2) heteroaryl, which is independently and optionally substituted from 1 to 10 times with $R^8$, and
  (3) $NR^{13}R^{14}$;
A is a ring selected from a group consisting of:
  (1) 3-, 4-, 5-, 6-, 7-, or 8-membered cycloalkyl optionally substituted from 1 to 12 times with $R^7$,
  (2) 4-, 5-, 6-, 7-, or 8-membered heterocycle containing 1 to 4 heteroatoms selected from the group consisting of oxygen, nitrogen, and sulfur, optionally substituted from 1 to 10 times with $R^7$, and (3) a cycloalkyl having the structure:

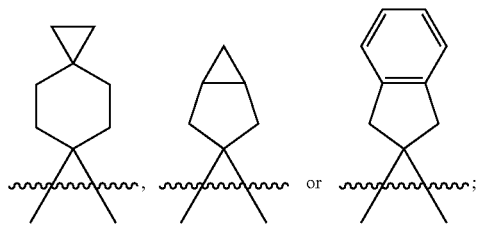

X is N or C, wherein C is optionally substituted with H or $C_1$-$C_3$ alkyl;
Y is N or C, wherein C is optionally substituted with H or $C_1$-$C_3$ alkyl;
$R^7$ is selected from the group consisting of:
  (1) hydrogen,
  (2) halogen,
  (3) deuterium,
  (4) gem-dialkyl,
  (5) gem-dihalo,
  (6) —$OR^9$, —$NR^{11}R^{13}$, —$NR^{11}C(O)_pR^{10}$, —$S(O)_pR^{10}$, —CN, —$NO_2$, —$C(O)_pR^{10}$, —$C(O)NR^{11}R^{12}$, or $NR^{11}C(S)R^{10}$,
  (7) 4-, 5- or 6-membered heterocycle containing 1 to 2 hetroatoms selected from the group consisting of oxygen, nitrogen and sulfur, optionally substituted from 1 to 10 times with $R^8$, and
  (8) oxo or thio;
$R^8$ is selected from the group consisting of:
  (1) hydrogen,
  (2) halogen,
  (3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$ cycloalkylalkyl is independently and optionally substituted from 1 to 11 times with $R^7$, and
  (4) —$OR^9$, —$NR^{11}R^{12}$, —$NR^{11}C(O)_pR^{10}$, —$S(O)_pR^{10}$, —CN, —$NO_2$, —$C(O)_pR^{10}$, —$C(O)NR^{11}R^{12}$, or —$NR^{11}C(S)R^{10}$;
$R^9$ is selected from the group consisting of hydrogen, $C_1$-$C_4$ alkyl, $C_3$-$C_7$ cycloalkyl, $C_4$-$C_7$ cycloalkylalkyl, —$C(O)NR^{11}R^{12}$, and —$C(O)_pR^{10}$, wherein each of $C_1$-$C_4$ alkyl, $C_3$-$C_7$ cycloalkyl, and $C_4$-$C_7$ cycloalkylalkyl is optionally substituted from 1 to 11 times with $R^7$;
$R^{10}$ is selected from the group consisting of hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$;
$R^{11}$ and $R^{12}$ are each independently selected from the group consisting of hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$, or
$R^{11}$ and $R^{12}$ are taken together with the nitrogen to which they are attached to form a saturated or partially saturated monocyclic or fused bicyclic heterocycle optionally substituted from 1 to 11 times with $R^7$;

$R^{13}$ and $R^{14}$ are each independently hydrogen or $C_1$-$C_3$ alkyl, wherein $C_1$-$C_3$ alkyl is optionally substituted from 1 to 10 times with $R^7$, or $R^{13}$ and $R^{14}$, together with the nitrogen atom to which they are attached, may form an azetidine or pyrrolidine ring optionally substituted from 1 to 10 times with $R^7$;

m is 0, 1, 2, 3 or 4, wherein when m is 2, 3 or 4, each of the $R^5$ substituents is independently chosen from the group listed above for $R^5$;

p is 1, or 2;

wherein any hydrogen atom attached to any carbon atom can be replaced with a deuterium atom;

when the carbon atom designated * is chiral, it is in the R or S configuration or the compounds of formula (I) exist as a mixture of R and S enantiomers;

with the following provisos that: (1) when $R^6$ is n-propyl, $R^1$ cannot be 2-cyanophenyl; (2) $R^6$ cannot be (a) 1H-1,2,3-triazol-4-yl, (b) 5-methylisoxazol-4-yl or (c) 3,3,3-trifluoropropyl; (3) A cannot be piperidin-4-yl; (4) when A is cyclopentyl and $R^6$ is n-propyl, $R^1$ cannot be (a) phenyl or (b) 4-toluoyl; (5) when A is cyclohexyl, $R^6$ cannot be benzyl; (6) when A is cycloheptyl and $R^6$ is ethyl, $R^1$ cannot be 4-fluoro-2-methoxyphenyl; (7) when A is tetrahydro-2H-pyran-4-yl, $R^6$ cannot be (a) 1-methyl-1H-pyrazol-4-yl; (8) when $R^6$ is 2-methyl-2H-1,2,3-triazol-4-yl, A cannot be tetrahydro-2H-pyran-4-yl or (b) cyclopentyl; (9) when A is tetrahydro-2H-pyran-4-yl and $R^3$ is H and $R^4$ is methyl, $R^6$ cannot be (a) cyclopropylmethyl or (b) 1-methyl-1H-imidazol-4-yl; (10) when $R^6$ is ethyl, $R^1$ cannot be 2,4-6-trimethoxyphenyl; (11) when A is 1,1-difluorocyclohexyl, $R^6$ cannot be diethylamino; and (12) when A is a 4-, 5-, 6-, 7-, or 8-membered heterocycle, $R^6$ cannot be $C_5$-$C_6$ alkyl which is optionally substituted from 1 to 11 times with $R^7$;

or an oxide thereof, a pharmaceutically acceptable salt thereof, a solvate thereof, prodrug thereof, or an individual enantiomer or diastereomer thereof.

The present invention is directed to compounds that inhibit the glycine transporter-1 (GlyT-1) and which are useful in the treatment of neurological and psychiatric disorders associated with glutamatergic neurotransmission dysfunction and diseases in which GlyT-1 is involved.

DETAILED DESCRIPTION OF THE INVENTION

The present invention relates to compounds represented by the formula (I) having the following structure:

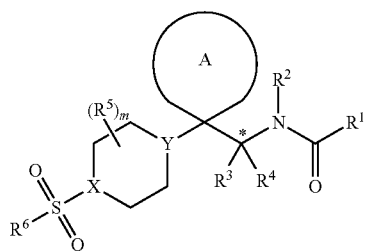

wherein:
$R^1$ is phenyl, which is independently and optionally substituted from 1 to 5 times with $R^{1a}$;
$R^{1a}$ is selected from the group consisting of:
(1) hydrogen,
(2) halogen,
(3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$ cycloalkylalkyl is optionally substituted from 1 to 11 times with $R^7$,
(4) aryl or heteroaryl which is independently and optionally substituted from 1 to 7 times with $R^8$,
(5) —$OR^9$,
(6) —$SR^{10}$,
(7) —$S(O)_pR^{10}$,
(8) —$S(O)NR^{11}R^{12}$,
(9) —$C(O)_pR^{10}$,
(10) —$C(O)NR^{11}R^{12}$,
(11) —CN,
(12) —$NO_2$,
(13) —$NR^{11}R^{12}$,
(14) —$NR^{11}C(O)_pR^{10}$, and
(15) —$NR^{11}C(S)R^{10}$;

$R^2$ is hydrogen;

$R^3$ and $R^4$ are each independently hydrogen or $C_1$-$C_3$ alkyl, or $R^3$ and $R^4$ together with the carbon atom to which they are attached form a 3-, 4-, 5- or 6-membered cycloalkyl optionally substituted from 1 to 10 times with $R^7$;

$R^5$ is selected from the group consisting of:
(1) hydrogen,
(2) $C_1$-$C_6$ alkyl which is optionally substituted from 1 to 11 times with $R^7$,
(3) gem-dialkyl, and
(4) gem-dihalo; or two $R^5$ substituents on the same carbon, together with the carbon atom to which they are attached, may form a 3-, 4-, or 5-membered cycloalkyl optionally substituted from 1 to 10 times with $R^7$; or two $R^5$ substituents on adjacent carbons of the ring to which they are attached, together may form a 3-, 4-, 5- or 6-membered cycloalkyl optionally substituted from 1 to 10 times with $R^7$;

two non-adjacent carbons of the ring

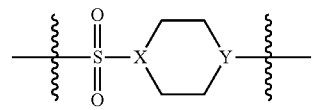

may form a —$CH_2$— or —$CH_2CH_2$-bridge;

$R^6$ is selected from the group consisting of:
(1) $C_1$-$C_6$ alkyl, $C_3$-$C_7$ cycloalkyl, or $C_4$-$C_7$ cycloalkylalkyl, wherein each of the $C_1$-$C_6$ alkyl, $C_3$-$C_7$ cycloalkyl, and $C_4$-$C_7$ cycloalkylalkyl is optionally substituted from 1 to 11 times with $R^7$,
(2) heteroaryl, which is independently and optionally substituted from 1 to 10 times with $R^8$, and
(3) $NR^{13}R^{14}$;

A is a ring selected from a group consisting of:
(1) 3-, 4-, 5-, 6-, 7-, or 8-membered cycloalkyl optionally substituted from 1 to 12 times with $R^7$,
(2) 4-, 5-, 6-, 7-, or 8-membered heterocycle containing 1 to 4 heteroatoms selected from the group consisting of oxygen, nitrogen, and sulfur, optionally substituted from 1 to 10 times with $R^7$, and (3) a cycloalkyl having the structure:

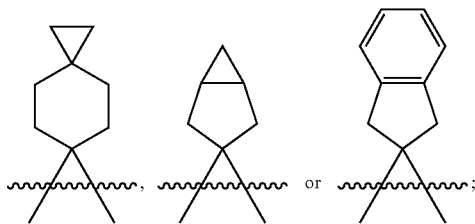

X is N or C, wherein C is optionally substituted with H or $C_1$-$C_3$ alkyl;
Y is N or C, wherein C is optionally substituted with H or $C_1$-$C_3$ alkyl;
$R^7$ is selected from the group consisting of:
  (1) hydrogen,
  (2) halogen,
  (3) deuterium,
  (4) gem-dialkyl,
  (5) gem-dihalo,
  (6) —$OR^9$, —$NR^{11}R^{12}$, —$NR^{11}C(O)_pR^{10}$, —$S(O)_pR^{10}$, —CN, —$NO_2$, —$C(O)_pR^{10}$, —$C(O)NR^{11}R^{12}$, or $NR^{11}C(s)R^{10}$,
  (7) 4-, 5- or 6-membered heterocycle containing 1 to 2 hetroatoms selected from the group consisting of oxygen, nitrogen and sulfur, optionally substituted from 1 to 10 times with $R^8$, and
  (8) oxo or thio;
$R^8$ is selected from the group consisting of:
  (1) hydrogen,
  (2) halogen,
  (3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$ cycloalkylalkyl is independently and optionally substituted from 1 to 11 times with $R^7$, and
  (4) —$OR^9$, —$NR^{11}R^{12}$, —$NR^{11}C(O)_pR^{10}$, —$S(O)_pR^{10}$, —CN, —$NO_2$, —$C(O)_pR^{10}$, —$C(O)NR^{11}R^{12}$, or —$NR^{11}C(S)R^{10}$;
$R^9$ is selected from the group consisting of hydrogen, $C_1$-$C_4$ alkyl, $C_3$-$C_7$ cycloalkyl, $C_4$-$C_7$ cycloalkylalkyl, —C(O)$NR^{11}R^{12}$, and —$C(O)_pR^{10}$, wherein each of $C_1$-$C_4$ alkyl, $C_3$-$C_7$ cycloalkyl, and $C_4$-$C_7$ cycloalkylalkyl is optionally substituted from 1 to 11 times with $R^7$;
$R^{10}$ is selected from the group consisting of hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$;
$R^{11}$ and $R^{12}$ are each independently selected from the group consisting of hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in $R^7$ and aryl or heteroaryl is optionally substituted from 1 to 10 times with $R^8$, or
$R^{11}$ and $R^{12}$ are taken together with the nitrogen to which they are attached to form a saturated or partially saturated monocyclic or fused bicyclic heterocycle optionally substituted from 1 to 11 times with $R^7$;

$R^{13}$ and $R^{14}$ are each independently hydrogen or $C_1$-$C_3$ alkyl, wherein $C_1$-$C_3$ alkyl is optionally substituted from 1 to 10 times with $R^7$, or
$R^{13}$ and $R^{14}$, together with the nitrogen atom to which they are attached, may form an azetidine or pyrrolidine ring optionally substituted from 1 to 10 times with $R^7$;
m is 0, 1, 2, 3 or 4, wherein when m is 2, 3 or 4, each of the $R^5$ substituents is independently chosen from the group listed above for $R^5$;
p is 1, or 2;
wherein any hydrogen atom attached to any carbon atom can be replaced with a deuterium atom;
when the carbon atom designated * is chiral, it is either in the R or S configuration or the compounds of formula (I) exist as a mixture of R and S enantiomers;
with the following provisos that (1) when $R^6$ is n-propyl, $R^1$ cannot be 2-cyanophenyl; (2) $R^6$ cannot be (a) 1H-1,2,3-triazol-4-yl, (b) 5-methylisoxazol-4-yl or (c) 3,3,3-trifluoropropyl; (3) A cannot be piperidin-4-yl; (4) when A is cyclopentyl and $R^6$ is n-propyl, $R^1$ cannot be (a) phenyl or (b) 4-toluoyl; (5) when A is cyclohexyl, $R^6$ cannot be benzyl; (6) when A is cycloheptyl and $R^6$ is ethyl, $R^1$ cannot be 4-fluoro-2-methoxyphenyl; (7) when A is tetrahydro-2H-pyran-4-yl, $R^6$ cannot be (a) 1-methyl-1H-pyrazol-4-yl; (8) when $R^6$ is 2-methyl-2H-1,2,3-triazol-4-yl, A cannot be tetrahydro-2H-pyran-4-yl or (b) cyclopentyl; (9) when A is tetrahydro-2H-pyran-4-yl and $R^3$ is H and $R^4$ is methyl, $R^6$ cannot be (a) cyclopropylmethyl or (b) 1-methyl-1H-imidazol-4-yl; (10) when $R^6$ is ethyl, $R^1$ cannot be 2,4-6-trimethoxyphenyl; (11) when A is 1,1-difluorocyclohexyl, $R^6$ cannot be diethylamino; and (12) when A is a 4-, 5-, 6-, 7-, or 8-membered heterocycle, $R^6$ cannot be $C_5$-$C_6$ alkyl which is optionally substituted from 1 to 11 times with $R^7$;
or an oxide thereof, a pharmaceutically acceptable salt thereof, a solvate thereof, or prodrug thereof, or an individual enantiomer or diastereomer thereof.

As used above, and throughout the description of the invention, the following terms, unless otherwise indicated, shall be understood to have the following meanings:

The term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Representative alkyl groups include methyl, ethyl, n-propyl, i-propyl, n-butyl, t-butyl, n-pentyl, and 3-pentyl and the like.

When an alkyl is substituted from 1 to 3 times with halogen, the substituted groups include $CF_3$, $CF_2H$, $CH_2CF_3$, $CH_2CF_2H$, and the like.

The term "gem-dialkyl" means two identical alkyl groups that substitute the two hydrogen atoms on a methylene group. Representative gem-dialkyl groups include gem-dimethyl, gem-diethyl, gem-dipropyl, and the like.

The term "alkenyl" means an aliphatic hydrocarbon group containing a carbon-carbon double bond and which may be straight or branched having 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Representative alkenyl groups include ethenyl, propenyl, n-butenyl, i-butenyl, and the like.

The term "alkynyl" means an aliphatic hydrocarbon group containing a carbon-carbon triple bond and which may be straight or branched having 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Representative alkynyl groups include ethynyl, propynyl, n-butynyl, 2-butynyl, 3-methylbutynyl, n-pentynyl, and the like.

The term "cycloalkyl" means a non-aromatic monocyclic ring system of about 3 to about 8 carbon atoms. Representative monocyclic cycloalkyl include cyclopropyl, cyclobutyl, cyclopentyl, cyclohexyl, cycloheptyl, and the like.

The term "cycloalkylalkyl" means a cycloalkyl-alkyl-group in which the cycloalkyl and alkyl are as defined herein. Representative cycloalkylalkyl groups include cyclopropylmethyl, cyclobutylmethyl, cyclopentylmethyl, and the like.

The term "halo" or "halogen" means fluoro, chloro, bromo, or iodo.

The term "gem-dihalo" means two halogen groups that substitute the two hydrogen atoms on a methylene group. Representative gem-dihalo groups include gem-difluoro, gem-dichloro, gem-dibromo, and gem-diiodo.

The term "aryl" means an aromatic monocyclic or multicyclic ring system of 6 to about 14 carbon atoms, preferably of 6 to about 10 carbon atoms. In the case of a multicyclic ring system, only one of the rings needs to be aromatic for the ring system to be defined as "aryl". Representative aryl groups include phenyl, naphthyl, indenyl, indanyl:

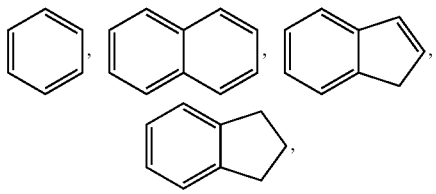

and the like.

The term "heteroaryl" means a means an aromatic monocyclic or multicyclic ring system of 6 to about 14 carbon atoms, preferably 5 to 10, in which one or more of the atoms in the ring system is/are element(s) other than carbon, for example, nitrogen, oxygen, or sulfur. In the case of multicyclic ring systems, only one of the rings needs to be aromatic for the ring system to be defined as "heteroaryl". The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. A sulfur atom of a heteroaryl is optionally oxidized to the corresponding sulfoxide or sulfone. Representative aromatic monocyclic ring systems include pyrrole, 1H-pyrazole, pyridinyl, pyrimidinyl, pyridazinyl, 2-oxo-pyridin-1(2H)-yl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, 1H-1,2,3-triazolyl, 2H-1,2,3-triazolyl, 4H-1,2,4-triazolyl, oxadiazolyl, thiadiazolyl, tetrazolyl, and the like. For lactam analogues of "aromatic monocyclic heterocycles" such as pyridin-2(1H)-one, pyridazin-3(2H)-one, and the like, when these lactams are structurally connected through the nitrogen atom adjacent to the lactam carbonyl, these lactams of aromatic monocyclic heterocycle are considered as "aromatic monocyclic heterocycle" in this invention. In addition, when a nitrogen containing heterocycle is substituted by hydroxyl group on the carbon adjacent to the nitrogen, the substituted heterocycle can be named as either tautomer as exemplified by the following examples:

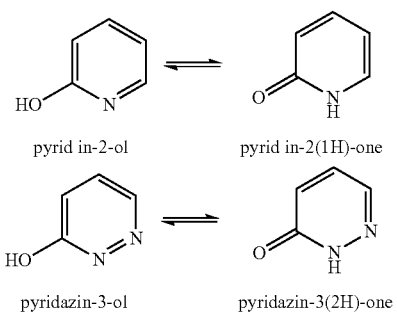

Two non-adjacent carbons of the ring

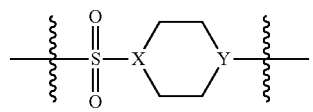

may form a —CH$_2$— or —CH$_2$CH$_2$— bridge as exemplified by the following examples:

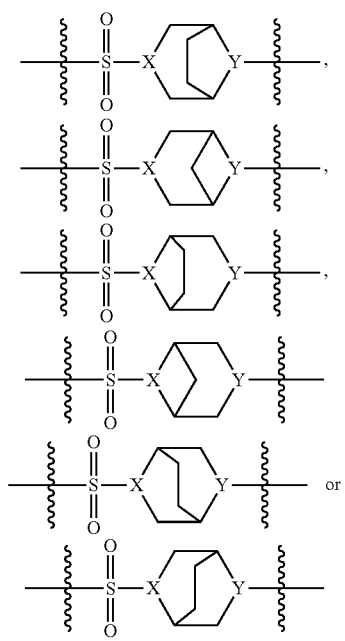

The term "heterocycle" means a nonaromatic, monocyclic ring system of about 4 to 8 ring atoms, preferably 5 or 6, in which one or more of the atoms in the ring system is/are element(s) other than carbon, for example, nitrogen, oxygen, or sulfur. The prefix aza, oxa, or thio before the heterocycle means that at least a nitrogen, oxygen, or sulfur atom, respectively, is present as a ring atom. A nitrogen atom in the ring is optionally oxidized to the corresponding N-oxide. A sulfur atom of a heterocycle is optionally oxidized to either the sulfoxide or sulfone. Representative monocyclic heterocycles include pyrrolidine, piperidine, piperazine, tetrahydrofuran, pyran, tetrahydropyran, oxetane, and the like.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto or oxo (i.e., =O), then two hydrogens on the atom are replaced. When a substituent is thio (i.e., =S), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, and quinateslaurylsulphonate salts, and the like. (See, for example Berge et al., *J. Pharm. Sci.*, 66:1-sup.19 (1977) and *Remington's Pharmaceutical Sciences*, 17th ed, p. 1418, Mack Publishing Company, Easton, Pa. (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as prodrugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs*, Elsevier (1985); Widder et al., *Methods in Enzymology*, ed., Academic Press, 42:309-396 (1985); "Design and Applications of Prodrugs," Krogsgaard-Larsen, ed., *A Textbook of Drug Design and Development*, Chapter 5:113-191 (1991); Bundgaard, "*Advanced Drug Delivery Reviews*," 8:1-38 (1992); Bundgaard et al., *Journal of Pharmaceutical Sciences*, 77:285 (1988); Nakeya et al., *Chem. Pharm. Bull.*, 32:692 (1984); Higuchi, "Pro-drugs as Novel Delivery Systems" Roche, ed., A.C.S. Symposium Series, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate, and benzoate derivatives of alcohol and amine functional groups in the compounds of the invention.

The term "therapeutically effective amounts" is meant to describe an amount of compound of the present invention effective in increasing the levels of glycine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

The term "pharmaceutical composition" means a composition comprising compounds of formula (I) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents, and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar, and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules. and suppositories, as well as liquid preparations for injections, including liposome preparations. Techniques and formulations generally may be found in Remington's Pharmaceutical Sciences, 17th ed, Easton, Pa., Mack Publishing Company (1985), which is hereby incorporated by reference in its entirety.

One embodiment of the present invention relates to the compound of formula (I), where X and Y are N.

Another embodiment of the present invention relates to the compound of formula (I), where X and Y are N and $R^3$ and $R^4$ are H.

Another embodiment of the present invention relates to the compound of formula (I), where X and Y are N and $R^3$ and $R^4$ are each individually H or $C_1$-$C_3$ alkyl.

Another embodiment of the present invention relates to the compound of formula (I), where X and Y are N and $R^3$ and $R^4$ are each individually H or $CH_3$.

Another embodiment of the present invention relates to the compound of formula (I), where X and Y are N, $R^3$ and $R^4$ are each individually H or $CH_3$, and m is 0.

Another embodiment of the present invention relates to the compound of formula (I), where X and Y are N, $R^3$ and $R^4$ are each individually H or $CH_3$, $R^5$ is $CH_3$, and m is 1 or 2.

Another embodiment of the present invention relates to the compound of formula (I), where X and Y are N, $R^3$ and $R^4$ are each individually H or $CH_3$, m is 0, and A is a 5-, 6- or 7-membered cycloalkyl optionally substituted 1 to 10 times with substituents as defined above in $R^7$.

Another embodiment of the present invention relates to the compound of formula (I), where X and Y are N, $R^3$ and $R^4$ are each individually H or $CH_3$, m is 0, and A is a 5-, 6-, or 7-membered heterocycle containing a heteroatom selected from the group consisting of oxygen, nitrogen, and sulfur, optionally substituted from 1 to 11 times with substituents as defined above in $R^7$.

Another embodiment of the present invention relates to the compound of formula (I), where X and Y are N, $R^3$ and $R^4$ are each individually H or $CH_3$, m is 0, A is a 5-, 6-, or 7-membered cycloalkyl optionally substituted 1 to 10 times with substituents as defined above in $R^7$, and $R^6$ is $C_1$-$C_6$ alkyl, $C_3$-$C_6$ cycloalkyl, or $C_4$-$C_7$ cycloalkylalkyl, where each of the $C_1$-$C_6$ alkyl, $C_3$-$C_6$ cycloalkyl, and $C_4$-$C_7$ cycloalkylalkyl is optionally substituted from 1 to 10 times with substituents as defined below in $R^7$.

Another embodiment of the present invention relates to the compound of formula (I), where X and Y are N, $R^3$ and $R^4$ are each individually H or $CH_3$, m is 0, and A is a 5-, 6-, or 7-membered cycloalkyl optionally substituted 1 to 10 times with substituents as defined above in $R^7$, and $R^6$ is heteroaryl, which is independently and optionally substituted from 1 to 4 times with $R^8$.

Another embodiment of the present invention relates to the compound of formula (I), where X and Y are N, $R^3$ and $R^4$ are each individually H or $CH_3$, m is 0, A is a 5-, 6-, or 7-membered heterocycle optionally substituted 1 to 10 times with substituents as defined above in $R^7$, and $R^6$ is $C_1$-$C_6$ alkyl, $C_3$-$C_6$ cycloalkyl, or $C_4$-$C_7$ cycloalkylalkyl, where each of the $C_1$-$C_6$ alkyl, $C_3$-$C_6$ cycloalkyl, and $C_4$-$C_7$ cycloalkylalkyl is optionally substituted from 1 to 10 times with substituents as defined below in $R^7$.

Another embodiment of the present invention relates to the compound of formula (I), where X and Y are N, $R^3$ and $R^4$ are each individually H or $CH_3$, m is 0, A is a 5-, 6-, or 7-membered heterocycle optionally substituted 1 to 10 times with substituents as defined above in $R^7$, and $R^6$ is heteroaryl, which is independently and optionally substituted from 1 to 4 times with $R^8$.

One embodiment of the present invention relates to the compound of formula (I) where:
X is N;
Y is N;
$R^1$ is phenyl, independently substituted from 1 to 5 times with halogen, $C_1$-$C_3$ alkyl, $C_3$-$C_6$ cycloalkyl, $OR^9$, or SIC, wherein $C_1$-$C_3$ alkyl and $C_3$-$C_6$ cycloalkyl are optionally substituted from 1 to 10 times with $R^7$;
$R^3$ and $R^4$ are each individually H or $CH_3$;
A is a 5-, 6-, or 7-membered cycloalkyl or a 4-, 5-, 6- or 7-membered heterocycle containing a heteroatom selected from the group consisting of oxygen, nitrogen, and sulfur, wherein the 5-, 6-, or 7-membered cycloalkyl or 4-, 5-, 6-, or 7-membered heterocycle are each optionally substituted from 1 to 10 times with substituents as defined in $R^7$;
m is 0; and
$R^6$ is $C_1$-$C_6$ alkyl, $C_3$-$C_6$ cycloalkyl, $C_4$-$C_7$ cycloalkylalkyl, or heteroaryl, wherein each of the $C_1$-$C_6$ alkyl, $C_3$-$C_6$ cycloalkyl, and $C_4$-$C_7$ cycloalkylalkyl is optionally substituted from 1 to 10 times with substituents as defined in $R^7$ and the heteroaryl is independently and optionally substituted from 1 to 4 times with $R^8$.

Another embodiment of the present invention relates to the compound of formula (I) where:
X is N;
Y is N;
$R^1$ is phenyl, independently substituted from 1 to 5 times with halogen, $C_1$-$C_3$ alkyl, $C_3$-$C_6$ cycloalkyl, $OR^9$, or $SR^{10}$, wherein $C_1$-$C_3$ alkyl and $C_3$-$C_6$ cycloalkyl are optionally substituted with 1 to 10 times with $R^7$;
$R^3$ and $R^4$ are each individually H or $CH_3$;

A is:

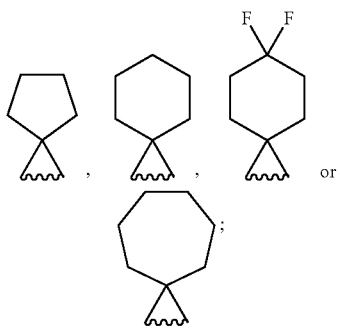

m is 0; and
R$^6$ is:

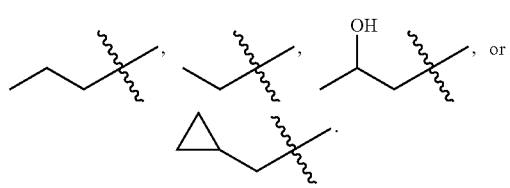

Another embodiment of the present invention relates to the compound of formula (I) where:
X is N;
Y is N;
R$^1$ is phenyl, independently substituted from 1 to 5 times with halogen, C$_1$-C$_3$ alkyl, C$_3$-C$_6$ cycloalkyl, OR$^9$, or SR$^{10}$, wherein C$_1$-C$_3$ alkyl and C$_3$-C$_6$ cycloalkyl are optionally substituted with 1 to 10 times with R$^7$;
R$^3$ and R$^4$ are each individually H or CH$_3$;
A is:

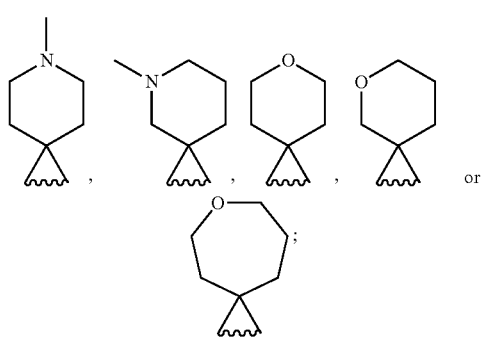

m is 0; and
R$^6$ is:

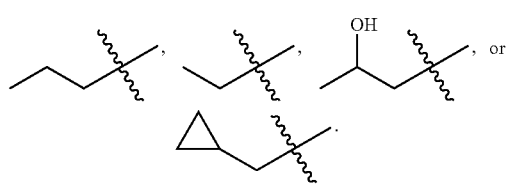

Yet another embodiment of the present invention relates to the compound of formula (I) where:
X is N;
Y is N;
R$^1$ is phenyl, independently substituted from 1 to 5 times with halogen, C$_1$-C$_3$ alkyl, C$_3$-C$_6$ cycloalkyl, OR$^9$, or SR$^{10}$, wherein C$_1$-C$_3$ alkyl and C$_3$-C$_6$ cycloalkyl are optionally substituted from 1 to 10 times with R$^7$;
R$^3$ and R$^4$ are each individually H or CH$_3$;
A is:

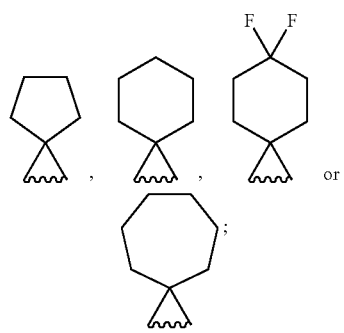

m is 0;
R$^6$ is heteroaryl represented by:

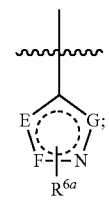

E, F, and G are each independently nitrogen or carbon; and
R$^{6a}$ is C$_1$-C$_2$ alkyl, which is optionally substituted 1 to 5 times with halogen or deuterium.

Another embodiment of the present invention relates to the compound of formula (I) where:
X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

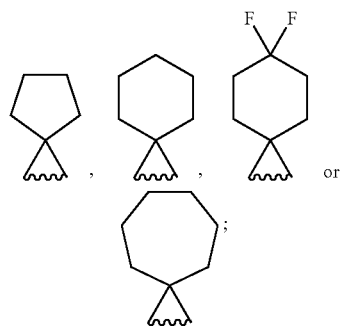

m is 0; and
R$^6$ is:

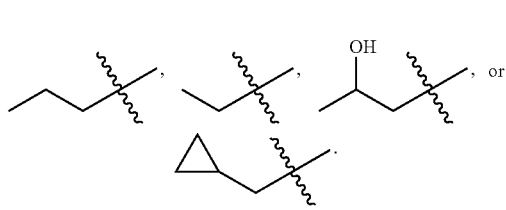

Another embodiment of the present invention relates to the compound of formula (I) where:

X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

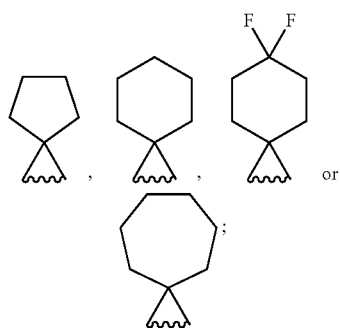

m is 0; and
R$^6$ is:

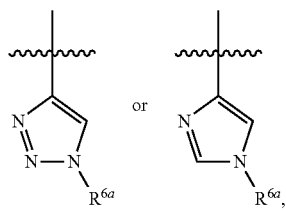

wherein R$^{6a}$ is C$_1$-C$_2$ alkyl, which is optionally substituted 1 to 5 times with halogen or deuterium.

Another embodiment of the present invention relates to the compound of formula (I) where:

X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

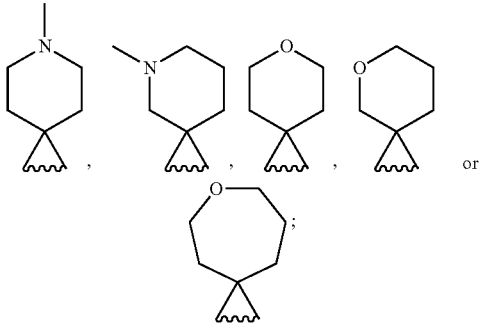

m is 0; and
R$^6$ is:

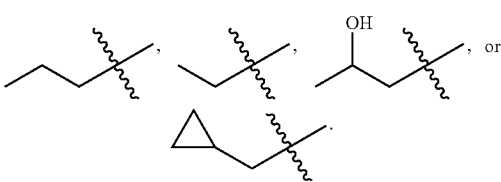

Another embodiment of the present invention relates to the compound of formula (I) where:

X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

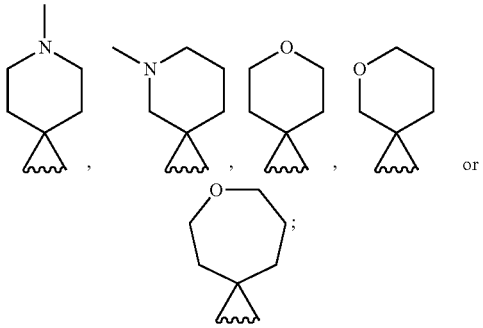

m is 0; and
R$^6$ is:

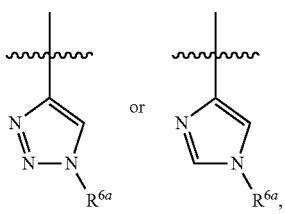

wherein R$^{6a}$ is C$_1$-C$_2$ alkyl, which is optionally substituted 1 to 5 times with halogen or deuterium.

Another embodiment of the present invention relates to the compound of formula (I) where:
X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

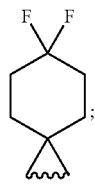

m is 0; and
R$^6$ is:

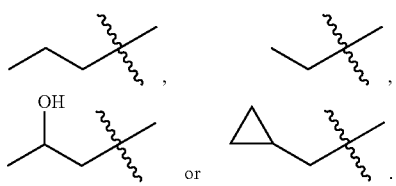

Another embodiment of the present invention relates to the compound of formula (I) where:
X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

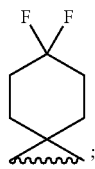

m is 0; and
R$^6$ is:

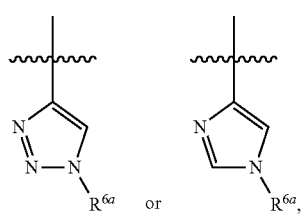

wherein R$^{6a}$ is CH$_3$, CF$_2$H, or CD$_3$.

Another embodiment of the present invention relates to the compound of formula (I) where:
X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

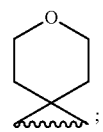

m is 0; and
R$^6$ is:

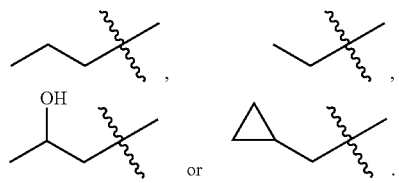

Another embodiment of the present invention relates to the compound of formula (I) where:
X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;
A is:

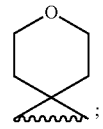

m is 0; and
R$^6$ is:

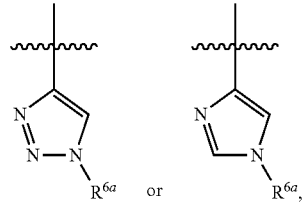

wherein R$^{6a}$ is CH$_3$, CF$_2$H, or CD$_3$.

Another embodiment of the present invention relates to the compound of formula (I) where:
X is N;
Y is N;
R$^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, CH$_3$, CF$_3$, OCH$_3$, CF$_2$H, SCH$_3$, NH$_2$, OCF$_3$, or OCF$_2$H;
R$^3$ and R$^4$ are each individually H or CH$_3$;

A is:

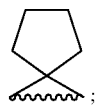

m is 0; and
R⁶ is:

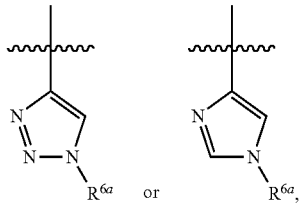

wherein $R^{6a}$ is $CH_3$, $CF_2H$, or $CD_3$.

Another embodiment of the present invention relates to the compound of formula (I) wherein A is a 5-, 6-, 7-, or 8-membered heterocycle.

A further embodiment of the present invention relates to the compound of formula (I) wherein A is a 4-, 5-, 6-, 7-, or 8-membered cycloalkyl.

Another embodiment of the present invention relates to the compound of formula (I) where:
X is N;
Y is N or CH;
$R^1$ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, $CH_3$, $CF_3$, $OCH_3$, $CF_2H$, $SCH_3$, $NH_2$, $OCF_3$, or $OCF_2H$;
$R^3$ and $R^4$ are each independently H or $CH_3$;
A is:

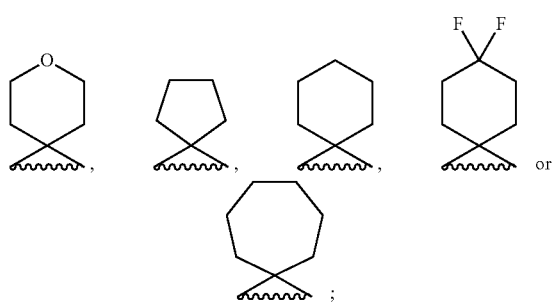

m is 0; and
R⁶ is:

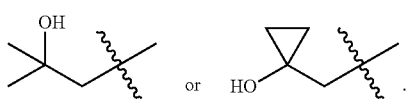

Specific compounds of formula (I) of the present invention include, but are not limited to, the following compounds:
2-Amino-6-chloro-N-((1-(4-(propylsulfonyl)piperazin-1-yl)cyclohexyl)methyl)benzamide;
2,4-Dichloro-N-((1-(4-(propylsulfonyl)piperazin-1-yl)cyclohexyl)methyl)benzamide;
2-Methoxy-6-methyl-N-((1-(4-(propylsulfonyl)piperazin-1-yl)cyclohexyl)methyl)benzamide;
N-((1-(4-(Propylsulfonyl)piperazin-1-yl)cyclohexyl)methyl)-2-(trifluoromethoxy)benzamide;
3-Chloro-2-fluoro-N-((1-(4-(propylsulfonyl)piperazin-1-yl)cyclohexyl)methyl)-6-(trifluoromethyl)benzamide;
N-((1-(4-(Propylsulfonyl)piperazin-1-yl)cyclohexyl)methyl)-4-(trifluoromethoxy)benzamide;
N-((1-(4-(Propylsulfonyl)piperazin-1-yl)cyclohexyl)methyl)-4-(trifluoromethyl)benzamide;
2-Chloro-N-((1-(4-(propylsulfonyl)piperazin-1-yl)cyclohexyl)methyl)benzamide;
4-Chloro-2-methyl-N-((1-(4-(propylsulfonyl)piperazin-1-yl)cyclohexyl)methyl)benzamide;
4-Fluoro-2-methyl-N-((1-(4-(propylsulfonyl)piperazin-1-yl)cyclohexyl)methyl)benzamide;
4-Bromo-N-((1-(4-(propylsulfonyl)piperazin-1-yl)cyclohexyl)methyl)benzamide;
2-Chloro-4-fluoro-N-((1-(4-(propylsulfonyl)piperazin-1-yl)cyclohexyl)methyl)benzamide;
2-(4-Chlorophenyl)-N-((1-(4-(propylsulfonyl)piperazin-1-yl)cyclohexyl)methyl)acetamide;
2-Fluoro-N-((1-(4-(propylsulfonyl)piperazin-1-yl)cyclohexyl)methyl)benzamide;
4-Fluoro-N-((1-(4-(propylsulfonyl)piperazin-1-yl)cyclohexyl)methyl)benzamide;
2,6-Difluoro-N-((1-(4-(propylsulfonyl)piperazin-1-yl)cyclohexyl)methyl)benzamide;
4-Cyano-N-((1-(4-(propylsulfonyl)piperazin-1-yl)cyclohexyl)methyl)benzamide;
4-Bromo-2-methyl-N-((1-(4-(propylsulfonyl)piperazin-1-yl)cyclohexyl)methyl)benzamide;
4-Fluoro-2-methoxy-6-methyl-N-((1-(4-(propylsulfonyl)piperazin-1-yl)cyclohexyl)methyl)benzamide;
4-Fluoro-2-methoxy-6-(methylthio)-N-((1-(4-(propylsulfonyl)piperazin-1-yl)cyclohexyl)methyl)benzamide;
2-Methoxy-N-((1(1-(4-(propylsulfonyl)piperazin-1-yl)cyclohexyl)methyl)-4,6-bis(trifluoromethyl)benzamide;
2-Chloro-N-((1-(4-(propylsulfonyl)piperazin-1-yl)cyclohexyl)methyl)-3-(trifluoromethyl)benzamide;
4-Methoxy-N-((1-(4-(propylsulfonyl)piperazin-1-yl)cyclohexyl)methyl)benzamide;
N-((1-(4-(Propylsulfonyl)piperazin-1-yl)cyclohexyl)methyl)benzamide;
4-Methyl-N-((1-(4-(propylsulfonyl)piperazin-1-yl)cyclohexyl)methyl)benzamide;
3,4-Dichloro-N-((1-(4-(propylsulfonyl)piperazin-1-yl)cyclohexyl)methyl)benzamide;
4-(Benzyloxy)-N-((1-(4-(propylsulfonyl)piperazin-1-yl)cyclohexyl)methyl)benzamide;
N-((1-(4-(Propylsulfonyl)piperazin-1-yl)cyclohexyl)methyl)-3-(trifluoromethyl)benzamide;
3-Methoxy-N-((1-(4-(propylsulfonyl)piperazin-1-yl)cyclohexyl)methyl)benzamide;
2,4-Dimethyl-N-((1-(4-(propylsulfonyl)piperazin-1-yl)cyclohexyl)methyl)benzamide;
3-Chloro-4-methyl-N-((1-(4-(propylsulfonyl)piperazin-1-yl)cyclohexyl)methyl)benzamide;
2,5-Dichloro-N-((1-(4-(propylsulfonyl)piperazin-1-yl)cyclohexyl)methyl)benzamide;
4-Isopropyl-N-((1-(4-(propylsulfonyl)piperazin-1-yl)cyclohexyl)methyl)benzamide;
N-((1-(4-(Propylsulfonyl)piperazin-1-yl)cyclohexyl)methyl)biphenyl-2-carboxamide;

3,4-Dimethyl-N-((1-(4-(propylsulfonyl)piperazin-1-yl)cyclohexyl)methyl)benzamide;
2,4,6-Trimethyl-N-((1-(4-(propylsulfonyl)piperazin-1-yl)cyclohexyl)methyl)benzamide;
3-Methyl-N-((1-(4-(propylsulfonyl)piperazin-1-yl)cyclohexyl)methyl)benzamide;
N-((1-(4-(Propylsulfonyl)piperazin-1-yl)cyclohexyl)methyl)biphenyl-4-carboxamide;
2,4-Difluoro-N-((1-(4-(propylsulfonyl)piperazin-1-yl)cyclohexyl)methyl)benzamide;
2-Methoxy-N-((1-(4-(propylsulfonyl)piperazin-1-yl)cyclohexyl)methyl)benzamide;
2-Amino-6-fluoro-N-((1-(4-(propylsulfonyl)piperazin-1-yl)cyclohexyl)methyl)benzamide;
2-Methyl-N-((1-(4-(propylsulfonyl)piperazin-1-yl)cyclohexyl)methyl)benzamide;
2,6-Dichloro-N-((1-(4-(propylsulfonyl)piperazin-1-yl)cyclohexyl)methyl)benzamide;
2-Fluoro-6-methoxy-N-((1-(4-(propylsulfonyl)piperazin-1-yl)cyclohexyl)methyl)benzamide;
4-Chloro-2-methoxy-N-((1-(4-(propylsulfonyl)piperazin-1-yl)cyclohexyl)methyl)benzamide;
4-Fluoro-2-methoxy-N-((1-(4-(propylsulfonyl)piperazin-1-yl)cyclohexyl)methyl)benzamide;
2,6-Dimethyl-N-((1-(4-(propylsulfonyl)piperazin-1-yl)cyclohexyl)methyl)benzamide;
2,4,6-Trifluoro-N-((1-(4-(propylsulfonyl)piperazin-1-yl)cyclohexyl)methyl)benzamide;
2-Fluoro-6-methyl-N-((1-(4-(propylsulfonyl)piperazin-1-yl)cyclohexyl)methyl)benzamide;
N-((1-(4-(Propylsulfonyl)piperazin-1-yl)cyclohexyl)methyl)-2-(trifluoromethyl)benzamide;
4-Chloro-2,6-difluoro-N-((1-(4-propylsulfonyl)piperazin-1-yl)cycloheptyl)methyl)benzamide;
4-Fluoro-2-methoxy-N-((1-(4-(propylsulfonyl)piperazin-1-yl)cycloheptyl)methyl)benzamide;
4-Chloro-2-methoxy-N-((1-(4-(propylsulfonyl)piperazin-1-yl)cycloheptyl)methyl)benzamide;
2-Chloro-3,6-difluoro-N-((1-(4-(propylsulfonyl)piperazin-1-yl)cycloheptyl)methyl)benzamide;
2-Fluoro-6-methoxy-N-((1-(4-(propylsulfonyl)piperazin-1-yl)cycloheptyl)methyl)benzamide;
2-Amino-6-chloro-N-((1-(4-(propylsulfonyl)piperazin-1-yl)cycloheptyl)methyl)benzamide;
4-Methyl-N-((1-(4-(propylsulfonyl)piperazin-1-yl)cycloheptyl)methyl)benzamide;
4-Chloro-N-((1-(4-(propylsulfonyl)piperazin-1-yl)cycloheptyl)methyl)benzamide;
2-Chloro-N-((1-(4-(propylsulfonyl)piperazin-1-yl)cycloheptyl)methyl)-3-(trifluoromethyl)benzamide;
2,4-Dichloro-N-((1-(4-(propylsulfonyl)piperazin-1-yl)cycloheptyl)methyl)benzamide;
N-((1-(4-(Propylsulfonyl)piperazin-1-yl)cycloheptyl)methyl)-4-(trifluoromethyl)benzamide;
N-((1-(4-(Propylsulfonyl)piperazin-1-yl)cycloheptyl)methyl)-4-(trifluoromethoxy)benzamide;
2-Fluoro-N-((1-(4-(propylsulfonyl)piperazin-1-yl)cycloheptyl)methyl)benzamide;
2,6-Dichloro-N-((1-(4-(propylsulfonyl)piperazin-1-yl)cycloheptyl)methyl)benzamide;
2-Chloro-3-methoxy-N-((1-(4-(propylsulfonyl)piperazin-1-yl)cycloheptyl)methyl)benzamide;
2,6-Difluoro-N-((1-(4-(propylsulfonyl)piperazin-1-yl)cycloheptyl)methyl)benzamide;
4-Methoxy-N-((1-(4-(propylsulfonyl)piperazin-1-yl)cycloheptyl)methyl)benzamide;
3,4-Dichloro-N-((1-(4-(propylsulfonyl)piperazin-1-yl)cycloheptyl)methyl)benzamide;
4-Fluoro-2-methoxy-6-methyl-N-((1-(4-(propylsulfonyl)piperazin-1-yl)cycloheptyl)methyl)benzamide;
2-Methoxy-N-((1-(4-(propylsulfonyl)piperazin-1-yl)cycloheptyl)methyl)-4,6-bis(trifluoromethyl)benzamide;
4-Fluoro-N-((1-(4-(propylsulfonyl)piperazin-1-yl)cycloheptyl)methyl)-2-(trifluoromethyl)benzamide;
4-Methyl-N-((1-(4-(propylsulfonyl)piperazin-1-yl)cyclopentyl)methyl)benzamide;
2,4-Dichloro-N-((1-(4-(propylsulfonyl)piperazin-1-yl)cyclopentyl)methyl)benzamide;
4-Chloro-N-((1-(4-(propylsulfonyl)piperazin-1-yl)cyclopentyl)methyl)benzamide;
4-Fluoro-2-methoxy-6-(methylthio)-N-((1-(4-(propylsulfonyl)piperazin-1-yl)cyclopentyl)methyl)benzamide;
4-Fluoro-2-methoxy-6-methyl-N-((1-(4-(propylsulfonyl)piperazin-1-yl)cyclopentyl)methyl)benzamide;
3,4-Dichloro-N-((1-(4-(propylsulfonyl)piperazin-1-yl)cyclopentyl)methyl)benzamide;
2-Amino-6-chloro-N-((1-(4-(propylsulfonyl)piperazin-1-yl)cyclopentyl)methyl)benzamide;
2-Amino-6-chloro-N-((1-(4-(propylsulfonyl)piperazin-1-yl)cyclobutyl)methyl)benzamide;
N-((1-(4-(Cyclopropylmethylsulfonyl)piperazin-1-yl)cyclohexyl)methyl)-4-fluoro-2-methoxy-6-methylbenzamide;
N-((1-(4-(Cyclopropylmethylsulfonyl)piperazin-1-yl)cyclohexyl)methyl)-2-fluoro-6-methylbenzamide;
N-((1-(4-(Cyclopropylmethylsulfonyl)piperazin-1-yl)cyclohexyl)methyl)-2,6-difluorobenzamide;
N-((1-(4-(Cyclopropylmethylsulfonyl)piperazin-1-yl)cyclohexyl)methyl)-4-fluoro-2-methoxy-6-(methylthio)benzamide;
N-((1-(4-(Cyclopropylmethylsulfonyl)piperazin-1-yl)cyclohexyl)methyl)-2-fluoro-6-methoxybenzamide;
2,4-Dichloro-N-((1-(4-(cyclopropylmethylsulfonyl)piperazin-1-yl)cyclohexyl)methyl)benzamide;
N-((1-(4-(Cyclopropylmethylsulfonyl)piperazin-1-yl)cycloheptyl)methyl)-4-fluoro-2-methylbenzamide;
N-((1-(4-(Cyclopropylmethylsulfonyl)piperazin-1-yl)cycloheptyl)methyl)-4-fluoro-2-methoxy-6-methylbenzamide;
N-((1-(4-(Ethylsulfonyl)piperazin-1-yl)cycloheptyl)methyl)-4-fluoro-2-methoxy-6-methylbenzamide;
2,6-Dichloro-N-((1-(4-(ethylsulfonyl)piperazin-1-yl)cycloheptyl)methyl)benzamide;
2-Amino-6-chloro-N-((1-(4-(phenylsulfonyl)piperazin-1-yl)cyclohexyl)methyl)benzamide;
2-Amino-6-chloro-N-((1-(4-(methylsulfonyl)piperazin-1-yl)cyclohexyl)methyl)benzamide;
2-Amino-6-chloro-N-((1-(4-(ethylsulfonyl)piperazin-1-yl)cyclohexyl)methyl)benzamide;
2-Amino-6-chloro-N-((1-(4-(isobutylsulfonyl)piperazin-1-yl)cyclohexyl)methyl)benzamide;
2,4-Dichloro-N-((1-(4-(cyclobutylsulfonyl)piperazin-1-yl)cyclohexyl)methyl)benzamide;
2,4-Dimethyl-N-((1-(4-(1-methyl-1H-imidazol-4-ylsulfonyl)piperazin-1-yl)cyclohexyl)methyl)benzamide;
2,6-Dimethyl-N-((1-(4-(1-methyl-1H-imidazol-4-ylsulfonyl)piperazin-1-yl)cyclohexyl)methyl)benzamide;
2-Fluoro-6-methoxy-N-((1-(4-(1-methyl-1H-imidazol-4-ylsulfonyl)piperazin-1-yl)cyclohexyl)methyl)benzamide;
2,4-Dichloro-N-((1-(4-(1-methyl-1H-imidazol-4-ylsulfonyl)piperazin-1-yl)cyclohexyl)methyl)benzamide;
2,6-Difluoro-N-((1-(4-(1-methyl-1H-imidazol-4-ylsulfonyl)piperazin-1-yl)cyclohexyl)methyl)benzamide;
2-Amino-6-chloro-N-((1-(4-(1-methyl-1H-imidazol-4-ylsulfonyl)piperazin-1-yl)cyclohexyl)methyl)benzamide;

2,4-Difluoro-N-((1-(4-(1-methyl-1H-imidazol-4-ylsulfonyl)piperazin-1-yl)cyclohexyl)methyl)benzamide;
2-Chloro-4-fluoro-N-((1-(4-(1-methyl-1H-imidazol-4-ylsulfonyl)piperazin-1-yl)cyclohexyl)methyl)benzamide;
4-Fluoro-2-methyl-N-((1-(4-(1-methyl-1H-imidazol-4-ylsulfonyl)piperazin-1-yl)cyclohexyl)methyl)benzamide;
4-Fluoro-2-methoxy-6-methyl-N-((1-(4-(1-methyl-1H-imidazol-4-ylsulfonyl)piperazin-1-yl)cyclopentyl)methyl)benzamide;
2,6-Difluoro-N-((1-(4-(1-methyl-1H-imidazol-4-ylsulfonyl)piperazin-1-yl)cyclopentyl)methyl)benzamide;
2,6-Dichloro-N-((1-(4-(1-methyl-1H-imidazol-4-ylsulfonyl)piperazin-1-yl)cyclopentyl)methyl)benzamide;
2,6-Dichloro-N-((1-(4-(1-methyl-1H-imidazol-4-ylsulfonyl)piperazin-1-yl)cycloheptyl)methyl)benzamide;
2,6-Difluoro-N-((1-(4-(1-methyl-1H-imidazol-4-ylsulfonyl)piperazin-1-yl)cycloheptyl)methyl)benzamide;
2,6-Difluoro-N-((1-(4-(1-methyl-1H-1,2,3-triazol-4-ylsulfonyl)piperazin-1-yl)cyclopentyl)methyl)benzamide;
2,6-Dichloro-N-((1-(4-(1-methyl-1H-1,2,3-triazol-4-ylsulfonyl)piperazin-1-yl)cyclopentyl)methyl)benzamide;
2,4-Dichloro-N-((1-(4-(1-methyl-1H-1,2,3-triazol-4-ylsulfonyl)piperazin-1-yl)cyclopentyl)methyl)benzamide;
2,4-Difluoro-N-((1-(4-(1-methyl-1H-1,2,3-triazol-4-ylsulfonyl)piperazin-1-yl)cyclopentyl)methyl)benzamide;
4-Fluoro-2-methoxy-6-methyl-N-((1-(4-(1-methyl-1H-1,2,3-triazol-4-ylsulfonyl)piperazin-1-yl)cyclopentyl)methyl)benzamide;
4-Fluoro-2-methoxy-N-((1-(4-(1-methyl-1H-1,2,3-triazol-4-ylsulfonyl)piperazin-1-yl)cyclopentyl)methyl)-6-(methylthio)benzamide;
2,6-Difluoro-N-((1-(4-(1-methyl-1H-1,2,3-triazol-4-ylsulfonyl)piperazin-1-yl)cyclohexyl)methyl)benzamide;
2-Amino-6-chloro-N-((2-(4-(propylsulfonyl)piperazin-1-yl)-2,3-dihydro-1H-inden-2-yl)methyl)benzamide;
2-Amino-6-chloro-N-((1-methyl-4-(4-(propylsulfonyl)piperazin-1-yl)piperidin-4-yl)methyl)benzamide;
2,6-Difluoro-N-((3-(4-(propylsulfonyl)piperazin-1-yl)quinuclidin-3-yl)methyl)benzamide;
2,6-Difluoro-N-(1-(1-(4-(1-methyl-1H-imidazol-4-ylsulfonyl)piperazin-1-yl)cyclohexyl)ethyl)benzamide;
N-((1-(4-(Cyclopropylmethylsulfonyl)-3-methylpiperazin-1-yl)cyclohexyl)methyl)-2,6-difluorobenzamide;
2,4-Dichloro-N-((4-(4-(propylsulfonyl)piperazin-1-yl)tetrahydro-2H-pyran-4-yl)methyl)benzamide;
2,6-Dichloro-N-((4-(4-(propylsulfonyl)piperazin-1-yl)tetrahydro-2H-pyran-4-yl)methyl)benzamide;
2,6-Dimethyl-N-((4-(4-(propylsulfonyl)piperazin-1-yl)tetrahydro-2H-pyran-4-yl)methyl)benzamide;
4-Fluoro-2-methoxy-6-methyl-N-((4-(4-(propylsulfonyl)piperazin-1-yl)tetrahydro-2H-pyran-4-yl)methyl)benzamide;
4-Fluoro-2-methoxy-6-(methylthio)-N-((4-(4-(propylsulfonyl)piperazin-1-yl)tetrahydro-2H-pyran-4-yl)methyl)benzamide;
2-Fluoro-6-methoxy-N-((4-(4-(propylsulfonyl)piperazin-1-yl)tetrahydro-2H-pyran-4-yl)methyl)benzamide;
2,6-Difluoro-N-((4-(4-(1-methyl-1H-imidazol-4-ylsulfonyl)piperazin-1-yl)tetrahydro-2H-pyran-4-yl)methyl)benzamide;
2,4-Dichloro-N-((3-(4-(propylsulfonyl)piperazin-1-yl)tetrahydro-2H-pyran-3-yl)methyl)benzamide;
N-((3-(4-(Cyclopropylmethylsulfonyl)piperazin-1-yl)tetrahydro-2H-pyran-3-yl)methyl)-2,6-difluorobenzamide;
2,6-Difluoro-N-((3-(4-(1-methyl-1H-imidazol-4-ylsulfonyl)piperazin-1-yl)tetrahydro-2H-pyran-3-yl)methyl)benzamide;
2,6-Difluoro-N-((4-(4-(1-methyl-1H-1,2,3-triazol-4-ylsulfonyl)piperazin-1-yl)tetrahydro-2H-pyran-4-yl)methyl)benzamide;
2,4-Dichloro-N-((4-(4-(1-methyl-1H-1,2,3-triazol-4-ylsulfonyl)piperazin-1-yl)tetrahydro-2H-pyran-4-yl)methyl)benzamide;
N-((4,4-Difluoro-1-(4-(propylsulfonyl)piperazin-1-yl)cyclohexyl)methyl)-2,6-difluorobenzamide;
N-((4,4-Difluoro-1-(4-(propylsulfonyl)piperazin-1-yl)cyclohexyl)methyl)-2-fluorobenzamide;
N-((4,4-Difluoro-1-(4-(propylsulfonyl)piperazin-1-yl)cyclohexyl)methyl)-2-(trifluoromethyl)benzamide;
N-((4,4-Difluoro-1-(4-(propylsulfonyl)piperazin-1-yl)cyclohexyl)methyl)-2-methoxybenzamide;
N-((4,4-Difluoro-1-(4-(propylsulfonyl)piperazin-1-yl)cyclohexyl)methyl)-2-methylbenzamide;
2,6-Dichloro-N-((4,4-difluoro-1-(4-(propylsulfonyl)piperazin-1-yl)cyclohexyl)methyl)benzamide;
2,4-Dichloro-N-((4,4-difluoro-1-(4-(propylsulfonyl)piperazin-1-yl)cyclohexyl)methyl)benzamide;
N-((4,4-Difluoro-1-(4-(propylsulfonyl)piperazin-1-yl)cyclohexyl)methyl)-4-fluoro-2-methoxy-6-methylbenzamide;
N-((4,4-Difluoro-1-(4-(propylsulfonyl)piperazin-1-yl)cyclohexyl)methyl)-4-fluoro-2-methoxy-6-(methylthio)benzamide;
2-Chloro-N-((4,4-difluoro-1-(4-(propylsulfonyl)piperazin-1-yl)cyclohexyl)methyl)benzamide;
N-((4,4-Difluoro-1-(4-(propylsulfonyl)piperazin-1-yl)cyclohexyl)methyl)-2,4-difluorobenzamide;
N-((4,4-Difluoro-1-(4-(propylsulfonyl)piperazin-1-yl)cyclohexyl)methyl)-2-(trifluoromethoxy)benzamide;
N-((4,4-Difluoro-1-(4-(propylsulfonyl)piperazin-1-yl)cyclohexyl)methyl)-2-(difluoromethoxy)benzamide;
4-Chloro-N-((4,4-difluoro-1-(4-(propylsulfonyl)piperazin-1-yl)cyclohexyl)methyl)-2-fluorobenzamide;
N-((4,4-Difluoro-1-(4-(propylsulfonyl)piperazin-1-yl)cyclohexyl)methyl)-2,4,6-trifluorobenzamide;
N-((4,4-Difluoro-1-(4-(propylsulfonyl)piperazin-1-yl)cyclohexyl)methyl)-4-fluoro-2-methylbenzamide;
N-((4,4-Difluoro-1-(4-(propylsulfonyl)piperazin-1-yl)cyclohexyl)methyl)-2,6-dimethylbenzamide;
N-((4,4-Difluoro-1-(4-(propylsulfonyl)piperazin-1-yl)cyclohexyl)methyl)-2-fluoro-6-methylbenzamide;
N-((4,4-Difluoro-1-(4-(propylsulfonyl)piperazin-1-yl)cyclohexyl)methyl)-4-fluoro-2-(trifluoromethyl)benzamide;
N-((4,4-Difluoro-1-(4-(propylsulfonyl)piperazin-1-yl)cyclohexyl)methyl)-2-fluoro-6-(trifluoromethyl)benzamide;
N-((4,4-Difluoro-1-(4-(propylsulfonyl)piperazin-1-yl)cyclohexyl)methyl)-2-fluoro-4-(trifluoromethyl)benzamide;
N-((4,4-Difluoro-1-(4-(propylsulfonyl)piperazin-1-yl)cyclohexyl)methyl)-2-chloro-4-(trifluoromethyl)benzamide;
2-Chloro-N-((4,4-difluoro-1-(4-(propylsulfonyl)piperazin-1-yl)cyclohexyl)methyl)-6-methoxybenzamide;
4-Chloro-N-((4,4-difluoro-1-(4-(propylsulfonyl)piperazin-1-yl)cyclohexyl)methyl)-2-methylbenzamide;
2-Chloro-N-((4,4-difluoro-1-(4-(propylsulfonyl)piperazin-1-yl)cyclohexyl)methyl)-4-fluorobenzamide;
2-Chloro-N-((4,4-difluoro-1-(4-(propylsulfonyl)piperazin-1-yl)cyclohexyl)methyl)-6-methylbenzamide;
2-Chloro-N-((4,4-difluoro-1-(4-(propylsulfonyl)piperazin-1-yl)cyclohexyl)methyl)-6-fluorobenzamide;
2-Chloro-N-((4,4-difluoro-1-(4-(propylsulfonyl)piperazin-1-yl)cyclohexyl)methyl)-6-(trifluoromethyl)benzamide;

N-((4,4-Difluoro-1-(4-(propylsulfonyl)piperazin-1-yl)cyclohexyl)methyl)-2-fluoro-6-(trifluoromethoxy)benzamide;
2-Chloro-N-((4,4-difluoro-1-(4-(propylsulfonyl)piperazin-1-yl)cyclohexyl)methyl)-6-(trifluoromethoxy)benzamide;
2-Chloro-N-((4,4-difluoro-1-(4-(1-methyl-1H-imidazol-4-ylsulfonyl)piperazin-1-yl)cyclohexyl)methyl)benzamide;
N-((4,4-difluoro-1-(4-(1-methyl-1H-imidazol-4-ylsulfonyl)piperazin-1-yl)cyclohexyl)methyl)-2-(trifluoromethoxy)benzamide;
N-((4,4-difluoro-1-(4-(1-methyl-1H-imidazol-4-ylsulfonyl)piperazin-1-yl)cyclohexyl)methyl)-2,4-difluorobenzamide;
N-((4,4-Difluoro-1-(4-(1-methyl-1H-imidazol-4-ylsulfonyl)piperazin-1-yl)cyclohexyl)methyl)-2,6-difluorobenzamide;
N-((4,4-Difluoro-1-(4-(1-methyl-1H-imidazol-4-ylsulfonyl)piperazin-1-yl)cyclohexyl)methyl)-2,6-dimethylbenzamide;
4-Chloro-N-((4,4-difluoro-1-(4-(1-methyl-1H-imidazol-4-ylsulfonyl)piperazin-1-yl)cyclohexyl)methyl)-2-fluorobenzamide;
2-Chloro-N-((4,4-difluoro-1-(4-(1-methyl-1H-imidazol-4-ylsulfonyl)piperazin-1-yl)cyclohexyl)methyl)-4-fluorobenzamide;
N-((4,4-Difluoro-1-(4-(1-methyl-1H-imidazol-4-ylsulfonyl)piperazin-1-yl)cyclohexyl)methyl)-2,4,6-trifluorobenzamide;
4-Chloro-N-((4,4-difluoro-1-(4-(1-methyl-1H-imidazol-4-ylsulfonyl)piperazin-1-yl)cyclohexyl)methyl)-2-methylbenzamide;
N-((4,4-Difluoro-1-(4-(1-methyl-1H-imidazol-4-ylsulfonyl)piperazin-1-yl)cyclohexyl)methyl)-4-fluoro-2-(trifluoromethyl)benzamide;
N-((4,4-Difluoro-1-(4-(1-methyl-1H-imidazol-4-ylsulfonyl)piperazin-1-yl)cyclohexyl)methyl)-2-fluoro-4-(trifluoromethyl)benzamide;
N-((4,4-Difluoro-1-(4-(1-methyl-1H-imidazol-4-ylsulfonyl)piperazin-1-yl)cyclohexyl)methyl)-2-chloro-4-(trifluoromethyl)benzamide;
N-((4,4-Difluoro-1-(4-(1-methyl-1H-imidazol-4-ylsulfonyl)piperazin-1-yl)cyclohexyl)methyl)-2-fluoro-6-(trifluoromethyl)benzamide;
2-Chloro-N-((4,4-Difluoro-1-(4-(1-methyl-1H-imidazol-4-ylsulfonyl)piperazin-1-yl)cyclohexyl)methyl)-6-methoxybenzamide;
2,6-Dichloro-N-((4,4-difluoro-1-(4-(1-methyl-1H-imidazol-4-ylsulfonyl)piperazin-1-yl)cyclohexyl)methyl)benzamide;
N-((4,4-Difluoro-1-(4-(1-methyl-1H-imidazol-4-ylsulfonyl)piperazin-1-yl)cyclohexyl)methyl)-2-fluorobenzamide;
N-((4,4-Difluoro-1-(4-(1-methyl-1H-imidazol-4-ylsulfonyl)piperazin-1-yl)cyclohexyl)methyl)-2-(trifluoromethyl)benzamide;
N-((4,4-Difluoro-1-(4-(1-methyl-1H-imidazol-4-ylsulfonyl)piperazin-1-yl)cyclohexyl)methyl)-2-methoxybenzamide;
2,4-Dichloro-N-((4,4-difluoro-1-(4-(1-methyl-1H-imidazol-4-ylsulfonyl)piperazin-1-yl)cyclohexyl)methyl)benzamide;
N-((4,4-difluoro-1-(4-(1-methyl-1H-imidazol-4-ylsulfonyl)piperazin-1-yl)cyclohexyl)methyl)-2-methylbenzamide;
2-Chloro-N-((4,4-difluoro-1-(4-(1-methyl-1H-imidazol-4-ylsulfonyl)piperazin-1-yl)cyclohexyl)methyl)-6-fluorobenzamide;
2-Chloro-N-((4,4-difluoro-1-(4-(1-methyl-1H-imidazol-4-ylsulfonyl)piperazin-1-yl)cyclohexyl)methyl)-6-methylbenzamide;
N-((4,4-Difluoro-1-(4-(1-methyl-1H-imidazol-4-ylsulfonyl)piperazin-1-yl)cyclohexyl)methyl)-2-fluoro-6-methylbenzamide;
N-((4,4-Difluoro-1-(4-(1-methyl-1H-imidazol-4-ylsulfonyl)piperazin-1-yl)cyclohexyl)methyl)-2-(difluoromethoxy)benzamide;
N-((4,4-Difluoro-1-(4-(1-methyl-1H-imidazol-4-ylsulfonyl)piperazin-1-yl)cyclohexyl)methyl)-4-fluoro-2-methylbenzamide;
2-Chloro-N-((4,4-difluoro-1-(4-(1-methyl-1H-imidazol-4-ylsulfonyl)piperazin-1-yl)cyclohexyl)methyl)-6-(trifluoromethyl)benzamide;
N-((4,4-Difluoro-1-(4-(1-methyl-1H-imidazol-4-ylsulfonyl)piperazin-1-yl)cyclohexyl)methyl)-2-fluoro-6-(trifluoromethoxy)benzamide;
2-Chloro-N-((4,4-difluoro-1-(4-(1-methyl-1H-imidazol-4-ylsulfonyl)piperazin-1-yl)cyclohexyl)methyl)-6-(trifluoromethoxy)benzamide;
N-((4,4-Difluoro-1-(4-(1-methyl-1H-imidazol-4-ylsulfonyl)piperazin-1-yl)cyclohexyl)methyl)-2-(difluoromethoxy)-6-fluorobenzamide;
N-((4,4-Difluoro-1-(4-(1-methyl-1H-1,2,3-triazol-4-ylsulfonyl)piperazin-1-yl)cyclohexyl)methyl)-2,6-difluorobenzamide;
2,6-Dichloro-N-((4,4-difluoro-1-(4-(1-methyl-1H-1,2,3-triazol-4-ylsulfonyl)piperazin-1-yl)cyclohexyl)methyl)benzamide;
2-Chloro-N-((4,4-difluoro-1-(4-(1-methyl-1H-1,2,3-triazol-4-ylsulfonyl)piperazin-1-yl)cyclohexyl)methyl)-6-(trifluoromethoxy)benzamide;
2-Chloro-N-((4,4-difluoro-1-(4-(1-methyl-1H-1,2,3-triazol-4-ylsulfonyl)piperazin-1-yl)cyclohexyl)methyl)-4-fluorobenzamide;
2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide;
N-(1-(4,4-Difluoro-1-(4-(1-methyl-1H-imidazol-4-ylsulfonyl)piperazin-1-yl)cyclohexyl)ethyl)-2,6-difluorobenzamide;
N-(1-(4,4-Difluoro-1-(4-(propylsulfonyl)piperazin-1-yl)cyclohexyl)ethyl)-2,6-difluorobenzamide;
2,6-Difluoro-N-((6-(4-(propylsulfonyl)piperazin-1-yl)spiro[2.5]octan-6-yl)methyl)benzamide;
2,6-Difluoro-N-((3-(4-(propylsulfonyl)piperazin-1-yl)bicyclo[3.1.0]hexan-3-yl)methyl)benzamide;
2,4-Dichloro-N-((1-(4-(cyclopropylmethylsulfonyl)piperidin-1-yl)cyclohexyl)methyl)benzamide;
N-((4,4-difluoro-1-(4-(propylsulfonyl)piperidin-1-yl)cyclohexyl)methyl)-2,6-difluorobenzamide;
4-Chloro-N-((1-(4-(propylsulfonyl)piperazin-1-yl)cyclohexyl)methyl)benzamide;
2-Chloro-N-((1-(4-(ethylsulfonyl)piperazin-1-yl)-4,4-difluorocyclohexyl)methyl)-4-(trifluoromethyl)benzamide;
2-Chloro-N-(1-(1-(4-(ethylsulfonyl)piperazin-1-yl)-4,4-difluorocyclohexyl)ethyl)-4-(trifluoromethyl)benzamide;
N-((1-(4-(Ethylsulfonyl)piperazin-1-yl)-4,4-difluorocyclohexyl)methyl)-2,4-bis(trifluoromethyl)benzamide;
2-Chloro-4-(1,1-difluoro ethyl)-N-((1-(4-(ethylsulfonyl)piperazin-1-yl)-4,4-difluorocyclohexyl)methyl)benzamide;
2-Chloro-N-((1-(4-(ethylsulfonyl)piperazin-1-yl)-4,4-difluorocyclohexyl)methyl)-4,6-bis(trifluoromethyl)benzamide;

2,6-Dichloro-N-((1-(4-(ethylsulfonyl)piperazin-1-yl)-4,4-difluorocyclohexyl)methyl)-4-(trifluoromethyl)benzamide;
4-Chloro-N-((1-(4-(ethylsulfonyl)piperazin-1-yl)-4,4-difluorocyclohexyl)methyl)-2,6-difluorobenzamide;
2,4,6-Trichloro-N-((1-(4-(ethylsulfonyl)piperazin-1-yl)-4,4-difluorocyclohexyl)methyl)benzamide;
2,4-Dichloro-N-((1-(4-(ethylsulfonyl)piperazin-1-yl)-4,4-difluorocyclohexyl)methyl)-6-fluorobenzamide;
N-((1-(4-(Ethylsulfonyl)piperazin-1-yl)-4,4-difluorocyclohexyl)methyl)-2,6-difluoro-3-(trifluoromethyl)benzamide;
2,4-Dichloro-N-((1-(4-(ethylsulfonyl)piperazin-1-yl)-4,4-difluorocyclohexyl)methyl)-5-fluorobenzamide;
3-Chloro-N-((1-(4-(ethylsulfonyl)piperazin-1-yl)-4,4-difluorocyclohexyl)methyl)-2,6-difluorobenzamide;
2-Chloro-N-((1-(4-(ethylsulfonyl)piperazin-1-yl)-4,4-difluorocyclohexyl)methyl)-4,5-difluorobenzamide;
2,6-Dichloro-N-((1-(4-(ethylsulfonyl)piperazin-1-yl)-4,4-difluorocyclohexyl)methyl)-3-(trifluoromethyl)benzamide;
N-((1-(4-(Ethylsulfonyl)piperazin-1-yl)-4,4-difluorocyclohexyl)methyl)-2,6-difluoro-4-methoxybenzamide;
N-((1-(4-(Ethylsulfonyl)piperazin-1-yl)-4,4-difluorocyclohexyl)methyl)-2,4,6-trimethylbenzamide;
N-((1-(4-(Ethylsulfonyl)-2-methylpiperazin-1-yl)-4,4-difluorocyclohexyl)methyl)-2,4-bis(trifluoromethyl)benzamide;
2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;
N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;
2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;
N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide;
2-Chloro-N-((4,4-difluoro-1-(3-methyl-4-(1-methyl-1H-1,2,3-triazol-4-ylsulfonyl)piperazin-1-yl)cyclohexyl)methyl)-4-(trifluoromethyl)benzamide;
2,4-Dichloro-N-((4,4-difluoro-1-(4-(1-methyl-1H-1,2,3-triazol-4-ylsulfonyl)piperazin-1-yl)cyclohexyl)methyl)benzamide;
N-((4,4-Difluoro-1-(4-(1-methyl-1H-1,2,3-triazol-4-ylsulfonyl)piperazin-1-yl)cyclohexyl)methyl)-2,4-difluorobenzamide;
4-Chloro-N-((4,4-difluoro-1-(4-(1-methyl-1H-1,2,3-triazol-4-ylsulfonyl)piperazin-1-yl)cyclohexyl)methyl)-2,6-difluorobenzamide;
2,4-Dichloro-N-((4,4-difluoro-1-(4-(1-methyl-1H-1,2,3-triazol-4-ylsulfonyl)piperazin-1-yl)cyclohexyl)methyl)-5-fluorobenzamide;
N-((4,4-Difluoro-1-(4-(1-methyl-1H-1,2,3-triazol-4-ylsulfonyl)piperazin-1-yl)cyclohexyl)methyl)-2-fluoro-4-(trifluoromethyl)benzamide;
N-((4,4-Difluoro-1-(4-(1-methyl-1H-1,2,3-triazol-4-ylsulfonyl)piperazin-1-yl)cyclohexyl)methyl)-4-fluoro-2-(trifluoromethyl)benzamide;
N-((4,4-Difluoro-1-(4-(1-methyl-1H-1,2,3-triazol-4-ylsulfonyl)piperazin-1-yl)cyclohexyl)methyl)-2,4,6-trifluorobenzamide;
2-Chloro-N-((4,4-difluoro-1-(4-(1-methyl-1H-1,2,3-triazol-4-ylsulfonyl)piperazin-1-yl)cyclohexyl)methyl)-4,5-difluorobenzamide;
2-Chloro-N-((1-(4-(1-(difluoromethyl)-1H-1,2,3-triazol-4-ylsulfonyl)piperazin-1-yl)-4,4-difluorocyclohexyl)methyl)-4-(trifluoromethyl)benzamide;
N-((1-(2,5-Dimethyl-4-(1-methyl-1H-1,2,3-triazol-4-ylsulfonyl)piperazin-1-yl)-4,4-difluorocyclohexyl)methyl)-2,4-bis(trifluoromethyl)benzamide;
4-Chloro-N-((4,4-difluoro-1-(4-(1-methyl-1H-1,2,3-triazol-4-ylsulfonyl)piperazin-1-yl)cyclohexyl)methyl)-2,5-difluorobenzamide;
N-((4,4-Difluoro-1-(4-(1-methyl-1H-1,2,3-triazol-4-ylsulfonyl)piperazin-1-yl)cyclohexyl)methyl)-2,5-difluoro-4-methylbenzamide;
2-Chloro-N-((4,4-difluoro-1-(4-(1-(tris-deutero)methyl-1H-1,2,3-triazol-4-ylsulfonyl)piperazin-1-yl)cyclohexyl)methyl)-4-(trifluoromethyl)benzamide;
2,4-Dichloro-N-((4,4-difluoro-1-(4-(1-methyl-1H-1,2,3-triazol-4-ylsulfonyl)piperazin-1-yl)cyclohexyl)methyl)-6-fluorobenzamide;
2-Chloro-N-((4,4-difluoro-1-(4-(1-methyl-1H-1,2,3-triazol-4-ylsulfonyl)piperazin-1-yl)cyclohexyl)methyl)-3-fluoro-4-methylbenzamide;
2,5-Dichloro-N-((4,4-difluoro-1-(4-(propylsulfonyl)piperazin-1-yl)cyclohexyl)methyl)benzamide;
2-Chloro-N-((4,4-difluoro-1-(4-(1-fluoropropylsulfonyl)piperazin-1-yl)cyclohexyl)methyl)-4-(trifluoromethyl)benzamide;
4-Chloro-N-((4,4-difluoro-1-(4-(propylsulfonyl)piperazin-1-yl)cyclohexyl)methyl)-2-(trifluoromethyl)benzamide;
N-((4,4-Difluoro-1-(4-(propylsulfonyl)piperazin-1-yl)cyclohexyl)methyl)-2,4-bis(trifluoromethyl)benzamide;
2-Chloro-4-cyclopropyl-N-((4,4-difluoro-1-(4-(propylsulfonyl)piperazin-1-yl)cyclohexyl)methyl)benzamide;
N-((4,4-Difluoro-1-(4-(propylsulfonyl)piperazin-1-yl)cyclohexyl)methyl)-2,5-bis(trifluoromethyl)benzamide;
4-Chloro-N-((4,4-difluoro-1-(4-(propylsulfonyl)piperazin-1-yl)cyclohexyl)methyl)-2-(difluoromethoxy)benzamide;
N-((4,4-Difluoro-1-(4-(propylsulfonyl)piperazin-1-yl)cyclohexyl)methyl)-2-(difluoromethoxy)-6-fluorobenzamide;
2-Chloro-N-((1-(4-(1,1-difluoropropylsulfonyl)piperazin-1-yl)-4,4-difluorocyclohexyl)methyl)-4-(trifluoromethyl)benzamide;
2-Chloro-N-((4,4-difluoro-1-(4-(2-hydroxypropylsulfonyl)piperazin-1-yl)cyclohexyl)methyl)-4-(trifluoromethyl)benzamide;
4-Chloro-2-cyclopropyl-N-((4,4-difluoro-1-(4-(propylsulfonyl)piperazin-1-yl)cyclohexyl)methyl)benzamide;
2-Chloro-N-((4,4-difluoro-1-(4-(propylsulfonyl)piperazin-1-yl)cyclohexyl)methyl)-4,6-bis(trifluoromethyl)benzamide;
2,4-Dichloro-N-((4,4-difluoro-1-(4-(propylsulfonyl)piperazin-1-yl)cyclohexyl)methyl)-6-fluorobenzamide;
2-Chloro-N-((4,4-difluoro-1-(3-methyl-4-(propylsulfonyl)piperazin-1-yl)cyclohexyl)methyl)-4-(trifluoromethyl)benzamide;
2-Chloro-N-((4,4-difluoro-1-(2-methyl-4-(propylsulfonyl)piperazin-1-yl)cyclohexyl)methyl)-4-(trifluoromethyl)benzamide;
2,6-Dichloro-N-((4,4-difluoro-1-(4-(propylsulfonyl)piperazin-1-yl)cyclohexyl)methyl)-4-(trifluoromethyl)benzamide;
4-Chloro-N-((4,4-difluoro-1-(4-(propylsulfonyl)piperazin-1-yl)cyclohexyl)methyl)-2,6-difluorobenzamide;
2,4,6-Trichloro-N-((4,4-difluoro-1-(4-(propylsulfonyl)piperazin-1-yl)cyclohexyl)methyl)benzamide;

2-Chloro-N-((4,4-difluoro-1-(3-(propylsulfonyl)-3,8-diazabicyclo[3.2.1]octan-8-yl)cyclohexyl)methyl)-4-(trifluoromethyl)benzamide;
N-((4,4-Difluoro-1-(4-(propylsulfonyl)piperazin-1-yl)cyclohexyl)methyl)-2,6-difluoro-3-(trifluoromethyl)benzamide;
2,4-Dichloro-N-((4,4-difluoro-1-(4-(propylsulfonyl)piperazin-1-yl)cyclohexyl)methyl)-5-fluorobenzamide;
2-Chloro-N-((4,4-difluoro-1-(4-(propylsulfonyl)piperazin-1-yl)cyclohexyl)methyl)-4,5-difluorobenzamide;
2,6-Dichloro-N-((4,4-difluoro-1-(4-(propylsulfonyl)piperazin-1-yl)cyclohexyl)methyl)-3-(trifluoromethyl)benzamide;
4-Chloro-N-((4,4-difluoro-1-(4-(propylsulfonyl)piperazin-1-yl)cyclohexyl)methyl)-2,6-dimethylbenzamide;
N-((4-(4-(propylsulfonyl)piperazin-1-yl)tetrahydro-2H-pyran-4-yl)methyl)-2,4-bis(trifluoromethyl)benzamide;
2,6-Difluoro-N-((4-(4-(propylsulfonyl)piperazin-1-yl)oxepan-4-yl)methyl)benzamide;
N-((4,4-Difluoro-1-(4-(pyridin-3-ylsulfonyl)piperazin-1-yl)cyclohexyl)methyl)-2,6-difluorobenzamide;
2-Chloro-N-((4,4-difluoro-1-(4-(pyrrolidin-1-ylsulfonyl)piperazin-1-yl)cyclohexyl)methyl)-4-(trifluoromethyl)benzamide;
N-((1-(4-(azetidin-1-ylsulfonyl)piperazin-1-yl)-4,4-difluorocyclohexyl)methyl)-2-chloro-4-(trifluoromethyl)benzamide;
2-Chloro-N-((1-(4-(N,N-dimethylsulfamoyl)piperazin-1-yl)-4,4-difluorocyclohexyl)methyl)-4-(trifluoromethyl)benzamide;
N-((4,4-Difluoro-1-(1-(1-methyl-1H-1,2,3-triazol-4-ylsulfonyl)piperidin-4-yl)cyclohexyl)methyl)-2,4-bis(trifluoromethyl)benzamide;
N-((1-(4-(1-Methyl-1H-1,2,3-triazol-4-ylsulfonyl)piperazin-1-yl)cyclopentyl)methyl)-2,4-bis(trifluoromethyl)benzamide;
N-((4-(4-(1-Methyl-1H-1,2,3-triazol-4-ylsulfonyl)piperazin-1-yl)tetrahydro-2H-pyran-4-yl)methyl)-2,4-bis(trifluoromethyl)benzamide;
2-Chloro-N-((4-(4-(1-methyl-1H-1,2,3-triazol-4-ylsulfonyl)piperazin-1-yl)tetrahydro-2H-pyran-4-yl)methyl)-4-(trifluoromethyl)benzamide;
2-Chloro-N-((4,4-difluoro-1-(4-(2-oxopropylsulfonyl)piperazin-1-yl)cyclohexyl)methyl)-4-(trifluoromethyl)benzamide;
2-Chloro-N-((4,4-difluoro-1-(4-(1-methyl-1H-1,2,4-triazol-3-ylsulfonyl)piperazin-1-yl)cyclohexyl)methyl)-4-(trifluoromethyl)benzamide;
2-Chloro-N-((1-(4-(1-methyl-1H-1,2,3-triazol-4-ylsulfonyl)piperazin-1-yl)cyclopentyl)methyl)-4-(trifluoromethyl)benzamide;
2-Chloro-4-fluoro-N-((1-(4-(1-methyl-1H-1,2,3-triazol-4-ylsulfonyl)piperazin-1-yl)cyclopentyl)methyl)benzamide;
2-Chloro-N-(1-(1-(4-(1-methyl-1H-1,2,3-triazol-4-ylsulfonyl)piperazin-1-yl)cyclopentyl)ethyl)-4-(trifluoromethyl)benzamide;
2-Chloro-4-fluoro-N-((4-(4-(1-methyl-1H-1,2,3-triazol-4-ylsulfonyl)piperazin-1-yl)tetrahydro-2H-pyran-4-yl)methyl)benzamide;
2-Chloro-N-(1-(4-(4-(1-methyl-1H-1,2,3-triazol-4-ylsulfonyl)piperazin-1-yl)tetrahydro-2H-pyran-4-yl)ethyl)-4-(trifluoromethyl)benzamide;
N-((4,4-difluoro-1-(4-(2-hydroxypropylsulfonyl)piperazin-1-yl)cyclohexyl)methyl)-2,4-bis(trifluoromethyl)benzamide;
N-((4,4-Difluoro-1-(1-(1-methyl-1H-1,2,3-triazol-4-ylsulfonyl)piperidin-4-yl)cyclohexyl)methyl)-2,4-bis(trifluoromethyl)benzamide;
2,4-Dichloro-N-((4,4-difluoro-1-(1-(1-methyl-1H-1,2,3-triazol-4-ylsulfonyl)piperidin-4-yl)cyclohexyl)methyl)benzamide;
2-Chloro-N-((4,4-difluoro-1-(1-(1-methyl-1H-1,2,3-triazol-4-ylsulfonyl)piperidin-4-yl)cyclohexyl)methyl)-4-fluorobenzamide;
N-(1-(4-(4-(1-Methyl-1H-1,2,3-triazol-4-ylsulfonyl)piperazin-1-yl)tetrahydro-2H-pyran-4-yl)ethyl)-2,4-bis(trifluoromethyl)benzamide;
2,4-Dichloro-N-((4,4-difluoro-1-(4-(2-hydroxypropylsulfonyl)piperazin-1-yl)cyclohexyl)methyl)benzamide;
N-(1-(1-(4-(1-Methyl-1H-1,2,3-triazol-4-ylsulfonyl)piperazin-1-yl)cyclopentyl)ethyl)-2,4-bis(trifluoromethyl)benzamide;
2-Chloro-N-((4,4-difluoro-1-(4-(2-hydroxypropylsulfonyl)piperazin-1-yl)cyclohexyl)methyl)-4-fluorobenzamide;
2-Chloro-N-(1-(4,4-difluoro-1-(4-(2-hydroxypropylsulfonyl)piperazin-1-yl)cyclohexyl)ethyl)-4-fluorobenzamide;
2-Chloro-N-(1-(4,4-difluoro-1-(4-(2-hydroxypropylsulfonyl)piperazin-1-yl)cyclohexyl)ethyl)-4-(trifluoromethyl)benzamide;
N-(1-(4,4-difluoro-1-(4-(2-hydroxypropylsulfonyl)piperazin-1-yl)cyclohexyl)ethyl)-2,4-bis(trifluoromethyl)benzamide;
2,4-Dichloro-N-(1-(4,4-difluoro-1-(4-(2-hydroxypropylsulfonyl)piperazin-1-yl)cyclohexyl)ethyl)benzamide;
2-Chloro-N-((3,3-difluoro-1-(4-(1-methyl-1H-1,2,3-triazol-4-ylsulfonyl)piperazin-1-yl)cyclopentyl)methyl)-4-fluorobenzamide;
2-Chloro-N-((3,3-difluoro-1-(4-(1-methyl-1H-1,2,3-triazol-4-ylsulfonyl)piperazin-1-yl)cyclopentyl)methyl)-4-(trifluoromethyl)benzamide;
N-((3,3-Difluoro-1-(4-(1-methyl-1H-1,2,3-triazol-4-ylsulfonyl)piperazin-1-yl)cyclopentyl)methyl)-2,4-bis(trifluoromethyl)benzamide;
2,4-Dichloro-N-((3,3-difluoro-1-(4-(1-methyl-1H-1,2,3-triazol-4-ylsulfonyl)piperazin-1-yl)cyclopentyl)methyl)benzamide;
2-Chloro-N-(1-(3,3-difluoro-1-(4-(1-methyl-1H-1,2,3-triazol-4-ylsulfonyl)piperazin-1-yl)cyclopentyl)ethyl)-4-fluorobenzamide;
2-Chloro-N-(1-(3,3-difluoro-1-(4-(1-methyl-1H-1,2,3-triazol-4-ylsulfonyl)piperazin-1-yl)cyclopentyl)ethyl)-4-(trifluoromethyl)benzamide;
N-(1-(3,3-Difluoro-1-(4-(1-methyl-1H-1,2,3-triazol-4-ylsulfonyl)piperazin-1-yl)cyclopentyl)ethyl)-2,4-bis(trifluoromethyl)benzamide; and
2,4-Dichloro-N-(1-(3,3-difluoro-1-(4-(1-methyl-1H-1,2,3-triazol-4-ylsulfonyl)piperazin-1-yl)cyclopentyl)ethyl)benzamide;
or an oxide thereof, a pharmaceutically acceptable salt thereof, a solvate thereof, or prodrug thereof.

Another embodiment of the present invention is a compound of formula (I) selected from the group consisting of:
2-Amino-6-chloro-N-((1-(4-(propylsulfonyl)piperazin-1-yl)cyclohexyl)methyl)benzamide;
2,4-Dichloro-N-((1-(4-(propylsulfonyl)piperazin-1-yl)cyclohexyl)methyl)benzamide;
N-((1-(4-(Propylsulfonyl)piperazin-1-yl)cyclohexyl)methyl)-2-(trifluoromethoxy)benzamide;
3-Chloro-2-fluoro-N-((1-(4-(propylsulfonyl)piperazin-1-yl)cyclohexyl)methyl)-6-(trifluoromethyl)benzamide;
2-Chloro-N-((1-(4-(propylsulfonyl)piperazin-1-yl)cyclohexyl)methyl)benzamide;

4-Chloro-2-methyl-N-((1-(4-(propylsulfonyl)piperazin-1-yl)cyclohexyl)methyl)benzamide;
4-Fluoro-2-methyl-N-((1-(4-(propylsulfonyl)piperazin-1-yl)cyclohexyl)methyl)benzamide;
2,6-Difluoro-N-((1-(4-(propylsulfonyl)piperazin-1-yl)cyclohexyl)methyl)benzamide;
4-Bromo-2-methyl-N-((1-(4-(propylsulfonyl)piperazin-1-yl)cyclohexyl)methyl)benzamide;
4-Fluoro-2-methoxy-6-methyl-N-((1-(4-(propylsulfonyl)piperazin-1-yl)cyclohexyl)methyl)benzamide;
4-Fluoro-2-methoxy-6-(methylthio)-N-((1-(4-(propylsulfonyl)piperazin-1-yl)cyclohexyl)methyl)benzamide;
2-Methoxy-N-((1(1-(4-(propylsulfonyl)piperazin-1-yl)cyclohexyl)methyl)-4,6-bis(trifluoromethyl)benzamide;
3-Methyl-N-((1-(4-(propylsulfonyl)piperazin-1-yl)cyclohexyl)methyl)benzamide;
2-Fluoro-6-methoxy-N-((1-(4-(propylsulfonyl)piperazin-1-yl)cyclohexyl)methyl)benzamide;
2,6-Dimethyl-N-((1-(4-(propylsulfonyl)piperazin-1-yl)cyclohexyl)methyl)benzamide;
2,4,6-Trifluoro-N-((1-(4-(propylsulfonyl)piperazin-1-yl)cyclohexyl)methyl)benzamide;
2-Fluoro-6-methyl-N-((1-(4-(propylsulfonyl)piperazin-1-yl)cyclohexyl)methyl)benzamide;
N-((1-(4-(Propylsulfonyl)piperazin-1-yl)cyclohexyl)methyl)-2-(trifluoromethyl)benzamide;
4-Chloro-2,6-difluoro-N-((1-(4-propyl sulfonyl)piperazin-1-yl)cycloheptyl)methyl)benzamide;
2-Chloro-3,6-difluoro-N-((1-(4-(propylsulfonyl)piperazin-1-yl)cycloheptyl)methyl)benzamide;
2-Fluoro-6-methoxy-N-((1-(4-(propylsulfonyl)piperazin-1-yl)cycloheptyl)methyl)benzamide;
2-Amino-6-chloro-N-((1-(4-(propylsulfonyl)piperazin-1-yl)cycloheptyl)methyl)benzamide;
2,4-Dichloro-N-((1-(4-(propylsulfonyl)piperazin-1-yl)cycloheptyl)methyl)benzamide;
2,6-Dichloro-N-((1-(4-(propylsulfonyl)piperazin-1-yl)cycloheptyl)methyl)benzamide;
2,6-Difluoro-N-((1-(4-(propylsulfonyl)piperazin-1-yl)cycloheptyl)methyl)benzamide;
4-Fluoro-2-methoxy-6-methyl-N-((1-(4-(propylsulfonyl)piperazin-1-yl)cycloheptyl)methyl)benzamide;
2-Methoxy-N-((1-(4-(propylsulfonyl)piperazin-1-yl)cycloheptyl)methyl)-4,6-bis(trifluoromethyl)benzamide;
4-Fluoro-N-((1-(4-(propylsulfonyl)piperazin-1-yl)cycloheptyl)methyl)-2-(trifluoromethyl)benzamide;
N-((1-(4-(Cyclopropylmethylsulfonyl)piperazin-1-yl)cyclohexyl)methyl)-4-fluoro-2-methoxy-6-methylbenzamide;
N-((1-(4-(Cyclopropylmethylsulfonyl)piperazin-1-yl)cyclohexyl)methyl)-2-fluoro-6-methylbenzamide;
N-((1-(4-(Cyclopropylmethylsulfonyl)piperazin-1-yl)cyclohexyl)methyl)-4-fluoro-2-methoxy-6-(methylthio)benzamide;
N-((1-(4-(Cyclopropylmethylsulfonyl)piperazin-1-yl)cyclohexyl)methyl)-2-fluoro-6-methoxybenzamide;
2,4-Dichloro-N-((1-(4-(cyclopropylmethylsulfonyl)piperazin-1-yl)cyclohexyl)methyl)benzamide;
2,4-Dimethyl-N-((1-(4-(1-methyl-1H-imidazol-4-ylsulfonyl)piperazin-1-yl)cyclohexyl)methyl)benzamide;
2,6-Dimethyl-N-((1-(4-(1-methyl-1H-imidazol-4-ylsulfonyl)piperazin-1-yl)cyclohexyl)methyl)benzamide;
2-Fluoro-6-methoxy-N-((1-(4-(1-methyl-1H-imidazol-4-ylsulfonyl)piperazin-1-yl)cyclohexyl)methyl)benzamide;
2,4-Dichloro-N-((1-(4-(1-methyl-1H-imidazol-4-ylsulfonyl)piperazin-1-yl)cyclohexyl)methyl)benzamide;
2,6-Difluoro-N-((1-(4-(1-methyl-1H-imidazol-4-ylsulfonyl)piperazin-1-yl)cyclohexyl)methyl)benzamide;
2-Amino-6-chloro-N-((1-(4-(1-methyl-1H-imidazol-4-ylsulfonyl)piperazin-1-yl)cyclohexyl)methyl)benzamide;
2,4-Difluoro-N-((1-(4-(1-methyl-1H-imidazol-4-ylsulfonyl)piperazin-1-yl)cyclohexyl)methyl)benzamide;
2-Chloro-4-fluoro-N-((1-(4-(1-methyl-1H-imidazol-4-ylsulfonyl)piperazin-1-yl)cyclohexyl)methyl)benzamide;
4-Fluoro-2-methyl-N-((1-(4-(1-methyl-1H-imidazol-4-ylsulfonyl)piperazin-1-yl)cyclohexyl)methyl)benzamide;
4-Fluoro-2-methoxy-6-methyl-N-((1-(4-(1-methyl-1H-imidazol-4-ylsulfonyl)piperazin-1-yl)cyclopentyl)methyl)benzamide;
2,6-Dichloro-N-((1-(4-(1-methyl-1H-imidazol-4-ylsulfonyl)piperazin-1-yl)cycloheptyl)methyl)benzamide;
2,6-Difluoro-N-((1-(4-(1-methyl-1H-imidazol-4-ylsulfonyl)piperazin-1-yl)cycloheptyl)methyl)benzamide;
2,6-Difluoro-N-((1-(4-(1-methyl-1H-1,2,3-triazol-4-ylsulfonyl)piperazin-1-yl)cyclopentyl)methyl)benzamide;
2,6-Dichloro-N-((1-(4-(1-methyl-1H-1,2,3-triazol-4-ylsulfonyl)piperazin-1-yl)cyclopentyl)methyl)benzamide;
2,4-Dichloro-N-((1-(4-(1-methyl-1H-1,2,3-triazol-4-ylsulfonyl)piperazin-1-yl)cyclopentyl)methyl)benzamide;
2,4-Difluoro-N-((1-(4-(1-methyl-1H-1,2,3-triazol-4-ylsulfonyl)piperazin-1-yl)cyclopentyl)methyl)benzamide;
4-Fluoro-2-methoxy-6-methyl-N-((1-(4-(1-methyl-1H-1,2,3-triazol-4-ylsulfonyl)piperazin-1-yl)cyclopentyl)methyl)benzamide;
4-Fluoro-2-methoxy-N-((1-(4-(1-methyl-1H-1,2,3-triazol-4-ylsulfonyl)piperazin-1-yl)cyclopentyl)methyl)-6-(methylthio)benzamide;
2,6-Difluoro-N-((1-(4-(1-methyl-1H-1,2,3-triazol-4-ylsulfonyl)piperazin-1-yl)cyclohexyl)methyl)benzamide;
2,6-Difluoro-N-((3-(4-(1-methyl-1H-imidazol-4-ylsulfonyl)piperazin-1-yl)tetrahydro-2H-pyran-3-yl)methyl)benzamide;
N-((4,4-Difluoro-1-(4-(propylsulfonyl)piperazin-1-yl)cyclohexyl)methyl)-2-fluorobenzamide;
N-((4,4-Difluoro-1-(4-(propylsulfonyl)piperazin-1-yl)cyclohexyl)methyl)-2-methoxybenzamide;
N-((4,4-Difluoro-1-(4-(propylsulfonyl)piperazin-1-yl)cyclohexyl)methyl)-2-methylbenzamide;
2,6-Dichloro-N-((4,4-difluoro-1-(4-(propylsulfonyl)piperazin-1-yl)cyclohexyl)methyl)benzamide;
2,4-Dichloro-N-((4,4-difluoro-1-(4-(propylsulfonyl)piperazin-1-yl)cyclohexyl)methyl)benzamide;
N-((4,4-Difluoro-1-(4-(propylsulfonyl)piperazin-1-yl)cyclohexyl)methyl)-4-fluoro-2-methoxy-6-methylbenzamide;
N-((4,4-Difluoro-1-(4-(propylsulfonyl)piperazin-1-yl)cyclohexyl)methyl)-4-fluoro-2-methoxy-6-(methylthio)benzamide;
N-((4,4-Difluoro-1-(4-(propylsulfonyl)piperazin-1-yl)cyclohexyl)methyl)-2,4-difluorobenzamide;
4-Chloro-N-((4,4-difluoro-1-(4-(propylsulfonyl)piperazin-1-yl)cyclohexyl)methyl)-2-fluorobenzamide;
N-((4,4-Difluoro-1-(4-(propylsulfonyl)piperazin-1-yl)cyclohexyl)methyl)-2,4,6-trifluorobenzamide;
N-((4,4-Difluoro-1-(4-(propylsulfonyl)piperazin-1-yl)cyclohexyl)methyl)-4-fluoro-2-methylbenzamide;
N-((4,4-Difluoro-1-(4-(propylsulfonyl)piperazin-1-yl)cyclohexyl)methyl)-2,6-dimethylbenzamide;
N-((4,4-Difluoro-1-(4-(propylsulfonyl)piperazin-1-yl)cyclohexyl)methyl)-2-fluoro-6-methylbenzamide;
N-((4,4-Difluoro-1-(4-(propylsulfonyl)piperazin-1-yl)cyclohexyl)methyl)-2-fluoro-4-(trifluoromethyl)benzamide;
N-((4,4-Difluoro-1-(4-(propylsulfonyl)piperazin-1-yl)cyclohexyl)methyl)-2-chloro-4-(trifluoromethyl)benzamide;

4-Chloro-N-((4,4-difluoro-1-(4-(propylsulfonyl)piperazin-1-yl)cyclohexyl)methyl)-2-methylbenzamide;
2-Chloro-N-((4,4-difluoro-1-(4-(propylsulfonyl)piperazin-1-yl)cyclohexyl)methyl)-4-fluorobenzamide;
2-Chloro-N-((4,4-difluoro-1-(4-(propylsulfonyl)piperazin-1-yl)cyclohexyl)methyl)-6-methylbenzamide;
2-Chloro-N-((4,4-difluoro-1-(4-(propylsulfonyl)piperazin-1-yl)cyclohexyl)methyl)-6-fluorobenzamide;
2-Chloro-N-((4,4-difluoro-1-(4-(propylsulfonyl)piperazin-1-yl)cyclohexyl)methyl)-6-(trifluoromethyl)benzamide;
N-((4,4-Difluoro-1-(4-(propylsulfonyl)piperazin-1-yl)cyclohexyl)methyl)-2-fluoro-6-(trifluoromethoxy)benzamide;
2-Chloro-N-((4,4-difluoro-1-(4-(propylsulfonyl)piperazin-1-yl)cyclohexyl)methyl)-6-(trifluoromethoxy)benzamide;
2-Chloro-N-((4,4-difluoro-1-(4-(1-methyl-1H-imidazol-4-ylsulfonyl)piperazin-1-yl)cyclohexyl)methyl)benzamide;
N-((4,4-difluoro-1-(4-(1-methyl-1H-imidazol-4-ylsulfonyl)piperazin-1-yl)cyclohexyl)methyl)-2-(trifluoromethoxy)benzamide;
N-((4,4-difluoro-1-(4-(1-methyl-1H-imidazol-4-ylsulfonyl)piperazin-1-yl)cyclohexyl)methyl)-2,4-difluorobenzamide;
N-((4,4-Difluoro-1-(4-(1-methyl-1H-imidazol-4-ylsulfonyl)piperazin-1-yl)cyclohexyl)methyl)-2,6-difluorobenzamide;
N-((4,4-Difluoro-1-(4-(1-methyl-1H-imidazol-4-ylsulfonyl)piperazin-1-yl)cyclohexyl)methyl)-2,6-dimethylbenzamide;
4-Chloro-N-((4,4-difluoro-1-(4-(1-methyl-1H-imidazol-4-ylsulfonyl)piperazin-1-yl)cyclohexyl)methyl)-2-fluorobenzamide;
2-Chloro-N-((4,4-difluoro-1-(4-(1-methyl-1H-imidazol-4-ylsulfonyl)piperazin-1-yl)cyclohexyl)methyl)-4-fluorobenzamide;
N-((4,4-Difluoro-1-(4-(1-methyl-1H-imidazol-4-ylsulfonyl)piperazin-1-yl)cyclohexyl)methyl)-2,4,6-trifluorobenzamide;
4-Chloro-N-((4,4-difluoro-1-(4-(1-methyl-1H-imidazol-4-ylsulfonyl)piperazin-1-yl)cyclohexyl)methyl)-2-methylbenzamide;
N-((4,4-Difluoro-1-(4-(1-methyl-1H-imidazol-4-ylsulfonyl)piperazin-1-yl)cyclohexyl)methyl)-4-fluoro-2-(trifluoromethyl)benzamide;
N-((4,4-Difluoro-1-(4-(1-methyl-1H-imidazol-4-ylsulfonyl)piperazin-1-yl)cyclohexyl)methyl)-2-fluoro-4-(trifluoromethyl)benzamide;
N-((4,4-Difluoro-1-(4-(1-methyl-1H-imidazol-4-ylsulfonyl)piperazin-1-yl)cyclohexyl)methyl)-2-chloro-4-(trifluoromethyl)benzamide;
N-((4,4-Difluoro-1-(4-(1-methyl-1H-imidazol-4-ylsulfonyl)piperazin-1-yl)cyclohexyl)methyl)-2-fluoro-6-(trifluoromethyl)benzamide;
2-Chloro-N-((4,4-Difluoro-1-(4-(1-methyl-1H-imidazol-4-ylsulfonyl)piperazin-1-yl)cyclohexyl)methyl)-6-methoxybenzamide;
2,6-Dichloro-N-((4,4-difluoro-1-(4-(1-methyl-1H-imidazol-4-ylsulfonyl)piperazin-1-yl)cyclohexyl)methyl)benzamide;
N-((4,4-Difluoro-1-(4-(1-methyl-1H-imidazol-4-ylsulfonyl)piperazin-1-yl)cyclohexyl)methyl)-2-fluorobenzamide;
N-((4,4-Difluoro-1-(4-(1-methyl-1H-imidazol-4-ylsulfonyl)piperazin-1-yl)cyclohexyl)methyl)-2-(trifluoromethyl)benzamide;
N-((4,4-Difluoro-1-(4-(1-methyl-1H-imidazol-4-ylsulfonyl)piperazin-1-yl)cyclohexyl)methyl)-2-methoxybenzamide;
2,4-Dichloro-N-((4,4-difluoro-1-(4-(1-methyl-1H-imidazol-4-ylsulfonyl)piperazin-1-yl)cyclohexyl)methyl)benzamide;
N-((4,4-difluoro-1-(4-(1-methyl-1H-imidazol-4-ylsulfonyl)piperazin-1-yl)cyclohexyl)methyl)-2-methylbenzamide;
2-Chloro-N-((4,4-difluoro-1-(4-(1-methyl-1H-imidazol-4-ylsulfonyl)piperazin-1-yl)cyclohexyl)methyl)-6-fluorobenzamide;
2-Chloro-N-((4,4-difluoro-1-(4-(1-methyl-1H-imidazol-4-ylsulfonyl)piperazin-1-yl)cyclohexyl)methyl)-6-methylbenzamide;
N-((4,4-Difluoro-1-(4-(1-methyl-1H-imidazol-4-ylsulfonyl)piperazin-1-yl)cyclohexyl)methyl)-2-fluoro-6-methylbenzamide;
N-((4,4-Difluoro-1-(4-(1-methyl-1H-imidazol-4-ylsulfonyl)piperazin-1-yl)cyclohexyl)methyl)-2-(difluoromethoxy)benzamide;
N-((4,4-Difluoro-1-(4-(1-methyl-1H-imidazol-4-ylsulfonyl)piperazin-1-yl)cyclohexyl)methyl)-4-fluoro-2-methylbenzamide;
2-Chloro-N-((4,4-difluoro-1-(4-(1-methyl-1H-imidazol-4-ylsulfonyl)piperazin-1-yl)cyclohexyl)methyl)-6-(trifluoromethyl)benzamide;
N-((4,4-Difluoro-1-(4-(1-methyl-1H-imidazol-4-ylsulfonyl)piperazin-1-yl)cyclohexyl)methyl)-2-fluoro-6-(trifluoromethoxy)benzamide;
2-Chloro-N-((4,4-difluoro-1-(4-(1-methyl-1H-imidazol-4-ylsulfonyl)piperazin-1-yl)cyclohexyl)methyl)-6-(trifluoromethoxy)benzamide;
N-((4,4-Difluoro-1-(4-(1-methyl-1H-imidazol-4-ylsulfonyl)piperazin-1-yl)cyclohexyl)methyl)-2-(difluoromethoxy)-6-fluorobenzamide;
N-((4,4-Difluoro-1-(4-(1-methyl-1H-1,2,3-triazol-4-ylsulfonyl)piperazin-1-yl)cyclohexyl)methyl)-2,6-difluorobenzamide;
2,6-Dichloro-N-((4,4-difluoro-1-(4-(1-methyl-1H-1,2,3-triazol-4-ylsulfonyl)piperazin-1-yl)cyclohexyl)methyl)benzamide;
2-Chloro-N-((4,4-difluoro-1-(4-(1-methyl-1H-1,2,3-triazol-4-ylsulfonyl)piperazin-1-yl)cyclohexyl)methyl)-6-(trifluoromethoxy)benzamide;
2-Chloro-N-((4,4-difluoro-1-(4-(1-methyl-1H-1,2,3-triazol-4-ylsulfonyl)piperazin-1-yl)cyclohexyl)methyl)-4-fluorobenzamide;
2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide;
N-(1-(4,4-Difluoro-1-(4-(1-methyl-1H-imidazol-4-ylsulfonyl)piperazin-1-yl)cyclohexyl)ethyl)-2,6-difluorobenzamide;
2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;
N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;
2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;
N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide;
2-Chloro-N-((4,4-difluoro-1-(3-methyl-4-(1-methyl-1H-1,2,3-triazol-4-ylsulfonyl)piperazin-1-yl)cyclohexyl)methyl)-4-(trifluoromethyl)benzamide;

2,4-Dichloro-N-((4,4-difluoro-1-(4-(1-methyl-1H-1,2,3-triazol-4-ylsulfonyl)piperazin-1-yl)cyclohexyl)methyl)benzamide;
N-((4,4-Difluoro-1-(4-(1-methyl-1H-1,2,3-triazol-4-ylsulfonyl)piperazin-1-yl)cyclohexyl)methyl)-2,4-difluorobenzamide;
4-Chloro-N-((4,4-difluoro-1-(4-(1-methyl-1H-1,2,3-triazol-4-ylsulfonyl)piperazin-1-yl)cyclohexyl)methyl)-2,6-difluorobenzamide;
2,4-Dichloro-N-((4,4-difluoro-1-(4-(1-methyl-1H-1,2,3-triazol-4-ylsulfonyl)piperazin-1-yl)cyclohexyl)methyl)-5-fluorobenzamide;
N-((4,4-Difluoro-1-(4-(1-methyl-1H-1,2,3-triazol-4-ylsulfonyl)piperazin-1-yl)cyclohexyl)methyl)-2-fluoro-4-(trifluoromethyl)benzamide;
N-((4,4-Difluoro-1-(4-(1-methyl-1H-1,2,3-triazol-4-ylsulfonyl)piperazin-1-yl)cyclohexyl)methyl)-4-fluoro-2-(trifluoromethyl)benzamide;
N-((4,4-Difluoro-1-(4-(1-methyl-1H-1,2,3-triazol-4-ylsulfonyl)piperazin-1-yl)cyclohexyl)methyl)-2,4,6-trifluorobenzamide;
2-Chloro-N-((4,4-difluoro-1-(4-(1-methyl-1H-1,2,3-triazol-4-ylsulfonyl)piperazin-1-yl)cyclohexyl)methyl)-4,5-difluorobenzamide;
2-Chloro-N-((1-(4-(1-(difluoromethyl)-1H-1,2,3-triazol-4-ylsulfonyl)piperazin-1-yl)-4,4-difluorocyclohexyl)methyl)-4-(trifluoromethyl)benzamide;
N-((1-(2,5-Dimethyl-4-(1-methyl-1H-1,2,3-triazol-4-ylsulfonyl)piperazin-1-yl)-4,4-difluorocyclohexyl)methyl)-2,4-bis(trifluoromethyl)benzamide;
4-Chloro-N-((4,4-difluoro-1-(4-(1-methyl-1H-1,2,3-triazol-4-ylsulfonyl)piperazin-1-yl)cyclohexyl)methyl)-2,5-difluorobenzamide;
N-((4,4-Difluoro-1-(4-(1-methyl-1H-1,2,3-triazol-4-ylsulfonyl)piperazin-1-yl)cyclohexyl)methyl)-2,5-difluoro-4-methylbenzamide;
2-Chloro-N-((4,4-difluoro-1-(4-(1-(tris-deutero)methyl-1H-1,2,3-triazol-4-ylsulfonyl)piperazin-1-yl)cyclohexyl)methyl)-4-(trifluoromethyl)benzamide;
2,4-Dichloro-N-((4,4-difluoro-1-(4-(1-methyl-1H-1,2,3-triazol-4-ylsulfonyl)piperazin-1-yl)cyclohexyl)methyl)-6-fluorobenzamide;
2-Chloro-N-((4,4-difluoro-1-(4-(1-methyl-1H-1,2,3-triazol-4-ylsulfonyl)piperazin-1-yl)cyclohexyl)methyl)-3-fluoro-4-methylbenzamide;
N-((4,4-Difluoro-1-(4-(propylsulfonyl)piperazin-1-yl)cyclohexyl)methyl)-2,6-difluorobenzamide;
2,5-Dichloro-N-((4,4-difluoro-1-(4-(propylsulfonyl)piperazin-1-yl)cyclohexyl)methyl)benzamide;
2-Chloro-N-((4,4-difluoro-1-(4-(1-fluoropropylsulfonyl)piperazin-1-yl)cyclohexyl)methyl)-4-(trifluoromethyl)benzamide;
4-Chloro-N-((4,4-difluoro-1-(4-(propylsulfonyl)piperazin-1-yl)cyclohexyl)methyl)-2-(trifluoromethyl)benzamide;
N-((4,4-Difluoro-1-(4-(propylsulfonyl)piperazin-1-yl)cyclohexyl)methyl)-2,4-bis(trifluoromethyl)benzamide;
2-Chloro-4-cyclopropyl-N-((4,4-difluoro-1-(4-(propylsulfonyl)piperazin-1-yl)cyclohexyl)methyl)benzamide;
4-Chloro-N-((4,4-difluoro-1-(4-(propylsulfonyl)piperazin-1-yl)cyclohexyl)methyl)-2-(difluoromethoxy)benzamide;
N-((4,4-Difluoro-1-(4-(propylsulfonyl)piperazin-1-yl)cyclohexyl)methyl)-2-(difluoromethoxy)-6-fluorobenzamide;
2-Chloro-N-((4,4-difluoro-1-(4-(2-hydroxypropylsulfonyl)piperazin-1-yl)cyclohexyl)methyl)-4-(trifluoromethyl)benzamide;
4-Chloro-2-cyclopropyl-N-((4,4-difluoro-1-(4-(propylsulfonyl)piperazin-1-yl)cyclohexyl)methyl)benzamide;
2-Chloro-N-((4,4-difluoro-1-(4-(propylsulfonyl)piperazin-1-yl)cyclohexyl)methyl)-4,6-bis(trifluoromethyl)benzamide;
2,4-Dichloro-N-((4,4-difluoro-1-(4-(propylsulfonyl)piperazin-1-yl)cyclohexyl)methyl)-6-fluorobenzamide;
2-Chloro-N-((4,4-difluoro-1-(2-methyl-4-(propylsulfonyl)piperazin-1-yl)cyclohexyl)methyl)-4-(trifluoromethyl)benzamide;
2,6-Dichloro-N-((4,4-difluoro-1-(4-(propylsulfonyl)piperazin-1-yl)cyclohexyl)methyl)-4-(trifluoromethyl)benzamide;
4-Chloro-N-((4,4-difluoro-1-(4-(propylsulfonyl)piperazin-1-yl)cyclohexyl)methyl)-2,6-difluorobenzamide;
2,4,6-Trichloro-N-((4,4-difluoro-1-(4-(propylsulfonyl)piperazin-1-yl)cyclohexyl)methyl)benzamide;
2,4-Dichloro-N-((4,4-difluoro-1-(4-(propylsulfonyl)piperazin-1-yl)cyclohexyl)methyl)-5-fluorobenzamide;
2-Chloro-N-((4,4-difluoro-1-(4-(propylsulfonyl)piperazin-1-yl)cyclohexyl)methyl)-4,5-difluorobenzamide;
4-Chloro-N-((4,4-difluoro-1-(4-(propylsulfonyl)piperazin-1-yl)cyclohexyl)methyl)-2,6-dimethylbenzamide;
N-((4-(4-(propylsulfonyl)piperazin-1-yl)tetrahydro-2H-pyran-4-yl)methyl)-2,4-bis(trifluoromethyl)benzamide;
2-Chloro-N-((4,4-difluoro-1-(4-(pyrrolidin-1-ylsulfonyl)piperazin-1-yl)cyclohexyl)methyl)-4-(trifluoromethyl)benzamide;
N-((1-(4-(1-Methyl-1H-1,2,3-triazol-4-ylsulfonyl)piperazin-1-yl)cyclopentyl)methyl)-2,4-bis(trifluoromethyl)benzamide;
N-((4-(4-(1-Methyl-1H-1,2,3-triazol-4-ylsulfonyl)piperazin-1-yl)tetrahydro-2H-pyran-4-yl)methyl)-2,4-bis(trifluoromethyl)benzamide;
2-Chloro-N-((4-(4-(1-methyl-1H-1,2,3-triazol-4-ylsulfonyl)piperazin-1-yl)tetrahydro-2H-pyran-4-yl)methyl)-4(trifluoromethyl)benzamide;
2-Chloro-N-((1-(4-(1-methyl-1H-1,2,3-triazol-4-ylsulfonyl)piperazin-1-yl)cyclopentyl)methyl)-4-(trifluoromethyl)benzamide;
2-Chloro-4-fluoro-N-((1-(4-(1-methyl-1H-1,2,3-triazol-4-ylsulfonyl)piperazin-1-yl)cyclopentyl)methyl)benzamide;
2-Chloro-N-(1-(1-(4-(1-methyl-1H-1,2,3-triazol-4-ylsulfonyl)piperazin-1-yl)cyclopentyl)ethyl)-4-(trifluoromethyl)benzamide;
2-Chloro-4-fluoro-N-((4-(4-(1-methyl-1H-1,2,3-triazol-4-ylsulfonyl)piperazin-1-yl)tetrahydro-2H-pyran-4-yl)methyl)benzamide;
2-Chloro-N-(1-(4-(4-(1-methyl-1H-1,2,3-triazol-4-ylsulfonyl)piperazin-1-yl)tetrahydro-2H-pyran-4-yl)ethyl)-4-(trifluoromethyl)benzamide;
N-((4,4-difluoro-1-(4-(2-hydroxypropylsulfonyl)piperazin-1-yl)cyclohexyl)methyl)-2,4-bis(trifluoromethyl)benzamide;
N-((4,4-Difluoro-1-(1-(1-methyl-1H-1,2,3-triazol-4-ylsulfonyl)piperidin-4-yl)cyclohexyl)methyl)-2,4-bis(trifluoromethyl)benzamide;
2,4-Dichloro-N-((4,4-difluoro-1-(1-(1-methyl-1H-1,2,3-triazol-4-ylsulfonyl)piperidin-4-yl)cyclohexyl)methyl)benzamide;
2-Chloro-N-((4,4-difluoro-1-(1-(1-methyl-1H-1,2,3-triazol-4-ylsulfonyl)piperidin-4-yl)cyclohexyl)methyl)-4-fluorobenzamide;
N-(1-(4-(4-(1-Methyl-1H-1,2,3-triazol-4-ylsulfonyl)piperazin-1-yl)tetrahydro-2H-pyran-4-yl)ethyl)-2,4-bis(trifluoromethyl)benzamide;

2,4-Dichloro-N-((4,4-difluoro-1-(4-(2-hydroxypropylsulfonyl)piperazin-1-yl)cyclohexyl)methyl)benzamide;
N-(1-(1-(4-(1-Methyl-1H-1,2,3-triazol-4-ylsulfonyl)piperazin-1-yl)cyclopentyl)ethyl)-2,4-bis(trifluoromethyl)benzamide;
2-Chloro-N-((4,4-difluoro-1-(4-(2-hydroxypropylsulfonyl)piperazin-1-yl)cyclohexyl)methyl)-4-fluorobenzamide;
2-Chloro-N-(1-(4,4-difluoro-1-(4-(2-hydroxypropylsulfonyl)piperazin-1-yl)cyclohexyl)ethyl)-4-fluorobenzamide;
2-Chloro-N-(1-(4,4-difluoro-1-(4-(2-hydroxypropylsulfonyl)piperazin-1-yl)cyclohexyl)ethyl)-4-(trifluoromethyl)benzamide;
N-(1-(4,4-difluoro-1-(4-(2-hydroxypropylsulfonyl)piperazin-1-yl)cyclohexyl)ethyl)-2,4-bis(trifluoromethyl)benzamide;
2,4-Dichloro-N-(1-(4,4-difluoro-1-(4-(2-hydroxypropylsulfonyl)piperazin-1-yl)cyclohexyl)ethyl)benzamide;
2-Chloro-N-((3,3-difluoro-1-(4-(1-methyl-1H-1,2,3-triazol-4-ylsulfonyl)piperazin-1-yl)cyclopentyl)methyl)-4-fluorobenzamide;
2-Chloro-N-((3,3-difluoro-1-(4-(1-methyl-1H-1,2,3-triazol-4-ylsulfonyl)piperazin-1-yl)cyclopentyl)methyl)-4-(trifluoromethyl)benzamide;
N-((3,3-Difluoro-1-(4-(1-methyl-1H-1,2,3-triazol-4-ylsulfonyl)piperazin-1-yl)cyclopentyl)methyl)-2,4-bis(trifluoromethyl)benzamide;
2,4-Dichloro-N-((3,3-difluoro-1-(4-(1-methyl-1H-1,2,3-triazol-4-ylsulfonyl)piperazin-1-yl)cyclopentyl)methyl)benzamide;
2-Chloro-N-(1-(3,3-difluoro-1-(4-(1-methyl-1H-1,2,3-triazol-4-ylsulfonyl)piperazin-1-yl)cyclopentyl)ethyl)-4-fluorobenzamide;
2-Chloro-N-(1-(3,3-difluoro-1-(4-(1-methyl-1H-1,2,3-triazol-4-ylsulfonyl)piperazin-1-yl)cyclopentyl)ethyl)-4-(trifluoromethyl)benzamide;
N-(1-(3,3-Difluoro-1-(4-(1-methyl-1H-1,2,3-triazol-4-ylsulfonyl)piperazin-1-yl)cyclopentyl)ethyl)-2,4-bis(trifluoromethyl)benzamide; and
2,4-Dichloro-N-(1-(3,3-difluoro-1-(4-(1-methyl-1H-1,2,3-triazol-4-ylsulfonyl)piperazin-1-yl)cyclopentyl)ethyl)benzamide.

Another embodiment of the present invention is a compound of formula (I) selected from the group consisting of:
N-((4,4-Difluoro-1-(4-(propylsulfonyl)piperazin-1-yl)cyclohexyl)methyl)-2,6-difluorobenzamide;
N-((4,4-Difluoro-1-(4-(propylsulfonyl)piperazin-1-yl)cyclohexyl)methyl)-2-chloro-4-(trifluoromethyl)benzamide;
N-((4,4-Difluoro-1-(4-(propylsulfonyl)piperazin-1-yl)cyclohexyl)methyl)-2,4-bis(trifluoromethyl)benzamide;
N-((4,4-difluoro-1-(4-(1-methyl-1H-imidazol-4-ylsulfonyl)piperazin-1-yl)cyclohexyl)methyl)-2,4-difluorobenzamide;
N-((4,4-Difluoro-1-(4-(1-methyl-1H-imidazol-4-ylsulfonyl)piperazin-1-yl)cyclohexyl)methyl)-2,6-difluorobenzamide;
N-((4,4-Difluoro-1-(4-(1-methyl-1H-1,2,3-triazol-4-ylsulfonyl)piperazin-1-yl)cyclohexyl)methyl)-2,6-difluorobenzamide;
2-Chloro-N-((4,4-difluoro-1-(4-(1-methyl-1H-1,2,3-triazol-4-ylsulfonyl)piperazin-1-yl)cyclohexyl)methyl)-4-fluorobenzamide;
2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide;
2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;
N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;
2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;
N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide;
N-((4,4-Difluoro-1-(4-(propylsulfonyl)piperazin-1-yl)cyclohexyl)methyl)-2,4-bis(trifluoromethyl)benzamide;
2-Chloro-N-((4,4-difluoro-1-(4-(2-hydroxypropylsulfonyl)piperazin-1-yl)cyclohexyl)methyl)-4-(trifluoromethyl)benzamide;
N-((4-(4-(propylsulfonyl)piperazin-1-yl)tetrahydro-2H-pyran-4-yl)methyl)-2,4-bis(trifluoromethyl)benzamide;
2-Chloro-N-((4,4-difluoro-1-(4-(1-methyl-1H-imidazol-4-ylsulfonyl)piperazin-1-yl)cyclohexyl)methyl)-4-fluorobenzamide;
2-Chloro-N-((1-(4-(1-methyl-1H-1,2,3-triazol-4-ylsulfonyl)piperazin-1-yl)cyclopentyl)methyl)-4-(trifluoromethyl)benzamide;
2-Chloro-4-fluoro-N-((1-(4-(1-methyl-1H-1,2,3-triazol-4-ylsulfonyl)piperazin-1-yl)cyclopentyl)methyl)benzamide;
2-Chloro-N-(1-(1-(4-(1-methyl-1H-1,2,3-triazol-4-ylsulfonyl)piperazin-1-yl)cyclopentyl)ethyl)-4-(trifluoromethyl)benzamide;
2-Chloro-4-fluoro-N-((4-(4-(1-methyl-1H-1,2,3-triazol-4-ylsulfonyl)piperazin-1-yl)tetrahydro-2H-pyran-4-yl)methyl)benzamide;
2-Chloro-N-(1-(4-(4-(1-methyl-1H-1,2,3-triazol-4-ylsulfonyl)piperazin-1-yl)tetrahydro-2H-pyran-4-yl)ethyl)-4-(trifluoromethyl)benzamide;
N-((4,4-difluoro-1-(4-(2-hydroxypropylsulfonyl)piperazin-1-yl)cyclohexyl)methyl)-2,4-bis(trifluoromethyl)benzamide;
N-((4,4-Difluoro-1-(1-(1-methyl-1H-1,2,3-triazol-4-ylsulfonyl)piperidin-4-yl)cyclohexyl)methyl)-2,4-bis(trifluoromethyl)benzamide;
2,4-Dichloro-N-((4,4-difluoro-1-(1-(1-methyl-1H-1,2,3-triazol-4-yl)piperidin-4-yl)cyclohexyl)methyl)benzamide;
2-Chloro-N-((4,4-difluoro-1-(1-(1-methyl-1H-1,2,3-triazol-4-ylsulfonyl)piperidin-4-yl)cyclohexyl)methyl)-4-fluorobenzamide;
N-(1-(4-(4-(1-Methyl-1H-1,2,3-triazol-4-ylsulfonyl)piperazin-1-yl)tetrahydro-2H-pyran-4-yl)ethyl)-2,4-bis(trifluoromethyl)benzamide;
2,4-Dichloro-N-((4,4-difluoro-1-(4-(2-hydroxypropylsulfonyl)piperazin-1-yl)cyclohexyl)methyl)benzamide;
N-(1-(1-(4-(1-Methyl-1H-1,2,3-triazol-4-ylsulfonyl)piperazin-1-yl)cyclopentyl)ethyl)-2,4-bis(trifluoromethyl)benzamide;
2-Chloro-N-((4,4-difluoro-1-(4-(2-hydroxypropylsulfonyl)piperazin-1-yl)cyclohexyl)methyl)-4-fluorobenzamide;
2-Chloro-N-(1-(4,4-difluoro-1-(4-(2-hydroxypropylsulfonyl)piperazin-1-yl)cyclohexyl)ethyl)-4-fluorobenzamide;
2-Chloro-N-(1-(4,4-difluoro-1-(4-(2-hydroxypropylsulfonyl)piperazin-1-yl)cyclohexyl)ethyl)-4-(trifluoromethyl)benzamide;
N-(1-(4,4-difluoro-1-(4-(2-hydroxypropylsulfonyl)piperazin-1-yl)cyclohexyl)ethyl)-2,4-bis(trifluoromethyl)benzamide;

2,4-Dichloro-N-(1-(4,4-difluoro-1-(4-(2-hydroxypropylsulfonyl)piperazin-1-yl)cyclohexyl)ethyl)benzamide;
2-Chloro-N-((3,3-difluoro-1-(4-(1-methyl-1H-1,2,3-triazol-4-ylsulfonyl)piperazin-1-yl)cyclopentyl)methyl)-4-fluorobenzamide;
2-Chloro-N-((3,3-difluoro-1-(4-(1-methyl-1H-1,2,3-triazol-4-ylsulfonyl)piperazin-1-yl)cyclopentyl)methyl)-4-(trifluoromethyl)benzamide;
N-((3,3-Difluoro-1-(4-(1-methyl-1H-1,2,3-triazol-4-ylsulfonyl)piperazin-1-yl)cyclopentyl)methyl)-2,4-bis(trifluoromethyl)benzamide;
2,4-Dichloro-N-((3,3-difluoro-1-(4-(1-methyl-1H-1,2,3-triazol-4-ylsulfonyl)piperazin-1-yl)cyclopentyl)methyl)benzamide;
2-Chloro-N-(1-(3,3-difluoro-1-(4-(1-methyl-1H-1,2,3-triazol-4-ylsulfonyl)piperazin-1-yl)cyclopentyl)ethyl)-4-fluorobenzamide;
2-Chloro-N-(1-(3,3-difluoro-1-(4-(1-methyl-1H-1,2,3-triazol-4-ylsulfonyl)piperazin-1-yl)cyclopentyl)ethyl)-4-(trifluoromethyl)benzamide;
N-(1-(3,3-Difluoro-1-(4-(1-methyl-1H-1,2,3-triazol-4-ylsulfonyl)piperazin-1-yl)cyclopentyl)ethyl)-2,4-bis(trifluoromethyl)benzamide; and
2,4-Dichloro-N-(1-(3,3-difluoro-1-(4-(1-methyl-1H-1,2,3-triazol-4-ylsulfonyl)piperazin-1-yl)cyclopentyl)ethyl)benzamide.

Another embodiment of the present invention is a compound of formula (I) selected from the group consisting of:
2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;
2-Chloro-N-((4,4-difluoro-1-(4-(1-methyl-1H-1,2,3-triazol-4-ylsulfonyl)piperazin-1-yl)cyclohexyl)methyl)-4-fluorobenzamide;
N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;
2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;
2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;
N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide;
N-((4,4-Difluoro-1-(4-(propylsulfonyl)piperazin-1-yl)cyclohexyl)methyl)-2-chloro-4-(trifluoromethyl)benzamide;
N-((4,4-Difluoro-1-(4-(propylsulfonyl)piperazin-1-yl)cyclohexyl)methyl)-2,4-bis(trifluoromethyl)benzamide;
2-Chloro-N-((4,4-difluoro-1-(4-(2-hydroxypropylsulfonyl)piperazin-1-yl)cyclohexyl)methyl)-4-(trifluoromethyl)benzamide;
2-Chloro-N-((1-(4-(1-methyl-1H-1,2,3-triazol-4-ylsulfonyl)piperazin-1-yl)cyclopentyl)methyl)-4-(trifluoromethyl)benzamide;
2-Chloro-4-fluoro-N-((1-(4-(1-methyl-1H-1,2,3-triazol-4-ylsulfonyl)piperazin-1-yl)cyclopentyl)methyl)benzamide;
2-Chloro-N-(1-(1-(4-(1-methyl-1H-1,2,3-triazol-4-ylsulfonyl)piperazin-1-yl)cyclopentyl)ethyl)-4-(trifluoromethyl)benzamide;
2-Chloro-4-fluoro-N-((4-(4-(1-methyl-1H-1,2,3-triazol-4-ylsulfonyl)piperazin-1-yl)tetrahydro-2H-pyran-4-yl)methyl)benzamide;
2-Chloro-N-(1-(4-(4-(1-methyl-1H-1,2,3-triazol-4-ylsulfonyl)piperazin-1-yl)tetrahydro-2H-pyran-4-yl)ethyl)-4-(trifluoromethyl)benzamide;
N-((4,4-difluoro-1-(4-(2-hydroxypropylsulfonyl)piperazin-1-yl)cyclohexyl)methyl)-2,4-bis(trifluoromethyl)benzamide;
N-((4,4-Difluoro-1-(4-(1-methyl-1H-1,2,3-triazol-4-ylsulfonyl)piperidin-4-yl)cyclohexyl)methyl)-2,4-bis(trifluoromethyl)benzamide;
2,4-Dichloro-N-((4,4-difluoro-1-(1-(1-methyl-1H-1,2,3-triazol-4-ylsulfonyl)piperidin-4-yl)cyclohexyl)methyl)benzamide;
2-Chloro-N-((4,4-difluoro-1-(1-(1-methyl-1H-1,2,3-triazol-4-ylsulfonyl)piperidin-4-yl)cyclohexyl)methyl)-4-fluorobenzamide;
N-(1-(4-(4-(1-Methyl-1H-1,2,3-triazol-4-ylsulfonyl)piperazin-1-yl)tetrahydro-2H-pyran-4-yl)ethyl)-2,4-bis(trifluoromethyl)benzamide;
2,4-Dichloro-N-((4,4-difluoro-1-(4-(2-hydroxypropylsulfonyl)piperazin-1-yl)cyclohexyl)methyl)benzamide;
N-(1-(1-(4-(1-Methyl-1H-1,2,3-triazol-4-ylsulfonyl)piperazin-1-yl)cyclopentyl)ethyl)-2,4-bis(trifluoromethyl)benzamide;
2-Chloro-N-((4,4-difluoro-1-(4-(2-hydroxypropylsulfonyl)piperazin-1-yl)cyclohexyl)methyl)-4-fluorobenzamide;
2-Chloro-N-(1-(4,4-difluoro-1-(4-(2-hydroxypropylsulfonyl)piperazin-1-yl)cyclohexyl)ethyl)-4-fluorobenzamide;
2-Chloro-N-(1-(4,4-difluoro-1-(4-(2-hydroxypropylsulfonyl)piperazin-1-yl)cyclohexyl)ethyl)-4-(trifluoromethyl)benzamide;
N-(1-(4,4-difluoro-1-(4-(2-hydroxypropylsulfonyl)piperazin-1-yl)cyclohexyl)ethyl)-2,4-bis(trifluoromethyl)benzamide;
2,4-Dichloro-N-(1-(4,4-difluoro-1-(4-(2-hydroxypropylsulfonyl)piperazin-1-yl)cyclohexyl)ethyl)benzamide;
2-Chloro-N-((3,3-difluoro-1-(4-(1-methyl-1H-1,2,3-triazol-4-ylsulfonyl)piperazin-1-yl)cyclopentyl)methyl)-4-fluorobenzamide;
2-Chloro-N-((3,3-difluoro-1-(4-(1-methyl-1H-1,2,3-triazol-4-ylsulfonyl)piperazin-1-yl)cyclopentyl)methyl)-4-(trifluoromethyl)benzamide;
N-((3,3-Difluoro-1-(4-(1-methyl-1H-1,2,3-triazol-4-ylsulfonyl)piperazin-1-yl)cyclopentyl)methyl)-2,4-bis(trifluoromethyl)benzamide;
2,4-Dichloro-N-((3,3-difluoro-1-(4-(1-methyl-1H-1,2,3-triazol-4-ylsulfonyl)piperazin-1-yl)cyclopentyl)methyl)benzamide;
2-Chloro-N-(1-(3,3-difluoro-1-(4-(1-methyl-1H-1,2,3-triazol-4-ylsulfonyl)piperazin-1-yl)cyclopentyl)ethyl)-4-fluorobenzamide;
2-Chloro-N-(1-(3,3-difluoro-1-(4-(1-methyl-1H-1,2,3-triazol-4-ylsulfonyl)piperazin-1-yl)cyclopentyl)ethyl)-4-(trifluoromethyl)benzamide;
N-(1-(3,3-Difluoro-1-(4-(1-methyl-1H-1,2,3-triazol-4-ylsulfonyl)piperazin-1-yl)cyclopentyl)ethyl)-2,4-bis(trifluoromethyl)benzamide; and
2,4-Dichloro-N-(1-(3,3-difluoro-1-(4-(1-methyl-1H-1,2,3-triazol-4-ylsulfonyl)piperazin-1-yl)cyclopentyl)ethyl)benzamide.

The compounds of the present invention may contain one or more chiral centers and can occur as racemic mixtures, single enantiomers, diastereomeric mixtures, and individual diastereomers. The present invention is meant to comprehend all isomeric forms of these compounds. Formula I shows the structure of the class of compounds without preferred stereochemistry.

Other embodiments of the present invention are compounds of formula (I) where $R^3$ and $R^4$ are different substituents and the carbon atom designated * is in the R configuration.

Other embodiments of the present invention are compounds of formula (I) where $R^3$ and $R^4$ are different substituents and the carbon atom designated * is in the S configuration.

Other embodiments of the present invention are compounds of formula (I) where $R^3$ and $R^4$ are different substituents and the compound is a (+) stereoisomer.

Other embodiments of the present invention are compounds of formula (I) where $R^3$ and $R^4$ are different substituents and the compound is a (−) stereoisomer.

Another embodiment of the present invention is a mixture of stereoisomeric compounds of formula (I) where $R^3$ and $R^4$ are different substituents and the compound is a mixture of (+) and (−) stereoisomers.

Another embodiment of the present invention is a mixture of stereoisomeric compounds of formula (I) where $R^3$ and $R^4$ are the same substituents and $R^5$ is any substituent other than H. The carbon atom to which $R^5$ is attached is in the R or S configuration when $R^5$ is any substituent other than H.

Other embodiments of the present invention are compounds of formula (I) where $R^3$ and $R^4$ are the same substituents and $R^5$ is any substituent other than H and the compound is a (+) stereoisomer.

Other embodiments of the present invention are compounds of formula (I) where $R^3$ and $R^4$ are the same substituents and $R^5$ is any substituent other than H and the compound is a (−) stereoisomer.

Another embodiment of the present invention is a mixture of stereoisomeric compounds of formula (I) where $R^3$ and $R^4$ are the same substituents and $R^5$ is any substituent other than H and the compound is a mixture of (+) and (−) stereoisomers.

Another embodiment of the present invention is a mixture of stereoisomeric compounds of formula (I) where $R^3$ and $R^4$ are different substituents and the carbon atom designated * is in the R or S configuration and $R^5$ is any substituent other than H. The carbon atom to which $R^5$ is attached is in the R or S configuration when $R^5$ is any substituent other than H.

Other embodiments of the present invention are compounds of formula (I) where $R^3$ and $R^4$ are different substituents and the carbon atom designated * is in the R or S configuration and $R^5$ is any substituent other than H. The carbon atom to which $R^5$ is attached is in the R or S configuration when $R^5$ is any substituent other than H and the compound is a (+) stereoisomer.

Other embodiments of the present invention are compounds of formula (I) where $R^3$ and $R^4$ are different substituents and the carbon atom designated * is in the R or S configuration and $R^5$ is any substituent other than H. The carbon atom to which $R^5$ is attached is in the R or S configuration when $R^5$ is any substituent other than H and the compound is a (−) stereoisomer.

Another embodiment of the present invention is a mixture of stereoisomeric compounds of formula (I) where $R^3$ and $R^4$ are different substituents and the carbon atom designated * is in the R or S configuration and $R^5$ is any substituent other than H. The carbon atom to which $R^5$ is attached is in the R or S configuration when $R^5$ is any substituent other than H and the compound is a mixture of (+) and (−) stereoisomers.

Another embodiment of the present invention is a mixture of stereoisomeric compounds of formula (I) where $R^3$ and $R^4$ are the same substituents and $R^5$ is any substituent other than H. When m is 2, 3 or 4, the compound might exists as a mixture of diastereomers and the carbon atom to which $R^5$ is attached may be in the R or S configuration.

Another embodiment of the present invention is a mixture of stereoisomeric compounds of formula (I) where $R^3$ and $R^4$ are different substituents and the carbon atom designated * is in the R or S configuration and $R^5$ is any substituent other than H. When m is 2, 3 or 4, the compound might exists as a mixture of diastereomers and the carbon atom to which $R^5$ is attached may be in the R or S configuration.

Within these embodiments, the selection of a particular preferred substituent at any one of $R^1$-$R^{14}$, $R^{1a}$, $R^{6a}$, A, X, x and Y does not affect the selection of a substituent at any of the others of $R^1$-$R^4$, $R^{1a}$, $R^{6a}$, A, X, and Y. That is, preferred compounds provided herein have any of the preferred substituents at any of the positions.

The scope of the present invention also encompasses active metabolites of the present compounds.

Another embodiment of the present invention is a compound of formula (I) wherein the compound is radiolabeled, i.e., where one or more of the atoms described are replaced by a radioactive isotope of that atom (e.g., C replaced by $^{14}C$ and H replaced by $^3H$ and S replaced by $^{35}S$). Radioisotopes of hydrogen, carbon, phosphorous, fluorine, iodine and chlorine include $^3H$, $^{14}C$, $^{35}S$, $^{18}F$, $^{32}P$, $^{33}P$, $^{125}I$, and $^{36}Cl$, respectively. Compounds that contain those radioisotopes and/or other radioisotopes of other atoms are within the scope of the invention. Radiolabeled compounds described herein and prodrugs thereof can generally be prepared by methods well known to those skilled in the art. Such compounds have a variety of potential uses, e.g., as standards and reagents in determining the ability of a potential pharmaceutical to bind to neurotransmitter proteins.

Another aspect of the present invention is a pharmaceutical composition containing a therapeutically effective amount of the compound of formula (I) and a pharmaceutically acceptable carrier.

The NMDA receptor plays a critical role in several CNS processes and dysfunction of this receptor is implicated in a variety of psychiatric diseases in humans. The function of GlyT-1 transporters is to modulate synaptic glycine levels in localized areas near to the NMDA receptor Inhibition of GlyT-1 will retard glycine removal and cause an increase in synaptic glycine levels. This increases binding to the GlyB site on the NMDA receptor, which in turn increases activation of the NMDA receptor following glutamate release from the pre-synaptic terminal Changes in NMDA receptor-mediated neurotransmission have been implicated in certain neuropsychiatric disorders such as dementia, depression, and psychoses, for example schizophrenia, and learning and memory disorders, for example attention deficit disorders and autism.

The compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phenylcyclidine, ketamine and dissociative anaesthetic, amphetamine and other psychostimulants and cocaine), psychosis psychotic disorder, psychosis associated with affective disorders, brief reactive psychosis, schizoaffective psychosis, "schizophrenia-spectrum" disorders such as schizoid or schizotypical personality disorders, or illness associated with psychosis (such as major depression, manic depressive (bipolar) disorder, Alzheimer's disease and post-traumatic stress syndrome), including both positive and negative symptoms of schizophrenia and other psychoses; cognitive disorders including dementia associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse; cognition impairment, delirium, amnestic disorders or age related cognitive decline; anxiety disorders such as attention deficit hyperactivity disorder (ADHD), generalized anxiety disorder (GAD), panic disorder, bipolar disorder or manic depression or manic-depressive disorder, obsessive compulsive disorder (OCD), posttraumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease or Parkinson's disease, supranuclear palsy, eating disorders, obesity, anorexia nervosa, bulimia nervosa, binge eating disorder, diabetes, ischemic diseases, pain, substance abuse disorders, chemical dependencies, nicotine addiction, cocaine addiction, amphetamine addiction, alcohol addiction, Lesch-Nyhan syndrome, neurodegenerative diseases, Parkinson's disease, late luteal phase syndrome or narcolepsy, insomnia, anger, rejection sensitivity, movement disorders, extrapyramidal syndrome, chorea, dystonia, myoclonus, Tic disorders, Gilles de la Tourette's syndrome, epilepsy, restless leg syndrome (RLS), tardive dyskinesia, supranuclear palsy, sleep related eating disorder (SRED), night eating syndrome (NES), stress urinary incontinence (SUI), migraine, neuropathic pain, diabetic neuropathy, lower back pain, fibromyalgia syndrome (FS), osteoarthritis pain, arthritis pain, chronic pain with memory impairment, chronic fatigue syndrome (CFS), emesis, hearing impairment, tinnitus, urinary incontinence, ocular damage, retinopathy or macular degeneration of the eye, drug induced parkinsonism; NMDA receptor-related disorders such as autism, depression, benign forgetfulness and childhood learning disorders.

The compounds provided herein are particularly useful in the treatment of these and other disorders due, at least in part, to their ability to selectively bind to the GlyT-1 with a greater affinity than to the transporter proteins for other neurochemicals.

Another embodiment of the present invention is a method of inhibiting synaptic glycine uptake in a patient in need thereof. The method involves administering a therapeutically effective inhibitory amount of a compound of formula (I).

Another embodiment of the present invention is a therapeutic method described herein, where the (+)-stereoisomer of the compound of formula (I) is employed, when $R^3$ and $R^4$ are different substituents and m is 0.

Another embodiment of the present invention is a therapeutic method described herein, where the (−)-stereoisomer of the compound of formula (I) is employed, when $R^3$ and $R^4$ are different substituents and m is 0.

Another embodiment of the present invention relates to a method of treating a neurological or psychiatric disorder associated with glutamatergic neurotransmission dysfunction (described above) in a patient in need thereof. The method involves administering a therapeutically effective amount of the compound of formula (I), which functions as a GlyT-1 inhibitor, under conditions effective to treat the neurological or psychiatric disorder. In accordance with the present invention, synaptic glycine uptake may thus be inhibited.

Another embodiment of the present invention relates to a method for inhibiting glycine uptake in mammals. The method involves administering to a mammal requiring increased NMDA receptor-mediated neurotransmission a pharmaceutically effective amount of the compound of formula (I).

Another embodiment of the present invention relates to a method of suppressing the desire of humans to smoke. The method involves administering to a human in need of such suppression an effective dose, to relieve the desire to smoke, of the compound of formula (I).

Another embodiment of the present invention relates to a method of suppressing the desire of humans to consume alcohol. The method involves administering to a human in need of such suppression an effective dose, to relieve the desire to consume alcohol, of the compound of formula (I).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates, or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula (I) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice (e.g., Wuts et al., *Protective Groups in Organic Chemistry* (4th Edition), Wiley (2006), and McOmie, *Protective Groups in Organic Chemistry*, Plenum Press (1973), which are hereby incorporated by reference in their entireties).

In the reaction schemes described hereinafter, the synthesis of compounds of the formula (I) are described.

Another aspect of the invention relates to the process of preparing a compound of formula I:

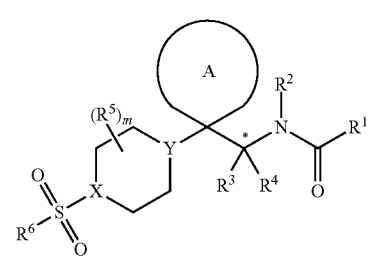

This process may involve treating an intermediate compound of formula II:

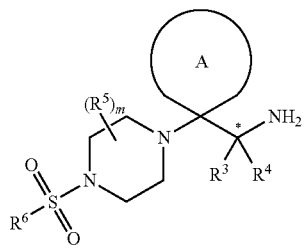

II wherein X and Y=N and $R^3$, $R^4$, $(R^5)_m$, $R^6$, and A are defined above.

The methods of synthesis of formula I involve standard amide bond formation conditions that are familiar to one skilled in the art of organic synthesis. This typically involves activation of the carboxyl component of a benzoic acid followed by reaction of the amine with the formula (II). Suitable activating groups for the benzoic acids include, but are not limited to, acyl halides, acyl azides, acylimidazoles, anhydrides and esters as described by Montalbetti et al., *Tetrahedron*, 61:10827 (2005), which is hereby incorporated by reference in its entirety. Preferred activating reagents include thionyl chloride ($SOCl_2$), oxalyl chloride ($COCl)_2$, phosphorus oxychloride ($POCl_3$), carbonyl diimidazole (CDI), dicyclohexyl carbodiimide (DCC), 1-ethyl-3-(3-dimethylaminopropyl)carbodiimide) (EDCI), 1-hydroxybenzotriazole (HOBt), O-(1H-benzotrial-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and 1-propanephosphonic acid cyclic anhydride (T3P).

Compounds of formula (II) may also be converted to compounds of formula (I) by reacting with an acid chloride in the presence of a base such as $Et_3N$, i-$PrNEt_2$ or pyridine in a halogenated solvent such as methylene chloride.

A further aspect of the present invention relates to a process of preparing a compound of formula I by treating an intermediate compound of formula III:

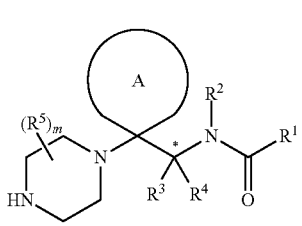

III

X=N, Y=N, and $R^3$, $R^4$, $(R^5)_m$, $R^6$, and A are defined above. Treating an intermediate compound of formula III with

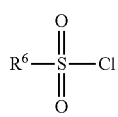

under effective conditions will produce the product compound of formula I. Such conditions are familiar to one skilled in the art of organic synthesis and are described, for example, in *Comprehensive Organic Transformations*, Larock, VCH Publishers, Inc. (1989), which is hereby incorporated by reference in its entirety Yet another aspect of the present invention relates to a process of preparing a compound of formula I by treating an intermediate compound of formula IV:

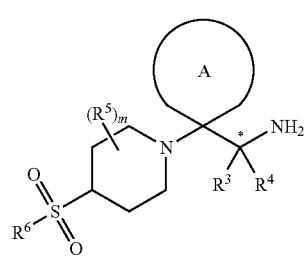

IV wherein X=CH, Y=N, and $R^3$, $R^4$, $(R^5)$, $R^6$, and A are defined above under conditions effective to produce the product compound.

The methods of synthesis of formula IV (X=CH) involve standard amide bond formation conditions that are familiar to one skilled in the art of organic synthesis. This typically involves activation of the carboxyl component of a benzoic acid followed by reaction of the amine with the formula (IV). Suitable activating groups for the benzoic acids include, but are not limited to, acyl halides, acyl azides, acylimidazoles, anhydrides and esters as described by Montalbetti et al., *Tetrahedron*, 61:10827 (2005), which is hereby incorporated by reference in its entirety. Preferred activating reagents include thionyl chloride ($SOCl_2$), oxalyl chloride ($COCl)_2$, phosphorus oxychloride ($POCl_3$), carbonyl diimidazole (CDI), dicyclohexyl carbodiimide (DCC), 1-ethyl-3-(3-dimethylaminopropyl)carbodiimide) (EDCI), 1-hydroxybenzotriazole (HOBt), O-(1H-benzotrial-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and 1-propanephosphonic acid cyclic anhydride (T3P).

A further aspect of the present invention relates to a process of preparing a compound of formula I by treating an intermediate compound of formula V:

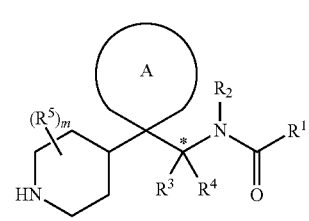

V wherein X=N, Y=CH, and $R^3$, $R^4$, $(R^5)$, $R^6$, and A are defined above. Treating an intermediate compound of formula III with

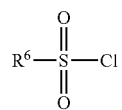

under effective conditions will produce the product compound of formula I. Such conditions are familiar to one skilled in the art of organic synthesis and are described, for example, in *Comprehensive Organic Transformations*, Larock, VCH Publishers, Inc (1989), which is hereby incorporated by reference in its entirety.

The amine intermediate II (wherein $R^3$ and $R^4$=H) may be prepared according to the reactions outlined in Scheme 1.

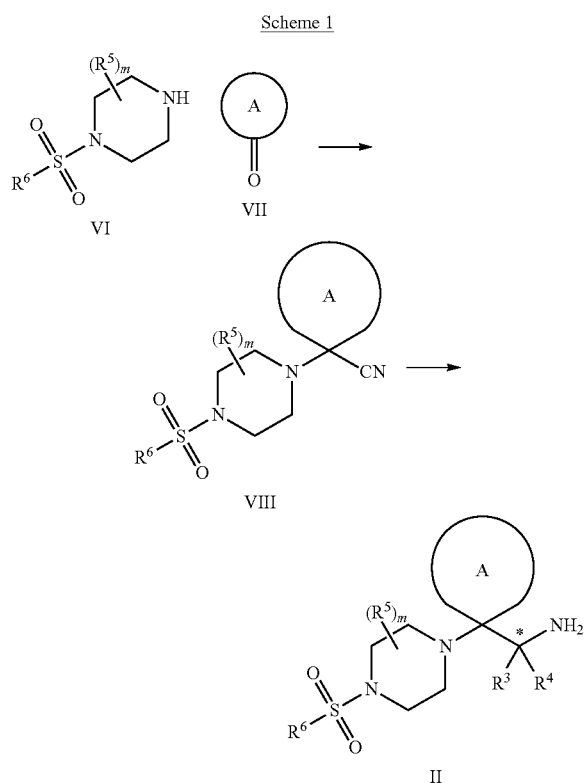

Strecker condensation of the piperazine intermediate (VI) with the appropriately substituted ketone (VII) in the presence of cyanide generates the amino nitrile adduct intermediate (VIII). The Strecker condensation may involve the use of various cyanide containing agents including, but not limited to, potassium cyanide (KCN), trimethylsilyl cyanide (TMSCN) and diethylaluminum cyanide ($Et_2AlCN$), and may be catalyzed by various reagents including, but not limited to, titanium(IV) iso-propoxide ($Ti(i-OPr)_4$), zinc iodide ($ZnI_2$) and sodium metabisulfite ($Na_2S_2O_5$). Intermediate VIII (wherein $R^3$ and $R^4$=H) can then be obtained via reduction of the nitrile to the amine using lithium aluminum hydride ($LiAlH_4$) or with other reducing agents and under a wide variety of conditions familiar to one skilled in the art of organic synthesis (see, e.g., Larock, *Comprehensive Organic Transformations*, Wiley-VCH publishers (1989), which is hereby incorporated by reference in its entirety). Intermediate II (wherein at least one of $R^3$ or $R^4$ is alkyl or aryl and the other is H) can then be obtained via addition to the Strecker adduct VIII with either an alkyl or aryl lithium reagents including, but not limited to methyl lithium (MeLi) and phenyl lithium (PhLi). The resulting intermediary imine is reduced to the amine intermediate II (wherein at least one of $R^3$ or $R^4$ is alkyl or aryl and the other is H) using sodium borohydride ($NaBH_4$) or with other reducing agents and under a wide variety of conditions familiar to one skilled in the art of organic synthesis (see, e.g., Larock, *Comprehensive Organic Transformations*, Wiley-VCH publishers (1989), which is hereby incorporated by reference in its entirety).

The amine intermediates (III) may be prepared according to the reaction outlined in Scheme 2.

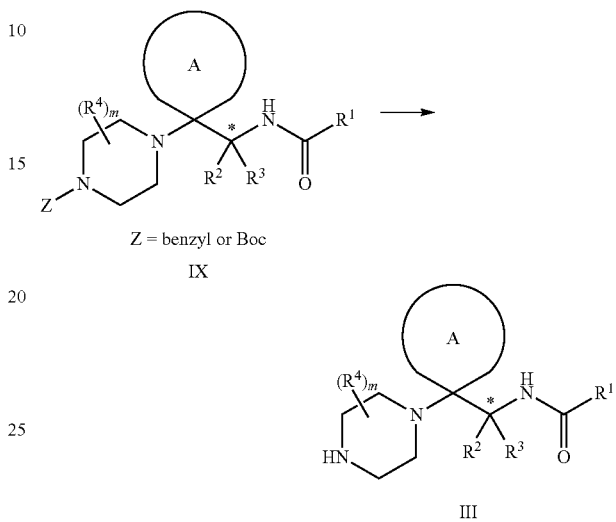

Compounds of formula IX (wherein Z is a benzyl group) may be converted to compounds of formula (III) by a de-benzylation procedure such as, but not limited to, hydrogenolysis in the presence of a metal catalyst such as palladium (Pd), platinum (Pt) or nickel (Ni) under an atmosphere of hydrogen ($H_2$) at various pressures and temperatures or with treatment with 1-chloroethyl chloroformate (ACE-Cl) in a halogenated solvent such as 1,2-dichloroethane (DCE) at reflux temperature followed by methanol ($CH_3OH$) at reflux temperature. One skilled in the art will understand the optimal combination of de-benzylation agents and reaction conditions needed or may seek guidance from the text of Wuts et al., *Protective Groups in Organic Chemistry* (4th Edition), Wiley (2006), which is hereby incorporated by reference in its entirety.

Compounds of formula IX (wherein Z is a Boc group) may be converted to compounds of formula (III) by a deprotection procedure such as, but not limited to, treatment with trifluoroacetic acid (TFA) in a halogenated solvent such as $CH_2Cl_2$ or with methanolic or aqueous hydrochloric acid (HCl) in a polar solvent such as 1,4-dioxane. One skilled in the art will understand the optimal combination of Boc-removing agents and reaction conditions needed or may seek guidance from the text of Wuts et al., *Protective Groups in Organic Chemistry* (4th Edition), Wiley (2006), which is hereby incorporated by reference in its entirety. Z is not limited to benzyl and Boc. Z can be other protecting groups such as but not limited to methyl carbamate, ethyl carbamate, isopropyl carbamate, p-methoxybenzyl, α-methylbenzyl, phenylethyl, acetamide, trimethylsilyl, tert-butyl-dimethylsilyl, and the like. One skilled in the art will understand the optimal combination of protecting group removing agents and reaction conditions needed or may seek guidance from the text of Wuts et al., *Protective Groups in Organic Chemistry* (4th Edition), Wiley (2006), which is hereby incorporated by reference in its entirety.

The amine intermediate IV (wherein $R^3$ and $R^4$=H) may be prepared according to the reactions outlined in Scheme 3.

The amine intermediates (V) may be prepared according to the reaction outlined in Scheme 4.

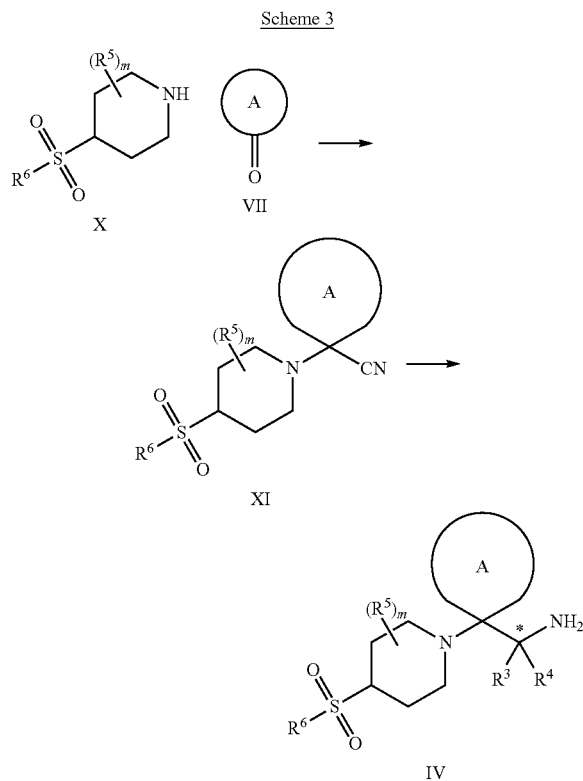

Scheme 3

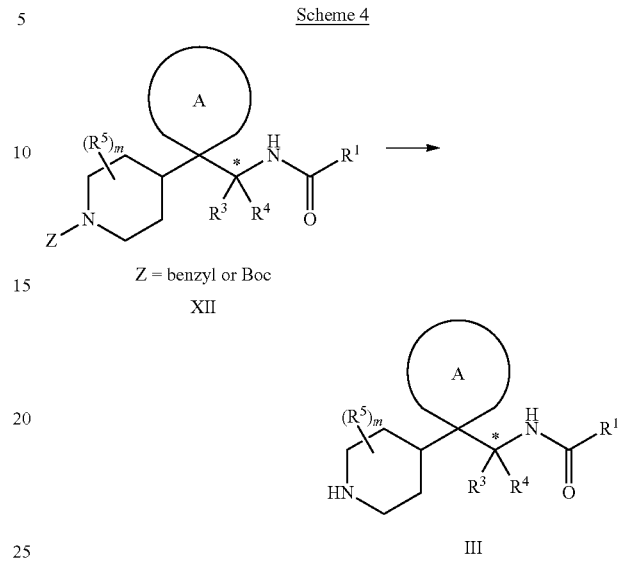

Scheme 4

Z = benzyl or Boc

Strecker condensation of the piperazine intermediate (X) with the appropriately substituted ketone (VII) in the presence of cyanide generates the amino nitrile adduct intermediate (XI). The Strecker condensation may involve the use of various cyanide containing agents including, but not limited to, potassium cyanide (KCN), trimethylsilyl cyanide (TM-SCN), and diethylaluminum cyanide ($Et_2AlCN$), and may be catalyzed by various reagents including, but not limited to, titanium(IV) iso-propoxide (Ti(i-$OPr)_4$), zinc iodide ($ZnI_2$), and sodium metabisulfite ($Na_2S_2O_5$). Intermediate IV (wherein $R^3$ and $R^4$=H) can then be obtained via reduction of the nitrile to the amine using lithium aluminum hydride (Li-$AlH_4$) or with other reducing agents and under a wide variety of conditions familiar to one skilled in the art of organic synthesis (see, e.g., Larock, *Comprehensive Organic Transformations*, Wiley-VCH publishers (1989), which is hereby incorporated by reference in its entirety). Intermediate IV (wherein at least one of $R^3$ or $R^4$ is alkyl or aryl and the other is H) can then be obtained via addition to the Strecker adduct XI with either an alkyl or aryl lithium reagents including, but not limited to methyl lithium (MeLi) and phenyl lithium (PhLi). The resulting intermediary imine is reduced to the amine intermediate IV (wherein at least one of $R^3$ or $R^4$ is alkyl or aryl and the other is H) using sodium borohydride ($NaBH_4$) or with other reducing agents and under a wide variety of conditions familiar to one skilled in the art of organic synthesis (see, e.g., Larock, *Comprehensive Organic Transformations*, Wiley-VCH publishers (1989), which is hereby incorporated by reference in its entirety).

Compounds of formula XII (wherein Z is a benzyl group) may be converted to compounds of formula (III) by a de-benzylation procedure such as, but not limited to, hydrogenolysis in the presence of a metal catalyst such as palladium (Pd), platinum (Pt) or nickel (Ni) under an atmosphere of hydrogen ($H_2$) at various pressures and temperatures or with treatment with 1-chloroethyl chloroformate (ACE-Cl) in a halogenated solvent such as 1,2-dichloroethane (DCE) at reflux temperature followed by methanol ($CH_3OH$) at reflux temperature. One skilled in the art will understand the optimal combination of de-benzylation agents and reaction conditions needed or may seek guidance from the text of Wuts et al., *Protective Groups in Organic Chemistry* (4th Edition), Wiley (2006), which is hereby incorporated by reference in its entirety.

Compounds of formula XII (wherein Z is a Boc group) may be converted to compounds of formula (III) by a deprotection procedure such as, but not limited to, treatment with trifluoroacetic acid (TFA) in a halogenated solvent such as $CH_2Cl_2$ or with methanolic or aqueous hydrochloric acid (HCl) in a polar solvent such as 1,4-dioxane. One skilled in the art will understand the optimal combination of Boc-removing agents and reaction conditions needed or may seek guidance from the text of Wuts et al., *Protective Groups in Organic Chemistry* (4th Edition), Wiley (2006), which is hereby incorporated by reference in its entirety. Z is not limited to benzyl and Boc. Z can be other protecting groups such as but not limited to methyl carbamate, ethyl carbamate, isopropyl carbamate, p-methoxybenzyl, α-methylbenzyl, phenylethyl, acetamide, trimethylsilyl, tert-butyl-dimethylsilyl, and the like. One skilled in the art will understand the optimal combination of protecting group removing agents and reaction conditions needed or may seek guidance from the text of Wuts et al., *Protective Groups in Organic Chemistry* (4th Edition), Wiley (2006), which is hereby incorporated by reference in its entirety.

Further synthetic schemes are illustrated in the Examples.

The compounds of formula (I) may be obtained in enantiomerically pure (R) and (S) form by crystallization with chiral salts as well known to one skilled in the art, or alternatively, may be isolated through chiral HPLC employing commercially available chiral columns or other chiral stationary phase methods.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formula (I) herein above. Such isomers can be separated from their mixtures, by the application or adaptation of known methods, for example chromatographic techniques and recrystallization techniques, or they are separately prepared from the appropriate isomers of their intermediates.

Radiolabeled compounds of the invention are synthesized by a number of techniques well known to those of ordinary skill in the art, e.g., by using starting materials incorporating therein one or more radioisotopes. Compounds of the present invention where a stable radioisotope, such as carbon-14 [$^{14}C$], deuterium [$^{2}H$], tritium [$^{3}H$], iodine-121 [$^{121}I$], or another radioisotope, has been introduced synthetically are useful diagnostic agents for identifying areas of the brain or central nervous system that may be affected by disorders where GlyT-1 is implicated.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formula (I) and the additional active ingredient (alone or in combination with diluent or carrier), as described above.

In practice, the compounds of the present invention may generally be administered parenterally, intravenously, subcutaneously, intramuscularly, colonically, nasally, intraperitoneally, rectally, topically (including dermal, buccal, sublingual and intraocular) or orally. The most suitable route may depend on the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or both and then, if necessary, shaping the product into the desired formulation.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate, and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions, or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride, and that they are sterilized by heating, irradiation, or microfiltration.

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula (I).

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents and the like. If desired, tablet dosages of the disclosed compositions may be coated by standard aqueous or nonaqueous techniques. "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes and the like. Any such optional ingredient must be compatible with the compound of formula I to ensure the stability of the formulation. The composition may contain other additives as needed, including for example lactose, glucose, fructose, galactose, tehalose, sucrose, maltose, raffinose, maltitol, melezitose, stachyose, lactitol, palatinate, starch, xylitol, mannitol, myoinostiol and the like and hydrates thereof, and amino acids, for example alanine, glycine, and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, antimicrobial agents, and coating agents.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic glycine uptake and are, therefore, believed to be useful in treating a disorder which is created by NMDA receptor hypofunction. The concentrations or doses at which a test compound inhibits synaptic glycine uptake are readily determined by the use of standard assay and techniques well known and appreciated by one of ordinary skill in the art. For example, the degree of inhibition at a particular dose in rats can be determined by the method of Dudley, *J Pharmacol Exp Ther,* 217:834-840 (1981), which is hereby incorporated by reference in its entirety.

The therapeutically effective inhibitory dose is one that is effective in substantially inhibiting synaptic glycine uptake. The therapeutically effective inhibitory dose can be determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to GlyT-1 inhibitors indirectly impacting NMDA receptor function.

The in vitro and in vivo affinity of the compounds to GlyT-1 is demonstrated by means well known to those of ordinary skill in the art, including, without limitation, those described in the Examples section below.

EXAMPLES

The following examples are provided to illustrate embodiments of the present invention but are by no means intended to limit its scope.

Example 1

General Synthetic Procedures for Preparing A3 with a Sulfonylated piperazine (GSP-1)

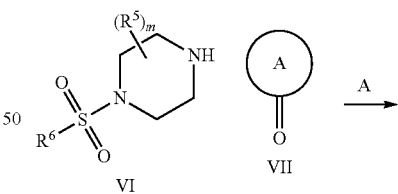

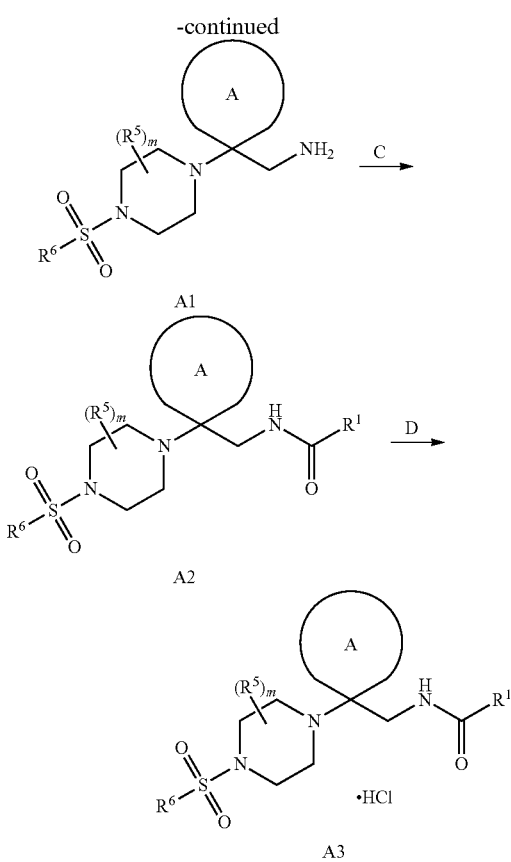

Conditions: A1) Na₂S₂O₅ or PPTS, H₂O, CH₃CN; A2) TMSCN, ZnI₂, Et₂O/CH₃OH; A3) Et₂AlCN, Ti(i-PrO)₄, toluene; B) LiAlH₄, THF; C1) carboxylic acid, HBTU, Et₃N, DMF; C2) acid chloride, Et₃N, CH₂Cl₂; D) 1.25 M HCl/CH₃OH, CH₂Cl₂

Example 2

General Synthetic Procedure for the Strecker Coupling Using $Na_2S_2O_5$ and KCN Cyclic ketone VII (1 eq) and $Na_2S_2O_5$ (0.5 eq) or PPTS (0.5 eq) were dissolved in a 1:1 mixture of $CH_3CN$ and $H_2O$ (0.2M) and stirred at room temperature for 1 to 16 h. To this was added sulfonylated piperazine VI (1 eq) and the mixture continued to stir for 2 hours. To this was added KCN (1.1 eq) and the mixture stirred at room temperature until the reaction was complete by LC-MS. The mixture was then extracted with $CH_2Cl_2$ and the combined organic extracts were washed with $H_2O$, brine, dried ($Na_2SO_4$), filtered and concentrated under reduced pressure. The resulting residue was purified by silica gel chromatography (typical eluents included hexanes and EtOAc) to afford the desired nitrile VIII. The product structure was verified by $^1$H NMR or by mass analysis.

Example 3

General Synthetic Procedure for the Strecker Coupling Using TMSCN and $ZnI_2$

To a solution of cyclic ketone VII (1 eq) and TMSCN (1 eq) in $Et_2O$ was added $ZnI_2$ (2 mol %). The mixture was allowed to stir for 15 minutes, then a solution of sulfonylated piperazine VI (1 eq) in $CH_3OH$ (0.8 M) and the mixture was heated at reflux for 3 hours, then room temperature until the reaction was complete by LC-MS. The mixture was concentrated and the resulting residue was purified by silica gel chromatography (typical eluents included hexanes and EtOAc) to afford the desired nitrile VIII. The product structure was verified by $^1$H NMR or by mass analysis.

Example 4

General Synthetic Procedure for the Strecker Coupling Using $Ti(i-PrO)_4$ and $Et_2AlCN$ To a 0° C. cooled solution of solution of cyclic ketone VII (1.0 eq) and sulfonylated piperazine VI (1 eq) in toluene (0.25 M) was added $Ti(i-PrO)_4$ (1.3 eq). The mixture was stirred for 2 hours and then $Et_2AlCN$ (1.5 eq) was slowly added. The mixture was allowed to stir at room temperature until the reaction was complete by LC-MS. The reaction was carefully quenched with $H_2O$ followed by addition of EtOAc. The mixture was filtered through Celite and the layers were separated. The aqueous layer was extracted with EtOAc and the combined organic extracts were washed with $H_2O$, brine, dried ($Na_2SO_4$), filtered and concentrated under reduced pressure. The resulting residue was purified by silica gel chromatography (typical eluents included hexanes and EtOAc) to afford the desired nitrile VIII. The product structure was verified by $^1$H NMR or by mass analysis.

Example 5

General Synthetic Procedure for the Nitrile Reduction

To a solution of lithium aluminum hydride (2.0 M in THF, 2 eq) in anhydrous THF (1.0 M) was slowly added a solution of VIII in anhydrous THF (0.13 M, 1 eq). The mixture was stirred at room temperature or was heated at a desired temperature until the reaction was complete by LC-MS. The reaction was carefully quenched with $H_2O$, followed by addition of 2 N NaOH until basic. After stirring at room temperature for 1 hours, the mixture was filtered through Celite and the filtrate was extracted with $Et_2O$. The combined organic extracts were washed with $H_2O$, brine, dried ($Na_2SO_4$), filtered and concentrated under reduced pressure. The resulting residue was purified by silica gel chromatography (typical eluents included $CH_2Cl_2$ and a 90:9:1 mixture of $CH_2Cl_2$/$CH_3OH$/concentrated $NH_4OH$) to afford the desired amine A1. The product structure was confirmed by $^1$H NMR or by mass analysis.

Example 6

General Synthetic Procedure for Carboxamide Formation Using a Carboxylic Acid and HBTU A mixture of amine A1 (1 eq), desired carboxylic acid (1 eq), $Et_3N$ (3 eq), and 2-(1H-benzotriazole-1-yl)-1,1,3,3-tetramethyluronium hexafluorophosphate (HBTU) (1.5 eq) in DMF (0.25 M) was stirred at room temperature until the reaction was complete by LC-MS. The mixture was diluted with $H_2O$ and extracted with ethyl acetate. The combined organic extracts were washed with $H_2O$, brine, dried ($Na_2SO_4$), filtered and concentrated under reduced pressure. The resulting residue was purified by silica gel chromatography (typical eluents included $CH_2Cl_2$ and a 90:9:1 mixture of CH$_2$Cl$_2$/CH$_3$OH/concentrated NH$_4$OH) to afford the desired carboxamide A2. The product structure was verified by $^1$H NMR or by mass analysis.

Example 7

General Synthetic Procedure for Carboxamide Formation Using an Acid Chloride and Base A mixture of amine A1 (1 eq), Et$_3$N (3 eq) and acid chloride (1.0 eq) in CH$_2$Cl$_2$ (0.25 M) was stirred at ambient temperature until the reaction was complete by LC-MS. The mixture was washed with H$_2$O, brine, dried (Na$_2$SO$_4$), filtered, and concentrated under reduced pressure. The resulting residue was purified by silica gel chromatography (typical eluents CH$_2$Cl$_2$ and a 90:9:1 mixture of CH$_2$Cl$_2$/CH$_3$OH/concentrated NH$_4$OH) to afford the desired carboxamide A2. The product structure was verified by $^1$H NMR or by mass analysis.

Example 8

General Synthetic Procedure for Hydrochloride Salt Formation

To an ice-cold solution of the carboxamide A2 (1 eq) in CH$_2$Cl$_2$ was added 1.25 M HCl in CH$_3$OH (1 to 3 eq). The mixture was concentrated under reduced pressure and the resulting solid was lyophilized from H$_2$O and CH$_3$CN to afford the desired hydrochloride salt A3. The product was verified by mass analysis and $^1$H NMR.

Example 9

General Synthetic Procedures for Preparing the Quaternary Core A1 with 1-Benzylpiperazine (GSP-2)

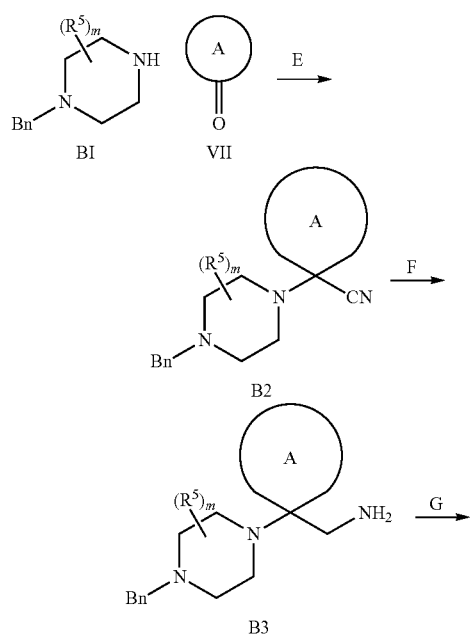

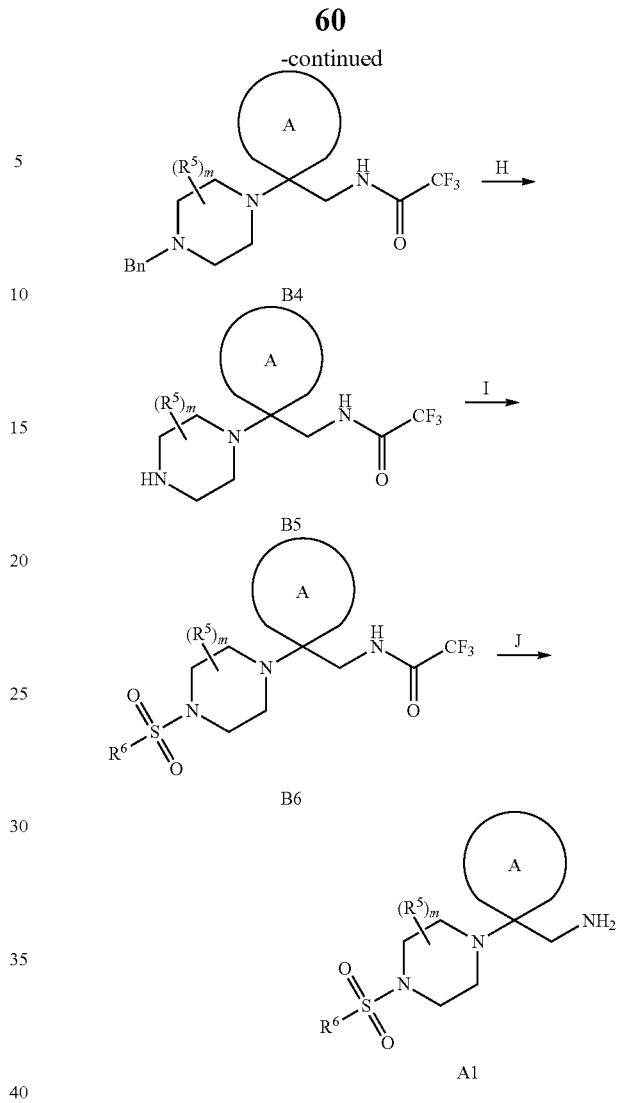

Conditions: E1) Na$_2$S$_2$O$_5$ or PPTS, H$_2$O, CH$_3$CN; E2) TMSCN, ZnI$_2$, Et$_2$O/CH$_3$OH; E3) Et$_2$AlCN, Ti(i-PrO)$_4$, toluene; F) LiAlH$_4$, THF; G) trifluoroacetic anhydride, Et$_3$N, CH$_2$Cl$_2$; H) 10% Pd/C, H$_2$, CH$_3$OH; I) sulfonyl chloride, Et$_3$N, CH$_2$Cl$_2$; J) K$_2$CO$_3$, H$_2$O, CH$_3$OH

Example 10

General Synthetic Procedure for the Strecker Coupling Using Na$_2$S$_2$O$_5$ and KCN Cyclic ketone VII (1 eq) and Na$_2$S$_2$O$_5$ (0.5 eq) or PPTS (0.5 eq) were dissolved in a 1:1 mixture of CH$_3$CN and H$_2$O (0.2M) and stirred at room temperature for 1 to 16 hours. To this was added sulfonylated piperazine B1 (1 eq) and the mixture continued to stir for 2 hours. To this was added KCN (1.1 eq) and the mixture was stirred at room temperature until the reaction was complete by LC-MS. The mixture was then extracted with CH$_2$Cl$_2$ and the combined organic extracts were washed with H$_2$O, brine, dried (Na$_2$SO$_4$), filtered and concentrated under reduced pressure. The resulting residue was purified by silica gel chromatography (typical eluents included hexanes and EtOAc) to afford the desired nitrile B2. The product structure was verified by $^1$H NMR or by mass analysis.

Example 11

General Synthetic Procedure for the Strecker Coupling Using TMSCN and ZnI$_2$ To a solution of cyclic ketone VII (1 eq) and TMSCN (1 eq) in Et$_2$O was added ZnI$_2$ (2 mol %). The mixture was allowed to stir for 15 minutes, then a solution of sulfonylated piperazine B1 (1 eq) in CH$_3$OH (0.8 M) and the mixture was heated at reflux for 3 hours, then room temperature until the reaction was complete by LC-MS. The mixture was concentrated and the resulting residue was purified by silica gel chromatography (typical eluents included hexanes and EtOAc) to afford the desired nitrile B2. The product structure was verified by $^1$H NMR or by mass analysis.

Example 12

General Synthetic Procedure for the Strecker Coupling Using Ti(i-PrO)$_4$ and Et$_2$AlCN To a 0° C. cooled solution of solution of cyclic ketone VII (1.0 eq) and sulfonylated piperazine B1 (1 eq) in toluene (0.25 M) was added Ti(i-PrO)$_4$ (1.3 eq). The mixture was stirred for 2 hours and then Et$_2$AlCN (1.5 eq) was slowly added. The mixture was allowed to stir at room temperature until the reaction was complete by LC-MS. The reaction was carefully quenched with H$_2$O followed by addition of EtOAc. The mixture was filtered through Celite and the layers were separated. The aqueous layer was extracted with EtOAc and the combined organic extracts were washed with H$_2$O, brine, dried (Na$_2$SO$_4$), filtered, and concentrated under reduced pressure. The resulting residue was purified by silica gel chromatography (typical eluents included hexanes and EtOAc) to afford the desired nitrile B2. The product structure was verified by $^1$H NMR or by mass analysis.

Example 13

General Synthetic Procedure for the Nitrile Reduction

To a solution of lithium aluminum hydride (2.0 M in THF, 2 eq) in anhydrous THF (1.0 M) was slowly added a solution of B2 in anhydrous THF (0.13 M, 1 eq). The mixture was stirred at room temperature or was heated at a desired temperature until the reaction was complete by LC-MS. The reaction was carefully quenched with H$_2$O, followed by addition of 2 N NaOH until basic. After stirring at room temperature for 1 hours, the mixture was filtered through Celite and the filtrate was extracted with diethyl ether. The combined organic extracts were washed with H$_2$O, brine, dried (Na$_2$SO$_4$), filtered, and concentrated under reduced pressure. The resulting residue was purified by silica gel chromatography (typical eluents CH$_2$Cl$_2$ and a 90:9:1 mixture of CH$_2$Cl$_2$/CH$_3$OH/concentrated NH$_4$OH) to afford the desired amine B3. The product structure was confirmed by $^1$H NMR or by mass analysis.

Example 14

General Synthetic Procedure for Trifluoromethyl Acetamide Formation

To an ice-cold solution of amine B3 (1 eq), and Et$_3$N (3 eq) in CH$_2$Cl$_2$ (0.25 M) was added trifluoroacetic anhydride (1 eq) and the mixture was stirred at room temperature until the reaction was complete by LC-MS. The mixture was washed with saturated NaHCO$_3$ solution, H$_2$O, brine, dried (Na$_2$SO$_4$), filtered, and concentrated under reduced pressure. The resulting residue was purified by silica gel chromatography (typical eluents included hexanes and EtOAc) to afford the desired carboxamide B4. The product structure was verified by $^1$H NMR or by mass analysis.

Example 15

General Synthetic Procedure for piperazine Deprotection via Hydrogenolysis

A mixture of carboxamide B4 (1 eq), and 10% Pd/C (0.10 eq) in CH$_3$OH (0.25 M) was subjected to an atmosphere of hydrogen gas at a pressure of 40 psi on a Parr Shaker apparatus at room temperature until the reaction was complete by LC-MS. The mixture was filtered through Celite and the filtrate was concentrated under reduced pressure. The resulting residue was purified by silica gel chromatography (typical eluents CH$_2$Cl$_2$ and a 90:9:1 mixture of CH$_2$Cl$_2$/CH$_3$OH/concentrated NH$_4$OH) to afford the desired carboxamide B5. The product structure was verified by $^1$H NMR or by mass analysis.

Example 16

General Synthetic Procedure for Sulfonamide Formation

To an ice-cold solution of carboxamide B5 (1 eq), and Et$_3$N (3 eq) CH$_2$Cl$_2$ (0.25 M) was added sulfonyl chloride (1 eq) and the mixture stirred at room temperature until the reaction was complete by LC-MS. The mixture was washed with saturated NaHCO$_3$ solution, H$_2$O, brine, dried (Na$_2$SO$_4$), filtered, and concentrated under reduced pressure. The resulting residue was purified by silica gel chromatography (typical eluents included hexanes and EtOAc) to afford the desired sulfonamide B6. The product structure was verified by $^1$H NMR or by mass analysis.

Example 17

General Synthetic Procedure for Trifluoromethyl Acetamide Removal

A mixture of sulfonamide B6 (1 eq), and K$_2$CO$_3$ (25 eq) in a 10:1 mixture of CH$_3$OH and water (0.25 M) was heated at 60° C. until the reaction was complete by LC-MS. The mixture was cooled to room temperature and was filtered through Celite. The filtrate was diluted with water and extracted with CH$_2$Cl$_2$. The combined organic extracts were washed with H$_2$O, brine, dried (Na$_2$SO$_4$), filtered, and concentrated under reduced pressure. The resulting residue was purified by silica gel chromatography (typical eluents included CH$_2$Cl$_2$ and a 90:9:1 mixture of CH$_2$Cl$_2$/CH$_3$OH/concentrated NH$_4$OH) to afford the desired amine A1. The product structure was verified by $^1$H NMR or by mass analysis.

Example 18

General Synthetic Procedures for Preparing the Quaternary Core VII with tert-Butyl piperazine-1-carboxylate (GSP-3)

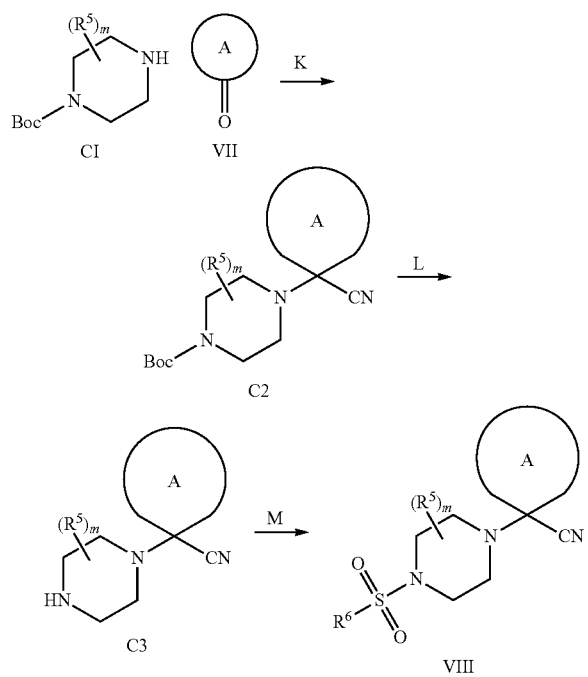

Conditions: K1) $Na_2S_2O_5$ or PPTS, $H_2O$, $CH_3CN$; K2) TMSCN, $ZnI_2$, $Et_2O/CH_3OH$; K3) $Et_2AlCN$, $Ti(i-PrO)_4$, toluene; L) TFA, $CH_2Cl_2$; M) sulfonyl chloride, $Et_3N$, $CH_2Cl_2$ Example 19

General Synthetic Procedure for the Strecker Coupling Using $Na_2S_2O_5$ and KCN Cyclic ketone VII (1 eq) and $Na_2S_2O_5$ (0.5 eq) or PPTS (0.5 eq) were dissolved in a 1:1 mixture of $CH_3CN$ and $H_2O$ (0.2M) and stirred at room temperature for 1 to 16 hours. To this was added sulfonylated piperazine Cl (1 eq) and the mixture continued to stir for 2 hours. To this was added KCN (1.1 eq) and the mixture was stirred at room temperature until the reaction was complete by LC-MS. The mixture was then extracted with $CH_2Cl_2$ and the combined organic extracts were washed with $H_2O$, brine, dried ($Na_2SO_4$), filtered, and concentrated under reduced pressure. The resulting residue was purified by silica gel chromatography (typical eluents included hexanes and EtOAc) to afford the desired nitrile C2. The product structure was verified by $^1$H NMR or by mass analysis.

Example 20

General Synthetic Procedure for the Strecker Coupling Using TMSCN and $ZnI_2$

To a solution of cyclic ketone VII (1 eq) and TMSCN (1 eq) in $Et_2O$ was added $ZnI_2$ (2 mol %). The mixture was allowed to stir for 15 minutes, then a solution of sulfonylated piperazine Cl (1 eq) in $CH_3OH$ (0.8 M) and the mixture was heated at reflux for 3 hours, then room temperature until the reaction was complete by LC-MS. The mixture was concentrated and the resulting residue was purified by silica gel chromatography (typical eluents included hexanes and EtOAc) to afford the desired nitrile C2. The product structure was verified by $^1$H NMR or by mass analysis.

Example 21

General Synthetic Procedure for the Strecker Coupling Using $Ti(i-PrO)_4$ and $Et_2AlCN$ To a 0° C. cooled solution of solution of cyclic ketone VII (1.0 eq) and sulfonylated piperazine Cl (1 eq) in toluene (0.25 M) was added $Ti(i-PrO)_4$ (1.3 eq). The mixture was stirred for 2 hours and then $Et_2AlCN$ (1.5 eq) was slowly added. The mixture was allowed to stir at room temperature until the reaction was complete by LC-MS. The reaction was carefully quenched with $H_2O$ followed by addition of EtOAc. The mixture was filtered through Celite and the layers were separated. The aqueous layer was extracted with EtOAc and the combined organic extracts were washed with $H_2O$, brine, dried ($Na_2SO_4$), filtered, and concentrated under reduced pressure. The resulting residue was purified by silica gel chromatography (typical eluents included hexanes and EtOAc) to afford the desired nitrile C2. The product structure was verified by $^1$H NMR or by mass analysis.

Example 22

General Synthetic Procedure for tert-Butyl Carbamate Removal Using TFA

To an ice-cold solution of nitrile C2 (1 eq) in $CH_2Cl_2$ (0.25 M) was added trifluoroacetic acid (10 eq) and the mixture was stirred at room temperature until the reaction was complete by LC-MS. The mixture was washed with saturated $NaHCO_3$ solution, $H_2O$, brine, dried ($Na_2SO_4$), filtered, and concentrated under reduced pressure. The resulting residue was purified by silica gel chromatography (typical eluents included $CH_2Cl_2$ and a 90:9:1 mixture of $CH_2Cl_2/CH_3OH$/concentrated $NH_4OH$) to afford the desired piperazine C3. The product structure was verified by $^1$H NMR or by mass analysis.

Example 23

General Synthetic Procedure for Sulfonamide Formation

To an ice-cold solution of piperazine C3 (1 eq), and $Et_3N$ (3 eq) $CH_2Cl_2$ (0.25 M) was added sulfonyl chloride (1 eq) and the mixture stirred at room temperature until the reaction was complete by LC-MS. The mixture was washed with saturated $NaHCO_3$ solution, $H_2O$, brine, dried ($Na_2SO_4$), filtered, and concentrated under reduced pressure. The resulting residue was purified by silica gel chromatography (typical eluents included hexanes and EtOAc) to afford the desired sulfonamide VIII. The product structure was verified by $^1$H NMR or by mass analysis.

Example 24

General Synthetic Procedures for Preparing the Quaternary Core D4 with tert-Butyl piperazine-1-carboxylate (GSP-4)

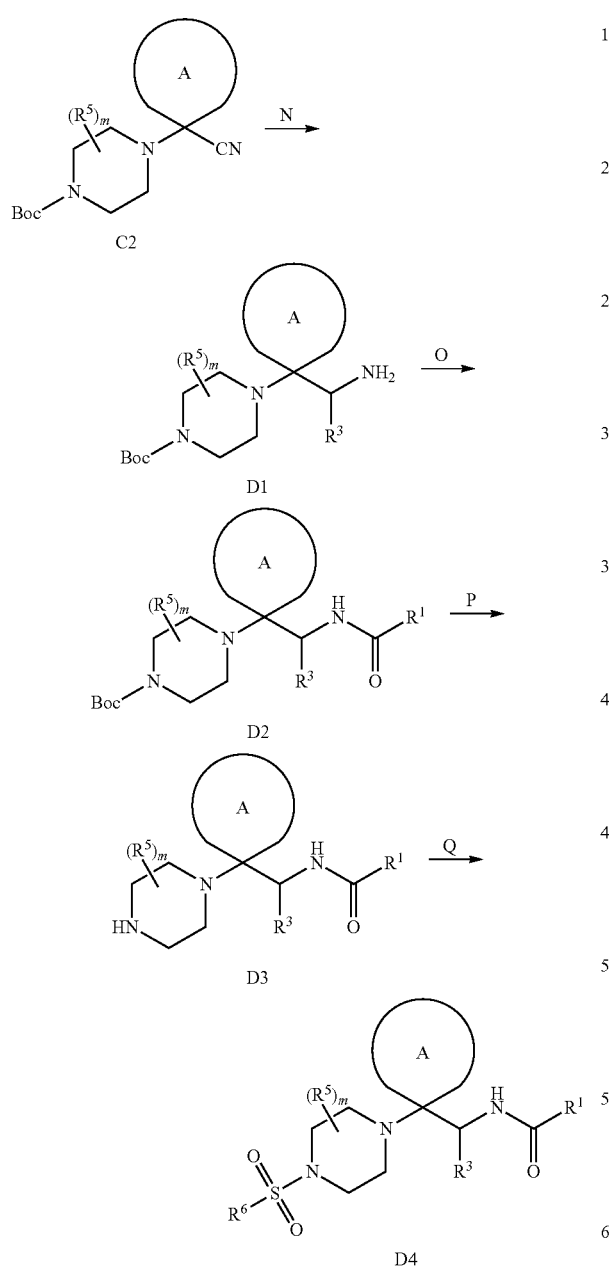

Conditions: N) i. R$^2$Li, Et$_2$O ii. NaBH$_4$, CH$_3$OH; O1) carboxylic acid, HBTU, Et$_3$N, DMF; O2) acid chloride, Et$_3$N, CH$_2$Cl$_2$; P) TFA, CH$_2$Cl$_2$; Q) sulfonyl chloride, Et$_3$N, CH$_2$Cl$_2$ Example 25

General Synthetic Procedure for Addition of R$^2$Li to the Strecker Adduct

To a solution of C2 (1 eq) in Et$_2$O (0.15 M) was added a solution of R$^2$Li (2 eq) drop wise. The resulting mixture was heated at reflux until the reaction was complete by LC-MS. The mixture was cooled to room temperature and then dissolved in CH$_3$OH (0.15 M). To this was added NaBH$_4$ (3 eq) and the mixture stirred at room temperature until the reaction was complete by LC-MS. The mixture was concentrated and the residue was partitioned between 2 N NaOH and CH$_2$Cl$_2$. the organic extracts were combined, washed with H$_2$O, brine, dried (Na$_2$SO$_4$), filtered, and concentrated under reduced pressure. The resulting residue was purified by silica gel chromatography (typical eluents included hexanes and EtOAc) to afford the desired amine D1. The product structure was verified by $^1$H NMR or by mass analysis.

Example 26

General Synthetic Procedure for Carboxamide Formation with HBTU

A mixture of amine D1 (1 eq), desired carboxylic acid (1 eq), Et$_3$N (3 eq), and 2-(1H-benzotriazole-1-yl)-1,1,3,3-tetramethyluronium hexafluorophosphate (HBTU) (1.5 eq) in DMF (0.25 M) was stirred at room temperature until the reaction was complete by LC-MS. The mixture was diluted with H$_2$O and extracted with ethyl acetate. The combined organic extracts were washed with H$_2$O, brine, dried (Na$_2$SO$_4$), filtered, and concentrated under reduced pressure. The resulting residue was purified by silica gel chromatography (typical eluents included hexanes and EtOAc) to afford the desired carboxamide D2. The product structure was verified by $^1$H NMR or by mass analysis.

Example 27

General Synthetic Procedure for Carboxamide Formation via an Acid Chloride

A mixture of amine D1 (1 eq), Et$_3$N (3 eq) and acid chloride (1.0 eq) in CH$_2$Cl$_2$ (0.25 M) was stirred at ambient temperature until the reaction was complete by LC-MS. The mixture was washed with H$_2$O, brine, dried (Na$_2$SO$_4$), filtered, and concentrated under reduced pressure. The resulting residue was purified by silica gel chromatography (typical eluents included hexanes and EtOAc) to afford the desired carboxamide D2. The product structure was verified by $^1$H NMR or by mass analysis.

Example 28

General Synthetic Procedure for the tert-Butyl Carbamate Removal with TFA

To an ice-cold solution of nitrile D2 (1 eq) in CH$_2$Cl$_2$ (0.25 M) was added trifluoroacetic acid (10 eq) and the mixture was stirred at room temperature until the reaction was complete by LC-MS. The mixture was washed with saturated NaHCO$_3$ solution, H$_2$O, brine, dried (Na$_2$SO$_4$), filtered, and concentrated under reduced pressure. The resulting residue was purified by silica gel chromatography (typical eluents included CH$_2$Cl$_2$ and a 90:9:1 mixture of CH$_2$Cl$_2$/CH$_3$OH/concen-

67 trated NH₄OH) to afford the desired piperazine D3. The product structure was verified by $^1$H NMR or by mass analysis.

Example 29

General Synthetic Procedure for Sulfonamide Formation

To an ice-cold solution of piperazine D3 (1 eq), and Et₃N (3 eq) CH₂Cl₂ (0.25 M) was added sulfonyl chloride (1 eq) and the mixture was stirred at room temperature until the reaction was complete by LC-MS. The mixture was washed with saturated NaHCO₃ solution, H₂O, brine, dried (Na₂SO₄), filtered, and concentrated under reduced pressure. The resulting residue was purified by silica gel chromatography (typical eluents included hexanes and EtOAc) to afford the desired sulfonamide D4. The product structure was verified by $^1$H NMR or by mass analysis.

Example 30

General Synthetic Procedures for Preparing the Quaternary Core E2 (GSP-5)

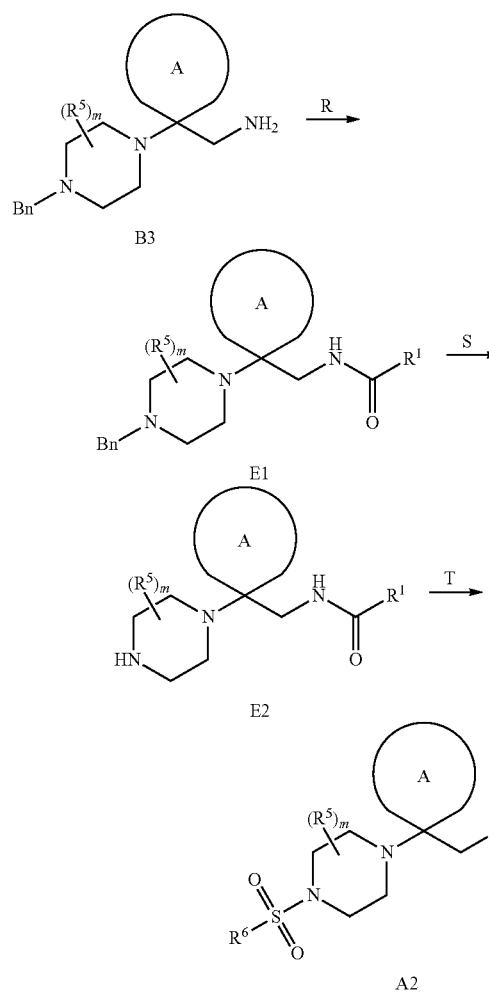

68

Conditions: R1) carboxylic acid, HBTU, Et₃N, DMF; R2) acid chloride, Et₃N, CH₂Cl₂; S1) H₂, 10% Pd/C, CH₃OH; S2) i. ACE-Cl, DCE, ii. CH₃OH; T) sulfonyl chloride, Et₃N, CH₂Cl₂

Example 31

General Synthetic Procedure for Carboxamide Formation

A mixture of amine B3 (1 eq), desired carboxylic acid (1 eq), Et₃N (3 eq), and 2-(1H-benzotriazole-1-yl)-1,1,3,3-tetramethyluronium hexafluorophosphate (HBTU) (1.5 eq) in DMF (0.25 M) was stirred at room temperature until the reaction was complete by LC-MS. The mixture was diluted with H₂Or and extracted with ethyl acetate. The combined organic extracts were washed with H₂O, brine, dried (Na₂SO₄), filtered, and concentrated under reduced pressure. The resulting residue was purified by silica gel chromatography (typical eluents included hexanes and EtOAc) to afford the desired carboxamide E1. The product structure was verified by $^1$H NMR or by mass analysis.

Example 32

General Synthetic Procedure for Carboxamide Formation

A mixture of amine B3 (1 eq), Et₃N (3 eq) and acid chloride (1.0 eq) in CH₂Cl₂ (0.25 M) was stirred at ambient temperature until the reaction was complete by LC-MS. The mixture was washed with H₂O, brine, dried (Na₂SO₄), filtered, and concentrated under reduced pressure. The resulting residue was purified by silica gel chromatography (typical eluents included hexanes and EtOAc) to afford the desired carboxamide E1. The product structure was verified by $^1$H NMR or by mass analysis.

Example 33

General Synthetic Procedure for De-Benzylation via Hydrogenolysis

A mixture of carboxamide E1 (1 eq), and 10% Pd/C (0.10 eq) in CH₃OH (0.25 M) was subjected to an atmosphere of hydrogen gas at a pressure of 40 psi on a Parr Shaker apparatus at room temperature until the reaction was complete by LC-MS. The mixture was filtered through Celite and the filtrate was concentrated under reduced pressure. The resulting residue was purified by silica gel chromatography (typical eluents CH₂Cl₂ and a 90:9:1 mixture of CH₂Cl₂/CH₃OH/concentrated NH₄OH) to afford the desired carboxamide E2. The product structure was verified by $^1$H NMR or by mass analysis.

Example 34

General Synthetic Procedure for De-Benzylation via ACE-Cl

A mixture of E1 (1 eq) and ACE-Cl (2 eq) in DCE (0.25 M) was heated at reflux until the reaction was complete by LC-MS. The mixture was concentrated under reduced pressure and the residue was taken up in CH₃OH (0.25 M). The resulting mixture was heated at reflux until the reaction was complete by LC-MS. The resulting residue was purified by silica gel chromatography (typical eluents included CH₂Cl₂ and a 90:9:1 mixture of $CH_2Cl_2/CH_3OH$/concentrated $NH_4OH$) to afford the desired amine E2. The product structure was verified by $^1H$ NMR or by mass analysis.

Example 35

General Synthetic Procedure for Sulfonamide Formation

To an ice-cold solution of piperazine E2 (1 eq) and $Et_3N$ (3 eq) $CH_2Cl_2$ (0.25 M) was added sulfonyl chloride (1 eq) and the mixture stirred at room temperature until the reaction was complete by LC-MS. The mixture was washed with saturated $NaHCO_3$ solution, $H_2O$, brine, dried ($Na_2SO_4$), filtered, and concentrated under reduced pressure. The resulting residue was purified by silica gel chromatography (typical eluents included hexanes and EtOAc) to afford the desired sulfonamide A2. The product structure was verified by $^1H$ NMR or by mass analysis.

Example 36

General Synthetic Procedures for Preparing the Quaternary Core F4 (GSP-6)

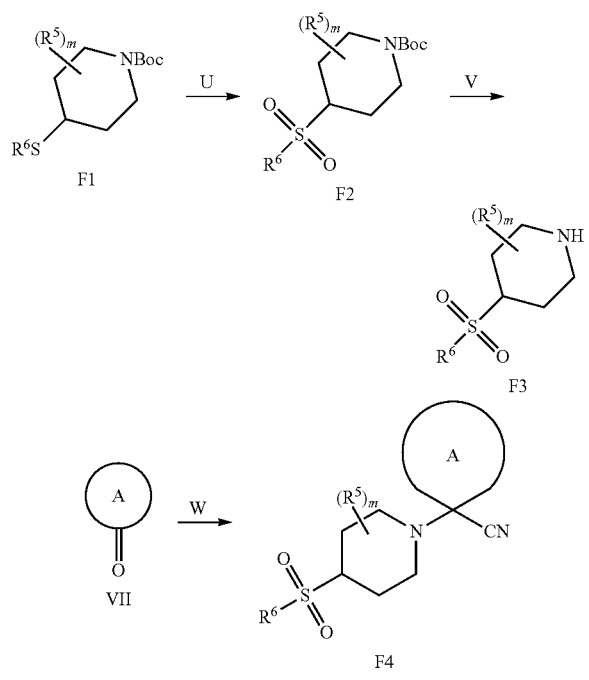

Conditions: U) m-CPBA, 1,2-dichloroethane; V) TFA, $CH_2Cl_2$; W) TMSCN, $ZnI_2$, $Et_2O/CH_3OH$ Example 37

General Synthetic Procedure for Sulfone Formation

To a solution of sulfide F1 (1 eq) in 1,2-dichloroethane (0.25 M) was added m-CPBA (1 eq) and the mixture was stirred at room temperature until the reaction was complete by LC-MS. The mixture was diluted with saturated aqueous $NaHCO_3$ and extracted with $CH_2Cl_2$. The combined organic extracts were washed with $H_2O$, brine, dried ($Na_2SO_4$), filtered, and concentrated under reduced pressure. The resulting residue was purified by silica gel chromatography (typical eluents included hexanes and EtOAc) to afford the desired sulfone F2. The product structure was verified by $^1H$ NMR or by mass analysis.

Example 38

General Synthetic Procedure for the tert-Butyl Carbamate Removal with TFA

To an ice-cold solution of sulfone F2 (1 eq) in $CH_2Cl_2$ (0.25 M) was added trifluoroacetic acid (10 eq) and the was mixture stirred at room temperature until the reaction was complete by LC-MS. The mixture was washed with saturated $NaHCO_3$ solution, $H_2O$, brine, dried ($Na_2SO_4$), filtered, and concentrated under reduced pressure. The resulting residue was purified by silica gel chromatography (typical eluents included $CH_2Cl_2$ and a 90:9:1 mixture of $CH_2Cl_2/CH_3OH$/concentrated $NH_4OH$) to afford the desired piperidine F3. The product structure was verified by $^1H$ NMR or by mass analysis.

Example 39

General Synthetic Procedure for the Strecker Coupling Using TMSCN and $ZnI_2$

To a solution of cyclic ketone VII (1 eq) and TMSCN (1 eq) in $Et_2O$ was added $ZnI_2$ (2 mol %). The mixture was allowed to stir for 15 minutes, then a solution of piperidine F2 (1 eq) in $CH_3OH$ (0.8 M) and the mixture was heated at reflux for 3 hours, then room temperature until the reaction was complete by LC-MS. The mixture was concentrated and the resulting residue was purified by silica gel chromatography (typical eluents included hexanes and EtOAc) to afford the desired nitrile F3. The product structure was verified by $^1H$ NMR or by mass analysis.

Example 40

General Synthetic Procedures for Preparing the Quaternary Core G5 (GSP-7)

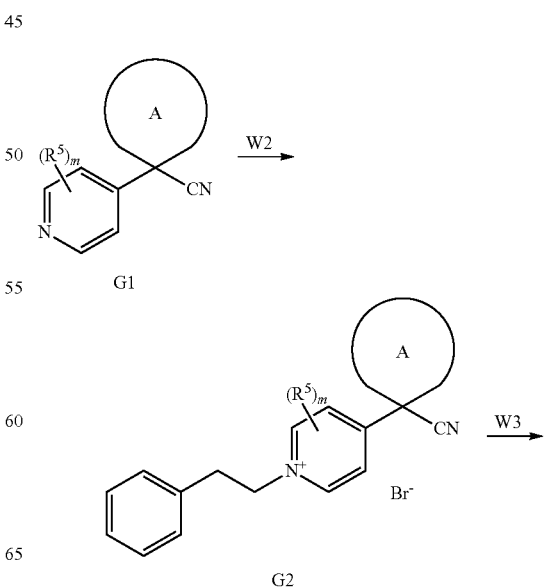

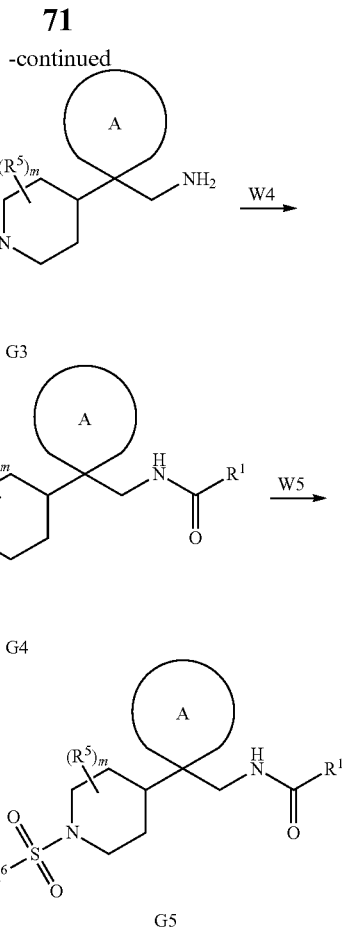

Conditions: W2) m-CPBA, 1,2-dichloroethane; W3) TFA, CH₂Cl₂; W4) carboxylic acid, HBTU, Et₃N, DMF; W5) i. ACE-Cl, DCE, ii. CH₃OH; ii. sulfonyl chloride, Et₃N, CH₂Cb

Example 41

General Synthetic Procedure for Pyridinium Salt Formation

To a solution of pyridine G1 (1 eq) in CH₃CN (0.50 M) was added phenethyl bromide (10 eq) and the mixture was concentrated under reduced pressure to afford the desired pyridinium salt G2. The product structure was verified by $^1$H NMR or by mass analysis.

Example 42

General Synthetic Procedure for the Pyridinium Salt Reduction

To a solution of G2 (1 eq) in EtOAc (0.25 M) was added PtO₂ (0.10 eq) and the was mixture stirred at room temperature under a balloon of H₂ gas (1 atmosphere) until the reaction was complete by LC-MS. The mixture was filtered through Celite and concentrated under reduced pressure. The resulting residue was purified by silica gel chromatography (typical eluents included CH₂Cl₂ and a 90:9:1 mixture of CH₂Cl₂/CH₃OH/concentrated NH₄OH) to afford the desired amino piperidine G3. The product structure was verified by $^1$H NMR or by mass analysis.

Example 43

General Synthetic Procedure for Carboxamide Formation

A mixture of amine G3 (1 eq), desired carboxylic acid (1 eq), Et₃N (3 eq), and 2-(1H-benzotriazole-1-yl)-1,1,3,3-tetramethyluronium hexafluorophosphate (HBTU) (1.5 eq) in DMF (0.25 M) was stirred at room temperature until the reaction was complete by LC-MS. The mixture was diluted with H₂Or and extracted with ethyl acetate. The combined organic extracts were washed with H₂O, brine, dried (Na₂SO₄), filtered, and concentrated under reduced pressure. The resulting residue was purified by silica gel chromatography (typical eluents included hexanes and EtOAc) to afford the desired carboxamide G4. The product structure was verified by $^1$H NMR or by mass analysis.

Example 44

General Synthetic Procedure for Removal of Phenethyl Group via ACE-Cl and Sulfonamide Formation A mixture of G4 (1 eq) and ACE-Cl (20 eq) in DCE (0.25 M) was heated at reflux until the reaction was complete by LC-MS. The mixture was concentrated under reduced pressure and the residue was taken up in CH₃OH (0.25 M). The resulting mixture was heated at reflux until the reaction was complete by LC-MS. The resulting residue was purified by silica gel chromatography (typical eluents included CH₂Cl₂ and a 90:9:1 mixture of CH₂Cl₂/CH₃OH/concentrated NH₄OH) to afford the desired amine. The product structure was verified by $^1$H NMR or by mass analysis. To an ice-cold solution of the amine intermediate (1 eq), and Et₃N (3 eq) CH₂Cl₂ (0.25 M) was added sulfonyl chloride (1 eq) and the mixture stirred at room temperature until the reaction was complete by LC-MS. The mixture was washed with saturated NaHCO₃ solution, H₂O, brine, dried (Na₂SO₄), filtered, and concentrated under reduced pressure. The resulting residue was purified by silica gel chromatography (typical eluents included hexanes and EtOAc) to afford the desired sulfonamide G5. The product structure was verified by $^1$H NMR or by mass analysis.

Example 45

Preparation of (1-(4-(Propylsulfonyl)piperazin-1-yl)cyclohexyl)methanamine (5)

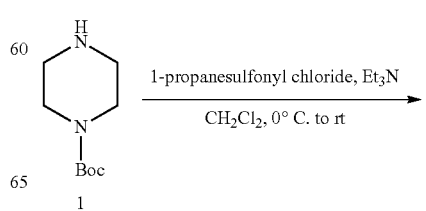

1

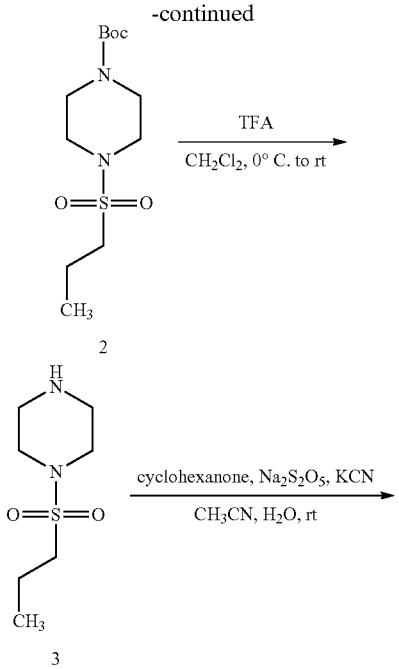

reduced pressure to afford 1-(propylsulfonyl)piperazine (3) as a crystalline solid (10.30 g quantitative): $^1$H NMR (500 MHz, CDCl$_3$) δ 7.91 (d, J=1.7 Hz, 1H), 7.48 (d, J=1.6 Hz, 1H), 7.21 (m, 1H), 7.14 (s, 1H), 7.09 (s, 1H), 3.96 (s, 3H), 3.75 (s, 3H).

Step C: Cyclohexanone and 1-(propylsulfonyl)piperazine (3) were converted to 1-(4-(propylsulfonyl)piperazin-1-yl)cyclohexanecarbonitrile (4): $^1$H NMR (500 MHz, DMSO-d$_6$) δ 10.03 (bs, 1H), 7.56 (d, J=8.1 Hz, 1H), 7.38 (d, J=7.1 Hz, 1H), 7.22 (m, 2H), 5.13 (dd, J=14.3 Hz, 1.0 Hz, 2H), 4.71 (m, 1H), 3.83 (s, 3H), 3.73 (m, 1H), 3.48 (m, 1H), 3.31-3.19 (m, 3H), 2.42 (m, 1H), 2.18 (m 1H), 1.99-1.97 (m, 3H); MS (ESI+) m/z 296 (M+H).

Step D: 1-(4-(Propylsulfonyl)piperazin-1-yl)cyclohexanecarbonitrile (4) was converted to (1-(4-(propylsulfonyl)piperazin-1-yl)cyclohexyl)methanamine (5): $^1$H NMR (500 MHz, DMSO-d$_6$) δ 10.03 (bs, 1H), 7.56 (d, J=8.1 Hz, 1H), 7.38 (d, J=7.1 Hz, 1H), 7.22 (m, 2H), 5.13 (dd, J=14.3 Hz, 1.0 Hz, 2H), 4.71 (m, 1H), 3.83 (s, 3H), 3.73 (m, 1H), 3.48 (m, 1H), 3.31-3.19 (m, 3H), 2.42 (m, 1H), 2.18 (m 1H), 1.99-1.97 (m, 3H); MS (ESI+) m/z 296 (M+H).

Example 46

Preparation of (1-(4-(Propylsulfonyl)piperazin-1-yl)cycloheptyl)methanamine (7)

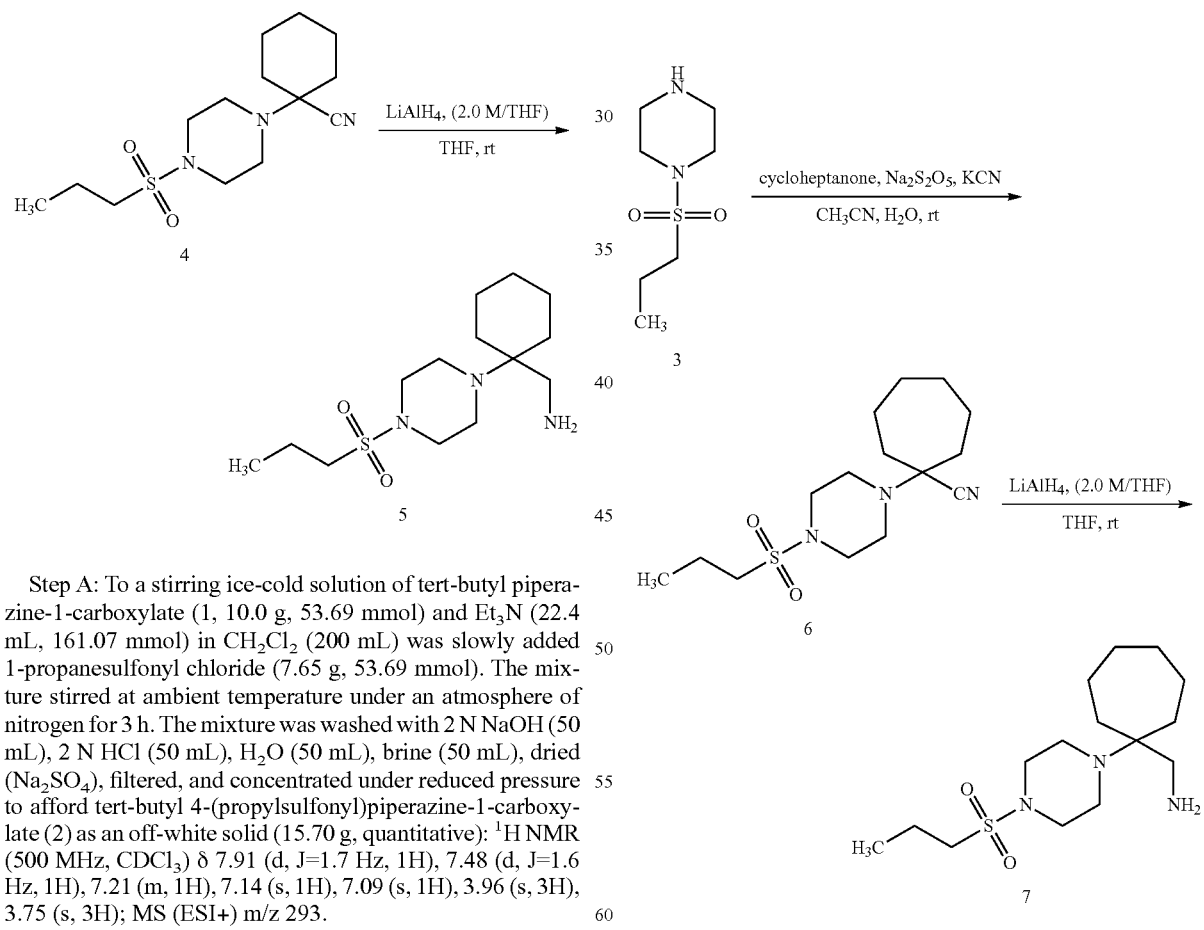

Step A: To a stirring ice-cold solution of tert-butyl piperazine-1-carboxylate (1, 10.0 g, 53.69 mmol) and Et$_3$N (22.4 mL, 161.07 mmol) in CH$_2$Cl$_2$ (200 mL) was slowly added 1-propanesulfonyl chloride (7.65 g, 53.69 mmol). The mixture stirred at ambient temperature under an atmosphere of nitrogen for 3 h. The mixture was washed with 2 N NaOH (50 mL), 2 N HCl (50 mL), H$_2$O (50 mL), brine (50 mL), dried (Na$_2$SO$_4$), filtered, and concentrated under reduced pressure to afford tert-butyl 4-(propylsulfonyl)piperazine-1-carboxylate (2) as an off-white solid (15.70 g, quantitative): $^1$H NMR (500 MHz, CDCl$_3$) δ 7.91 (d, J=1.7 Hz, 1H), 7.48 (d, J=1.6 Hz, 1H), 7.21 (m, 1H), 7.14 (s, 1H), 7.09 (s, 1H), 3.96 (s, 3H), 3.75 (s, 3H); MS (ESI+) m/z 293.

Step B: To a stirring ice-cold solution of tert-butyl 4-(propylsulfonyl)piperazine-1-carboxylate (2, 15.70 g, 53.69 mmol) in CH$_2$Cl$_2$ (200 mL) was slowly added trifluoroacetic acid (21.4 mL, 268.45 mmol). The mixture stirred at room temperature for 16 h under an atmosphere of N$_2$. The mixture was washed with 2 N NaOH (3×50 mL), H$_2$O (50 mL), brine (50 mL), dried (Na$_2$SO$_4$), filtered, and concentrated under Step A: Cycloheptanone and 1-(propylsulfonyl)piperazine (3) were converted to 1-(4-(propylsulfonyl)piperazin-1-yl)cycloheptanecarbonitrile (6): MS (ESI+) m/z 314 (M+H).

Step B: 1-(4-(Propylsulfonyl)piperazin-1-yl)cycloheptanecarbonitrile (6) was converted to (1-(4-(propylsulfonyl)piperazin-1-yl)cycloheptyl)methanamine (7): MS (ESI+) m/z 318 (M+H).

Example 47

Preparation of (1-(4-(Propylsulfonyl)piperazin-1-yl)cyclopentyl)methanamine (9)

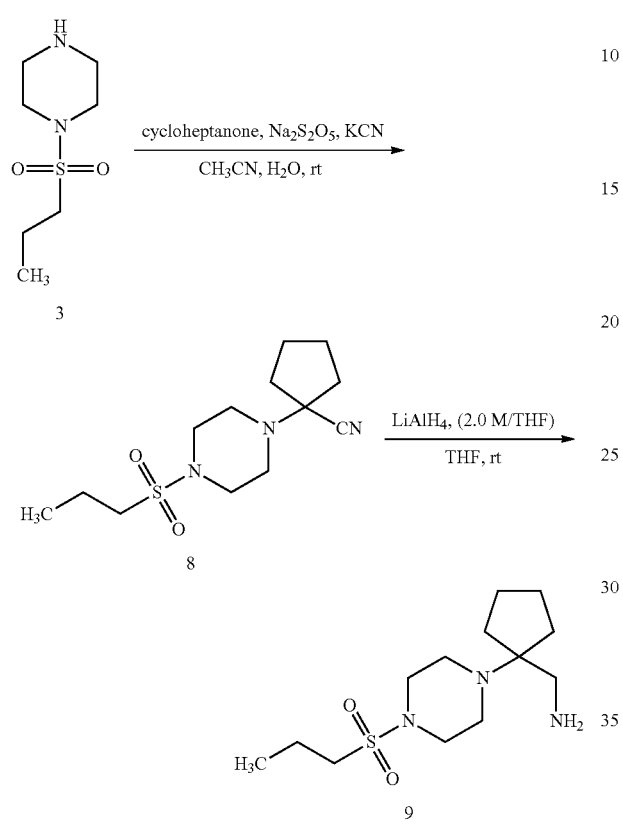

Step A: Cyclopentanone and 1-(propylsulfonyl)piperazine (3) were converted to 1-(4-(propylsulfonyl)piperazin-1-yl)cyclopentanecarbonitrile (8): MS (ESI+) m/z 286 (M+H).

Step B: 1-(4-(Propylsulfonyl)piperazin-1-yl)cyclopentanecarbonitrile (8) was converted to (1-(4-(propylsulfonyl)piperazin-1-yl)cyclopentyl)methanamine (9): MS (ESI+) m/z 290 (M+H).

Example 48

Preparation of 2,2,2-Trifluoro-N-((1-(piperazin-1-yl)cyclohexyl)methyl)acetamide (14)

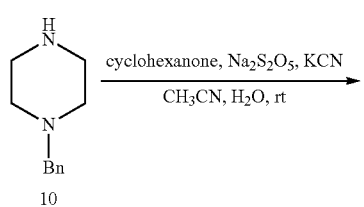

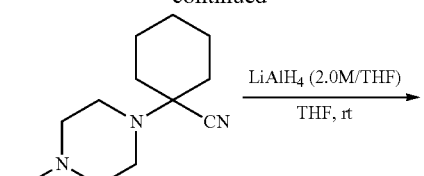

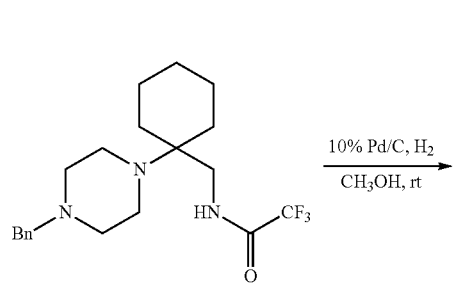

Step A: Cyclohexanone and 1-benzylpiperazine (10) were converted to 1-(4-benzylpiperazin-1-yl)cyclohexanecarbonitrile (11): MS (ESI+) m/z 284 (M+H).

Step B: 1-(4-Benzylpiperazin-1-yl)cyclohexanecarbonitrile (11) was converted to (1-(4-benzylpiperazin-1-yl)cyclohexyl)methanamine (12): MS (ESI+) m/z 288 (M+H).

Step C: (1-(4-Benzylpiperazin-1-yl)cyclohexyl)methanamine (12) was converted to N-((1-(4-benzylpiperazin-1-yl)cyclohexyl)methyl)-2,2,2-trifluoroacetamide (13): MS (ESI+) m/z 384 (M+H).

Step D: N-((1-(4-Benzylpiperazin-1-yl)cyclohexyl)methyl)-2,2,2-trifluoroacetamide (13) was converted to 2,2,2- trifluoro-N-((1-(piperazin-1-yl)cyclohexyl)methyl)acetamide (14): MS (ESI+) m/z 294 (M+H).

Example 49

Preparation of 1-(piperazin-1-yl)cyclohexanecarbonitrile (17)

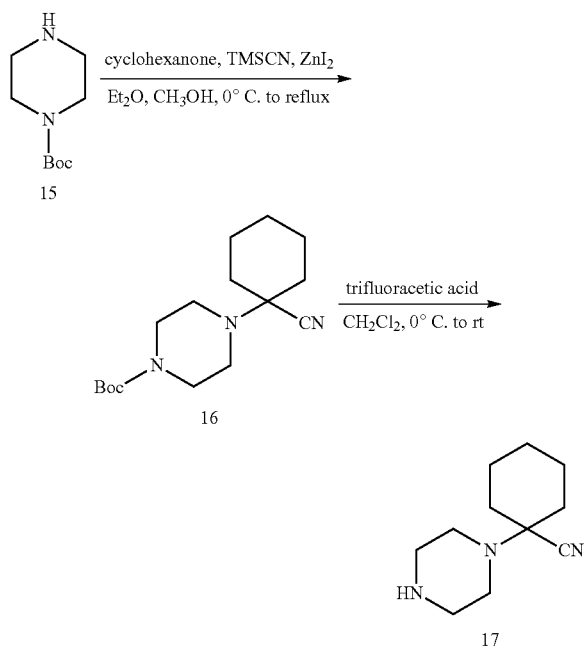

Step A: 1-Boc-piperazine and cyclohexanone were converted to tert-butyl 4-(1-cyanocyclohexyl)piperazine-1-carboxylate (16): MS (ESI+) m/z 294 (M+H).

Step B: tert-Butyl 4-(1-cyanocyclohexyl)piperazine-1-carboxylate (16) was converted to 1-(piperazin-1-yl)cyclohexanecarbonitrile (17): MS (ESI+) m/z 194 (M+H).

Example 50

Preparation of (1-(4-(Cyclopropylmethylsulfonyl)piperazin-1-yl)cyclohexyl)methanamine (19)

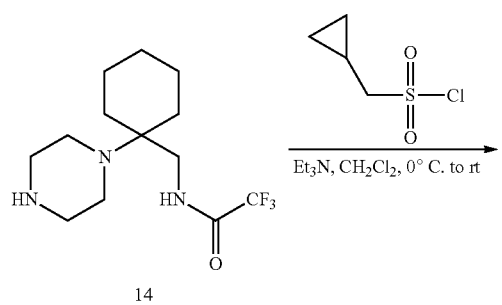

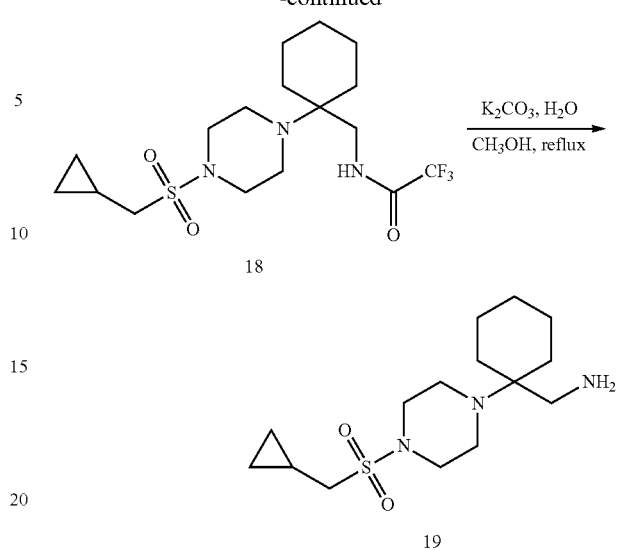

Step A: To a stirring ice-cold solution of 14 (10.0 g, 34.09 mmol) and Et₃N (14.2 mL, 102.27 mmol) in CH₂Cl₂ (200 mL) was slowly added 1-cyclopropylmethylsulfonyl chloride (5.27 g, 34.09 mmol). The mixture stirred at ambient temperature under an atmosphere of nitrogen for 3 h. The mixture was washed with 2 N NaOH (50 mL), 2 N HCl (50 mL), H₂O (50 mL), brine (50 mL), dried (Na₂SO₄), filtered, and concentrated under reduced pressure to afford N-((1-(4-(cyclopropylmethylsulfonyl)piperazin-1-yl)cyclohexyl)methyl)-2,2,2-trifluoroacetamide (18) as an off-white solid (14.00 g, quantitative): MS (ESI+) m/z 412.

Step B: N-((1-(4-(Cyclopropylmethylsulfonyl)piperazin-1-yl)cyclohexyl)methyl)-2,2,2-trifluoroacetamide (18) was converted to (1-(4-(cyclopropylmethylsulfonyl)piperazin-1-yl)cyclohexyl)methanamine (19): MS (ESI+) m/z 316.

Example 51

Preparation of (1-(4-(Cyclopropylmethylsulfonyl)piperazin-1-yl)cycloheptyl)methanamine (25)

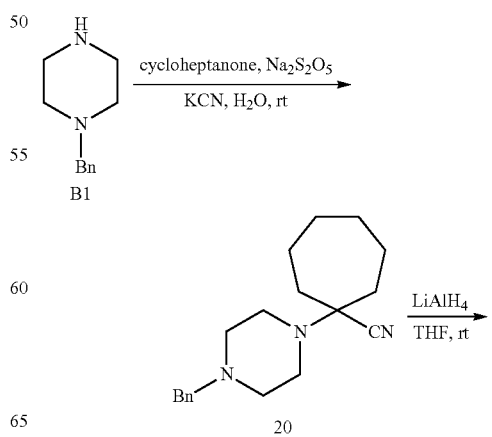

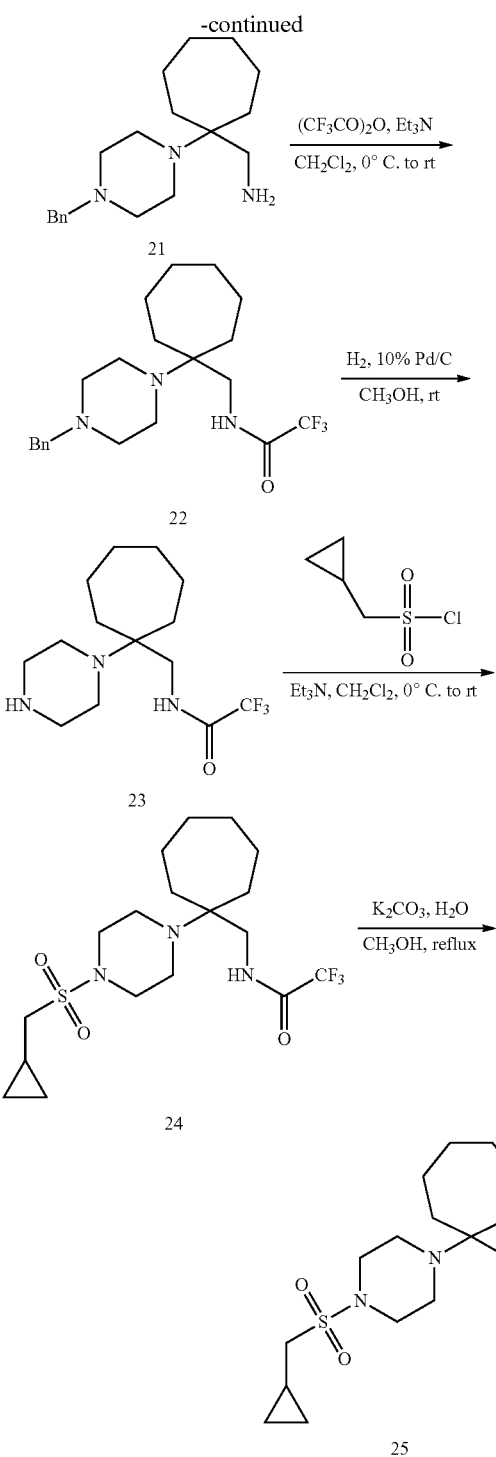

Step D: N-((1-(4-Benzylpiperazin-1-yl)cycloheptyl)methyl)-2,2,2-trifluoroacetamide (22) was converted to 2,2,2-trifluoro-N-((1-(piperazin-1-yl)cycloheptyl)methyl)acetamide (23): $^1$H NMR (300 MHz, CDCl$_3$) δ 7.28-7.20 (bs, 1H), 6.90-6.75 (bs, 1H), 3.47 (s, 2H), 3.36 (d, J=5.4 Hz, 2H), 3.20-3.13 (m, 2H), 2.91 (t, J=4.8 Hz, 4H), 1.95-1.85 (m, 2H), 1.83-1.71 (m, 2H), 1.65-1.42 (m, 8H).

Step E: 2,2,2-Trifluoro-N-((1-(piperazin-1-yl)cycloheptyl)methyl)acetamide (23) was converted to N-((1-(4-(cyclopropylmethylsulfonyl)piperazin-1-yl)cycloheptyl)methyl)-2,2,2-trifluoroacetamide (24): $^1$H NMR (400 MHz, CDCl$_3$): δ 7.02 (bs, 1H), 3.35 (d, J=4.8 Hz, 2H), 3.30 (bs, 4H), 2.87 (d, J=7.2 Hz, 2H), 2.65 (t, J=4.8 Hz, 4H), 1.80-1.70 (m, 2H), 1.60-1.40 (m, 10H), 1.18-1.05 (m, 1H), 0.75-0.65 (m, 2H), 0.40-0.34 (m, 2H).

Step F: N-((1-(4-(Cyclopropylmethylsulfonyl)piperazin-1-yl)cycloheptyl)methyl)-2,2,2-trifluoroacetamide (24) was converted to (1-(4-(cyclopropylmethylsulfonyl)piperazin-1-yl)cycloheptyl)methanamine (25): $^1$H NMR (300 MHz, CDCl$_3$): δ 3.27 (t, J=4.8 Hz, 4H), 2.85 (d, J=6.9 Hz, 2H), 2.70-2.60 (m, 6H), 1.80-1.67 (m, 2H), 1.60-1.35 (m, 10H), 1.18-1.05 (m, 1H), 0.75-0.65 (m, 2H), 0.40-0.35 (m, 2H).

Example 52

Preparation of (1-(4-(ethanesulfonyl)piperazin-1-yl)cycloheptyl)methanamine (27)

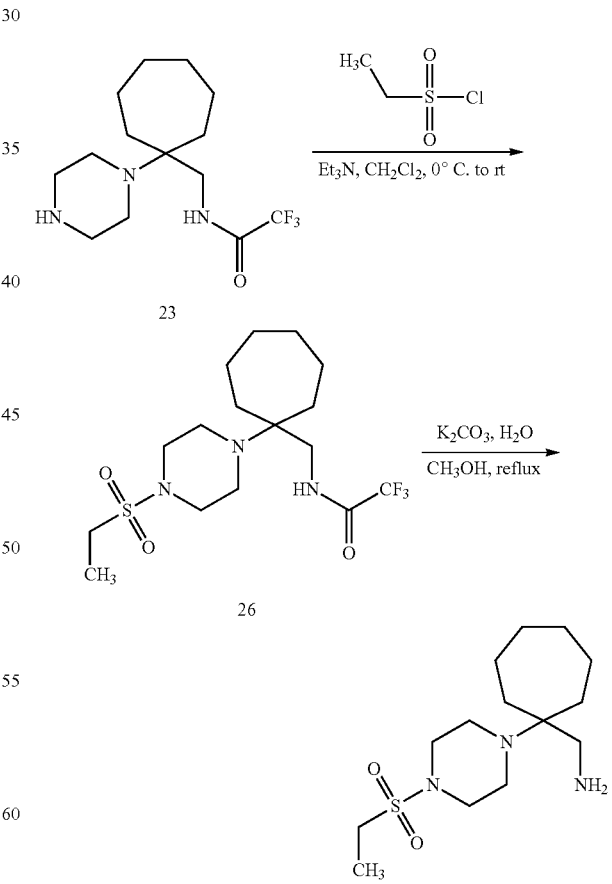

Step A: 1-Benzylpiperazine and cycloheptanone were converted to 1-(4-benzylpiperazin-1-yl)cycloheptanecarbonitrile (20): $^1$H NMR (300 MHz, CDCl$_3$) δ 7.35-7.20 (m, 5H), 3.53-4.90 (m, 2H), 2.89 (t, J=4.8 Hz, 2H), 2.70-2.35 (m, 8H), 2.15-2.05 (m, 1H), 1.95-1.85 (m, 1H), 1.75-1.50 (m, 8H).

Step B: 1-(4-Benzylpiperazin-1-yl)cycloheptanecarbonitrile (20) was converted to (1-(4-benzylpiperazin-1-yl)cycloheptyl)methanamine (21).

Step C: (1-(4-Benzylpiperazin-1-yl)cycloheptyl)methanamine (21) was converted to N-((1-(4-benzylpiperazin-1-yl)cycloheptyl)methyl)-2,2,2-trifluoroacetamide (22).

Step A: 2,2,2-trifluoro-N-((1-(piperazin-1-yl)cycloheptyl)methyl)acetamide (23) was converted to N-((1-(4-(ethylsulfonyl)piperazin-1-yl)cycloheptyl)methyl)-2,2,2-trifluoroacetamide (26): ¹H NMR (400 MHz, CDCl₃) δ 7.02 (bs, 1H), 3.35 (d, J=4.4 Hz, 2H), 3.26 (t, J=4.4 Hz, 4H), 2.96 (q, J=7.6 Hz, 2H), 2.66 (t, J=4.8 Hz, 4H), 1.85-1.75 (m, 2H), 1.63-1.40 (m, 10H), 1.37 (t, J=7.6 Hz, 3H), Step B: N-((1-(4-(Ethylsulfonyl)piperazin-1-yl)cycloheptyl)methyl)-2,2,2-trifluoroacetamide (26) was converted to (1-(4-(ethylsulfonyl)piperazin-1-yl)cycloheptyl)methanamine (27): ¹H NMR (300 MHz, CDCl₃) δ 3.24 (t, J=4.8 Hz, 4H), 2.94 (q, J=7.5 Hz, 2H), 2.70-2.60 (m, 6H), 1.80-1.67 (m, 2H), 1.60-1.34 (m, 10H), 1.36 (t, J=7.6 Hz, 3H).

Example 53

Preparation of (1-(4-(1-methyl-1H-imidazol-4-ylsulfonyl)piperazin-1-yl)cyclohexyl)methanamine (29)

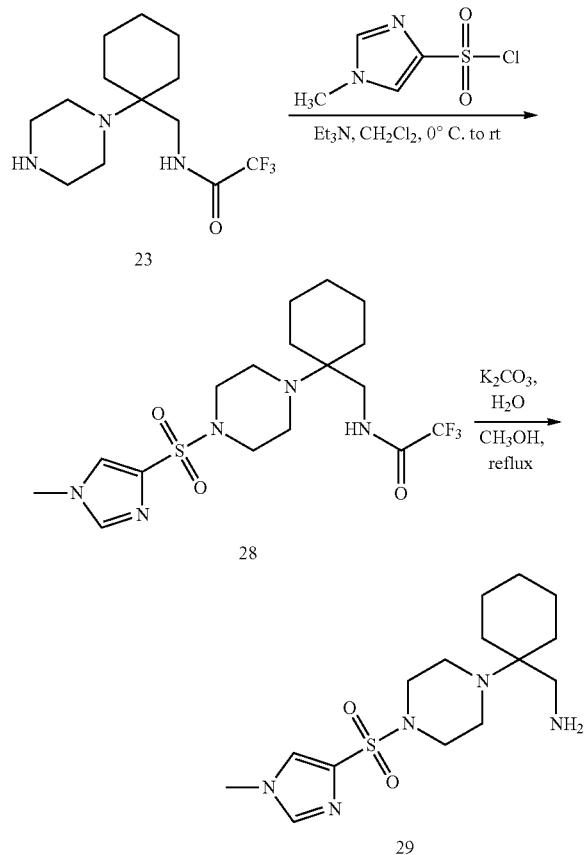

Step A: 2,2,2-Trifluoro-N-((1-(piperazin-1-yl)cyclohexyl) methyl)acetamide and 1-methyl-1H-imidazole-4-sulfonyl chloride were converted to 2,2,2-trifluoro-N-methyl-N-(1-(4-(1-methyl-1H-imidazol-4-ylsulfonyl)piperazin-1-yl)cyclohexyl)acetamide (28): ¹H NMR (300 MHz, CDCl₃) δ 7.51 (d, J=1.5 Hz, 1H), 7.44 (d, J=1.5 Hz, 1H), 6.93 (bs, 1H), 3.77 (s, 3H), 3.41 (dd, J=5.7 Hz, J=11.1 Hz, 2H), 3.25-3.16 (m, 4H), 2.73-2.65 (m, 4H), 1.68-1.47 (m, 5H), 1.46-1.28 (m, 4H), 1.27-1.09 (m, 1H).

Step B: 2,2,2-Trifluoro-N-methyl-N-(1-(4-(1-methyl-1H-imidazol-4-ylsulfonyl)piperazin-1-yl)cyclohexyl)acetamide (28) was converted to (1-(4-(1-methyl-1H-imidazol-4-ylsulfonyl)piperazin-1-yl)cyclohexyl)methanamine (29): MS (ESI+) m/z 342 (M+H).

Example 54

Preparation of 1-(1-Methyl-1H-1,2,3-triazol-4-ylsulfonyl)piperazine (33)

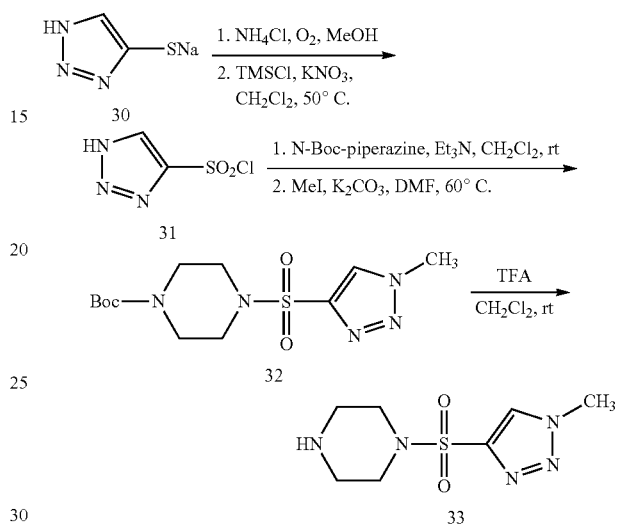

Step A: Sodium 1H-1,2,3-triazole-4-thiolate (30, 7.0 g, 56.70 mmol) was added in small portions to ice-cooled methanol (50 mL) followed by NH₄Cl (4.55 g, 85.05 mmol) with H₂O (20 mL). The reaction mixture was air bubbled for 5 hours at room temperature. It was then concentrated under reduced pressure to afford the intermediate disulfide, which was dissolved in CH₂Cl₂ (160 mL). To this mixture was added potassium nitrate (14.35 g, 141.75 mmol) and trimethylsilyl chloride (TMSCl) (15.4 g, 141.75 mmol) and the mixture was placed in a sealed flask. The heterogeneous mixture was stirred vigorously at 50° C. until the reaction was complete by LC-MS. The reaction mixture was cooled to room temperature and filtered. The filtrate was concentrated under reduced pressure to afford the 1H-1,2,3-triazole-4-sulfonyl chloride (31) as a white solid (4.50 g, 48%). This material was used as is in the next step.

Step B: N-Boc-piperazine and 1H-1,2,3-triazole-4-sulfonyl chloride were converted to tert-butyl 4-(1H-1,2,3-triazol-4-ylsulfonyl)piperazine-1-carboxylate. This material was used as is in the next step.

Step C: To a solution tert-butyl 4-(1H-1,2,3-triazol-4-ylsulfonyl)piperazine-1-carboxylate (0.54 g, 1.15 mmol) in DMF (10 mL) at 0° C. was added K₂CO₃ (0.32 g, 2.30 mmol) followed by MeI (0.09 mL, 1.49 mmol) drop wise. Then the reaction mixture was stirred at room temperature for 16 hours. Then the reaction mixture was concentrated under reduced pressure and dissolved in CH₂Cl₂ (20 mL), washed with H₂O (20 mL), dried (Na₂SO₄), filtered and concentrated under reduced pressure. The resulting residue was chromatographed over silica gel (Isco CombiFlash Companion unit, 12 g Redisep column, 9:1 mixture of CH₂Cl₂/CH₃OH) to give tert-butyl 4-(1-methyl-1H-1,2,3-triazol-4-ylsulfonyl)piperazine-1-carboxylate as a white foam (32, 0.30 g, 57%): MS (ESI+) m/z 332.

Step D: tert-Butyl 4-(1-methyl-1H-1,2,3-triazol-4-ylsulfonyl)piperazine-1-carboxylate was converted to 1-(1-methyl-1H-1,2,3-triazol-4-ylsulfonyl)piperazine (33): MS (ESI+) m/z 232.

Example 55

Preparation of (4,4-difluoro-1-(4-(propylsulfonyl)piperazin-1-yl)cyclohexyl)methanamine (35)

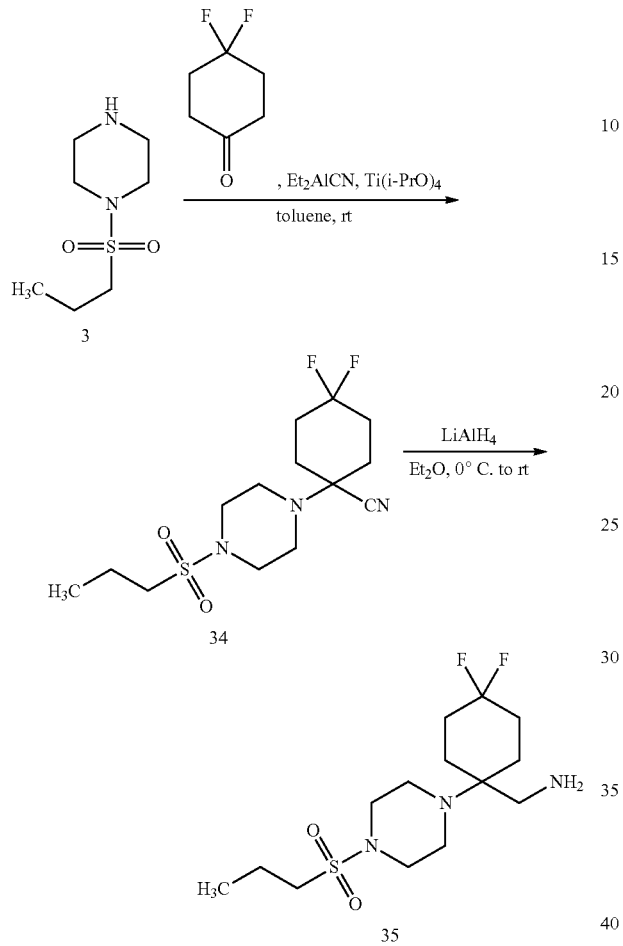

Step A: 4,4-Difluorocyclohexanone and 1-(propylsulfonyl)piperazine (3) were converted to 4,4-difluoro-1-(4-(propylsulfonyl)piperazin-1-yl)cyclohexanecarbonitrile (34): MS (ESI+) m/z 336 (M+H).

Step B: 4,4-Difluoro-1-(4-(propylsulfonyl)piperazin-1-yl)cyclohexanecarbonitrile (34) was converted to (4,4-difluoro-1-(4-(propylsulfonyl)piperazin-1-yl)cyclohexyl)methanamine (35): MS (ESI+) m/z 340 (M+H).

Example 56

Preparation of (4,4-difluoro-1-(4-(1-methyl-1H-imidazol-4-ylsulfonyl)piperazin-1-yl)cyclohexyl)methanamine (39)

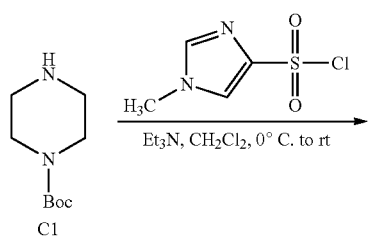

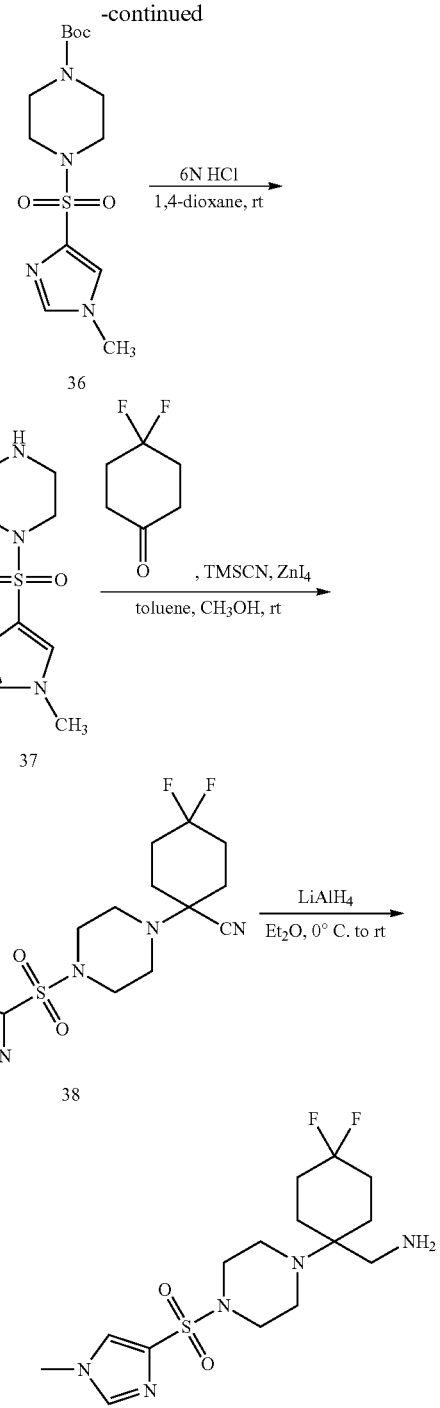

Step A: To a stirred ice-cold solution of tert-butyl piperazine-1-carboxylate (C1, 10.0 g, 53.76 mmol) in $CH_2Cl_2$ (50 mL) at 0° C. was added $Et_3N$ (22.66 mL, 161.29 mmol) and a solution of 1-methyl-1H-imidazole-4-sulfonyl chloride (11.61 g, 64.51 mmol) in $CH_2Cl_2$ (50 mL) drop wise over 30 minutes while maintaining the temperature of the reaction mixture below 5° C. and under an atmosphere of $N_2$. The reaction mixture was warmed to room temperature and stirred for an additional 5 h then quenched with a saturated solution of $NaHCO_3$ (50 mL). The aqueous mixture was extracted with $CH_2Cl_2$ (3×100 mL), and the combined organic extracts were washed with brine (1×50 mL), dried (Na$_2$SO$_4$), filtered and concentrated under reduced pressure to give a crude solid. The solids were suspended in Et$_2$O and stirred for 30 minutes at room temperature then filtered, washed with cold diethyl ether and dried under vacuum to afford tert-butyl 4-(1-methyl-1H-imidazol-4-ylsulfonyl)piperazine-1-carboxylate (36) as an off-white solid (16.8, 95%): $^1$H NMR (300 MHz, CDCl$_3$) δ (dd, J=1.5 Hz, 14.56 Hz, 2H), 3.76 (s, 3H), 3.55-3.45 (m, 4H), 3.20-3.10 (m, 4H), 1.43 (s, 9H); MS (ESI+) m/z 331 (M+H).

Step B: To an ice-cold solution of tert-butyl 4-(1-methyl-1H-imidazol-4-ylsulfonyl)piperazine-1-carboxylate (36, 6.0 g, 18.18 mmol) in 1,4-dioxane (30 mL) was slowly added concentrated HCl (30 mL) drop wise over 30 minutes. The reaction mixture was warmed to room temperature and stirred for 2 h. The reaction mixture was concentrated under vacuum, azeotroped with toluene (3×100 mL) and the resultant solids dissolved in H$_2$O (100 mL). The aqueous mixture was washed with CH$_2$Cl$_2$ (2×100 mL) then carefully neutralized with solid K$_2$CO$_3$ (15 g). The aqueous mixture was then extracted with CH$_2$Cl$_2$ (4×100 mL) and combined organic extracts were washed with brine (1×50 mL), dried (Na$_2$SO$_4$), filtered and concentrated under reduced pressure to afford 1-(1-methyl-1H-imidazol-4-ylsulfonyl)piperazine (37) as off-white foam (3.8 g, 90%): $^1$H NMR (400 MHz, CDCl$_3$) δ (dd, J=1.1 Hz, 16.8 Hz, 2H), 3.80-3.75 (m, 5H), 3.74-3.65 (m, 2H), 3.37-3.1 (m, 2H), 3.0-3.25 (m, 2H); MS (ESI+) m/z 231 (M+H).

Step C: 1-(1-Methyl-1H-imidazol-4-ylsulfonyl)piperazine and 4,4-difluorocyclohexanone were converted to 4,4-difluoro-1-(4-(1-methyl-1H-imidazol-4-ylsulfonyl)piperazin-1-yl)cyclohexanecarbonitrile (38): $^1$H NMR (300 MHz, CDCl$_3$) δ (d, J=1.1 Hz, 1H), 7.45 (d, J=1.4 Hz, 1H), 3.76 (s, 3H), 3.35-3.25 (m, 4H), 2.73-2.67 (m, 4H), 2.17-1.94 (m, 8H); MS (ESI+) m/z 375 (M+H).

Step D: 4,4-Difluoro-1-(4-(1-methyl-1H-imidazol-4-ylsulfonyl)piperazin-1-yl)cyclohexanecarbonitrile was converted to (4,4-difluoro-1-(4-(1-methyl-1H-imidazol-4-ylsulfonyl)piperazin-1-yl)cyclohexyl)methanamine (39): MS (ESI+) m/z 378 (M+H).

Example 57

Preparation (4,4-Difluoro-1-(4-(1-methyl-1H-1,2,3-triazol-4-ylsulfonyl)piperazin-1-yl)cyclohexyl)methanamine (42)

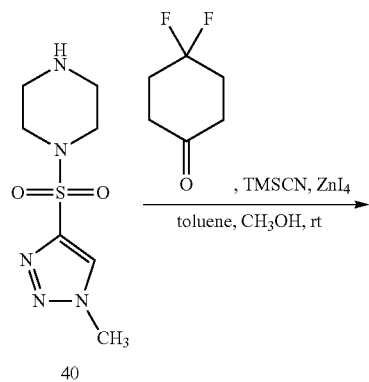

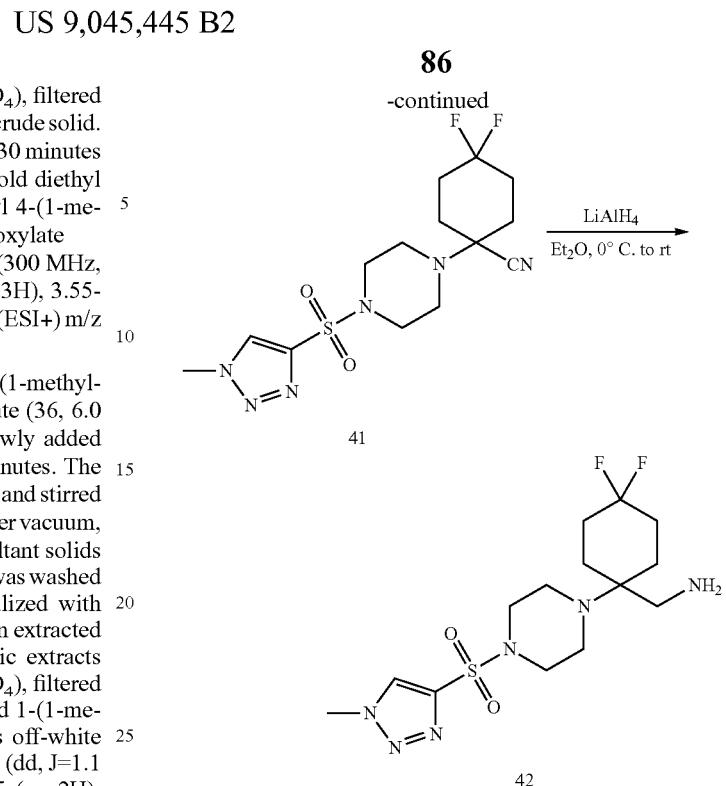

Step A: 1-(1-Methyl-1H-1,2,3-triazol-4-ylsulfonyl)piperazine and 4,4-difluorocyc lohexanone were converted to 4,4-difluoro-1-(4-(1-methyl-1H-1,2,3-triazol-4-ylsulfonyl)piperazin-1-yl)cyclohexanecarbonitrile (41): MS (ESI+) m/z 376 (M+H).

Step B: 4,4-Difluoro-1-(4-(1-methyl-1H-1,2,3-triazol-4-yl sulfonyl)piperazin-1-yl)cyclohexanecarbonitrile was converted to (4,4-difluoro-1-(4-(1-methyl-1H-1,2,3-triazol-4-ylsulfonyl)piperazin-1-yl)cyclohexyl)methanamine (42): MS (ESI+) m/z 379 (M+H).

Example 58

Preparation of 4-Fluoro-2-methoxy-6-methylbenzoic acid (45)

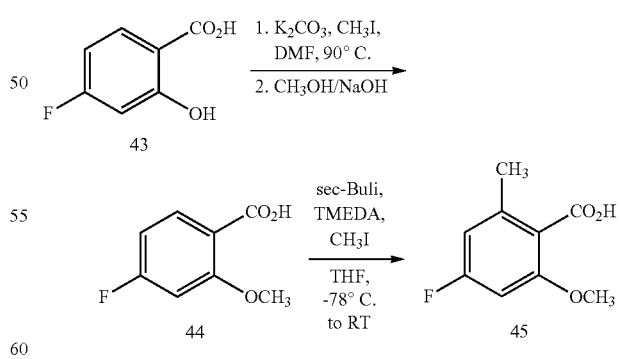

Step A: To a stirring suspension of 4-fluorosalycylic acid (43, 10.0 g, 64 mmol) and K$_2$CO$_3$ (22.0 g, 160 mmol) in DMF (200 mL) was slowly added methyl iodide (20.0 g, 140 mmol) at room temperature. The mixture was heated to 90° C. while stirring overnight. After cooling to room temperature, solvent was removed under reduced pressure, and the resulting white solid was purified on silica column eluting with 100% CH$_2$Cl$_2$ to afford intermediate methyl 4-fluoro-2-methoxybenzoate (10.0 g, 92%) as clear oil. The intermediate was immediately taken to the next step without any further analysis.

Step B: To a solution of 4-fluoro-2-methoxybenzoate (10.0 g, 58.8 mmol) in methanol (50 mL) was slowly added 6 M NaOH solution (30 mL). White solid immediately precipitated and the mixture was stirred for another hour at room temperature before it was re-dissolved in H$_2$O and acidified with 6 M HCl solution until precipitation occurred. The white solid was collected by vacuum filtration and dried on vacuum oven overnight to afford 4-fluoro-2-methyl benzoic acid (44, 9.2 g, 85%) $^1$H NMR (300 MHz, CDCl$_3$) δ 8.21 (dd, J=9.0 Hz, 6.9 Hz, 1H), 6.82-6.88 (m, 1H), 6.79 (dd, J=7.8 Hz, 2.1 Hz, 1H), 4.07 (s, 1H).

Step C: To a solution of TMEDA (1.95 mL, 19.2 mmol) in anhydrous THF (8 mL) at −78° C. was slowly added a solution of sec-BuLi (1.4 M solution in cyclohexane, 18.5 mL, 25.8 mmol), followed by a solution of 4-fluoro-2-methyl-benzoic acid (44, 1.0 g, 5.88 mmol) in anhydrous THF (2 mL) at −78° C. under an atmosphere of N$_2$. The mixture stirred at −78° C. for 2 h before a solution of methyl iodide (1.46 mL, 23.5 mmol) in anhydrous THF (2 mL) was added slowly. The mixture was stirred at same temperature for 1 h before it was warmed up to room temperature and quenched with H$_2$O. The crude mixture was diluted with H$_2$O (10 mL) and extracted with EtOAc (10 mL). Aqueous layer was collected and acidified with 2 M HCl, followed by extraction by EtOAc (2×20 mL). The combined organic layers were dried over Na$_2$SO$_4$, filtered, and concentrated under reduced pressure. The resulting residue was chromatographed over silica gel (Isco CombiFlash Companion unit, 40 g Redisep column, 20% to 50% EtOAc/hexane) to give 4-fluoro-2-methoxy-6-methyl benzoic acid as a white solid (45, 0.18 g, 16%): $^1$H NMR (300 MHz, CDCl$_3$) δ 6.53-6.62 (m, 2H), 3.90 (s, 1H), 2.48 (s, 1H); MS (ESI+) m/z 185 (M+H).

Example 59

Preparation of 4-fluoro-2-methoxy-6-(methylthio)benzoic acid (46)

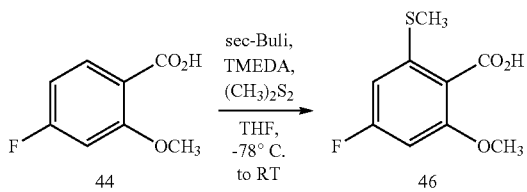 [SMILES: COc1cc(F)ccc1C(=O)O ; COc1cc(F)cc(SC)c1C(=O)O]

Step A: To a solution of TMEDA (1.95 mL, 12.9 mmol) in anhydrous THF (8 mL) was slowly added a solution of sec-BuLi (1.4 M solution in cyclohexane, 18.5 mL, 25.8 mmol) at −78° C., followed by a solution of 4-fluoro-2-methoxy-benzoic acid (44, 1.0 g, 5.88 mmol) in anhydrous THF (2 mL) at −78° C. under an atmosphere of N$_2$. The mixture stirred at −78° C. for 2 h before a solution of dimethyl disulfide (2.1 mL, 23.5 mmol) in anhydrous THF (2 mL) was added slowly. The mixture was stirred at same temperature for 1 h before it was warmed up to room temperature and quenched with H$_2$O. The crude mixture was diluted with H$_2$O (10 mL) and extracted with EtOAc (10 mL). Aqueous layer was collected and acidified with 2 M HCl, followed by extraction by EtOAc (2×20 mL). The combined organic layers were dried over Na$_2$SO$_4$, filtered, and concentrated under reduced pressure. The resulting residue was chromatographed over silica gel (Isco CombiFlash Companion unit, 40 g Redisep column, 20% to 50% EtOAc/hexane) to give 4-fluoro-2-methoxy-6-(methylthio) benzoic acid as a white solid (46, 0.22 g, 17%):

$^1$H NMR (300 MHz, CDCl$_3$) δ 8.07 (dd, J=15.3, 4.5 Hz, 1H), 7.03 (t, J=8.7 Hz, 1H), 4.11 (s, 3H), 2.49 (s, 1H); MS (ESI+) m/z 217 (M+H).

Example 60

Preparation of 2-methoxy-4,6-bis(trifluoromethy)benzoic acid (49)

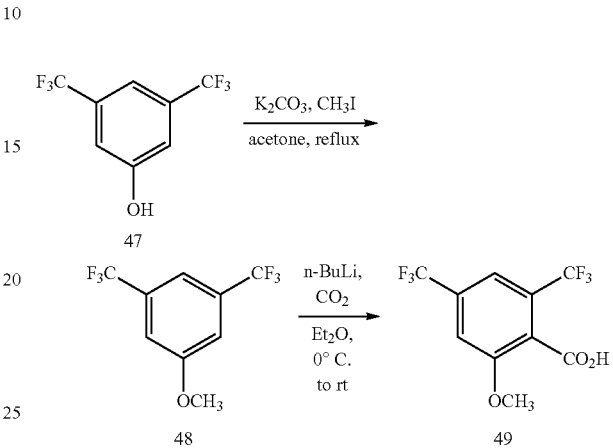

Step A: A mixture of 3,5-bis(trifluoromethyl)phenol (47, 1.0 g, 4.35 mmol), methyl iodide (0.7 mL, 10.8 mmol) and K$_2$CO$_3$ (3 g, 21.75 mmol) in acetone (10 mL) was heated to reflux while stirring overnight. Solid residue was filtered off and the filtrate was concentrated on warm water bath at atmospheric pressure (Caution: product was volatile) to afford 1-methoxy-3,5-bis(trifluoromethyl)benzene (48, 0.6 g, 56%) as clear oil: $^1$H NMR (300 MHz, CDCl$_3$) δ 7.46 (s, 1H), 7.30 (s, 1H), 3.90 (s, 1H).

Step B: To a solution of 1-methoxy-3,5-bis(trifluoromethyl)benzene (48, 0.56 g, 2.33 mmol) in anhydrous ether (5 mL) was slowly added n-BuLi (1.6 M solution in hexanes, 3 mL, 4.66 mmol) at 0° C. The reaction mixture was stirred at room temperature for 1 h. Dry ice was added into the yellow suspension until the starting material was completely consumed as monitored by TLC. The reaction was quenched with H$_2$O (3 mL) and organic layer was separated. The aqueous layer was acidified with concentrated HCl, and then extracted with Et$_2$O (3×5 mL). The combined organic layers were dried over Na$_2$SO$_4$, filtered, and concentrated under reduced pressure to afford 2-methoxy-4,6-bis(trifluoromethyl)benzoic acid (49, 0.38 g, 50%): $^1$H NMR (300 MHz, DMSO-d$_6$) δ 13.94 (s, 1H), 7.76 (s, 1H), 3.97 (s, 1H).

Example 61

Preparation of 4-(Cyclopropylmethylsulfonyl)piperidine (54)

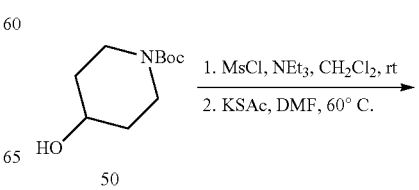

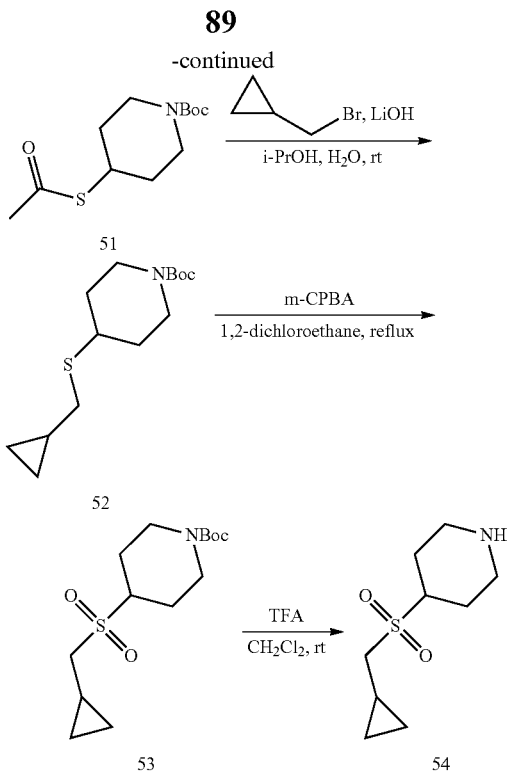

Step A: To an ice-cooled solution of tert-butyl-4-hydroxypiperidine-1-carboxylate (50, 2.20 g, 10.93 mmol) and Et$_3$N (7.5 mL, 54.65 mmol) in CH$_2$Cl$_2$ (25 mL) was added a solution of mesyl chloride (1.5 g, 13.12 mmol) in CH$_2$Cl$_2$ (5 mL). The mixture stirred at room temperature for 3 h then washed with saturated aqueous NaHCO$_3$ (3×5 mL) solution. The organic layer was washed with water (10 mL), brine (10 mL), dried over Na$_2$SO$_4$, filtered and concentrated under reduced pressure to give tert-butyl-4-(methylsulfonyloxy)piperidine-1-carboxylate as a colorless syrup (3.30 g). The residue was dissolved in anhydrous DMF (25 mL) followed by addition of KSAc (2.77 g, 24.3 mmol). The mixture was heated at 60° C. for 16 h then cooled to room temperature and poured over ice-water (225 mL). The aqueous mixture was extracted with Et$_2$O (3×25 mL). The organic layer was washed with H$_2$O (10 mL), brine (10 mL), dried over Na$_2$SO$_4$, filtered and concentrated under reduced pressure to give tert-butyl-4-(acetylthio)piperidine-1-carboxylate as a white solid (51, 1.5 g, 48% over two steps); $^1$H NMR (300 MHz, CDCl$_3$): δ 3.91 (m, 1H), 3.08-2.94 (m, 2H), 1.89-1.78 (m, 2H), 1.59 (s, 3H), 1.54-1.39 (m, 4H), 1.46 (s, 9H).

Step B: To an argon purged solution of tert-butyl-4-(acetylthio)piperidine-1-carboxylate (51, 1.50 g, 5.86 mmol) in a 5:1 mixture of isopropanol-water (55 mL) was added cyclopropyl bromide (1.52 g, 11.72 mmol) followed by solid LiOH H$_2$O (1.0 g, 68.67 mmol). The mixture stirred at room temperature and stirred for 16 h and was concentrated under reduced pressure. The residue was dissolved in EtOAc (90 mL) and washed with H$_2$O (25 mL), brine (25 mL), dried over Na$_2$SO$_4$, filtered and concentrated under reduced pressure to give tert-butyl 4-(cyclopropylmethylthio) piperidine-1-carboxylate as a colorless syrup (52, 1.1 g, 69%); $^1$H NMR (300 MHz, CDCl$_3$) δ 2.98-2.75 (m, 3H), 2.61 (m, 1H), 2.48 (d, J=6.9 Hz, 2H), 2.39-2.28 (m, 1H), 1.74-2.01 (m, 2H), 1.43-1.55 (m, 2H), 1.45 (s, 9H), 1.01-0.88 (m, 1H), 0.52-0.59 (m, 2H), 0.15-0.25 (m, 2H);

Step C: To a solution of tert-butyl 4-(cyclopropylmethylthio) piperidine-1-carboxylate (52, 2.60 g, 9.58 mmol) in 1,2-dichloroethane (60 mL) was added m-CPBA (4.95 g, 28.73 mmol) portion-wise. The mixture was heated to reflux for 16 h then cooled to room temperature and was diluted with CH$_2$Cl$_2$ (20 mL). The organic layer was washed with saturated NaHCO$_3$ solution (50 mL), H$_2$O (25 mL), brine (25 mL), dried over Na$_2$SO$_4$, filtered and concentrated under reduced pressure. The residue was chromatographed over silica gel (Isco CombiFlash Companion unit, 40 g Redisep column, 20% to 30% EtOAc in hexanes) to give tert-butyl 4-(cyclopropylmethylsulfonyl)piperidine-1-carboxylate as a white solid (53, 1.67 g, 56%); $^1$H NMR (300 MHz, CDCl$_3$): δ 4.38-4.30 (m, 2H), 3.15-3.03 (m, 1H), 2.89 (d, J=7.2 Hz, 2H), 2.81-2.70 (m, 2H), 2.09-2.28 (m, 2H), 1.85-1.70 (m, 2H), 1.46 (s, 9H), 1.25-1.10 (m, 1H), 0.81-0.62 (m, 2H), 0.43-0.35 (m, 2H).

Step D: To an ice-cold solution of tert-butyl 4-(cyclopropylmethylsulfonyl)piperidine-1-carboxylate (53, 0.9 g, 2.96 mmol) in CH$_2$Cl$_2$ (15 mL) was added TFA (3.0 mL). The mixture stirred at room temperature and stirred for 3 h and was concentrated under reduced pressure. The residue was dissolved in CH$_2$Cl$_2$ (25 mL) and the organic layer was washed with saturated NaHCO$_3$ solution (10 mL), H$_2$O (15 mL) brine (15 mL), dried over Na$_2$SO$_4$, filtered and concentrated under reduced pressure. The residue was chromatographed over silica gel (Isco CombiFlash Companion unit, 40 g Redisep column, 30% to 50% EtOAc in hexanes) to give 4-(cyclopropylmethylsulfonyl)piperidine as a white foam (54, 0.38 g, 63%); $^1$H NMR (300 MHz, MeOH-d$_4$): δ 3.27-3.24 (m, 1H), 3.23-3.12 (m, 2H), 2.99 (d, J=7.2 Hz, 2H), 2.63 (dt, J=2.4, 12.0 Hz, 2H), 2.10-2.01 (m, 2H), 1.77-1.60 (m, 2H), 1.27-1.14 (m, 1H), 0.83-0.64 (m, 2H), 0.45-0.39 (m, 2H);

Example 62

Preparation of 1-Methyl-1H-1,2,3-triazole-4-sulfonyl chloride (57)

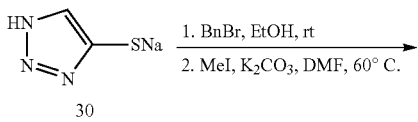

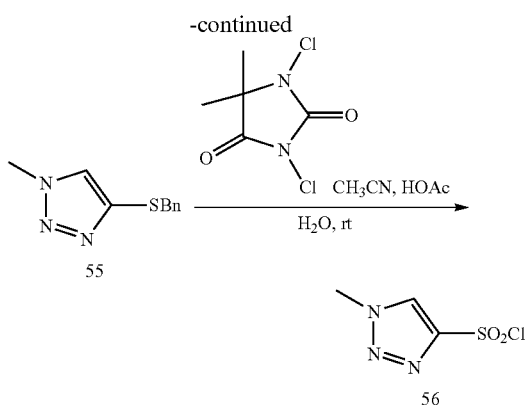

Step A: To an ice-cooled solution of sodium 1H-1,2,3-triazole-4-thiolate (30, 1.0 g, 8.13 in EtOH (10 mL) was added benzyl bromide (1.4 g, 8.13 mmol) drop-wise. The mixture stirred at room temperature for 20 minutes then diluted with EtOAc and washed with water (10 mL), brine (10 mL), dried over Na$_2$SO$_4$, filtered and concentrated under reduced pressure to give 4-(benzylthio)-1-methyl-1H-1,2,3-triazole as a white solid (55, 1.5 g, 93%); $^1$H NMR (300 MHz, CDCl$_3$): δ 13.37 (bs, 1H), 7.48 (s, 1H), 7.21 (m, 5H), 4.09 (s, 2H).

Step B: To a 4-(benzylthio)-1-methyl-1H-1,2,3-triazole (140 g, 732 mmol) in DMF (1.4 L) at 0° C. was added K$_2$CO$_3$ (126 g, 1.6 mol) followed by dimethylsulfate (202 g, 1.4 mol) drop wise. Then the reaction mixture was stirred at room temperature for 16 hours. Then the reaction mixture was concentrated under reduced pressure and dissolved in CH$_2$Cl$_2$ (1 L), washed with H$_2$O (1 L), dried over Na$_2$SO$_4$, filtered and concentrated under reduced pressure. The resulting residue was chromatographed over silica gel (Isco CombiFlash Companion unit, 9:1 mixture of CH$_2$Cl$_2$/CH$_3$OH) to give 4-(benzylthio)-1-methyl-1H-1,2,3-triazole as a white solid (56, 34.1 g, 23%): $^1$H NMR (400 MHz, CDCl$_3$): δ 7.27 (m, 6H), 4.09 (s, 2H), 3.98 (s, 3H).

Step C: To a 0° C. cooled mixture of 4-(benzylthio)-1-methyl-1H-1,2,3-triazole (4.2 g, 26.4 mmol), CH$_3$CN (200 mL), HOAc (7.5 mL) and H$_2$O (5 mL) was added 1,3-dichloro-5,5-dimethylimidazolidine-2,4-dione (8.0 g, 40.9 mmol) portion wise so as to maintain the internal temperature of the reaction below 5° C. Upon complete addition, the mixture stirred for an additional for 2 h at 0° C., then quenched slowly with the additional of aqueous 5% NaHCO$_3$ solution (100 mL). The resulting mixture stirred for 15 minutes and was then diluted with CH$_2$Cl$_2$ (500 mL). The organic layer was separated, washed with brine, dried over Na$_2$SO$_4$, filtered and concentrated under reduced pressure. The resulting crude 1-methyl-1H-1,2,3-triazole-4-sulfonyl chloride (7.4 g) was used as is in the next step without further purification or characterization.

Example 63

Additional Compound Synthesis and Spectral Data

Additional compounds within the scope of the invention can be produced in accordance with the procedures described in Examples 1-62, above. Table 1 describes examples of compounds produced in accordance with the present invention, including general synthetic procedures and spectral data:

TABLE 1

Examples, General Synthetic Procedures (GSP) and Spectral Data

| Cpd | Name | Structure | General Synthetic Procedure and Spectral Data |
|---|---|---|---|
| 1 | 2-Amino-6-chloro-N-((1-(4-(propylsulfonyl)piperazin-1-yl)cyclohexyl)methyl)benzamide Hydrochloride | 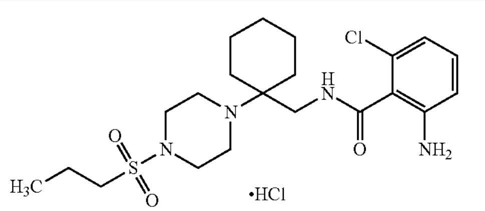 [SMILES: CCCS(=O)(=O)N1CCN(C2(CNC(=O)c3c(N)cccc3Cl)CCCCC2)CC1 ; Cl] | GSP-1<br>$^1$H NMR (500 MHz, DMSO-d$_6$) δ 10.03 (bs, 1H), 7.56 (d, J = 8.1 Hz, 1H), 7.38 (d, J = 7.1 Hz, 1H), 7.22 (m, 2H), 5.13 (dd, J = 14.3 Hz, 1.0 Hz, 2H), 4.71 (m, 1H), 3.83 (s, 3H), 3.73 (m, 1H), 3.48 (m, 1H), 3.31-3.19 (m, 3H), 2.42 (m, 1H), 2.18 (m 1H), 1.99-1.97 (m, 3H); MS (ESI+) m/z 458 (M + H). |
| 2 | 2,4-Dichloro-N-((1-(4-(propylsulfonyl)piperazin-1-yl)cyclohexyl)methyl)benzamide Hydrochloride | 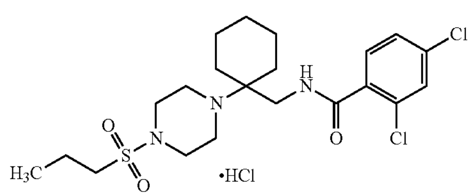 [SMILES: CCCS(=O)(=O)N1CCN(C2(CNC(=O)c3ccc(Cl)cc3Cl)CCCCC2)CC1 ; Cl] | GSP-1<br>$^1$H NMR (500 MHz, DMSO-d$_6$) δ 10.03 (bs, 1H), 7.56 (d, J = 8.1 Hz, 1H), 7.38 (d, J = 7.1 Hz, 1H), 7.22 (m, 2H), 5.13 (dd, J = 14.3 Hz, 1.0 Hz, 2H), 4.71 (m, 1H), 3.83 (s, 3H), 3.73 (m, 1H), 3.48 (m, 1H), 3.31-3.19 (m, 3H), 2.42 (m, 1H), 2.18 (m 1H), 1.99-1.97 (m, 3H); MS (ESI+) m/z 478 (M + H). |
| 3 | 2-Methoxy-6-methyl-N-((1-(4-(propylsulfonyl)piperazin-1-yl)cyclohexyl)methyl)benzamide Hydrochloride | 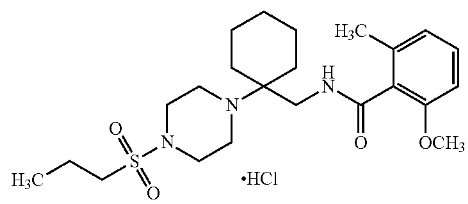 [SMILES: CCCS(=O)(=O)N1CCN(C2(CNC(=O)c3c(C)cccc3OC)CCCCC2)CC1 ; Cl] | GSP-1<br>$^1$H NMR (500 MHz, DMSO-d$_6$) δ 10.86 (bs, 1H), 8.63 (bs (1H), 7.34 (m, 2H), 7.10 (m, 1H), 3.73 (s, 3H), 3.72-3.70 (m, 2H), 3.70 (m, 2H), 3.51 (m, 2H), 3.35 (m, 1H), 3.12 (m, 2H), 2.50 (s, 3H), 2.08 (m, 2H), 1.96 (m, 2H), 1.75-1.60 (m, 5H), 0.95 (m, 3H); MS (ESI+) m/z 452. |

TABLE 1-continued

Examples, General Synthetic Procedures (GSP) and Spectral Data

| Cpd | Name | Structure | General Synthetic Procedure and Spectral Data |
|---|---|---|---|
| 4 | N-((1-(4-(Propylsulfonyl)piperazin-1-yl)cyclohexyl)methyl)-2-(trifluoromethoxy) benzamide Hydrochloride | 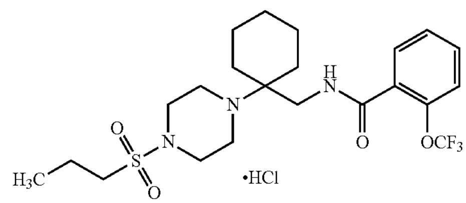 [SMILES: CCCS(=O)(=O)N1CCN(C2(CNC(=O)c3ccccc3OC(F)(F)F)CCCCC2)CC1 ; Cl] | GSP-1<br>$^1$H NMR (500 MHz, DMSO-$d_6$) δ 10.82 (bs, 1H), 8.87 (bs (1H), 7.65 (m, 2H), 7.50 (m, 2H), 3.75-3.56 (m, 9H), 3.25 (m, 2H), 3.12 (m, 2H), 2.07 (m, 2H), 1.94 (m, 2H), 1.70-1.54 (m, 7H), 0.95 (s, 3H); MS (ESI+) m/z 492. |
| 5 | 3-Chloro-2-fluoro-N-((1-(4-(propylsulfonyl) piperazin-1-yl)cyclohexyl)methyl)-6-(trifluoromethyl)benzamide Hydrochloride | 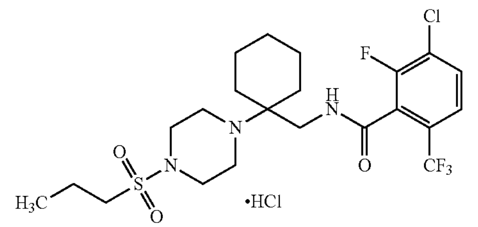 [SMILES: CCCS(=O)(=O)N1CCN(C2(CNC(=O)c3c(C(F)(F)F)ccc(Cl)c3F)CCCCC2)CC1 ; Cl] | GSP-1<br>$^1$H NMR (300 MHz, DMSO-$d_6$) δ 10.70-10.60 (m, 1H), 9.25-9.23 (m, 1H), 7.98 (t, J = 7.8 Hz, 1H), 7.70 (d, J = 8.7 Hz, 1H), 3.85-3.50 (m, 8H), 3.25-3.05 (m, 4H), 2.15-2.00 (m, 2H), 1.98-1.85 (m, 2H), 1.80-1.45 (m, 8H), 0.97 (t, J = 7.5 Hz, 3H); MS (ESI$^+$) m/z 528 (M + H). |
| 6 | N-((1-(4-(Propylsulfonyl)piperazin-1-yl)cyclohexyl)methyl)-4-(trifluoromethoxy) benzamide Hydrochloride | 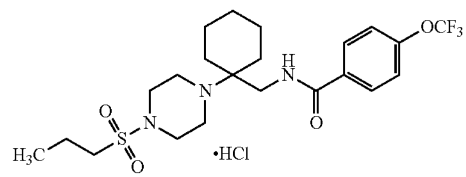 [SMILES: CCCS(=O)(=O)N1CCN(C2(CNC(=O)c3ccc(OC(F)(F)F)cc3)CCCCC2)CC1 ; Cl] | GSP-1<br>$^1$H NMR (300 MHz, CD$_3$OD) δ 8.09 (d, J = 8.7 Hz, 2H), 7.48 (d, J = 8.7 Hz, 2H), 4.15-3.85 (m, 6H), 3.55-3.27 (m, 4H), 3.22-3.10 (m, 2H), 2.15-2.00 (m, 2H), 2.00-1.80 (m, 8H), 1.72-1.55 (m, 2H), 1.13 (t, J = 7.5 Hz, 3H); MS (ESI$^+$) m/z 492 (M + H); $^{19}$F NMR (300 MHz, MeOH-$d_4$): −61.31 (OCF$_3$); MS (ESI$^+$) m/z 492 (M + H). |
| 7 | N-((1-(4-(Propylsulfonyl)piperazin-1-yl)cyclohexyl)methyl)-4-(trifluoromethyl) benzamide Hydrochloride | 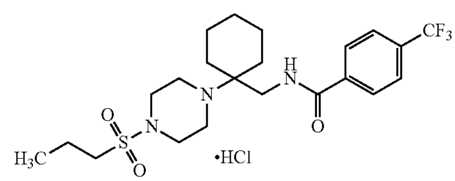 [SMILES: CCCS(=O)(=O)N1CCN(C2(CNC(=O)c3ccc(C(F)(F)F)cc3)CCCCC2)CC1 ; Cl] | GSP-1<br>$^1$H NMR (300 MHz, CD$_3$OD) δ 8.16 (d, J = 8.1 Hz, 2H), 7.87 (d, J = 8.1 Hz, 2H), 4.20-3.95 (m, 6H), 3.55-3.20 (m, 4H), 3.15-3.05 (m, 2H), 2.41-2.10 (m, 2H), 2.05-1.65 (m, 10H), 1.12 (t, J = 7.5Hz, 3H); $^{19}$F NMR (300 MHz, CD$_3$OD) −66.5 (CF$_3$); MS (ESI$^+$) m/z 476 (M + H). |
| 8 | 2-Chloro-N-((1-(4-(propylsulfonyl)piperazin-1-yl)cyclohexyl)methyl) benzamide Hydrochloride | 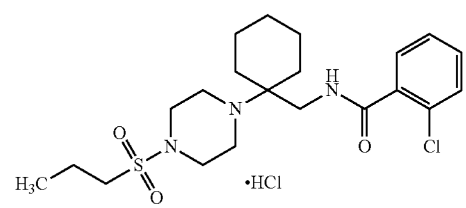 [SMILES: CCCS(=O)(=O)N1CCN(C2(CNC(=O)c3ccccc3Cl)CCCCC2)CC1 ; Cl] | GSP-1<br>$^1$H NMR (300 MHz, DMSO-$d_6$) δ 10.74-10.72 (m, 1H), 8.87 (t, J = 6.3 Hz, 1H), 7.55-7.40 (m, 4H), 3.75-3.63 (m, 6H), 3.60-3.58 (m, 2H), 3.29-3.27 (m, 2H), 3.11-3.09 (m, 2H), 2.09-2.07 (m, 2H), 1.90-1.88 (m, 2H), 1.77-1.49 (m, 7H), 1.16-1.14 (m, 1H), 0.97 (t, J = 1.5 Hz, 3H); MS (ESI+) m/z 442 (M + H). |
| 9 | 4-Chloro-2-methyl-N-((1-(4-(propylsulfonyl)piperazin-1-yl)cyclohexyl)methyl) benzamide Hydrochloride | 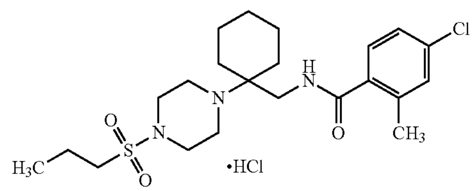 [SMILES: CCCS(=O)(=O)N1CCN(C2(CNC(=O)c3ccc(Cl)cc3C)CCCCC2)CC1 ; Cl] | GSP-1<br>$^1$H NMR (300 MHz, DMSO-$d_6$) δ 10.52-10.50 (m, 1H), 8.68 (t, J = 6.0 Hz, 1H), 7.45 (d, J = 8.4 Hz, 1H), 7.38-7.32 (m, 2H), 3.75-3.63 (m, 6H), 3.60-3.58 (m, 2H), 3.26-3.24 (m, 2H), 3.12-3.10 (m, 2H), 2.34 (s, 3H). 2.09-2.07 (m, 2H), 1.90-1.88 (m, 2H), 1.77-1.49 (m, 7H), 1.16-1.14 (m, 1H), 0.97 (t, J = 7.5 Hz, 3H); MS (ESI+) m/z 456 (M + H). |
| 10 | 4-Fluoro-2-methyl-N-((1-(4-(propylsulfonyl) piperazin-1-yl)cyclohexyl)methyl) benzamide Hydrochloride | 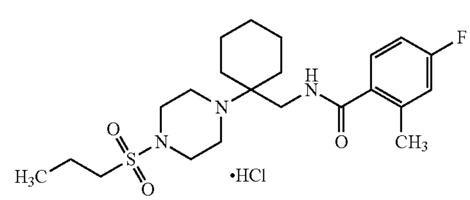 | GSP-1<br>$^1$H NMR (300 MHz, DMSO-$d_6$) δ 10.54-10.52 (m, 1H), 8.64 (t, J = 6.0 Hz, 1H), 7.50 (dd, J = 6.0, 8.4 Hz, 1H), 7.17-7.07 (m, 2H), 3.75-3.70 (m, 6H), 3.57-3.55 (m, 2H), 3.26-3.24 (m, 2H), 3.11-3.09 (m, 2H), 2.36 (s, 3H), 2.06-2.04 (m, 2H), 1.87-1.85 (m, 2H), 1.75-1.45 (m, 7H), 1.16-1.14 (m, 1H), 0.98 (t, J = 7.5 Hz, 3H); MS (ESI+) m/z 440 (M + H). |

TABLE 1-continued

Examples, General Synthetic Procedures (GSP) and Spectral Data

| Cpd | Name | Structure | General Synthetic Procedure and Spectral Data |
|---|---|---|---|
| 11 | 4-Bromo-N-((1-(4-(propylsulfonyl)piperazin-1-yl)cyclohexyl)methyl)benzamide Hydrochloride | 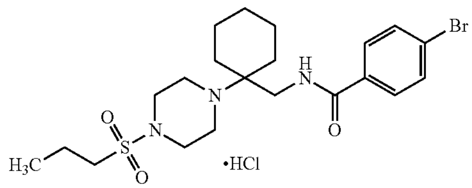 [SMILES: CCCS(=O)(=O)N1CCN(C2(CNC(=O)c3ccc(Br)cc3)CCCCC2)CC1 ; Cl] | GSP-1<br>$^1$H NMR (300 MHz, DMSO-d$_6$) δ 10.40-10.38 (m, 1H), 8.82 (t, J = 6.0 Hz, 1H), 7.88 (d, J = 8.4 Hz, 2H), 7.72 (d, J = 8.4 Hz, 2H), 3.80-3.70 (m, 6H), 3.54-3.52 (m, 2H), 3.29-3.27 (m, 2H), 3.13-3.11 (m, 2H), 2.05-2.03 (m, 2H), 1.88-1.86 (m, 2H), 1.77-1.49 (m, 7H), 1.16-1.14 (m, 1H), 0.99 (t, J = 7.5 Hz, 3H); MS (ESI+) m/z 486 (M + H). |
| 12 | 2-Chloro-4-fluoro-N-((1-(4-(propylsulfonyl)piperazin-1-yl)cyclohexyl)methyl)benzamide Hydrochloride | 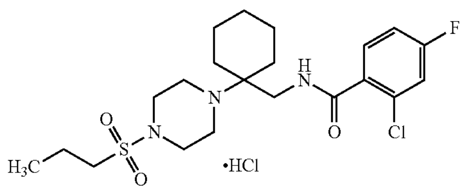 [SMILES: CCCS(=O)(=O)N1CCN(C2(CNC(=O)c3ccc(F)cc3Cl)CCCCC2)CC1 ; Cl] | GSP-1<br>$^1$H NMR (300 MHz, DMSO-d$_6$) δ 10.76-10.74 (m, 1H), 8.80 (t, J = 6.0 Hz, 1H), 7.69-7.67 (m, 1H), 7.60 (dd, J = 1.8, 9.9 Hz), 7.41 (dd J = 1.8, 8.1 Hz), 3.76-3.65 (m, 6H), 3.58-3.56 (m, 2H), 3.26-3.24 (m, 2H), 3.09-3.07 (m, 2H), 2.06-2.04 (m, 2H), 1.90-1.88 (m, 2H), 1.77-1.49 (m, 7H), 1.16-1.14 (m, 1H), 0.98 (t, J = 7.5 Hz, 3H); MS (ESI+) m/z 460 (M + H). |
| 13 | 2-(4-Chlorophenyl)-N-((1-(4-(propylsulfonyl)piperazin-1-yl)cyclohexyl)methyl)acetamide Hydrochloride | 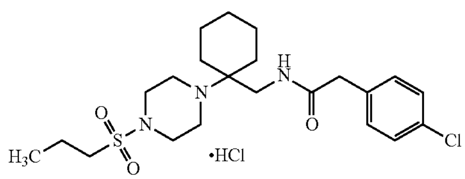 [SMILES: CCCS(=O)(=O)N1CCN(C2(CNC(=O)Cc3ccc(Cl)cc3)CCCCC2)CC1 ; Cl] | GSP-1<br>$^1$H NMR (300 MHz, DMSO-d$_6$) δ 10.44-10.42 (m, 1H), 8.58 (t, J = 6.0 Hz, 1H), 7.35-7.33 (m, 4H), 3.63-3.48 (m, 10H), 3.06-3.04 (m, 4H), 1.97-10.95 (m, 2H), 1.83-1.59 (m, 7H), 1.46-10.44 (m, 2H), 1.16-1.14 (m, 1H), 0.98 (t, J = 7.5 Hz, 3H); MS (ESI+) m/z 456 (M + H). |
| 14 | 2-Fluoro-N-((1-(4-(propylsulfonyl)piperazin-1-yl)cyclohexyl)methyl)benzamide Hydrochloride | 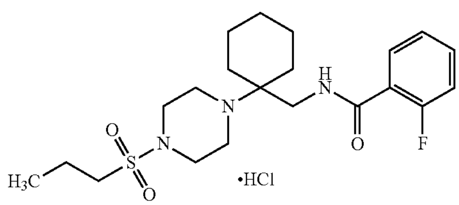 [SMILES: CCCS(=O)(=O)N1CCN(C2(CNC(=O)c3ccccc3F)CCCCC2)CC1 ; Cl] | GSP-1<br>$^1$H NMR (300 MHz, DMSO-d$_6$) δ 10.45 (bs, 1H), 8.74 (t, J = 6.0 Hz, 1H), 7.68-7.52 (m, 2H), 7.35-7.25 (m, 2H), 3.80-3.68 (m, 5H), 3.60-3.40 (m, 4H), 3.38-3.06 (m, 4H), 2.12-2.01 (m, 2H), 1.93-1.50 (m, 9H), 0.97 (t, J = 7.5 Hz, 3H); MS (ESI+) m/z 426 (M + H). |
| 15 | 4-Fluoro-N-((1-(4-(propylsulfonyl)piperazin-1-yl)cyclohexyl)methyl)benzamide Hydrochloride | 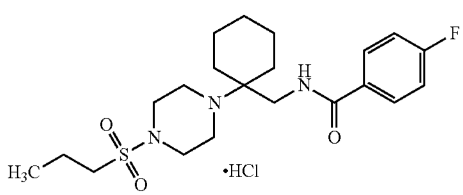 [SMILES: CCCS(=O)(=O)N1CCN(C2(CNC(=O)c3ccc(F)cc3)CCCCC2)CC1 ; Cl] | GSP-1<br>$^1$H NMR (300 MHz, DMSO-d$_6$) δ 10.28 (bs, 1H), 8.76 (t, J = 6.0 Hz, 1H), 8.05-7.97 (m, 2H), 7.38-7.28 (m, 2H), 3.83-3.68 (m, 5H), 3.60-3.40 (m, 4H), 3.32-3.08 (m, 4H), 2.10-1.98 (m, 2H), 1.91-1.50 (m, 9H), 0.99 (t, J = 7.5 Hz, 3H); MS (ESI+) m/z 426 (M + H). |
| 16 | 2,6-Difluoro-N-((1-(4-(propylsulfonyl)piperazin-1-yl)cyclohexyl)methyl)benzamide Hydrochloride | 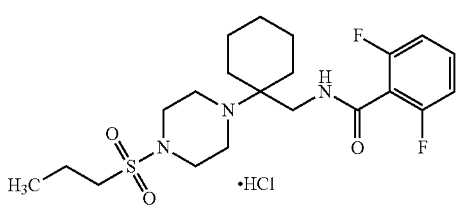 [SMILES: CCCS(=O)(=O)N1CCN(C2(CNC(=O)c3c(F)cccc3F)CCCCC2)CC1 ; Cl] | GSP-1<br>$^1$H NMR (300 MHz, DMSO-d$_6$) δ 10.53 (bs, 1H), 9.15 (t, J = 6.0 Hz, 1H), 7.62-7.50 (m, 1H), 7.21 (t, J = 8.1 Hz, 2H), 3.79 (d, J = 6.3 Hz, 2H), 3.75-3.65 (m, 3H), 3.55 (t, J = 11.4 Hz, 2H), 3.46 (s, 2H), 3.35-3.05 (m, 4H), 2.10-2.02 (m, 2H), 1.86 (dd, J = 12.9 Hz, 9.6 Hz, 2H), 1.80-1.48 (m, 7H), 0.97 (t, J = 7.5 Hz, 3H); MS (ESI+) m/z 444 (M + H). |
| 17 | 4-Cyano-N-((1-(4-(propylsulfonyl)piperazin-1-yl)cyclohexyl)methyl)benzamide Hydrochloride | 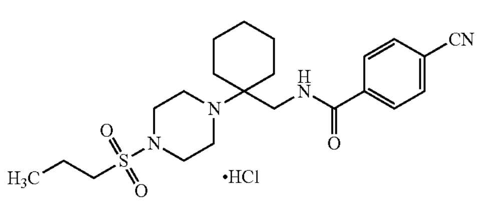 [SMILES: CCCS(=O)(=O)N1CCN(C2(CNC(=O)c3ccc(C#N)cc3)CCCCC2)CC1 ; Cl] | GSP-1<br>$^1$H NMR (300 MHz, DMSO-d$_6$) δ 10.57 (bs, 1H), 9.00 (t, J = 6.0 Hz, 1H), 8.08 (d, J = 8.4 Hz, 2H), 8.00 (d, J = 8.4 Hz, 2H), 3.87-3.68 (m, 5H), 3.60 (t, J = 11.4 Hz, 2H), 3.46 (s, 2H), 3.35-3.07 (m, 4H), 2.10-1.98 (m, 2H), 1.94-1.50 (m, 9H), 0.99 (t, J = 7.5 Hz, 3H); MS (ESI+) m/z 433 (M + H). |

TABLE 1-continued

Examples, General Synthetic Procedures (GSP) and Spectral Data

| Cpd | Name | Structure | General Synthetic Procedure and Spectral Data |
|---|---|---|---|
| 18 | 4-Bromo-2-methyl-N-((1-(4-(propylsulfonyl)piperazin-1-yl)cyclohexyl)methyl)benzamide Hydrochloride | 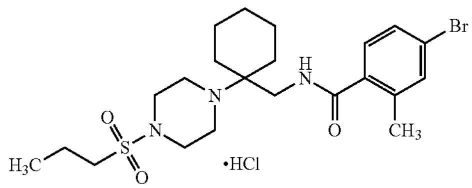 [SMILES: CCCS(=O)(=O)N1CCN(C2(CNC(=O)c3ccc(Br)cc3C)CCCCC2)CC1 ; Cl] | GSP-1<br>$^1$H NMR (300 MHz, DMSO-d$_6$) δ 10.58 (bs, 1H), 8.69 (t, J = 6.0 Hz, 1H), 7.53 (s, 1H), 7.47 (dd, J = 8.1 Hz, 1.5 Hz, 1H), 7.37 (d, J = 8.1 Hz, 1H), 3.80-3.65 (m, 5H), 3.57 (t, J = 11.4 Hz, 2H), 3.46 (s, 2H), 3.35-3.07 (m, 4H), 2.33 (s, 3H), 2.10-2.02 (m, 2H), 1.95-1.48 (m, 9H), 0.97 (t, J = 7.5 Hz, 3H); MS (ESI+) m/z 501 (M + H). |
| 19 | 4-Fluoro-2-methoxy-6-methyl-N-((1-(4-(propylsulfonyl)piperazin-1-yl)cyclohexyl)methyl)benzamide Hydrochloride | 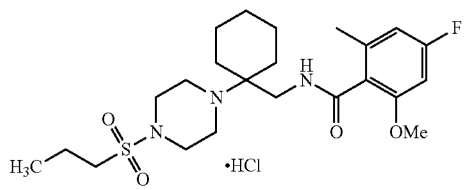 [SMILES: CCCS(=O)(=O)N1CCN(C2(CNC(=O)c3c(C)cc(F)cc3OC)CCCCC2)CC1 ; Cl] | GSP-1<br>$^1$H NMR (300 MHz, DMSO-d$_6$) δ 10.7-10.9 (m, 1H), 8.55-8.63 (m, 1H), 6.8 (dd, J = 11.7 Hz, 7.5 Hz, 1H), 6.75 (dd, J = 11.7 Hz, 7.5 Hz, 1H), 4.57 (bs, 1H), 3.89 (s, 3H), 3.55-3.87 (m, 7H), 3.28-3.42 (m, 2H), 3.08-3.17 (m, 2H), 2.49-2.51 (m, 3H), 2.18-2.22 (m, 2H), 2.01-2.12 (m, 2H), 1.85-1.99 (m, 2H), 1.48-1.81 (m, 7H), 0.97 (t, J = 7.5 Hz, 3H); MS (ESI+) m/z 470 (M + H). |
| 20 | 4-Fluoro-2-methoxy-6-(methylthio)-N-((1-(4-(propylsulfonyl)piperazin-1-yl)cyclohexyl)methyl)benzamide Hydrochloride | 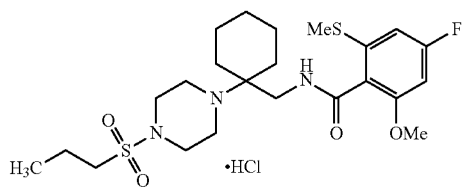 [SMILES: CCCS(=O)(=O)N1CCN(C2(CNC(=O)c3c(OC)cc(F)cc3SC)CCCCC2)CC1 ; Cl] | GSP-2<br>$^1$H NMR (300 MHz, CD$_3$OD) δ 8.68 (bs, 1H), 6.79-6.86 (m, 2H), 3.77 (s, 3H), 3.67-3.69 (m, 6H), 3.4-3.55 (m, 3H), 4.71 (m, 1H), 2.44 (s, 3H), 2.09-2.14 (m, 2H), 1.57-1.77 (m, 9H), 0.98 (t, J = 7.5 Hz, 3H); MS (ESI+) m/z 502 (M + H). |
| 21 | 2-Methoxy-N-((1(1-(4-(propylsulfonyl)piperazin-1-yl)cyclohexyl)methyl)-4,6-bis(trifluoromethyl)benzamide Hydrochloride | 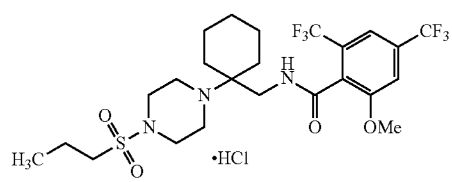 [SMILES: CCCS(=O)(=O)N1CCN(C2(CNC(=O)c3c(OC)cc(C(F)(F)F)cc3C(F)(F)F)CCCCC2)CC1 ; Cl] | GSP-1<br>$^1$H NMR (300 MHz, CD$_3$OD) δ 10.25 (bs, 1H), 8.90 (s, 1H), 7.77 (s, 1H), 7.67 (s, 1H), 3.95 (s, 3H), 3.48-3.55 (m, 7H), 3.27-3.29 (m, 2H), 3.10-3.12 (m, 2H), 2.08-2.11 (m, 2H); 1.56-1.79 (m, 10H), 0.97-0.99 (m, 3H); MS (ESI+) m/z 574 (M + H). |
| 22 | 2-Chloro-N-((1-(4-(propylsulfonyl)piperazin-1-yl)cyclohexyl)methyl)-3-(trifluoromethyl)benzamide Hydrochloride | 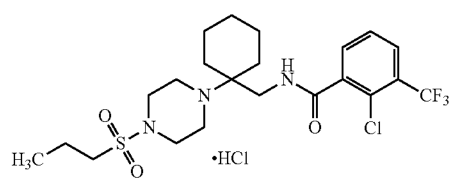 [SMILES: CCCS(=O)(=O)N1CCN(C2(CNC(=O)c3cccc(C(F)(F)F)c3Cl)CCCCC2)CC1 ; Cl] | GSP-1<br>$^1$H NMR (300 MHz, CD$_3$OD) δ 7.92 (d, J = 7.7 Hz, 1H), 7.7 (d, J = 7.3 Hz, 1H), 7.65-7.57 (m, 1H), 4.10-3.80 (m, 6H), 3.50-3.35 (m, 4H), 3.15-3.05 (m, 2H), 2.22-2.04 (m, 2H), 1.95 1.70 (m, 7H), 1.70-1.50 (m, 2H), 1.40-1.20 (m, 1H), 1.10-1.01 (t, J = 7.5 Hz, 3H); MS (ESI+) m/z 510 (M + H). |
| 23 | 4-Methoxy-N-((1-(4-(propylsulfonyl)piperazin-1-yl)cyclohexyl)methyl)benzamide Hydrochloride | 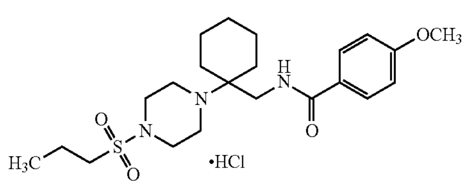 [SMILES: CCCS(=O)(=O)N1CCN(C2(CNC(=O)c3ccc(OC)cc3)CCCCC2)CC1 ; Cl] | GSP-2<br>$^1$H NMR (300 MHz, CD$_3$OD) δ 7.94-7.89 (m, 2H), 7.05-7.01 (m, 2H), 4.0 (d, J = 13.1 Hz, 2H), 3.9-3.80 (m, 7H), 3.40-3.20 (m, 4H); 3.15-3.08 (m, 2H), 2.0-1.92 (m, 2H), 1.91-1.70 (m, 7H), 1.68-1.55 (m, 2H), 1.35-1.28 (m, 1H), 1.11-1.05 (t, J = 7.4 Hz, 3H); MS (ESI+) m/z 438 (M + H). |
| 24 | N-((1-(4-(Propylsulfonyl)piperazin-1-yl)cyclohexyl)methyl)benzamide Hydrochloride | 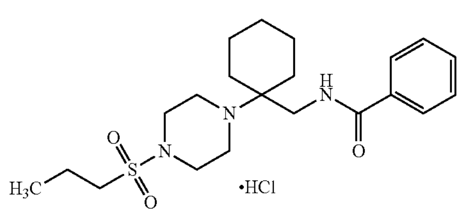 [SMILES: CCCS(=O)(=O)N1CCN(C2(CNC(=O)c3ccccc3)CCCCC2)CC1 ; Cl] | GSP-1<br>$^1$H NMR (300 MHz, CD$_3$OD) δ 7.98-7.90 (m, 2H), 7.65-7.40 (m, 3H), 4.03-3.80 (m, 6H), 3.45-3.30 (m, 4H), 3.15-3.04 (m, 2H), 2.08-1.98 (m, 2H), 1.95-1.50 (m, 9H), 1.04-1.20 (m, 1H), 1.10-1.02 (t, J = 7.4 Hz 3H); MS (ESI+) m/z 408 (M + H). |

TABLE 1-continued

Examples, General Synthetic Procedures (GSP) and Spectral Data

| Cpd | Name | Structure | General Synthetic Procedure and Spectral Data |
|---|---|---|---|
| 25 | 4-Methyl-N-((1-(4-(propylsulfonyl)piperazin-1-yl)cyclohexyl)methyl)benzamide Hydrochloride | 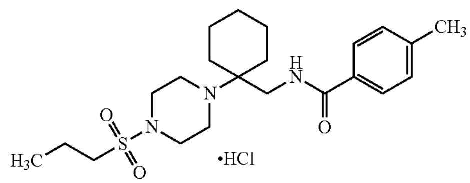 [SMILES: CCCS(=O)(=O)N1CCN(C2(CNC(=O)c3ccc(C)cc3)CCCCC2)CC1 ; Cl] | GSP-1<br>$^1$H NMR (300 MHz, CD$_3$OD) δ 7.82 (d, J = 8.2 Hz, 2H), 7.33 (d, J = 8.0 Hz, 2H), 4.02 (d, J = 12.3 Hz, 2H), 3.9-3.8 (m, 4H), 3.38-3.20 (m, 4H), 3.15-3.0 (m, 2H), 2.41 (s, 3H), 2.0-1.92 (m, 2H), 1.92-1.72 (m, 7H), 1.68-1.58 (m, 3H), 1.01-0.95 (t, J = 7.4 Hz, 3H); MS (ESI+) m/z 422 (M + H). |
| 26 | 3,4-Dichloro-N-((1-(4-(propylsulfonyl)piperazin-1-yl)cyclohexyl)methyl)benzamide Hydrochloride | 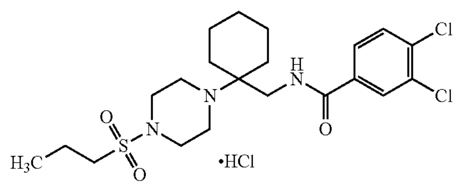 [SMILES: CCCS(=O)(=O)N1CCN(C2(CNC(=O)c3ccc(Cl)c(Cl)c3)CCCCC2)CC1 ; Cl] | GSP-1<br>$^1$H NMR (300 MHz, CD$_3$OD) δ 8.11 (d, J = 1.8 Hz, 1H), 7.85 (dd, J = 1.7 Hz, 8.3 Hz, 1H), 7.69 (d, J = 8.4 Hz, 1H), 4.02 (d, J = 10.4 Hz, 2H), 3.95-3.80 (m, 4H), 3.38-3.20 (m, 4H), 3.15-3.05 (m, 2H), 2.07-1.98 (m, 2H), 1.94-1.70 (m, 8H), 1.70-1.55 (m, 2H), 1.1-1.03 (t, J = 7.5 Hz, 3H); MS (ESI+) m/z 476 (M + H). |
| 27 | 4-(Benzyloxy)-N-((1-(4-(propylsulfonyl)piperazin-1-yl)cyclohexyl)methyl)benzamide Hydrochloride | 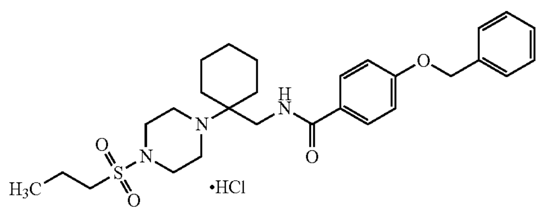 [SMILES: CCCS(=O)(=O)N1CCN(C2(CNC(=O)c3ccc(OCc4ccccc4)cc3)CCCCC2)CC1 ; Cl] | GSP-1<br>$^1$H NMR (300 MHz, DMSO-d$_6$) δ 10.46 (bs, 1H), 8.60 (t, J = 6.0 Hz, 1 H), 7.9 (d, J = 7.0 Hz, 2H), 7.48-7.31 (m, 5H), 7.11 (d, J = 8.9 Hz, 2H), 3.78-3.67 (m, 6H), 3.60-3.40 (m, 4H), 3.45-3.20 (m, 2H), 3.15-3.08 (m, 2H), 2.05-1.98 (m, 2H), 1.88-1.78 (m, 2H), 1.75-1.50 (m, 8H), 1.03-0.98 (t, J = 7.5 Hz, 3H); MS (ESI+) m/z 514 (M + H). |
| 28 | N-((1-(4-(Propylsulfonyl)piperazin-1-yl)cyclohexyl)methyl)-3-(trifluoromethyl)benzamide Hydrochloride | 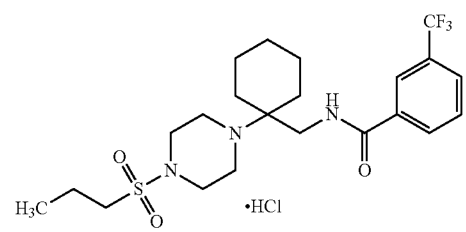 [SMILES: CCCS(=O)(=O)N1CCN(C2(CNC(=O)c3cccc(C(F)(F)F)c3)CCCCC2)CC1 ; Cl] | GSP-1<br>$^1$H NMR (300 MHz, DMSO-d$_6$) δ 11.0 (bs, 1H), 9.0 (t, J = 5.5 Hz, 1H), 8.27 (d, J = 7.3 Hz, 2H), 7.95 (d, J = 7.8 Hz, 1H), 7.77 (t, J = 8.2 Hz, 1H), 3.83 (d, J = 6.1 Hz, 2H), 3.79-3.68 (m, 2H), 3.68-3.54 (m, 2H), 3.53-3.35 (m, 2H), 3.32-3.20 (m, 2H), 3.18-3.05 (m, 2H), 2.15-2.0 (m, 2H), 1.90-1.80 (m 2H); 1.76-1.50 (m, 6H), 1.48-1.1 (m, 2H), 1.02-0.95 (t, J = 7.4 Hz, 3 H); MS (ESI+) m/z 476(M + H). |
| 29 | 3-Methoxy-N-((1-(4-(propylsulfonyl)piperazin-1-yl)cyclohexyl)methyl)benzamide Hydrochloride | 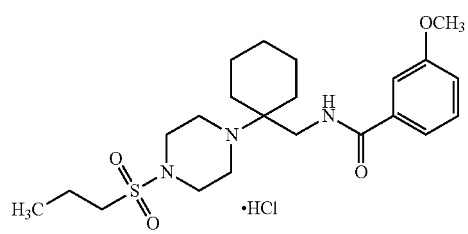 [SMILES: CCCS(=O)(=O)N1CCN(C2(CNC(=O)c3cccc(OC)c3)CCCCC2)CC1 ; Cl] | GSP-1<br>$^1$H NMR (300 MHz, DMSO-d$_6$) δ 10.73 (bs, 1H), 8.78 (bs, 1H), 7.50 (m, 2H), 7.41 (t, J = 8.0 Hz, 1 H), 7.14 (dd, J = 2.5 Hz, 8.2 Hz, 1H), 3.82 (s, 3H), 3.8-3.58 (m, 8H), 3.35-3.20 (m, 2H), 3.18-3.07 (m, 2H), 2.08-1.98 (m, 2H), 1.95-1.80 (m, 2H), 1.8-1.5 (m, 8 H), 1.02-0.98 (t, J = 7.4 Hz 3H); MS (ESI+) m/z 438 (M + H). |
| 30 | 2,4-Dimethyl-N-((1-(4-(propylsulfonyl)piperazin-1-yl)cyclohexyl)methyl)benzamide Hydrochloride | 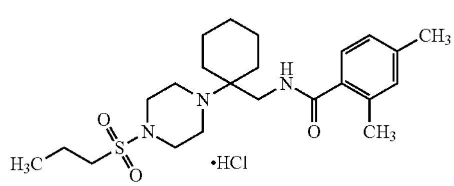 [SMILES: CCCS(=O)(=O)N1CCN(C2(CNC(=O)c3ccc(C)cc3C)CCCCC2)CC1 ; Cl] | GSP-1<br>$^1$H NMR (300 MHz, DMSO-d$_6$) δ 10.95 (t, J = 8.5 Hz, 1H), 8.58 (t, J = 6.2 Hz, 1H), 7.33 (d, J = 7.5 Hz, 1H), 7.05 (m, 2H), 3.80-3.58 (m, 8H), 3.36-3.20 (m, 2H), 3.15-3.05 (m, 2H), 2.31 (s, 3H), 2.29 (s, 3H), 2.08-2.0 (m, 2H), 1.98-1.85 (m, 2H), 1.78-1.50 (m, 8H), 1.01-0.97 (t, J = 7.4 Hz, 3H); MS (ESI+) m/z 436 (M + H). |
| 31 | 3-Chloro-4-methyl-N-((1-(4-(propylsulfonyl)piperazin-1-yl)cyclohexyl)methyl)benzamide Hydrochloride | 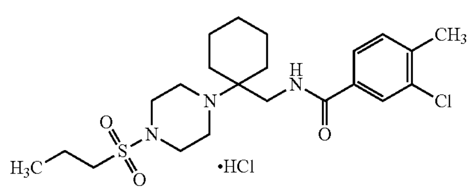 [SMILES: CCCS(=O)(=O)N1CCN(C2(CNC(=O)c3ccc(C)c(Cl)c3)CCCCC2)CC1 ; Cl] | GSP-1<br>$^1$H NMR (300 MHz, DMSO-d$_6$) δ 10.50 (bs, 1H), 8.82 (t, J = 5.8 Hz, 1H), 7.98 (d, J = 1.6 Hz, 1H), 7.82 (dd, J = 1.7 Hz, 8.0 Hz, 1H), 7.50 (d, J = 8.1 Hz, 1H), 3.85-3.65 (m, 6H), 3.62-3.48 (m, 2H), 3.35-3.20 (m, 2H), 3.18-3.08 (m, 2H), 2.10-1.94 (m, 2H), 1.90-1.50 (m, 10H), 1.05-0.98 (t, J = 7.4 Hz, 3H); MS (ESI+) m/z 456 (M + H). |

TABLE 1-continued

Examples, General Synthetic Procedures (GSP) and Spectral Data

| Cpd | Name | Structure | General Synthetic Procedure and Spectral Data |
|---|---|---|---|
| 32 | 2,5-Dichloro-N-((1-(4-(propylsulfonyl)piperazin-1-yl)cyclohexyl)methyl)benzamide Hydrochloride | 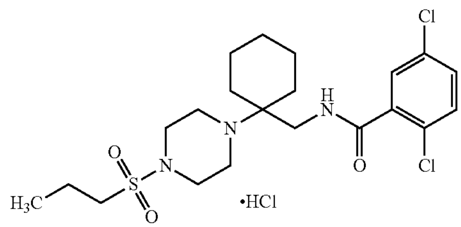 | GSP-1<br>$^1$H NMR (300 MHz, DMSO-$d_6$) δ 10.67 (bs, 1H), 7.64-7.55 (m, 3H), 3.80-3.50 (m, 8H), 3.35-3.05 (m, 4H), 2.13-2.03 (m, 2H), 1.98-1.80 (m, 2H), 1.80-1.50 (m, 8H), 1.02-0.98 (t, J = 7.3 Hz, 3H); MS (ESI+) m/z 416 (M + H). |
| 33 | 4-Isopropyl-N-((1-(4-(propylsulfonyl)piperazin-1-yl)cyclohexyl)methyl)benzamide Hydrochloride | 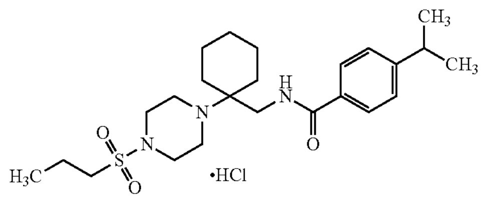 [SMILES: CCCS(=O)(=O)N1CCN(C2(CNC(=O)c3ccc(C(C)C)cc3)CCCCC2)CC1 ; Cl] | GSP-1<br>$^1$H NMR (300 MHz, DMSO-$d_6$) δ 10.43 (bs, 1H), 8.59 (t, J = 5.6 Hz, 1H), 7.90 (d, J = 8.8 Hz, 2H), 7.0 (d, J = 8.8 Hz, 2H), 4.70 (m, 1H), 3.80-3.65 (m, 6H), 3.60-3.48 (m, 2H), 3.35-3.20 (m, 2H), 3.15-3.05 (m, 2H), 2.05-1.97 (m, 2H), 1.90-1.50 (m, 10H), 1.29 (s 3H), 1.27 (s, 3H) 1.02-0.97 (t, J = 7.3 Hz, 3H); MS (ESI+) m/z 450 (M + H). |
| 34 | N-((1-(4-(Propylsulfonyl)piperazin-1-yl)cyclohexyl)methyl)biphenyl-2-carboxamide Hydrochloride | 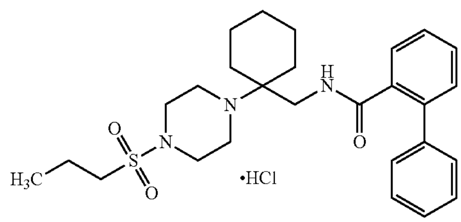 [SMILES: CCCS(=O)(=O)N1CCN(C2(CNC(=O)c3ccccc3-c3ccccc3)CCCCC2)CC1 ; Cl] | GSP-1<br>$^1$H NMR (300 MHz, DMSO-$d_6$) δ 10.34 (t, J = 8.4 Hz 1H), 8.51 (t, J = 5.8 Hz, 1 H), 7.58-7.33 (m, 9H), 3.70-3.33 (m, 10H), 3.10-3.0 (m, 4H), 1.90-1.40 (m, 14H), 1.01-0.97 (t, J = 7.4 Hz, 3H); MS (ESI+) m/z 484 (M + H). |
| 35 | 3,4-Dimethyl-N-((1-(4-(propylsulfonyl)piperazin-1-yl)cyclohexyl)methyl)benzamide Hydrochloride | 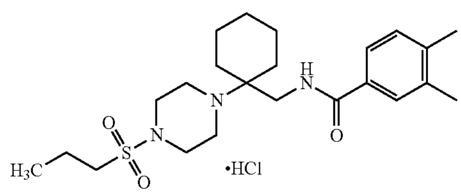 [SMILES: CCCS(=O)(=O)N1CCN(C2(CNC(=O)c3ccc(C)c(C)c3)CCCCC2)CC1 ; Cl] | GSP-1<br>$^1$H NMR (300 MHz, DMSO-$d_6$) δ 10.46 (bs, 1H), 8.64 (t, J = 5.9 Hz, 1H), 7.73 (bs, 1 H), 7.66 (d, J = 7.8 Hz, 1H), 7.25 (d, J = 7.9 Hz, 1H), 3.80-3.50 (m, 8H), 3.35-3.20 (m, 2H), 3.15-3.05 (m, 2H), 2.27 (s, 6H), 2.08-1.95 (m, 2H), 1.90-1.50 (m, 10H), 1.03-0.95 (t, J = 7.4 Hz, 3H); MS (ESI+) m/z 436 (M + H). |
| 36 | 2,4,6-Trimethyl-N-((1-(4-(propylsulfonyl)piperazin-1-yl)cyclohexyl)methyl)benzamide Hydrochloride | 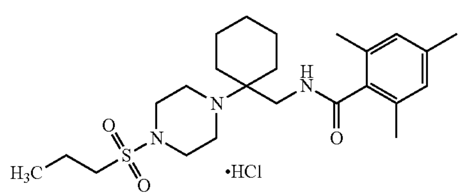 [SMILES: CCCS(=O)(=O)N1CCN(C2(CNC(=O)c3c(C)cc(C)cc3C)CCCCC2)CC1 ; Cl] | GSP-1<br>$^1$H NMR (300 MHz, DMSO-$d_6$) δ 10.75 (bs, 1H), 8.52 (t, J = 5.9 Hz 1H), 6.87 (s, 2H), 3.80-3.50 (m, 8H), 3.35-3.20 (m, 2H), 3.18-3.08 (m, 2H), 2.08-1.95 (m, 2H), 1.90-1.50 (m, 10H), 1.05-0.98 (t, J = 7.4 Hz, 3H); MS (ESI+) m/z 450 (M + H). |
| 37 | 3-Methyl-N-((1-(4-(propylsulfonyl)piperazin-1-yl)cyclohexyl)methyl)benzamide Hydrochloride | 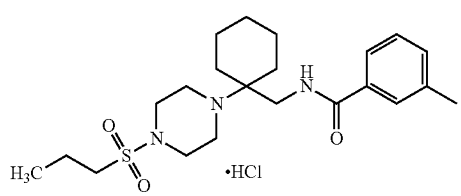 [SMILES: CCCS(=O)(=O)N1CCN(C2(CNC(=O)c3cccc(C)c3)CCCCC2)CC1 ; Cl] | GSP-1<br>$^1$H NMR (300 MHz, DMSO-$d_6$) δ 10.43 (bs, 1H), 8.71 (t, J = 6.0 Hz, 1 H), 7.74 (m, 2 H), 7.38 (d, J = 5.1 Hz, 2 H), 3.80-3.67 (m, 4 H), 3.65-3.50 (m, 4 H), 3.35-3.20 (m, 2H), 3.18-3.08 (m, 2H), 2.37 (s, 3 H), 2.08-2.0 (m, 2H), 1.90-1.50 (m, 10H), 1.03-0.98 (t, J = 7.4 Hz, 3H); MS (ESI+) m/z 422 (M + H). |
| 38 | N-((1-(4-(Propylsulfonyl)piperazin-1-yl)cyclohexyl)methyl)biphenyl-4-carboxamide Hydrochloride | 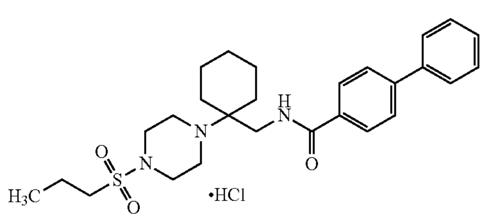 [SMILES: CCCS(=O)(=O)N1CCN(C2(CNC(=O)c3ccc(-c4ccccc4)cc3)CCCCC2)CC1 ; Cl] | GSP-1<br>$^1$H NMR (300 MHz, DMSO-$d_6$) δ 10.38 (bs, 1H), 8.80 (t, J = 6.0 Hz, 1 H), 8.03 (d, J = 8.4 Hz, 2H), 7.81 (d, J = 8.4 Hz, 2H), 7.74 (d, J = 7.2 Hz, 2H), 7.45 (m, 3H), 3.85-3.70 (m, 4H), 3.65-3.50 (m, 4H), 3.48-3.22 (m, 2H), 3.18-3.08 (m, 2H), 2.1-2.0 (m, 2H), 1.92-1.55 (m, 10H), 1.03-0.98 (t, J = 7.3 Hz 3H); MS (ESI+) m/z 484 (M + H). |

TABLE 1-continued

Examples, General Synthetic Procedures (GSP) and Spectral Data

| Cpd | Name | Structure | General Synthetic Procedure and Spectral Data |
|---|---|---|---|
| 39 | 2,4-Difluoro-N-((1-(4-(propylsulfonyl)piperazin-1-yl)cyclohexyl)methyl)benzamide Hydrochloride | 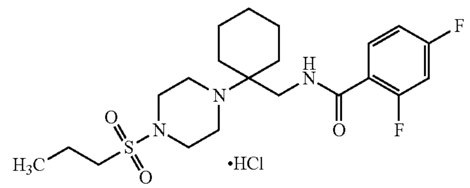 | GSP-1<br>$^1$H NMR (300 MHz, DMSO-$d_6$) δ 10.85 (t, J = 8.8 Hz, 1H), 8.75 (t, J = 6.1 Hz, 1H), 7.73 (dd, J = 6.7 Hz, 8.5 Hz, 15.1 Hz, 1H), 7.40 (dd, J = 2.5 Hz, 9.5 Hz, 11.8 Hz, 1H), 7.24-7.15 (m, 1H), 3.78-3.58 (m, 8H), 3.35-3.18 (m, 2H), 3.15-3.05 (m, 2H), 2.1-2.0 (m, 2H), 2.0-1.84 (m, 2H), 1.80-1.50 (m, 8H), 1.01-0.94 (t, J = 7.4 Hz, 3H); MS (ESI+) m/z 444 (M + H). |
| 40 | 2-Methoxy-N-((1-(4-(propylsulfonyl)piperazin-1-yl)cyclohexyl)methyl)benzamide Hydrochloride | 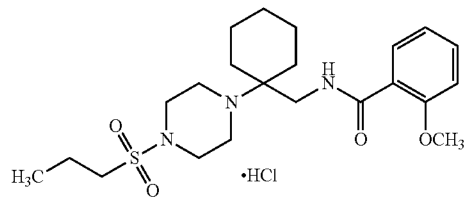 [SMILES: CCCS(=O)(=O)N1CCN(C2(CNC(=O)c3ccccc3OC)CCCCC2)CC1 ; Cl] | GSP-1<br>$^1$H NMR (300 MHz, DMSO-$d_6$) δ 10.41 (bs, 1H), 8.53 (t, J = 6.3 Hz, 1 H), 7.6 (dd, J = 4.5 Hz, 6.2 Hz, 1H), 7.53-7.45 (m, 1 H), 7.16 (d, J = 8.2 Hz, 1H), 7.04 (m, 1H), 3.86 (s, 3H), 3.80-3.65 (m, 6H), 3.65-3.45 (m, 4H), 3.40-3.25 (m, 2H), 3.15-3.05 (m, 2H), 2.12-2.0 (m, 2H), 1.90-1.45 (m, 10H), 1.0-0.95 (t, J = 7.4 Hz, 3H); MS (ESI+) m/z 438 (M + H). |
| 41 | 2-Amino-6-fluoro-N-((1-(4-(propylsulfonyl)piperazin-1-yl)cyclohexyl)methyl)benzamide Hydrochloride | 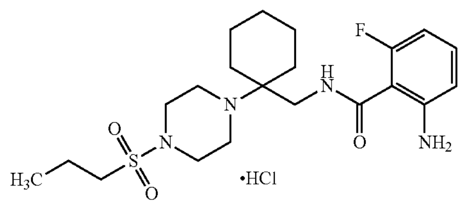 [SMILES: CCCS(=O)(=O)N1CCN(C2(CNC(=O)c3c(N)cccc3F)CCCCC2)CC1 ; Cl] | GSP-1<br>$^1$H NMR (300 MHz, DMSO-$d_6$) δ 10.83 (bs, 1H), 7.19-7.10 (m, 2H), 6.60 (d, J = 8.1 Hz, 1H), 6.47-6.38 (m, 1H), 3.80-3.58 (m, 8H), 3.40-3.20 (m, 2H), 3.15-3.05 (m, 2H), 2.12-1.85 (m, 4H), 1.80-1.50 (m, 7H), 1.25-1.05 (m, 1H), 1.02-0.95 (t, J = 7.4 Hz, 3H); MS (ESI+) m/z 441 (M + H). |
| 42 | 2-Methyl-N-((1-(4-(propylsulfonyl)piperazin-1-yl)cyclohexyl)methyl)benzamide Hydrochloride | 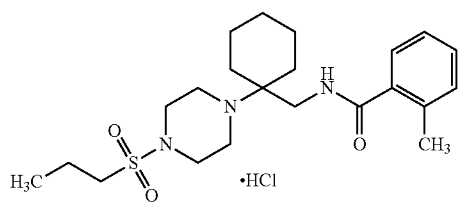 [SMILES: CCCS(=O)(=O)N1CCN(C2(CNC(=O)c3ccccc3C)CCCCC2)CC1 ; Cl] | GSP-1<br>$^1$H NMR (300 MHz, DMSO-$d_6$) δ 10.6 (bs, 1H), 8.63 (t, J = 6.1 Hz, 1H), 7.44-7.23 (m, 4H), 3.80-3.68 (m, 6H), 3.62-3.50 (m, 2H), 3.45-3.30 (m, 2H), 3.15-3.06 (m, 2H), 2.35 (s, 3H), 2.10-2.0 (m, 2H); 1.95-1.80 (m, 2H), 1.80-1.50 (m, 10H), 1.02-0.95 (t, J = 7.4 Hz 3H); MS (ESI+) m/z 422 (M + H). |
| 43 | 2,6-Dichloro-N-((1-(4-(propylsulfonyl)piperazin-1-yl)cyclohexyl)methyl)benzamide Hydrochloride | 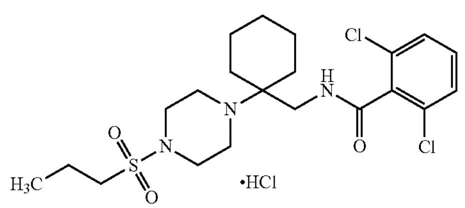 | GSP-1<br>$^1$H NMR (300 MHz, DMSO-$d_6$) δ 10.69 (bs, 1H), 7.56-7.43 (m, 3H), 3.76 (d, J = 6.2 Hz, 2H), 3.74-3.50 (m, 6H), 3.40-3.20 (m, 2H), 3.15-3.05 (m, 2H), 2.18-2.07 (m, 2H), 1.98-1.80 (m, 2H), 1.80-1.50 (m, 8H), 1.02-0.97 (t, J = 7.4 Hz, 3H); MS (ESI+) m/z 476 (M + H). |
| 44 | 2-Fluoro-6-methoxy-N-((1-(4-(propylsulfonyl)piperazin-1-yl)cyclohexyl)methyl)benzamide Hydrochloride | 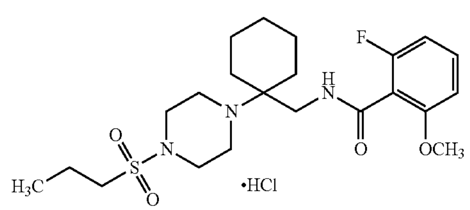 [SMILES: CCCS(=O)(=O)N1CCN(C2(CNC(=O)c3c(F)cccc3OC)CCCCC2)CC1 ; Cl] | GSP-1<br>$^1$H NMR (300 MHz, DMSO-$d_6$) δ 10.31 (bs, 1H), 8.8 (t, J = 6.5 Hz, 1H), 7.48-7.38 (m, 1H), 6.98-6.82 (m, 2H), 3.8 (s, 3H), 3.78-3.65 (m, 4H), 3.64-3.40 (m, 4H), 3.38-3.28 (m, 2H), 3.13-3.09 (m 2H), 2.13-2.05 (m, 2H); 1.85-1.50 (m, 10H), 1.02-0.98 (t, J = 7.4 Hz, 3H); MS (ESI+) m/z 456 (M + H). |
| 45 | 4-Chloro-2-methoxy-N-((1-(4-(propylsulfonyl)piperazin-1-yl)cyclohexyl)methyl)benzamide Hydrochloride | 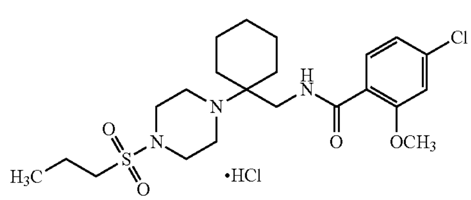 | GSP-1<br>$^1$H NMR (400 MHz, DMSO-$d_6$) δ 10.75 (t, J = 8.5 Hz, 1H), 8.51 (t, J = 6.3 Hz, 1 H), 7.59 (d, J = 8.2 Hz, 1H), 7.25 (d, J = 1.9 Hz, 1H), 7.11 (dd, J = 1.9 Hz, 8.2 Hz, 1H), 3.88 (s, 3H), 3.75-3.65 (m, 6H), 3.64-3.42 (m, 2H), 3.35-3.28 (m, 2H), 3.13-3.09 (m 2H), 2.09-2.0 (m, 2H), 1.95-1.85 (m, 2H) 1.78-1.50 (m, 8 H), 1.02-0.98 (t, J = 7.4 Hz, 3H); MS (ESI+) m/z 472 (M + H). |

TABLE 1-continued

Examples, General Synthetic Procedures (GSP) and Spectral Data

| Cpd | Name | Structure | General Synthetic Procedure and Spectral Data |
|---|---|---|---|
| 46 | 4-Fluoro-2-methoxy-N-((1-(4-(propyl-sulfonyl)piperazin-1-yl)cyclohexyl)methyl) benzamide Hydrochloride | 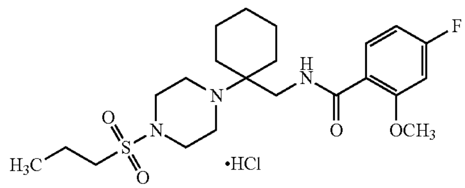 [SMILES: CCCS(=O)(=O)N1CCN(C2(CNC(=O)c3ccc(F)cc3OC)CCCCC2)CC1 ; Cl] | GSP-1<br>$^1$H NMR (400 MHz, DMSO-$d_6$) δ 10.63 (bs, 1H), 8.46 (t, J = 6.4 Hz, 1H), 7.67 (t, J = 7.7 Hz, 1H), 7.09 (dd, J = 1.9 Hz, 11.3 Hz, 1H), 6.88 (m, 1H), 3.88 (s, 3H), 3.80-3.60 (m, 6H), 3.60-3.20 (m, 4H), 3.18-3.08 (m, 2H), 2.10-2.00 (m 2H), 1.90-1.50 (m, 10H) 1.02-0.98 (t, J = 7.3 Hz, 3H); MS (ESI+) m/z 456 (M + H). |
| 47 | 2,6-Dimethyl-N-((1-(4-(propylsulfonyl)piperazin-1-yl)cyclohexyl)methyl) benzamide Hydrochloride | 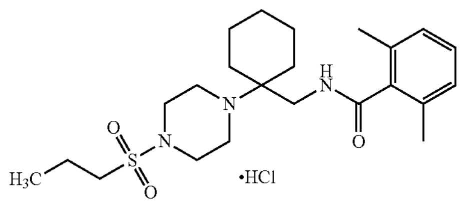 [SMILES: CCCS(=O)(=O)N1CCN(C2(CNC(=O)c3c(C)cccc3C)CCCCC2)CC1 ; Cl] | GSP-1<br>$^1$H NMR (300 MHz, DMSO-$d_6$) δ 10.83 (bs, 1H), 8.60 (t, J = 5.3 Hz 1H), 7.23-7.15 (m, 1H), 7.09-7.02 (d, J = 7.5 Hz, 2H), 3.82-3.76 (d, J = 6.2 Hz, 2H), 3.75-3.65 (m, 4H), 3.65-3.40 (m, 2H), 3.37-3.21 (m, 2H), 3.16-3.05 (m, 2H), 2.22 (s, 6H), 2.10-2.0 (m, 2H), 1.98-1.50 (m, 10H), 1.03-0.97 (t, J = 7.4 Hz, 3H); MS (ESI+) m/z 436 (M + H). |
| 48 | 2,4,6-Trifluoro-N-((1-(4-(propylsulfonyl) piperazin-1-yl)cyclohexyl)methyl) benzamide Hydrochloride | 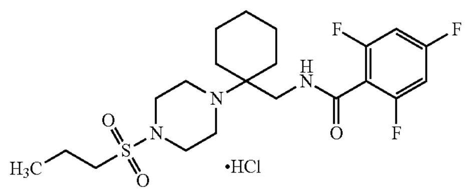 [SMILES: CCCS(=O)(=O)N1CCN(C2(CNC(=O)c3c(F)cc(F)cc3F)CCCCC2)CC1 ; Cl] | GSP-1<br>$^1$H NMR (300 MHz, DMSO-$d_6$) δ 10.71 (bs, 1H), 9.15 (t, J = 6.1 Hz, 1H), 7.29-7.39 (t, J = 9.1 Hz, 2H), 3.83-3.75 (d, J = 6.2 Hz 2H), 3.74-3.51 (m, 6H), 3.30-3.14 (m, 2H), 3.13-3.05 (m, 2H), 2.10-2.0 (m, 2H), 1.98-1.80 (m, 2H), 1.80-1.42 (m, 8H), 1.0-0.92 (t, J = 7.4 Hz 3H); MS (ESI+) m/z 462 (M + H). |
| 49 | 2-Fluoro-6-methyl-N-((1-(4-(propylsulfonyl) piperazin-1-yl)cyclohexyl)methyl) benzamide Hydrochloride | 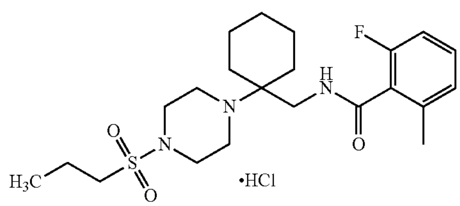 [SMILES: CCCS(=O)(=O)N1CCN(C2(CNC(=O)c3c(C)cccc3F)CCCCC2)CC1 ; Cl] | GSP-1<br>$^1$H NMR (300 MHz, DMSO-$d_6$) δ 10.50 (bs, 1H), 8.90 (t, J = 5.8 Hz, 1H), 7.40-7.30 (m, 1H), 7.15-7.05 (m, 2H), 3.80-3.75 (d, J = 6.1 Hz, 2H), 3.74-3.62 (m, 4H), 3.62-3.46 (m, 2H), 3.36-3.20 (m, 2H), 3.15-3.05 (m, 2H), 2.28 (s, 3H), 2.12-2.0 (m, 2H), 1.96-1.79 (m 2H), 1.78-1.48 (m, 8H) 0.97-0.95 (t, J = 7.5 Hz 3H); MS (ESI+) m/z 440 (M + H). |
| 50 | N-((1-(4-(Propylsulfonyl)piperazin-1-yl)cyclohexyl)methyl)-2-(trifluoromethyl)benzamide Hydrochloride | 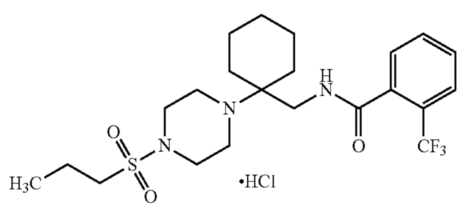 [SMILES: CCCS(=O)(=O)N1CCN(C2(CNC(=O)c3ccccc3C(F)(F)F)CCCCC2)CC1 ; Cl] | GSP-1<br>$^1$H NMR (300 MHz, DMSO-$d_6$) δ 10.46 (bs, 1H), 8.89 (t, J = 5.97 Hz 1H), 7.85-7.60 (m, 4H), 3.80-3.65 (m, 6H), 3.63-3.50 (m, 2H), 3.32-3.18 (m, 2H), 3.15-3.05 (m, 2H), 2.12-2.02 (m, 2H), 1.92-1.78 (m, 2H), 1.77-1.50 (m, 8H), 1.01-0.92 (t, J = 7.34 Hz, 3H); MS (ESI+) m/z 476 (M + H). |
| 51 | 4-Chloro-2,6-difluoro-N-((1-(4-propylsulfonyl)piperazin-1-yl)cycloheptyl)methyl) benzamide Hydrochloride | 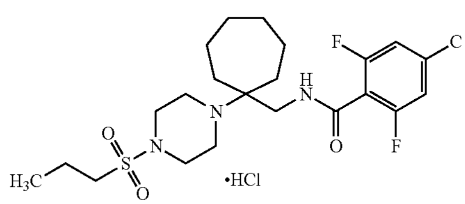 | GSP-1<br>$^1$H NMR (300 MHz, DMSO-$d_6$) δ 10.06 (bs, 1H), 9.27 bs, 1H), 7.50 (d, J = 7.4 Hz, 2H), 3.78-3.32 (m, 8H), 3.30-3.08 (m, 4H), 2.18-2.05 (m, 2H), 1.92-1.80 (m, 2H), 1.80-1.65 (m, 6H), 1.64-1.40 (m, 6H), 1.03-0.98 (t, J = 7.4 Hz 1H); MS (ESI+) m/z 492 (M + H). |
| 52 | 4-Fluoro-2-methoxy-N-((1-(4-(propylsulfonyl)piperazin-1-yl)cycloheptyl)methyl) benzamide Hydrochloride | 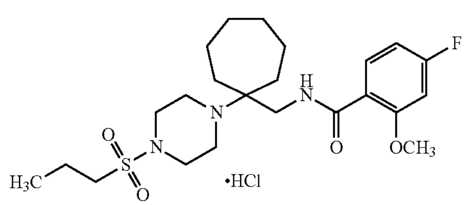 [SMILES: CCCS(=O)(=O)N1CCN(C2(CNC(=O)c3ccc(F)cc3OC)CCCCCC2)CC1 ; Cl] | GSP-1<br>$^1$H NMR (300 MHz, DMSO-$d_6$) δ 9.93 (bs, 1H), 8.62 (t, J = 6.2 Hz, 1H), 7.80 (dd, J = 7.2 Hz, 8.6 Hz, 1H), 7.10 (dd, J =2.3 Hz, 11.4 Hz, 1H), 6.89 (dd, J = 2.3 Hz, 8.3 Hz, 1H), 3.91 (s, 3H), 3.80-3.60 (m, 6H), 3.58-3.42 (m, 2H), 3.38-3.20 (m, 2H), 3.18-3.10 (m, 2H) 2.15-2.05 (m, 2H), 1.93-1.63 (m, 6H), 1.60-1.43 (m 6H), 1.02-0.98 (t, 7.4 Hz, 3H); MS (ESI+) m/z 470 (M + H). |

TABLE 1-continued

Examples, General Synthetic Procedures (GSP) and Spectral Data

| Cpd | Name | Structure | General Synthetic Procedure and Spectral Data |
|---|---|---|---|
| 53 | 4-Chloro-2-methoxy-N-((1-(4-(propylsulfonyl)piperazin-1-yl)cycloheptyl)methyl)benzamide Hydrochloride | 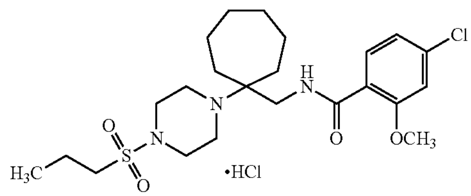 [SMILES: CCCS(=O)(=O)N1CCN(C2(CNC(=O)c3ccc(Cl)cc3OC)CCCCCC2)CC1 ; Cl] | GSP-1<br>$^1$H NMR (300 MHz, DMSO-d$_6$) δ 9.69 (bs, 1H), 8.64 (t, J = 6.3 Hz 1H), 7.73 (d, J = 8.3 Hz, 1H), 7.27 (d, J = 1.7 Hz 1H), 7.13 (dd J = 1.9 Hz, 8.5 Hz, 1H), 3.92 (s, 3H), 3.80-3.60 (m, 6H), 3.50-3.40 (m, 2H), 3.38-3.20 (m, 2H), 3.18-3.10 (m, 2H), 2.15-2.03 (m, 2H), 1.92-1.82 (m, 2H), 1.80-1.64 (m, 4H), 1.60-1.5 (m, 6H), 1.02-0.98 (t, J = 7.4 Hz, 3H); MS (ESI+) m/z 486 (M + H). |
| 54 | 2-Chloro-3,6-difluoro-N-((1-(4-(propylsulfonyl)piperazin-1-yl)cycloheptyl)methyl)benzamide Hydrochloride | 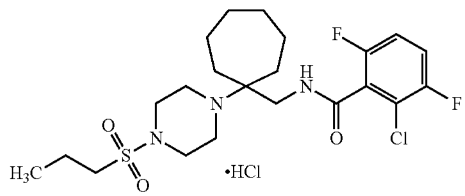 [SMILES: CCCS(=O)(=O)N1CCN(C2(CNC(=O)c3c(F)ccc(F)c3Cl)CCCCCC2)CC1 ; Cl] | GSP-1<br>$^1$H NMR (300 MHz, DMSO-d$_6$) δ 10.14 (bs, 1H), 9.29 (bs, 1H), 7.65-7.54 (m, 1H), 7.48-7.38 (m, 1H), 3.78-3.53 (m, 8H), 3.32-3.18 (m, 2H), 3.15-3.08 (m, 2H), 2.20-2.08 (m, 2H), 1.96-1.82 (m, 2H), 1.80-1.65 (m, 3H), 1.60-1.40 (m 6H), 1.12-0.98 (t, J = 7.4 Hz, 3H); MS (ESI+) m/z 492 (M + H). |
| 55 | 2-Fluoro-6-methoxy-N-((1-(4-(propylsulfonyl)piperazin-1-yl)cycloheptyl)methyl)benzamide Hydrochloride | 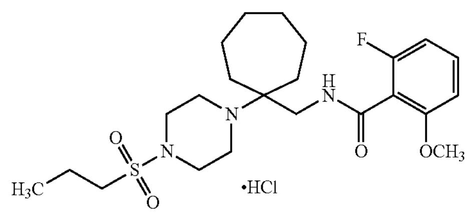 [SMILES: CCCS(=O)(=O)N1CCN(C2(CNC(=O)c3c(F)cccc3OC)CCCCCC2)CC1 ; Cl] | GSP-1<br>$^1$H NMR (300 MHz, DMSO-d$_6$) δ 9.95 (bs, 1H), 8.88 (t, J = 6.3 Hz, 1H), 7.42 (dd, J = 8.4 Hz, 15.4 Hz, 1H), 6.95 (d, J = 8.5 Hz, 1H), 6.87 (t, J = 8.7 Hz, 1H), 3.80 (s, 3H), 3.72-3.54 (m, 8H), 3.35-3.25 (m, 2H), 3.18-3.08 (m, 2H), 2.15-2.08 (m, 2H), 1.95-1.85 (m, 2H), 1.82-1.68 (m 4H), 1.62-1.1.45 (m, 6H), 1.12-0.98 (t, J = 7.4 Hz, 3H); MS (ESI+) m/z 470 (M + H). |
| 56 | 2-Amino-6-chloro-N-((1-(4-(propylsulfonyl)piperazin-1-yl)cycloheptyl)methyl)benzamide Hydrochloride | 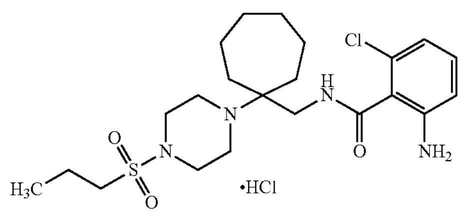 [SMILES: CCCS(=O)(=O)N1CCN(C2(CNC(=O)c3c(N)cccc3Cl)CCCCCC2)CC1 ; Cl] | GSP-1<br>$^1$H NMR (300 MHz, DMSO-d$_6$) δ 8.82 (t, J = 6.0 Hz, 1H), 7.08 (t, J = 8.1 Hz, 1H), 6.71-6.63 (m, 2H), 4.25 (bs, 3H), 3.80-3.50 (m, 8H), 3.40-3.07 (m, 4H), 2.21-2.05 (m, 2H), 1.93-1.45 (m, 12H), 0.99 (t, J = 7.5 Hz, 3H); MS (ESI+) m/z 471 (M + H). |
| 57 | 4-Methyl-N-((1-(4-(propylsulfonyl)piperazin-1-yl)cycloheptyl)methyl)benzamide Hydrochloride | 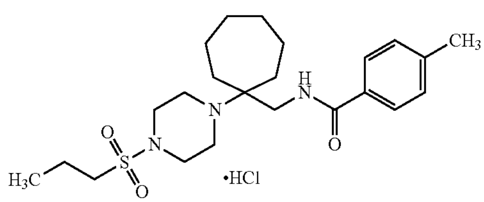 [SMILES: CCCS(=O)(=O)N1CCN(C2(CNC(=O)c3ccc(C)cc3)CCCCCC2)CC1 ; Cl] | GSP-1<br>$^1$H NMR (300 MHz, DMSO-d$_6$) δ 10.45 (bs, 1H), 8.95 (t, J = 6.0 Hz, 1H), 7.91 (d, J = 8.1 Hz, 2H), 7.29 (d, J = 8.1 Hz, 2H), 3.78-3.55 (m, 7H), 3.40-3.10 (m, 5H), 2.36 (s, 3H), 2.18-2.03 (m, 2H), 1.90-1.40 (m, 12H), 1.00 (t, J = 7.5 Hz, 3H); MS (ESI+) m/z 436 (M + H). |
| 58 | 4-Chloro-N-((1-(4-(propylsulfonyl)piperazin-1-yl)cycloheptyl)methyl)benzamide Hydrochloride | 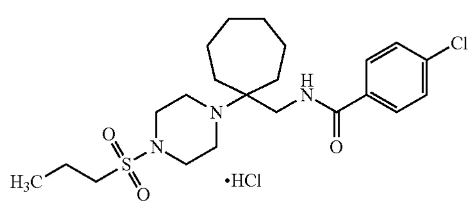 | GSP-1<br>$^1$H NMR (300 MHz, DMSO-d$_6$) δ 10.21 (bs, 1H), 9.06 (t, J = 6.0 Hz, 1H), 8.03 (d, J = 8.4 Hz, 2H), 7.56 (d, J = 8.4 Hz, 2H), 3.78-3.55 (m, 7H), 3.40-3.10 (m, 5H), 2.36 (s, 3H), 2.18-2.05 (m, 2H), 1.90-1.40 (m, 12H), 1.00 (t, J = 7.5 Hz, 3H); MS (ESI+) m/z 436 (M + H). |
| 59 | 2-Chloro-N-((1-(4-(propylsulfonyl)piperazin-1-yl)cycloheptyl)methyl)-3-(trifluoromethyl)benzamide Hydrochloride | 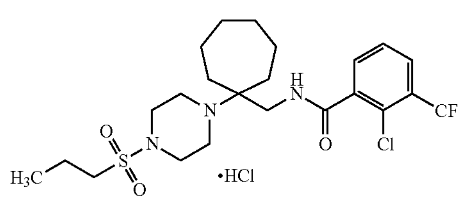 | GSP-1<br>$^1$H NMR (300 MHz, DMSO-d$_6$) δ 10.29 (bs, 1H), 9.10 (t, J = 6.0 Hz, 1H), 7.95 (d, J = 7.8 Hz, 1H), 7.90 (d, J = 7.2 Hz, 1H), 7.64 (t, J = 7.8 Hz, 1H), 3.78-3.55 (m, 8H), 3.35-3.10 (m, 4H), 2.23-2.08 (m, 2H), 1.95-1.40 (m, 12H), 0.99 (t, J = 7.5 Hz, 3H); MS (ESI+) m/z 524 (M + H). |

TABLE 1-continued

Examples, General Synthetic Procedures (GSP) and Spectral Data

| Cpd | Name | Structure | General Synthetic Procedure and Spectral Data |
|---|---|---|---|
| 60 | 2,4-Dichloro-N-((1-(4-(propylsulfonyl)piperazin-1-yl)cycloheptyl)methyl)benzamide Hydrochloride | 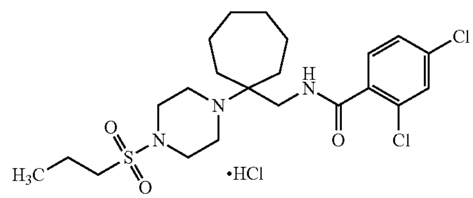 [SMILES: CCCS(=O)(=O)N1CCN(C2(CNC(=O)c3ccc(Cl)cc3Cl)CCCCCC2)CC1 ; Cl] | GSP-1<br>$^1$H NMR (300 MHz, DMSO-d$_6$) δ 10.13 (bs, 1H), 8.97 (t, J = 6.0 Hz, 1H), 7.72 (d, J = 1.8 Hz, 1H), 7.63 (d, J = 8.1 Hz, 1H), 7.52 (dd, J = 8.1 Hz, 1.8 Hz, 1H), 3.78-3.52 (m, 8H), 3.35-3.10 (m, 4H), 2.23-2.08 (m, 2H), 1.95-1.40 (m, 12H), 0.99 (t, J = 7.5 Hz, 3H); MS (ESI+) m/z 524 (M + H). |
| 61 | N-((1-(4-(Propylsulfonyl)piperazin-1-yl)cycloheptyl)methyl)-4-(trifluoromethyl)benzamide Hydrochloride | 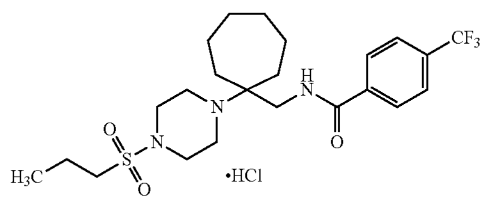 [SMILES: CCCS(=O)(=O)N1CCN(C2(CNC(=O)c3ccc(C(F)(F)F)cc3)CCCCCC2)CC1 ; Cl] | GSP-1<br>$^1$H NMR (300 MHz, DMSO-d$_6$) δ 10.23 (bs, 1H), 9.21 (t, J = 6.0 Hz, 1H), 8.21 (d, J = 8.1 Hz, 2H), 7.87 (d, J = 8.1 Hz, 2H), 3.80-3.55 (m, 7H), 3.40-3.10 (m, 5H), 2.18-2.05 (m, 2H), 1.90-1.40 (m, 12H), 1.00 (t, J = 1.5 Hz, 3H); MS (ESI+) m/z 490 (M + H). |
| 62 | N-((1-(4-(Propylsulfonyl)piperazin-1-yl)cycloheptyl)methyl)-4-(trifluoromethoxy)benzamide Hydrochloride | 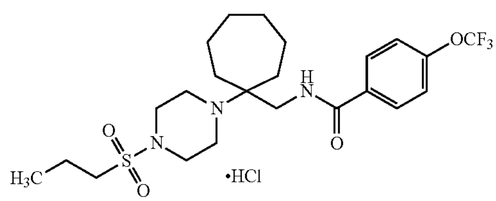 [SMILES: CCCS(=O)(=O)N1CCN(C2(CNC(=O)c3ccc(OC(F)(F)F)cc3)CCCCCC2)CC1 ; Cl] | GSP-1<br>$^1$H NMR (300 MHz, DMSO-d$_6$) δ 10.14 (bs, 1H), 9.08 (t, J = 6.0 Hz, 1H), 8.15 (d, J = 8.1 Hz, 2H), 7.49 (d, J = 8.1 Hz, 2H), 3.80-3.55 (m, 7H), 3.40-3.10 (m, 5H), 2.18-2.05 (m, 2H), 1.90-1.40 (m, 12H), 1.00 (t, J = 7.5 Hz, 3H); MS (ESI+) m/z 506 (M + H). |
| 63 | 2-Fluoro-N-((1-(4-(propylsulfonyl)piperazin-1-yl)cycloheptyl)methyl)benzamide Hydrochloride | 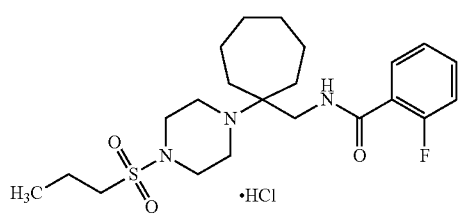 [SMILES: CCCS(=O)(=O)N1CCN(C2(CNC(=O)c3ccccc3F)CCCCCC2)CC1 ; Cl] | GSP-1<br>$^1$H NMR (300 MHz, DMSO-d$_6$) δ 10.15 (bs, 1H), 8.84 (t, J = 6.0 Hz, 1H), 7.72 (dd, J = 7.5 Hz, 1.8 Hz, 1H), 7.61-7.52 (m, 1H), 7.35-7.27 (m, 2H), 3.78-3.52 (m, 8H), 3.35-3.10 (m, 4H), 2.20-2.05 (m, 2H), 1.93-1.40 (m, 12H), 0.99 (t, J = 7.5 Hz, 3H); MS (ESI+) m/z 440 (M + H). |
| 64 | 2,6-Dichloro-N-((1-(4-(propylsulfonyl)piperazin-1-yl)cycloheptyl)methyl)benzamide Hydrochloride | 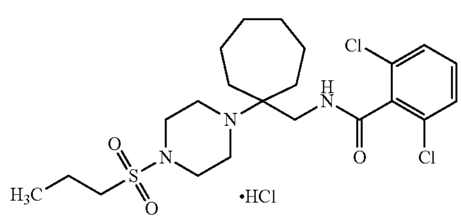 [SMILES: CCCS(=O)(=O)N1CCN(C2(CNC(=O)c3c(Cl)cccc3Cl)CCCCCC2)CC1 ; Cl] | GSP-1<br>$^1$H NMR (300 MHz, DMSO-d$_6$) δ 10.34 (bs, 1H), 9.16 (t, J = 6.0 Hz, 1H), 7.56-7.43 (m, 3H), 3.74-3.60 (m, 7H), 3.40-3.08 (m, 5H), 2.23-2.10 (m, 2H), 1.95-1.40 (m, 12H), 0.99 (t, J = 7.5 Hz, 3H); MS (ESI+) m/z 490 (M + H). |
| 65 | 2-Chloro-3-methoxy-N-((1-(4-(propylsulfonyl)piperazin-1-yl)cycloheptyl)methyl)benzamide Hydrochloride | 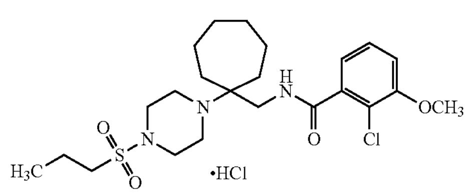 [SMILES: CCCS(=O)(=O)N1CCN(C2(CNC(=O)c3cccc(OC)c3Cl)CCCCCC2)CC1 ; Cl] | GSP-1<br>$^1$H NMR (300 MHz, DMSO-d$_6$) δ 10.39 (bs, 1H), 8.89-8.87 (m, 1H), 7.37 (dd, J = 8.0, 7.8 Hz, 1H), 7.22 (dd, J = 1.3, 8.4 Hz, 1H), 7.08 (dd, J = 1.2, 7.4 Hz, 1H), 3.94 (s, 2H), 3.88 (s, 3H), 3.69-3.67 (m, 6H), 3.26-3.24 (m, 2H), 3.13-3.11 (m, 2H), 2.50 (t, J = 1.8 Hz, 2H), 2.14-2.12 (m, 2H), 1.91-1.49 (m, 8H), 0.99 (t, J = 7.4 Hz, 3H); MS (ESI+) m/z 486 (M + H). |
| 66 | 2,6-Difluoro-N-((1-(4-(propylsulfonyl)piperazin-1-yl)cycloheptyl)methyl)benzamide Hydrochloride | 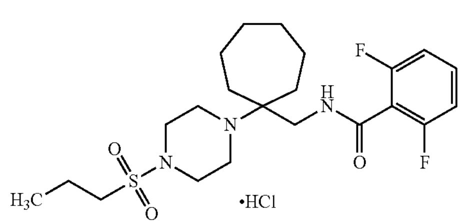 [SMILES: CCCS(=O)(=O)N1CCN(C2(CNC(=O)c3c(F)cccc3F)CCCCCC2)CC1 ; Cl] | GSP-1<br>$^1$H NMR (300 MHz, DMSO-d$_6$) δ 9.19 (bs, 1H), 7.55 (t, J = 7.2 Hz, 1H), 7.20 (t, J = 8.1 Hz, 2H), 3.80-3.33 (m, 8H), 3.32-3.04 (m, 4H), 2.21-2.01 (m, 2H), 1.95-1.35 (m, 2H), 1.95-1.35 (m, 10H), 0.99 (t, J = 7.5 Hz, 3H); MS (ESI$^+$) m/z 458 (M + H). |

TABLE 1-continued

Examples, General Synthetic Procedures (GSP) and Spectral Data

| Cpd | Name | Structure | General Synthetic Procedure and Spectral Data |
|---|---|---|---|
| 67 | 4-Methoxy-N-((1-(4-(propylsulfonyl)piperazin-1-yl)cycloheptyl)methyl)benzamide Hydrochloride | 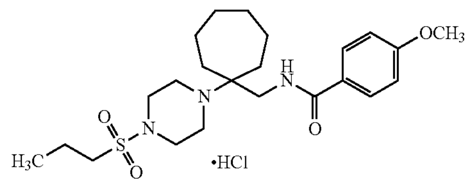 [SMILES: CCCS(=O)(=O)N1CCN(C2(CNC(=O)c3ccc(OC)cc3)CCCCCC2)CC1 ; Cl] | GSP-1<br>$^1$H NMR (300 MHz, DMSO-$d_6$) δ 10.14 (bs, 1H), 9.08 (t, J = 6.0 Hz, 1H), 8.15 (d, J = 8.1 Hz, 2H), 7.49 (d, J = 8.1 Hz, 2H), 3.80-3.55 (m, 7H), 3.40-3.10 (m, 5H), 2.18-2.05 (m, 2H), 1.90-1.40 (m, 12H), 1.00 (t, J = 7.5 Hz, 3H); MS (ESI+) m/z 506 (M + H). MS (ESI+) m/z 452 (M + H). |
| 68 | 3,4-Dichloro-N-((1-(4-(propylsulfonyl)piperazin-1-yl)cycloheptyl)methyl)benzamide Hydrochloride | 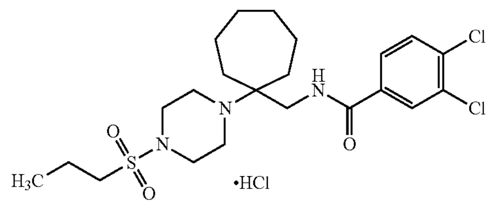 [SMILES: CCCS(=O)(=O)N1CCN(C2(CNC(=O)c3ccc(Cl)c(Cl)c3)CCCCCC2)CC1 ; Cl] | GSP-1<br>$^1$H NMR (300 MHz, DMSO-$d_6$): δ 10.14-10.12 (m, 1H), 9.13 (t, J = 6.0 Hz, 1H), 8.30 (d, J = 2.1 Hz, 1H), 7.99 (dd, J = 2.1, 8.4 Hz, 1H), 7.79 (d, J = 8.4 Hz), 3.77-3.71 (m, 6H), 3.61 (t, J = 12.0 Hz, 2H), 3.25-3.23 (m, 2H), 3.16-3.14 (m, 2H), 2.13-2.11 (m, 2H), 1.86-1.66 (m, 6H), 1.55-1.49 (m, 6H), 1.00 (t, J = 7.5 Hz, 3H); MS (ESI+) m/z 491 (M + H). |
| 69 | 4-Fluoro-2-methoxy-6-methyl-N-((1-(4-(propylsulfonyl)piperazin-1-yl)cycloheptyl)methyl)benzamide Hydrochloride | 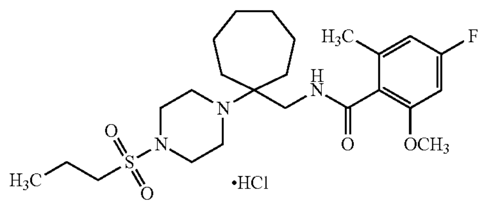 | GSP-1<br>$^1$H NMR (300 MHz, DMSO-$d_6$): δ 10.37-10.35 (m, 1H), 8.66 (t, J = 6.0 Hz, 1H), 6.82 (d, J = 10.1 Hz, 1H), 6.68 (d, J = 10.1 Hz, 1H), 3.76 (s, 3H), 3.75-3.63 (m, 6H), 3.51-3.49 (m, 2H), 3.30-3.28 (m, 2H), 3.14-3.12 (m, J = 7.2 Hz, 2H), 2.20 (s, 3H), 2.10-2.08 (m, 2H), 1.92-1.65 (m, 6H), 1.55-1.51 (m, 6H), 1.00 (t, J = 7.5 Hz, 3H); MS (ESI+) m/z 491 (M + H). |
| 70 | 2-Methoxy-N-((1-(4-(propylsulfonyl)piperazin-1-yl)cycloheptyl)methyl)-4,6-bis(trifluoromethyl)benzamide Hydrochloride | 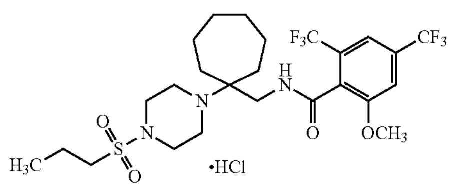 [SMILES: CCCS(=O)(=O)N1CCN(C2(CNC(=O)c3c(OC)cc(C(F)(F)F)cc3C(F)(F)F)CCCCCC2)CC1 ; Cl] | GSP-1<br>$^1$H NMR (300 MHz, DMSO-$d_6$): δ 10.41-10.39 (m, 1H), 9.04-9.02 (m, 1H), 7.77 (s, 1H), 7.67 (s, 1H), 3.95 (s, 3H), 3.55-3.52 (m, 8H), 3.29-3.27 (m, 2H), 3.12-3.10 (m, 2H), 2.13-2.11 (m, 2H), 1.93-1.65 (m, 6H), 1.52-1.49 (m, 6H), 0.98 (t, J = 7.5 Hz, 3H); MS (ESI+) m/z 588 (M + H). |
| 71 | 4-Fluoro-N-((1-(4-(propylsulfonyl)piperazin-1-yl)cycloheptyl)methyl)-2-(trifluoromethyl)benzamide Hydrochloride | 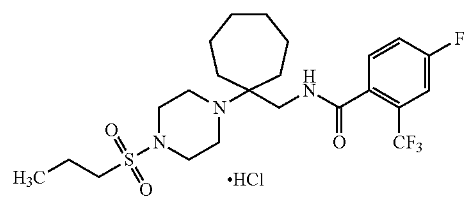 [SMILES: CCCS(=O)(=O)N1CCN(C2(CNC(=O)c3ccc(F)cc3C(F)(F)F)CCCCCC2)CC1 ; Cl] | GSP-1<br>$^1$H NMR (300 MHz, DMSO-$d_6$): δ 9.02-9.00 (m, 1H), 7.88-7.86 (m, 1H), 7.75 (d, J = 9.3Hz), 7.66-7.64 (m, 1H), 3.73-3.51 (m, 8H), 3.23-3.21 (m, 2H), 3.14-3.12 (m, 2H), 2.12-2.10 (m, 2H), 1.91-1.65 (m, 6H), 1.55-1.51 (m, 6H), 0.99 (t, J = 7.5 Hz, 3H); MS (ESI+) m/z 508 (M + H). |
| 72 | 2,4-Dichloro-N-((1-(4-(propylsulfonyl)piperazin-1-yl)cyclopentyl)methyl)benzamide Hydrochloride | 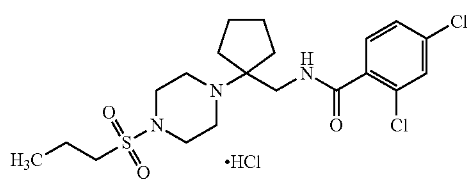 [SMILES: CCCS(=O)(=O)N1CCN(C2(CNC(=O)c3ccc(Cl)cc3Cl)CCCC2)CC1 ; Cl] | GSP-1<br>$^1$H NMR (300 MHz, DMSO-$d_6$): δ 10.98 (bs, 1H), 8.93 (bs, 1H), 7.73 (m, 1H), 7.52 (m, 2H), 3.78-3.67 (d, J = 12.3 Hz, 1.0 Hz, 2H), 3.65-3.48 (m, 6H), 3.47-3.32 (m, 2H), 3.18-3.08 (m, 2H), 2.18-2.02 (m, 2H), 2.01-1.90 (m, 2H), 1.83-1.65 (m, 6H), 1.03-0.97 (t, J = 7.4 Hz 3H); MS (ESI+) m/z 462 (M + H). |
| 73 | 4-Chloro-N-((1-(4-(propylsulfonyl)piperazin-1-yl)cyclopentyl)methyl)benzamide Hydrochloride | 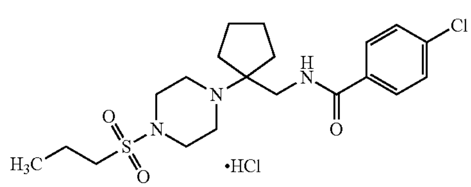 [SMILES: CCCS(=O)(=O)N1CCN(C2(CNC(=O)c3ccc(Cl)cc3)CCCC2)CC1 ; Cl] | GSP-1<br>$^1$H NMR (300 MHz, DMSO-$d_6$) δ 10.98 (bs, 1H), 8.90 (bs, 1H), 7.98-7.90 (d, J = 8.5 Hz, 2H), 7.62-7.55 (d, J = 8.4 Hz, 2H), 3.78-3.67 (d, J = 12.7 Hz, 2H), 3.65-3.48 (m, 6H), 3.47-3.32 (m, 2H), 3.18-3.08 (m, 2H), 2.18-2.02 (m, 2H), 2.01-1.90 (m, 2H), 1.83-1.65 (m, 6H), 1.03-0.97 (t, J = 7.4 Hz, 3H); MS (ESI+) m/z 427 (M + H). |

TABLE 1-continued

Examples, General Synthetic Procedures (GSP) and Spectral Data

| Cpd | Name | Structure | General Synthetic Procedure and Spectral Data |
|---|---|---|---|
| 74 | 4-Fluoro-2-methoxy-6-(methylthio)-N-((1-(4-(propylsulfonyl)piperazin-1-yl)cyclopentyl)methyl)benzamide Hydrochloride | 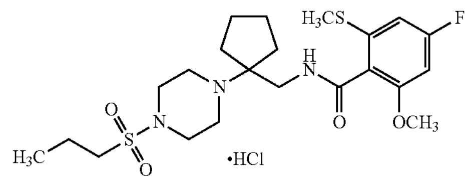 | GSP-1<br>$^1$H NMR (300 MHz, DMSO-$d_6$) δ 10.85 (bs, 1H), 8.72 (t, J = 5.6 Hz 1H), 6.88-6.79 (m, 2H), 3.76 (s, 3H), 3.75-3.67 (d, J = 9.6 Hz, 2H), 3.58-3.40 (m, 8H), 3.16-3.07 (m, 2H), 2.44 (s, 3H), 2.08-1.98 (m, 4H), 1.84-1.64 (m, 6H), 1.02-0.95 (t, J = 7.4 Hz 3H); MS (ESI+) m/z 488 (M + H). |
| 75 | 4-Fluoro-2-methoxy-6-methyl-N-((1-(4-(propylsulfonyl)piperazin-1-yl)cyclopentyl)methyl)benzamide Hydrochloride | 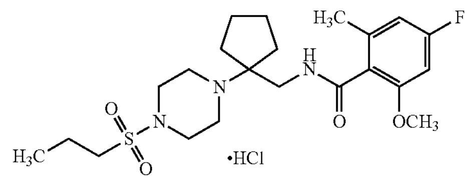 [SMILES: CCCS(=O)(=O)N1CCN(C2(CNC(=O)c3c(C)cc(F)cc3OC)CCCC2)CC1 ; Cl] | GSP-1<br>$^1$H NMR (300 MHz, DMSO-$d_6$) δ 10.50 (bs, 1H), 8.67 (t, J = 6.3 Hz, 1H), 6.87-6.80 (dd, J = 1.9 Hz, 11.3 Hz, 1H), 6.73-6.67 (dd, J = 2.1 Hz, 9.6 Hz, 1H), 3.75 (s, 3H), 3.74-3.70 (m, 2H), 3.62-3.42 (m, 8H), 3.18-3.08 (m, 2H), 2.18 (s, 3H), 2.08-1.92 (m, 4H), 1.82-1.63 (m, 6H), 1.02-0.93 (t, J = 7.4 Hz, 3H); MS (ESI+) m/z 456 (M + H). |
| 76 | 3,4-Dichloro-N-((1-(4-(propylsulfonyl)piperazin-1-yl)cyclopentyl)methyl)benzamide Hydrochloride | 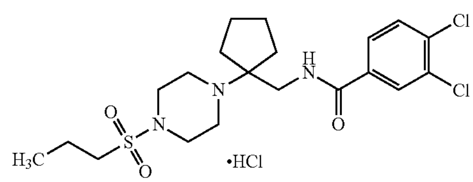 [SMILES: CCCS(=O)(=O)N1CCN(C2(CNC(=O)c3ccc(Cl)c(Cl)c3)CCCC2)CC1 ; Cl] | GSP-1<br>$^1$H NMR (300 MHz, DMSO-$d_6$) δ 10.64 (bs, 1H), 8.98 (bs, 1H), 8.16 (m, 1H), 7.93-7.86 (m, 1H), 7.83-7.78 (d, J = 8.4 Hz, 1.0 Hz, 1H), 3.78-3.69 (d, J = 12.2 Hz 2H), 3.68-3.30 (m, 8H), 3.29-3.09 (m, 2H), 2.20-2.02 (m, 2H) 2.01-1.90 (m, 2H), 1.85-1.64 (m, 6H), 1.03-0.98 (t, J = 7.5 Hz 3H); MS (ESI+) m/z 462 (M + H). |
| 77 | 2-Amino-6-chloro-N-((1-(4-(propylsulfonyl)piperazin-1-yl)cyclopentyl)methyl)benzamide Hydrochloride | 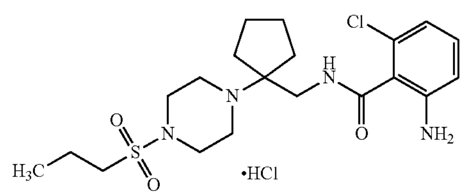 [SMILES: CCCS(=O)(=O)N1CCN(C2(CNC(=O)c3c(N)cccc3Cl)CCCC2)CC1 ; Cl] | GSP-1<br>$^1$H NMR (300 MHz, CD$_3$OD) δ 7.31 (t, J = 8.1 Hz, 1H), 7.10 (d, J = 7.8 Hz, 1H), 7.03 (d, J = 8.1 Hz, 1H), 4.01-3.40 (m, 10H), 3.15-3.05 (m, 2H), 2.18-1.74 (m, 10H), 1.06 (t, J = 7.5 Hz, 3H); MS (ESI+) m/z 443 (M + H). |
| 78 | 2-Amino-6-chloro-N-((1-(4-(propylsulfonyl)piperazin-1-yl)cyclobutyl)methyl)benzamide Hydrochloride | 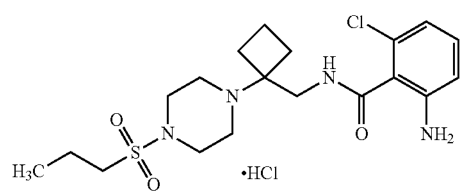 [SMILES: CCCS(=O)(=O)N1CCN(C2(CNC(=O)c3c(N)cccc3Cl)CCC2)CC1 ; Cl] | GSP-1<br>$^1$H NMR (300 MHz, DMSO-$d_6$) δ 8.89 (t, J = 6.0 Hz, 1H), 7.08-7.06 (m, 1H), 6.68 (dd, J = 0.6, 8.1 Hz, 1H), 6.63 (dd J = 0.6, 8.1 Hz, 1H), 3.76-3.31 (m, 13H), 3.14-3.12 (m, 2H), 2.61-2.59 (m, 1H), 2.17-2.15 (m, 3H), 1.84-1.82 (m, 2H), 1.71-1.69 (m, 2H), 0.99 (t, J = 7.5 Hz, 3H); MS (ESI+) m/z 429 (M + H). |
| 79 | N-((1-(4-(Cyclopropylmethyl-sulfonyl)piperazin-1-yl)cyclohexyl)methyl)-4-fluoro-2-methoxy-6-methylbenzamide Hydrochloride | 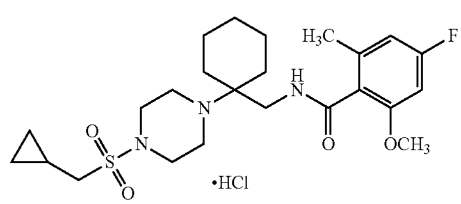 [SMILES: COc1cc(F)cc(C)c1C(=O)NCC1(N2CCN(S(=O)(=O)CC3CC3)CC2)CCCCC1 ; Cl] | GSP-1<br>$^1$H NMR (300 MHz, DMSO-$d_6$) δ 10.77 (bs, 1H), 8.63 (t, J = 5.7 Hz, 1H), 6.82 (d, J = 11.1 Hz, 1H), 6.69 (d, J = 9.6 Hz, 1H), 3.82-3.60 (m, 10H), 3.35 (s, 3H), 3.10 (d, J = 6.9 Hz, 2H), 2.19 (s, 3H), 2.10-2.05 (m, 2H), 1.95-1.87 (m, 2H), 1.72-1.45 (m, 5H), 1.22-0.95 (m, 2H), 0.57 (d, J = 7.8 Hz, 2H), 0.38 (d, J = 4.8 Hz, 2H); MS (APCI+) m/z 482 (M + H). |
| 80 | N-((1-(4-(Cyclopropylmethyl-sulfonyl)piperazin-1-yl)cyclohexyl)methyl)-2-fluoro-6-methylbenzamide Hydrochloride | 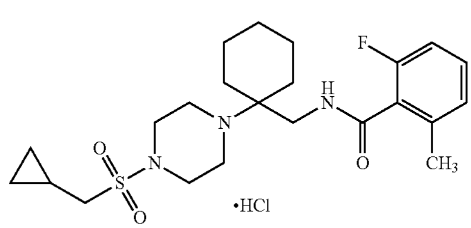 [SMILES: Cc1cccc(F)c1C(=O)NCC1(N2CCN(S(=O)(=O)CC3CC3)CC2)CCCCC1 ; Cl] | GSP-1<br>$^1$H NMR (300 MHz, DMSO-$d_6$) δ 10.75 (bs, 1H), 8.91 (t, J = 6.0 Hz, 1H), 7.40-7.32 (m, 1H), 7.15-7.03 (m, 2H), 3.87-3.60 (m, 10H), 3.10 (d, J = 6.9 Hz, 2H), 2.28 (s, 3H), 2.12-2.04 (m, 2H), 1.96-1.84 (m, 2H), 1.77-1.47 (m, 5H), 1.22-0.95 (m, 2H), 0.62-0.55 (m, 2H), 0.41-0.35 (m, 2H); MS (ESI+) m/z 452 (M + H). |

TABLE 1-continued

Examples, General Synthetic Procedures (GSP) and Spectral Data

| Cpd | Name | Structure | General Synthetic Procedure and Spectral Data |
|---|---|---|---|
| 81 | N-((1-(4-(Cyclopropylmethyl-sulfonyl)piperazin-1-yl)cyclohexyl)methyl)-2,6-difluorobenzamide Hydrochloride | 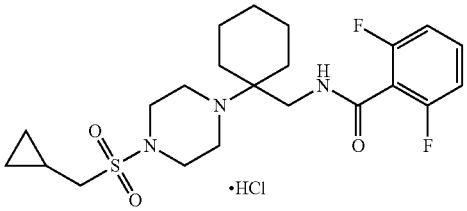 [SMILES: O=C(NCC1(N2CCN(S(=O)(=O)CC3CC3)CC2)CCCCC1)c1c(F)cccc1F ; Cl] | GSP-1<br>$^1$H NMR (300 MHz, DMSO-$d_6$) δ 10.86 (bs, 1H), 9.17 (t, J = 6.0 Hz, 1H), 7.60-7.48 (m, 1H), 7.21 (d, J = 8.1 Hz, 1H), 7.19 (d, J = 7.8 Hz, 1H), 3.83-3.40 (m, 10H), 3.11 (d, J = 6.9 Hz, 2H), 2.12-1.85 (m, 4H), 1.79-1.45 (m, 5H), 1.25-0.95 (m, 2H), 0.62-0.55 (m, 2H), 0.41-0.36 (m, 2H); MS (ESI+) m/z 456 (M + H). |
| 82 | N-((1-(4-(Cyclopropylmethyl-sulfonyl)piperazin-1-yl)cyclohexyl)methyl)-4-fluoro-2-methoxy-6-(methylthio)benzamide Hydrochloride | 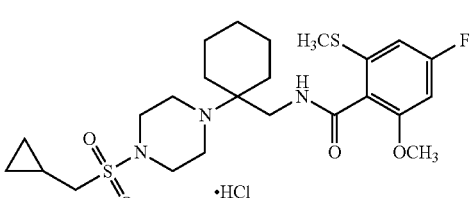 | GSP-1<br>$^1$H NMR (300 MHz, DMSO-$d_6$) δ 10.52 (bs, 1H), 8.68 (t, J = 6.0 Hz, 1H), 6.88-6.75 (m, 2H), 3.81-3.52 (m, 10H), 3.35 (s, 3H), 3.11 (d, J = 6.9 Hz, 2H), 2.44 (s, 3H), 2.18-2.05 (m, 2H), 1.95-1.45 (m, 7H), 1.22-0.95 (m, 2H), 0.62-0.55 (m, 2H), 0.40-0.35 (m, 2H); MS (ESI+) m/z 514 (M + H). |
| 83 | N-((1-(4-(Cyclopropylmethyl-sulfonyl)piperazin-1-yl)cyclohexyl)methyl)-2-fluoro-6-methoxybenzamide Hydrochloride | 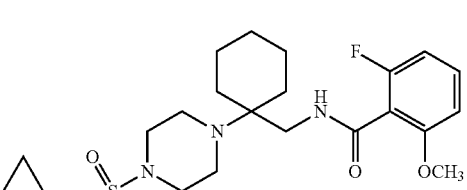 | GSP-1<br>$^1$H NMR (300 MHz, DMSO-$d_6$) δ 10.87 (bs, 1H), 8.88 (t, J = 6.0 Hz, 1H), 7.42 (q, J = 8.4 Hz, 1H), 6.94 (d, J = 8.4 Hz, 1H), 6.86 (t, J = 8.7 Hz, 1H), 3.86-3.61 (m, 10H), 3.38 (s, 3H), 3.10 (d, J = 6.9 Hz, 2H), 2.12-1.85 (m, 4H), 1.77-1.47 (m, 5H), 1.22-0.97 (m, 2H), 0.65-0.55 (m, 2H), 0.42-0.35 (m, 2H); MS (ESI+) m/z 468 (M + H). |
| 84 | 2,4-Dichloro-N-((1-(4-(cyclopropylmethyl-sulfonyl)piperazin-1-yl)cyclohexyl)methyl) benzamide Hydrochloride | 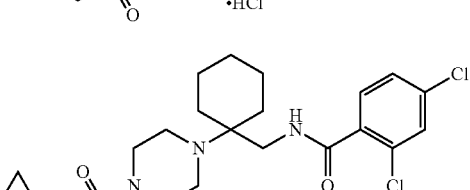 | GSP-1<br>NMR (300 MHz, DMSO-$d_6$) δ 11.01 (bs, 1H), 8.92 (t, J = 6.0 Hz, 1H), 7.72 (d, J = 1.2 Hz, 1H), 7.57-7.50 (m, 2H), 3.83-3.40 (m, 10H), 3.11 (d, J = 6.9 Hz, 2H), 2.12-1.85 (m, 4H), 1.77-1.46 (m, 5H), 1.22-0.95 (m, 2H), 0.62-0.55 (m, 2H), 0.42-0.35 (m, 2H); MS (ESI+) m/z 488 (M + H). |
| 85 | N-((1-(4-(Cyclopropylmethyl-sulfonyl)piperazin-1-yl)cycloheptyl)methyl)-4-fluoro-2-methylbenzamide Hydrochloride | 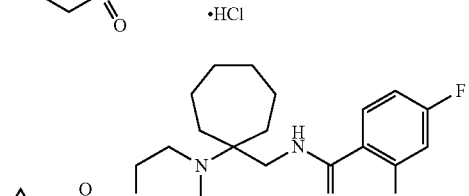 | GSP-2<br>$^1$H NMR (300 MHz, DMSO-$d_6$): δ 10.32-10.30 (m, 1H), 8.78-8.76 (m, 1H), 7.60 (dd, J = 6.0, 8.4 Hz), 1H), 7.15-7.05 (m, 2H), 3.75-3.71 (m, 8H), 3.22-3.20 (m, 2H), 3.13 (d, J = 7.2 Hz, 2H), 2.38 (s, 3H), 2.14-2.12 (m, 2H), 1.88-1.86 (m, 2H), 1.73-1.71 (m, 2H), 1.55-1.51 (m, 6H), 1.02-1.00 (m, 1H), 0.60-0.58 (m, 2H), 0.40-0.38 (m, 2H); MS (ESI+) m/z 466 (M + H). |
| 86 | N-((1-(4-(Cyclopropylmethyl-sulfonyl)piperazin-1-yl)cycloheptyl)methyl)-4-fluoro-2-methoxy-6-methylbenzamide Hydrochloride | 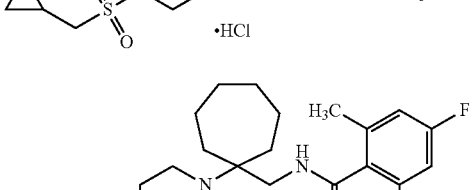 | GSP-2<br>$^1$H NMR (300 MHz, DMSO-$d_6$): δ 9.98-9.96 (m, 1H), 8.66-8.64 (m, 1H), 6.83 (d, J = 10.1, 1H), 6.69 (d, J = 10.1, 1H), 3.76 (s, 3H), 3.75-3.71 (m, 8H), 3.31-3.29 (m, 2H), 3.13 (d, J = 7.2 Hz, 2H), 2.20 (s, 3H), 2.10-2.08 (m, 2H), 1.90-1.88 (m, 2H), 1.73-1.71 (m, 2H), 1.55-1.51 (m, 6H), 1.02-1.00 (m, 1H), 0.59 (d, J = 8.1 Hz, 2H), 0.37 (d, J = 8.1 Hz, 2H); MS (ESI+) m/z 496 (M + H). |
| 87 | N-((1-(4-(Ethylsulfonyl)piperazin-1-yl)cycloheptyl)methyl)-4-fluoro-2-methoxy-6-methylbenzamide Hydrochloride | 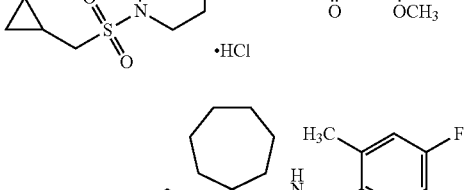 | GSP-2<br>$^1$H NMR (300 MHz, DMSO-$d_6$): δ 9.98-9.96 (m, 1H), 8.66-8.64 (m, 1H), 6.83 (d, J = 10.1, 1H), 6.69 (d, J = 10.1, 1H), 3.76 (s, 3H), 3.75-3.71 (m, 8H), 3.30-3.28 (m, 2H), 3.16 (q, J = 7.2 Hz, 2H), 2.18-2.16 (m, 2H), 1.93-1.91 (m, 2H), 1.77-1.75 (m, 2H), 1.55-1.51 (m, 6H), 1.24 (t, J = 7.2 Hz, 3H); MS (ESI+) m/z 470 (M + H). |

TABLE 1-continued

Examples, General Synthetic Procedures (GSP) and Spectral Data

| Cpd | Name | Structure | General Synthetic Procedure and Spectral Data |
|---|---|---|---|
| 88 | 2,6-Dichloro-N-((1-(4-(ethylsulfonyl)piperazin-1-yl)cycloheptyl)methyl)benzamide Hydrochloride | 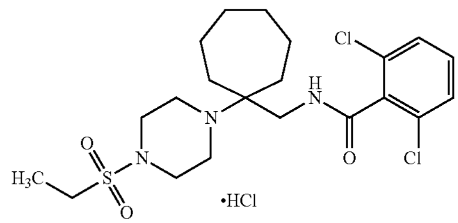 [SMILES: CCS(=O)(=O)N1CCN(C2(CNC(=O)c3c(Cl)cccc3Cl)CCCCCC2)CC1 ; Cl] | GSP-2<br>$^1$H NMR (300 MHz, DMSO-d$_6$): δ 10.42-10.40 (m, 1H), 9.14 (t, J = 6 Hz, 1H), 7.55-7.43 (m, 3H), 3.70-3.68 (m, 8H), 3.30-3.28 (m, 2H), 3.16 (q, J = 7.2 Hz, 2H), 2.18-2.16 (m, 2H), 1.93-1.91 (m, 2H), 1.77-1.75 (m, 2H), 1.55-1.51 (m, 6H), 1.24 (t, J = 7.2 Hz, 3H); MS (ESI+) m/z 477 (M + H). |
| 89 | 2-Amino-6-chloro-N-((1-(4-(phenylsulfonyl)piperazin-1-yl)cyclohexyl)methyl)benzamide Hydrochloride | 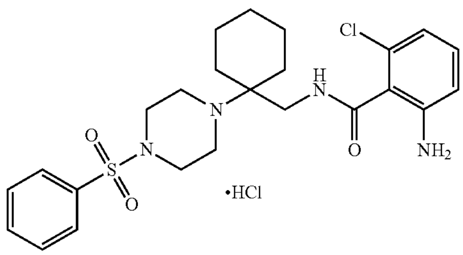 [SMILES: Nc1cccc(Cl)c1C(=O)NCC1(N2CCN(S(=O)(=O)c3ccccc3)CC2)CCCCC1 ; Cl] | GSP-3<br>1H NMR (300 MHz, DMSO-d6) δ 8.77 (bs, 1H), 7.80-7.66 (m, 5H), 7.12-7.06 (m, 1H), 6.73-6.65 (m, 2H), 3.88-3.28 (m, 8H), 3.30-2.76 (m, 2H), 2.16-1.91 (m, 2H), 1.86-1.37 (m, 7H), 1.15-1.00 (m, 1H); MS (APCI$^+$) m/z 491 (M + H). |
| 90 | 2-Amino-6-chloro-N-((1-(4-(methylsulfonyl)piperazin-1-yl)cyclohexyl)methyl)benzamide Hydrochloride | 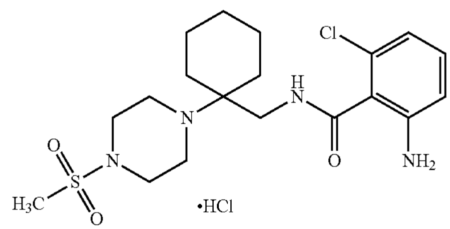 [SMILES: CS(=O)(=O)N1CCN(C2(CNC(=O)c3c(N)cccc3Cl)CCCCC2)CC1 ; Cl] | GSP-3<br>$^1$H NMR (300 MHz, DMSO-d$_6$) δ 8.80 (bs, 1H), 7.08 (t, J = 8.1 Hz, 1H), 6.72-6.64 (m, 2H), 6.23 (bs, 2H), 3.84-3.27 (m, 10H), 2.91 (s, 3H), 2.17-2.01 (m, 2H), 1.80-1.44 (m, 7H), 1.25-1.02 (m, 1H); MS (ESI$^+$) m/z 429 (M + H). |
| 91 | 2-Amino-6-chloro-N-((1-(4-(ethylsulfonyl)piperazin-1-yl)cyclohexyl)methyl)benzamide Hydrochloride | 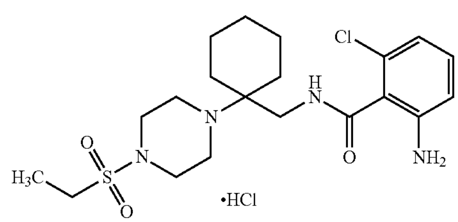 [SMILES: CCS(=O)(=O)N1CCN(C2(CNC(=O)c3c(N)cccc3Cl)CCCCC2)CC1 ; Cl] | GSP-3<br>$^1$H NMR (400 MHz, MeOH-d$_4$) δ 7.36 (d, J = 2.0 Hz, 1H), 7.18 (s, 1H), 7.09 (s, 1H), 4.04-3.82 (m, 6H), 3.55-3.33 (m, 4H), 3.15 (q, J = 7.4 Hz, 2H), 2.18 (d, J = 11.8 Hz, 2H), 1.93-1.72 (m, 5H), 1.70-1.54 (m, 2H), 1.34 (t, J = 7.6 Hz, 3H), 1.30-1.25 (m, 1H); MS (ESI$^+$) m/z 443 (M + H). |
| 92 | 2-Amino-6-chloro-N-((1-(4-(isobutylsulfonyl)piperazin-1-yl)cyclohexyl)methyl)benzamide Hydrochloride | 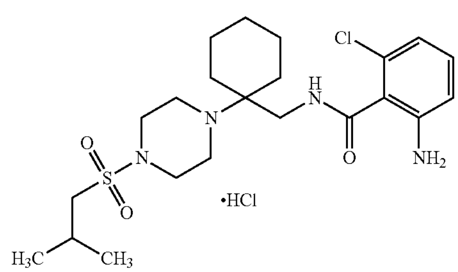 [SMILES: CC(C)CS(=O)(=O)N1CCN(C2(CNC(=O)c3c(N)cccc3Cl)CCCCC2)CC1 ; Cl] | GSP-3<br>$^1$H NMR (300 MHz, DMSO-d$_6$) δ 8.79 (s, 1H), 7.07 (t, J = 7.8 Hz, 1H), 6.66 (q, J = 8.1 Hz, 2H), 5.78 (bs, 2H), 3.88-3.18 (m, 10H), 2.98 (d, J = 6.6 Hz, 2H), 2.25-2.06 (m, 3H), 1.98-1.39 (m, 7H), 1.23-1.08 (m, 1H), 1.03 (d, J = 6.6 Hz, 6H); MS (APCI$^+$) m/z 471 (M + H). |
| 93 | 2,4-Dichloro-N-((1-(4-(cyclobutylsulfonyl)piperazin-1-yl)cyclohexyl)methyl)benzamide Hydrochloride | 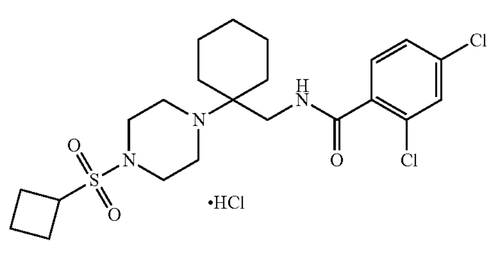 [SMILES: O=C(NCC1(N2CCN(S(=O)(=O)C3CCC3)CC2)CCCCC1)c1ccc(Cl)cc1Cl ; Cl] | GSP-1<br>$^1$H NMR (300 MHz, DMSO-d$_6$) δ 10.57 (bs, 1H), 8.87 (t, J = 5.7 Hz, 1H), 7.73 (s, 1H), 7.53 (d, J = 0.6 Hz, 2H), 4.10 (quintet, J = 8.4 Hz, 1H), 3.80-3.51 (m, 8H), 3.30-3.05 (m, 2H), 2.40-2.18 (m, 4H), 2.12-1.45 (m, 12H); MS (ESI$^+$) m/z 488 (M + H). |

TABLE 1-continued

Examples, General Synthetic Procedures (GSP) and Spectral Data

| Cpd | Name | Structure | General Synthetic Procedure and Spectral Data |
|---|---|---|---|
| 94 | 2,4-Dimethyl-N-((1-(4-(1-methyl-1H-imidazol-4-ylsulfonyl)piperazin-1-yl)cyclohexyl)methyl)benzamide Hydrochloride | 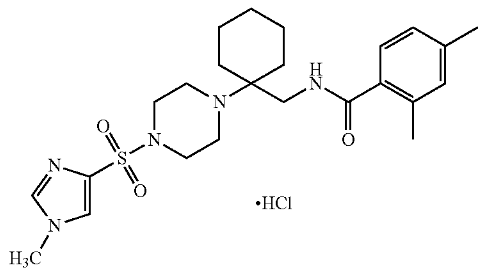 [SMILES: Cc1ccc(C(=O)NCC2(N3CCN(S(=O)(=O)c4cn(C)cn4)CC3)CCCCC2)c(C)c1 ; Cl] | GSP-2<br>$^1$H NMR (400 MHz, DMSO-$d_6$) δ 9.98 (bs, 1H), 8.52 (s, 1H), 7.90 (d, J = 12.0 Hz, 2H), 7.31 (d, J = 7.6 Hz, 1H), 7.07 (d, J = 9.2 Hz, 2H), 3.77-3.67 (m, 9H), 3.35-3.13 (m, 4H), 2.31 (s, 3H), 2.30 (s, 3H), 1.99 (d, J = 12.0 Hz, 2H), 1.82-1.48 (m, 7H), 1.17-1.02 (m, 1H); MS (ESI$^+$) m/z 474 (M + H). |
| 95 | 2,6-Dimethyl-N-((1-(4-(1-methyl-1H-imidazol-4-ylsulfonyl)piperazin-1-yl)cyclohexyl)methyl)benzamide Hydrochloride | 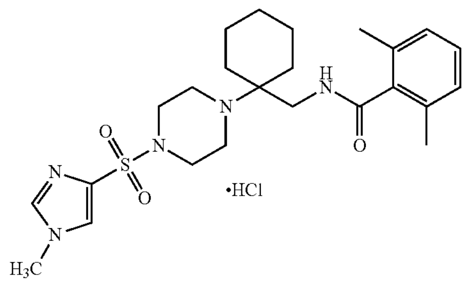 [SMILES: Cc1cccc(C)c1C(=O)NCC1(N2CCN(S(=O)(=O)c3cn(C)cn3)CC2)CCCCC1 ; Cl] | GSP-2<br>$^1$H NMR (400 MHz, DMSO-$d_6$) δ 9.86 (bs, 1H), 8.52 (s, 1H), 7.90 (d, J = 10.0 Hz, 2H), 7.19 (t, J = 7.6 Hz, 1H), 7.06 (d, J = 7.2 Hz, 2H), 3.77 (d, J = 7.2 Hz, 2H), 3.74-3.63 (m, 5H), 3.40-3.26 (m, 4H), 3.14-2.98 (m, 4H), 2.22 (s, 6H), 2.05-1.93 (m, 2H), 1.80-1.50 (m, 7H), 1.18-1.03 (m, 1H); MS (ESI$^+$) m/z 474 (M + H). |
| 96 | 2-Fluoro-6-methoxy-N-((1-(4-(1-methyl-1H-imidazol-4-ylsulfonyl)piperazin-1-yl)cyclohexyl)methyl)benzamide Hydrochloride | 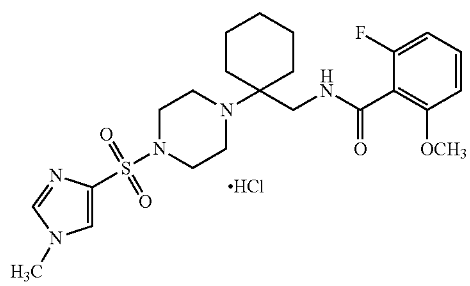 [SMILES: COc1cccc(F)c1C(=O)NCC1(N2CCN(S(=O)(=O)c3cn(C)cn3)CC2)CCCCC1 ; Cl] | GSP-2<br>$^1$H NMR (300 MHz, DMSO-$d_6$) δ 9.59 (bs, 1H), 8.85 (s, 1H), 7.91 (d, J = 6.9 Hz, 2H), 7.47-7.39 (m, 1H), 6.96 (d, J = 8.4 Hz, 1H), 6.88 (d, J = 8.7 Hz, 1H), 3.81 (s, 3H), 3.76-3.62 (m, 9H), 3.44-3.27 (m, 2H), 3.14-2.96 (m, 2H), 2.11-1.98 (m, 2H), 1.76-1.42 (m, 7H), 1.15-1.01 (m, 1H); MS (ESI$^+$) m/z 494 (M + H). |
| 97 | 2,4-Dichloro-N-((1-(4-(1-methyl-1H-imidazol-4-ylsulfonyl)piperazin-1-yl)cyclohexyl)methyl)benzamide Hydrochloride | 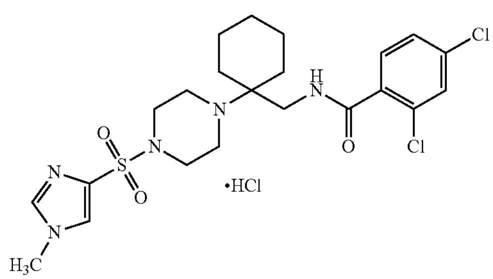 [SMILES: Cn1cnc(S(=O)(=O)N2CCN(C3(CNC(=O)c4ccc(Cl)cc4Cl)CCCCC3)CC2)c1 ; Cl] | GSP-2<br>$^1$H NMR (300 MHz, DMSO-$d_6$) δ 10.14 (bs, 1H), 8.86 (s, 1H), 7.89 (d, J = 8.4 Hz, 2H), 7.73 (s, 1H), 7.52 (s, 2H), 3.79-3.58 (m, 9H), 3.42-3.07 (m, 4H), 2.11-1.94 (m, 2H), 1.87-1.41 (m, 7H), 1.21-0.99 (m, 1H); MS (ESI$^+$) m/z 514 (M + H). |
| 98 | 2,6-Difluoro-N-((1-(4-(1-methyl-1H-imidazol-4-ylsulfonyl)piperazin-1-yl)cyclohexyl)methyl)benzamide Hydrochloride | 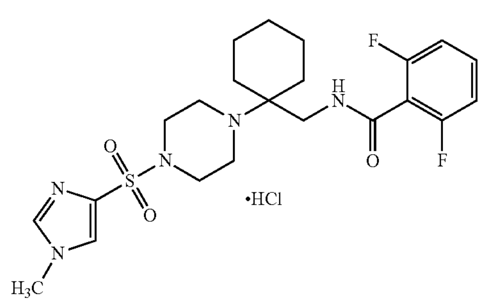 [SMILES: Cn1cnc(S(=O)(=O)N2CCN(C3(CNC(=O)c4c(F)cccc4F)CCCCC3)CC2)c1 ; Cl] | GSP-2<br>$^1$H NMR (300 MHz, DMSO-$d_6$) δ 10.30 (bs, 1H), 9.12 (s, 1H), 7.89 (dd, J = 1.2 Hz, J = 7.5 Hz, 2H), 7.61-7.51 (m, 1H), 7.21 (t, J = 7.8 Hz, 2H), 3.83-3.57 (m, 9H), 3.36-3.10 (m, 4H), 2.08-1.92 (m, 2H), 1.87-1.41 (m, 7H), 1.18-0.98 (m, 1H); MS (ESI$^+$) m/z 482 (M + H). |

TABLE 1-continued

Examples, General Synthetic Procedures (GSP) and Spectral Data

| Cpd | Name | Structure | General Synthetic Procedure and Spectral Data |
|---|---|---|---|
| 99 | 2-Amino-6-chloro-N-((1-(4-(1-methyl-1H-imidazol-4-ylsulfonyl)piperazin-1-yl)cyclohexyl)methyl)benzamide Hydrochloride | 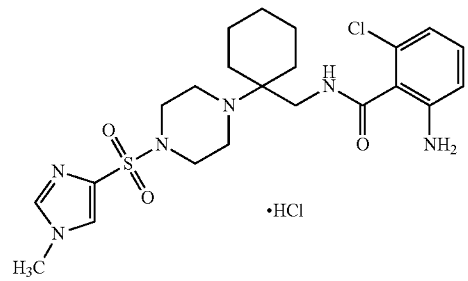 [SMILES: Cn1cnc(S(=O)(=O)N2CCN(C3(CNC(=O)c4c(N)cccc4Cl)CCCCC3)CC2)c1 ; Cl] | GSP-2<br>$^1$H NMR (300 MHz, DMSO-$d_6$) δ 8.79 (s, 1H), 7.90 (d, 5.4 Hz, 2H), 7.09 (t, J = 7.8 Hz, 1H), 6.71-6.64 (m, 2H), 3.83-3.53 (m, 9H), 3.47-3.28 (m, 2H), 3.28-3.21 (m, 2H), 2.14-1.96 (m, 2H), 1.86-1.42 (m, 7H), 1.19-0.98 (m, 1H); MS (ESI$^+$) m/2 495 (M + H). |
| 100 | 2,4-Difluoro-N-((1-(4-(1-methyl-1H-imidazol-4-ylsulfonyl)piperazin-1-yl)cyclohexyl)methyl)benzamide Hydrochloride | 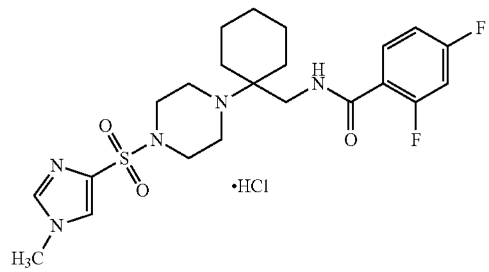 [SMILES: Cn1cnc(S(=O)(=O)N2CCN(C3(CNC(=O)c4ccc(F)cc4F)CCCCC3)CC2)c1 ; Cl] | GSP-1<br>$^1$H NMR (300 MHz, DMSO-$d_6$) δ 10.61 (bs, 1H), 8.75 (t, J = 6.0 Hz, 1H), 7.91 (d, J = 1.2 Hz, 1H), 7.88 (d, J = 0.9 Hz, 1H), 7.77-7.69 (m, 1H), 7.44-7.36 (m, 1H), 7.20 (dd, J = 8.1 Hz, 2.1 Hz, 1H), 3.73 (s, 3H), 3.73-3.60 (m, 6H), 3.35-3.17 (m, 4H), 2.08-1.48 (m, 9H), 1.15-1.03 (m, 1H); MS (APCI+) m/z 482 (M + H). |
| 101 | 2-Chloro-4-fluoro-N-((1-(4-(1-methyl-1H-imidazol-4-ylsulfonyl)piperazin-1-yl)cyclohexyl)methyl)benzamide Hydrochloride | 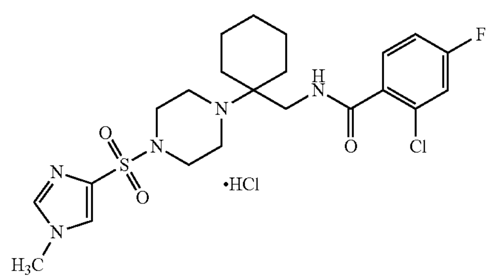 [SMILES: Cn1cnc(S(=O)(=O)N2CCN(C3(CNC(=O)c4ccc(F)cc4Cl)CCCCC3)CC2)c1 ; Cl] | GSP-1<br>$^1$H NMR (300 MHz, DMSO-$d_6$) δ 10.32 (bs, 1H), 8.83 (t, J = 6.0 Hz, 1H), 7.90 (d, J = 0.9 Hz, 1H), 7.88 (s, 1H), 7.63-7.53 (m, 2H), 7.32 (dd, J = 8.4 Hz, 2.7 Hz, 1H), 3.73 (s, 3H), 3.73-3.61 (m, 6H), 3.37-3.13 (m, 4H), 2.11-1.45 (m, 9H), 1.17-1.03 (m, 1H); MS (APCI+) m/z 499 (M + H). |
| 102 | 4-Fluoro-2-methyl-N-((1-(4-(1-methyl-1H-imidazol-4-ylsulfonyl)piperazin-1-yl)cyclohexyl)methyl)benzamide Hydrochloride | 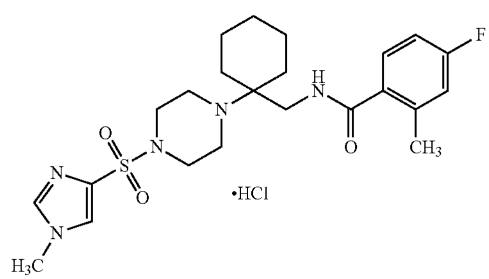 [SMILES: Cc1cc(F)ccc1C(=O)NCC1(N2CCN(S(=O)(=O)c3cn(C)cn3)CC2)CCCCC1 ; Cl] | GSP-1<br>$^1$H NMR (300 MHz, DMSO-$d_6$) δ 10.18 (bs, 1H), 8.62 (t, J = 6.0 Hz, 1H), 7.90 (s, 1H), 7.88 (s, 1H), 7.48 (dd, J = 8.4 Hz, 6.0 Hz, 1H), 7.17-7.05 (m, 2H), 3.72 (s, 3H), 3.72-3.61 (m, 6H), 3.37-3.10 (m, 4H), 2.35 (s, 3H), 2.08-1.45 (m, 9H), 1.20-1.01 (m, 1H); MS (APCI+) m/z 478 (M + H). |
| 103 | 4-Fluoro-2-methoxy-6-methyl-N-((1-(4-(1-methyl-1H-imidazol-4-ylsulfonyl)piperazin-1-yl)cyclopentyl)methyl)benzamide Hydrochloride | 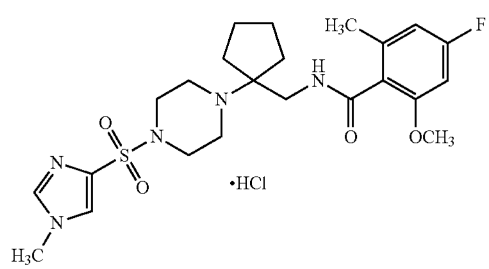 [SMILES: COc1cc(F)cc(C)c1C(=O)NCC1(N2CCN(S(=O)(=O)c3cn(C)cn3)CC2)CCCC1 ; Cl] | GSP-1<br>$^1$H NMR (300 MHz, DMSO-$d_6$): δ 10.25 (bs, 1H), 8.63 (bs, 1H), 7.91 (dd, J = 7.2, 1.2 Hz, 2H), 6.84 (dd, J = 11.4, 2.1 Hz, 1H), 6.70 (dd J = 9.6, 2.1 Hz, 1H), 3.76 (s, 3H), 3.73 (s, 3H), 3.66 (s, 2H), 3.54 (s, 4H), 3.06-3.09 (m, 2H), 2.18 (s, 2H), 1.92 (bs, 4H), 1.73 (bs, 4H); MS (ESI+) m/z 493 (M + H); MS (APCI+) m/z 494 (M + H). |

TABLE 1-continued

Examples, General Synthetic Procedures (GSP) and Spectral Data

| Cpd | Name | Structure | General Synthetic Procedure and Spectral Data |
|---|---|---|---|
| 104 | 2,6-Difluoro-N-((1-(4-(1-methyl-1H-imidazol-4-ylsulfonyl)piperazin-1-yl)cyclopentyl)methyl)benzamide Hydrochloride | 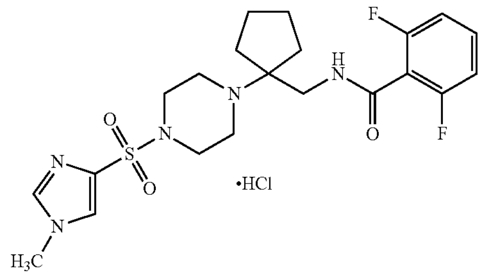 [SMILES: Cn1cnc(S(=O)(=O)N2CCN(C3(CNC(=O)c4c(F)cccc4F)CCCC3)CC2)c1 ; Cl] | GSP-1<br>$^1$H NMR (300 MHz, DMSO-$d_6$): δ 10.92 (bs, 1H), 9.17 (bs, 1H), 7.89 (dd, J = 6.9, 1.2 Hz, 2H), 7.51-7.61 (m, 1H), 7.21 (t, J = 11.1 Hz, 2H), 4.46 (s, 3H), 3.61-3.69 (m, 4H), 3.50-3.54 (m, 2H), 3.38-3.42 (m, 2H), 3.16-3.24 (m, 2H), 2.04-2.08 (m, 2H), 1.90-1.92 (m, 2H), 1.72 (bs, 4H); MS (ESI+) m/z 467 (M + H); MS (APCI+) m/z 468 (M + H). |
| 105 | 2,6-Difluoro-N-((1-(4-(1-methyl-1H-imidazol-4-ylsulfonyl)piperazin-1-yl)cyclopentyl)methyl)benzamide Hydrochloride | 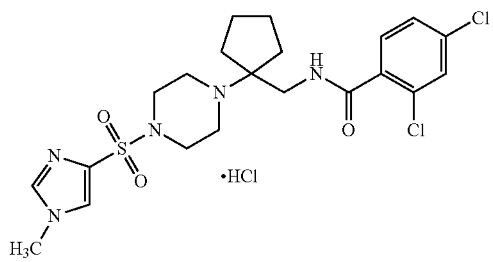 [SMILES: Cn1cnc(S(=O)(=O)N2CCN(C3(CNC(=O)c4ccc(Cl)cc4Cl)CCCC3)CC2)c1 ; Cl] | GSP-1<br>$^1$H NMR (300 MHz, DMSO-$d_6$): δ 10.79 (bs, 1H), 8.93 (bs, 1H), 7.91 (d, J = 0.9 Hz, 2H), 7.88 (s, 1H), 7.52 (d, J = 1.5 Hz, 2H), 3.70 (s, 3H), 3.56-3.58 (m, 4H), 3.36-3.39 (m, 2H), 3.14-3.18 (m, 4H), 1.89-2.07 (m, 4H), 1.73 (s, 4H); MS (ESI+) m/z 500 (M + H); MS (APCI+) m/z 501 (M + H). |
| 106 | 2,6-Dichloro-N-((1-(4-(1-methyl-1H-imidazol-4-ylsulfonyl)piperazin-1-yl)cycloheptyl)methyl)benzamide Hydrochloride | 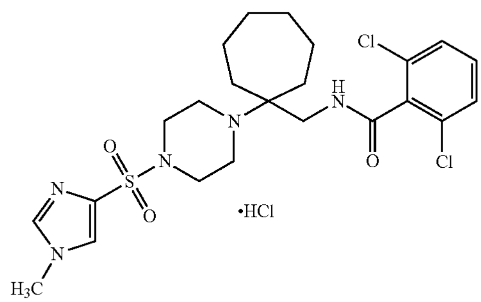 [SMILES: Cn1cnc(S(=O)(=O)N2CCN(C3(CNC(=O)c4c(Cl)cccc4Cl)CCCCCC3)CC2)c1 ; Cl] | GSP-1<br>$^1$H NMR (300 MHz, DMSO-$d_6$) δ 10.02 (bs, 1H), 9.10 (t, J = 5.8 Hz, 1H), 7.91 (d, J = 1.2 Hz, 2 H) 7.55-7.42 (m, 3H), 3.72 (s, 3H), 3.70-3.58 (m, 6H) 3.38-3.20 (m, 4H), 2.10-2.0 (m, 2H), 1.90-1.78 (m, 2H), 1.75-1.60 (m, 2H), 1.60-1.40 (m, 6H); MS (ESI+) m/z 528 (M + H). |
| 107 | 2,6-Difluoro-N-((1-(4-(1-methyl-1H-imidazol-4-ylsulfonyl)piperazin-1-yl)cycloheptyl)methyl)benzamide Hydrochloride | 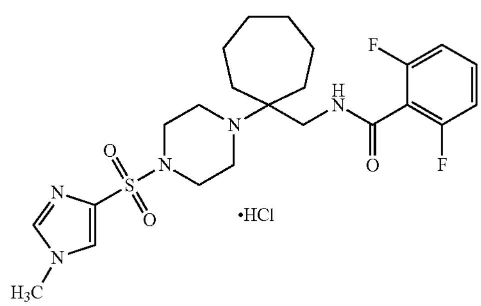 [SMILES: Cn1cnc(S(=O)(=O)N2CCN(C3(CNC(=O)c4c(F)cccc4F)CCCCCC3)CC2)c1 ; Cl] | GSP-1<br>$^1$H NMR (300 MHz, DMSO-$d_6$) δ 9.80 (bs, 1H), 9.16 (bs, 1H), 7.90 (d, J = 8.4 Hz, 2 H) 7.60-7.50 (m, 1H), 7.22-7.12 (m, 2H), 3.72 (s, 3H), 3.70-3.60 (m, 6H) 3.32-3.12 (m, 4H), 2.10-2.0 (m, 2H), 1.90-1.78 (m, 2H), 1.75-1.60 (m, 2H), 1.60-1.40 (m, 6H); MS (ESI+) m/z 496 (M + H). |
| 108 | 2,6-Difluoro-N-((1-(4-(1-methyl-1H-1,2,3-triazol-4-ylsulfonyl)piperazin-1-yl)cyclopentyl)methyl)benzamide Hydrochloride | 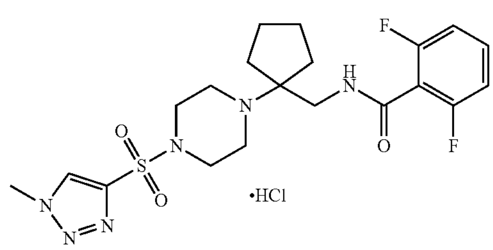 | GSP-1<br>$^1$H NMR (300 MHz, CD$_3$OD) δ 8.56 (s, 1H), 7.63-7.47 (m, 1H), 7.17-7.03 (m, 2H), 4.16 (s, 3H), 4.10-3.95 (m, 2H), 3.81-3.52 (m, 6H), 3.25-3.05 (m, 2H), 2.19-1.76 (m, 8H); MS (APCI$^+$) m/z 469 (M + H). |

TABLE 1-continued

Examples, General Synthetic Procedures (GSP) and Spectral Data

| Cpd | Name | Structure | General Synthetic Procedure and Spectral Data |
|---|---|---|---|
| 109 | 2,6-Dichloro-N-((1-(4-(1-methyl-1H-1,2,3-triazol-4-ylsulfonyl)piperazin-1-yl)cyclopentyl)methyl)benzamide Hydrochloride | 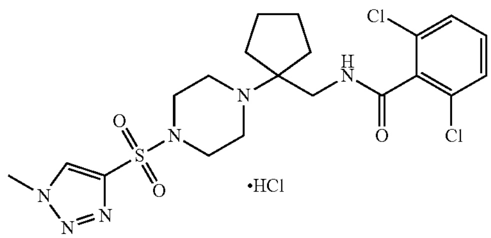 | GSP-1<br>$^1$H NMR (300 MHz, DMSO-d$_6$) δ 10.15 (bs, 1H), 9.08 (bs, 1H), 8.88 (s, 1H), 7.71-7.37 (m, 3H), 4.14 (s, 3H), 3.83-3.70 (m, 2H), 3.70-3.49 (m, 6H), 3.22-2.98 (m, 2H), 2.08-1.43 (m, 8H); MS (APCI$^+$) m/z 501 (M + H). |
| 110 | 2,4-Dichloro-N-((1-(4-(1-methyl-1H-1,2,3-triazol-4-ylsulfonyl)piperazin-1-yl)cyclopentyl)methyl)benzamide Hydrochloride | 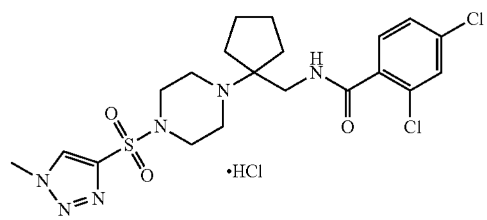 [SMILES: Cn1cc(S(=O)(=O)N2CCN(C3(CNC(=O)c4ccc(Cl)cc4Cl)CCCC3)CC2)nn1 ; Cl] | GSP-1<br>$^1$H NMR (300 MHz, DMSO-d$_6$) δ 10.35 (bs, 1H), 8.88 (bs, 1H), 8.40 (bs, 1H), 7.73 (s, 1H), 7.55-7.50 (m, 2H), 4.14 (s, 3H), 3.83-3.70 (m, 2H), 3.66-3.43 (m, 6H), 3.25-3.03 (m, 2H), 2.07-1.84 (m, 4H), 1.81-1.65 (m, 4H); MS (APCI$^+$) m/z 501 (M + H). |
| 111 | 2,4-Difluoro-N-((1-(4-(1-methyl-1H-1,2,3-triazol-4-ylsulfonyl)piperazin-1-yl)cyclopentyl)methyl)benzamide Hydrochloride | 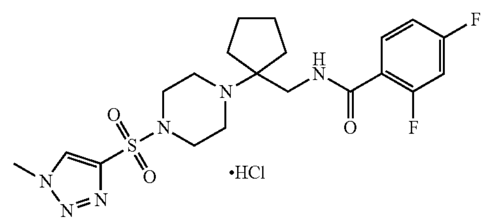 [SMILES: Cn1cc(S(=O)(=O)N2CCN(C3(CNC(=O)c4ccc(F)cc4F)CCCC3)CC2)nn1 ; Cl] | GSP-1<br>$^1$H NMR (300 MHz, DMSO-d$_6$): δ 10.09 (bs, 1H), 8.89 (bs, 1H), 8.74 (bs, 1H), 7.78-7.62 (m, 1H), 7.47-7.35 (m, 1H), 7.27-7.15 (m, 1H), 4.14 (s, 3H), 3.83-3.70 (m, 2H), 3.66-3.43 (m, 6H), 3.20-2.90 (m, 2H), 2.06-1.44 (m, 8H); MS (APCI$^+$) m/z 469 (M + H). |
| 112 | 4-Fluoro-2-methoxy-6-methyl-N-((1-(4-(1-methyl-1H-1,2,3-triazol-4-ylsulfonyl)piperazin-1-yl)cyclopentyl)methyl)benzamide Hydrochloride | 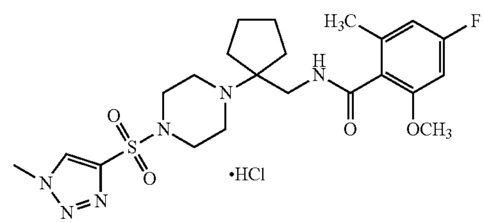 [SMILES: COc1cc(F)cc(C)c1C(=O)NCC1(N2CCN(S(=O)(=O)c3cn(C)nn3)CC2)CCCC1 ; Cl] | GSP-1<br>$^1$H NMR (300 MHz, DMSO-d$_6$): δ 10.22 (bs, 1H), 8.88 (s, 1H), 8.64 (bs, 1H), 6.85-6.82 (m, 1H), 6.72-6.69 (m, 1H), 4.14 (s, 3H), 3.84-3.70 (m, 5H), 3.64-3.47 (m, 6H), 3.19-3.03 (m, 2H), 2.18 (s, 3H), 2.02-1.85 (m, 4H), 1.79-1.65 (m, 4H); MS (APCI$^+$) m/z 495 (M + H). |
| 113 | 4-Fluoro-2-methoxy-N-((1-(4-(1-methyl-1H-1,2,3-triazol-4-ylsulfonyl)piperazin-1-yl)cyclopentyl)methyl)-6-(methylthio)benzamide Hydrochloride | 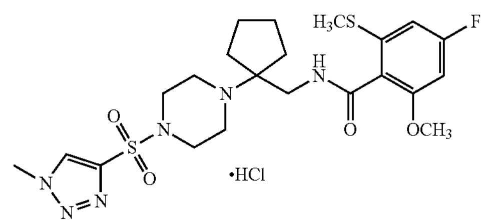 | GSP-1<br>$^1$H NMR (300 MHz, DMSO-d$_6$) δ 9.87 (bs, 1H), 8.76 (s, 1H), 8.61 (bs, 1H), 6.92-6.71 (m, 2H), 4.14 (s, 3H), 3.87-3.69 (m, 5H), 3.62-3.45 (m, 6H), 3.17-2.89 (m, 2H), 2.45 (s, 3H), 2.10-1.38 (m, 8H); MS (APCI$^+$) m/z 527 (M + H). |
| 114 | 2,6-Difluoro-N-((1-(4-(1-methyl-1H-1,2,3-triazol-4-ylsulfonyl)piperazin-1-yl)cyclohexyl)methyl)benzamide Hydrochloride | 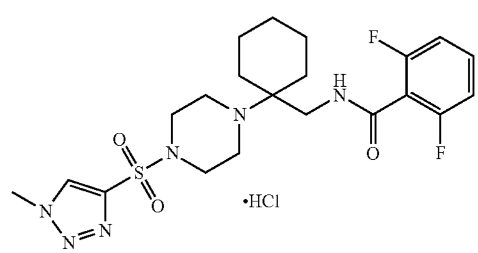 [SMILES: Cn1cc(S(=O)(=O)N2CCN(C3(CNC(=O)c4c(F)cccc4F)CCCCC3)CC2)nn1 ; Cl] | GSP-1<br>$^1$H NMR (300 MHz, DMSO-d$_6$): δ 10.50 (bs, 1H), 9.16 (bs, 1H), 8.87 (s, 1H), 7.59-7.54 (m, 1H), 7.24-7.19 (m, 2H), 4.14 (s, 3H), 3.78-3.67 (m, 6H), 3.34-3.19 (m, 4H), 2.08-1.46 (m, 9H), 1.14-1.06 (m, 1H); MS (APCI+) m/z 483 (M + H). |

TABLE 1-continued

Examples, General Synthetic Procedures (GSP) and Spectral Data

| Cpd | Name | Structure | General Synthetic Procedure and Spectral Data |
|---|---|---|---|
| 115 | 2-Amino-6-chloro-N-((2-(4-(propylsulfonyl)piperazin-1-yl)-2,3-dihydro-1H-inden-2-yl)methyl)benzamide Hydrochloride | 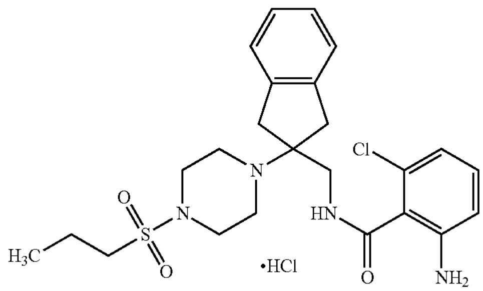 [SMILES: CCCS(=O)(=O)N1CCN(C2(CNC(=O)c3c(N)cccc3Cl)Cc3ccccc3C2)CC1 ; Cl] | GSP-1<br>$^1$H NMR (300 MHz, DMSO-d$_6$) δ 8.93-8.91 (m, 1H), 7.23-7.21 (m, 4H), 7.06-7.04 (m, 1H), 6.64-6.62 (m, 2H), 3.69-3.57 (m, 13H), 3.32 (d, J = 16.2 Hz, 2H), 3.12 (dd, J = 7.5, 9.6 Hz), 1.72-1.70 (m, 2H), 0.99 (t, J = 7.5 Hz, 3H); MS (ESI+) m/z 491 (M + H). |
| 116 | 2-Amino-6-chloro-N-((1-methyl-4-(4-(propylsulfonyl)piperazin-1-yl)piperidin-4-yl)methyl)benzamide Hydrochloride | 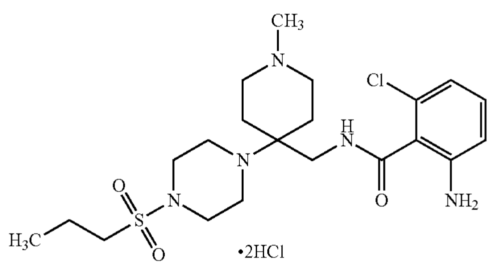 [SMILES: CCCS(=O)(=O)N1CCN(C2(CNC(=O)c3c(N)cccc3Cl)CCN(C)CC2)CC1 ; "·2HCl"] | GSP-1<br>$^1$H NMR (400 MHz, DMSO-d$_6$) δ 7.16-7.14 (m, 1H), 6.73-6.71 (m, 2H), 3.89 (d, J = 8 Hz, 2H), 3.53-3.51 (m, 4H), 3.50-3.48 (m, 4H), 3.35-3.33 (m, 2H), 3.12-3.10 (m, 2H), 2.88-2.86 (m, 2H), 2.78 (d, J = 4 Hz, 3H), 2.48-2.28 (m, 4H), 1.72-1.70 (m, 2H), 0.99 (dd, J = 3.2, 7.2 Hz, 6H); MS (ESI+) 472 (M + H). |
| 117 | N-((1-(4-(Cyclopropylmethyl-sulfonyl)-3-methylpiperazin-1-yl)cyclohexyl)methyl)-2,6-difluorobenzamide Hydrochloride | 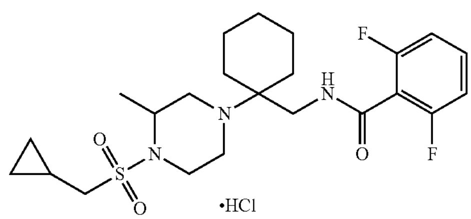 [SMILES: CC1CN(C2(CNC(=O)c3c(F)cccc3F)CCCCC2)CCN1S(=O)(=O)CC1CC1 ; Cl] | GSP-1<br>$^1$H NMR (300 MHz, DMSO-d$_6$) δ 10.71 (bs, 0.4H), 9.52 (bs, 0.6H), 9.27 (t, J = 6.0 Hz, 0.6H), 9.21 (t, J = 6.0 Hz, 0.4H), 7.62-7.51 (m, 1H), 7.22 (t, J = 7.8 Hz, 2H), 4.31-4.20 (m, 1H), 3.95-3.45 (m, 6H), 3.25-3.01 (m, 4H), 2.20-1.45 (m, 10H), 1.40-0.91 (m, 4H), 0.65-0.52 (m, 2H), 0.45-0.28 (m, 2H); MS (APCI$^+$) m/z 470 (M + H). |
| 118 | 2,4-Dichloro-N-((4-(4-(propylsulfonyl)piperazin-1-yl)tetrahydro-2H-pyran-4-yl)methyl)benzamide Hydrochloride | 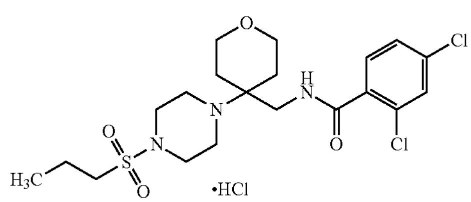 [SMILES: CCCS(=O)(=O)N1CCN(C2(CNC(=O)c3ccc(Cl)cc3Cl)CCOCC2)CC1 ; Cl] | GSP-1<br>$^1$H NMR (400 MHz, DMSO-d$_6$): δ 10.55 (bs, 1H), 8.934 (s, 1H), 7.74 (s, 1H), 7.55 (m, 2H ), 3.95-3.80 (m, 4H) 3.80-3.40 (m, 8H), 3.42-3.25 (m, 2H ), 3.25-3.15 (m, 2H), 225-2.00 (m, 2H), 2.00-1.8 (m, 2 H), 1.70 (m, 2H), 0.9 (t, J = 7.2 Hz, 3H); MS (ESI$^+$) m/z 479 (M + H). |
| 119 | 2,6-Dichloro-N-((4-(4-(propylsulfonyl)piperazin-1-yl)tetrahydro-2H-pyran-4-yl)methyl)benzamide Hydrochloride | 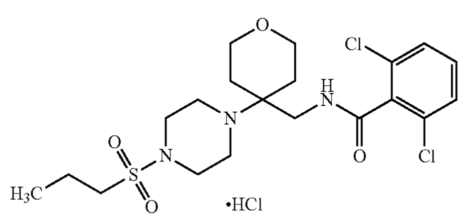 [SMILES: CCCS(=O)(=O)N1CCN(C2(CNC(=O)c3c(Cl)cccc3Cl)CCOCC2)CC1 ; Cl] | GSP-1<br>$^1$H NMR (300 MHz, DMSO-d$_6$): δ 10.8 (s, 1H), 9.10-9.12 (m, 1H), 7.45-7.57 (m, 3H), 4.08 (s, 4H), 3.89-3.92 (d, J = 9 Hz, 6H), 3.65-3.73 (m, 4H), 3.22-3.25 (m, 2H), 2.27-2.30 (m, 2H), 2.0-2.18 (m, 2H), 1.64-1.76 (m, 2H), 0.96-1.01 (t, J = 7.2 Hz, 3H); MS (ESI+) m/z 477 (M + H). |
| 120 | 2,6-Dimethyl-N-((4-(4-(propylsulfonyl)piperazin-1-yl)tetrahydro-2H-pyran-4-yl)methyl)benzamide Hydrochloride | 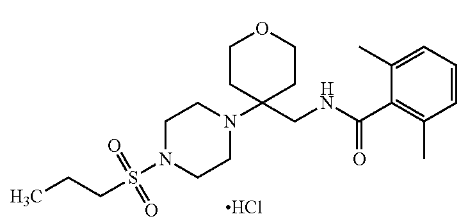 [SMILES: CCCS(=O)(=O)N1CCN(C2(CNC(=O)c3c(C)cccc3C)CCOCC2)CC1 ; Cl] | GSP-1<br>$^1$H NMR (300 MHz, DMSO-d$_6$) δ 10.75 (bs, 1H), 8.65 (bs, 1H), 7.17-7.25 (m, 1H), 7.06-7.08 (m, 2H), 3.85-3.92 (m, 4H), 3.68-3.74 (m, 6H), 3.52-3.56 (m, 2H), 3.31-3.37 (m, 2H), 3.09-3.14 (m, 2H), 2.21 (s, 6H), 2.10-2.14 (m, 2H), 1.90-1.99 (m, 2H), 1.65-1.74 (m, 2H), 0.99 (t, J = 6.6 Hz, 3H); MS (ESI+) m/z 436 (M + H). |

TABLE 1-continued

Examples, General Synthetic Procedures (GSP) and Spectral Data

| Cpd | Name | Structure | General Synthetic Procedure and Spectral Data |
|---|---|---|---|
| 121 | 4-Fluoro-2-methoxy-6-methyl-N-((4-(4-(propylsulfonyl)piperazin-1-yl)tetrahydro-2H-pyran-4-yl)methyl)benzamide Hydrochloride | 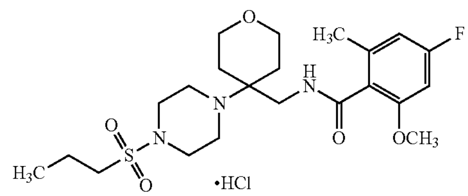 [SMILES: CCCS(=O)(=O)N1CCN(C2(CNC(=O)c3c(C)cc(F)cc3OC)CCOCC2)CC1 ; Cl] | GSP-1<br>$^1$H NMR (300 MHz, DMSO-d$_6$) δ 10.77 (bs, 1H), 8.69-8.73 (m, 1H), 6.82-6.86 (m, 1H), 6.70-6.73 (m, 1H), 3.81-3.89 (m, 4H), 3.78 (s, 3H), 3.61-3.69 (m, 8H), 3.48-3.57 (m, 2H), 3.09-3.17 (m, 2H), 2.18 (s, 3H), 2.10-2.15 (m, 2H), 1.94-1.98 (m, 2H), 1.67-1.77 (m, 2H), 0.98 (t, J = 6.6 Hz, 3H); MS (ESI+) m/z 470 (M + H). |
| 122 | 4-Fluoro-2-methoxy-6-(methylthio)-N-((4-(4-(propylsulfonyl)piperazin-1-yl)tetrahydro-2H-pyran-4-yl)methyl)benzamide Hydrochloride | 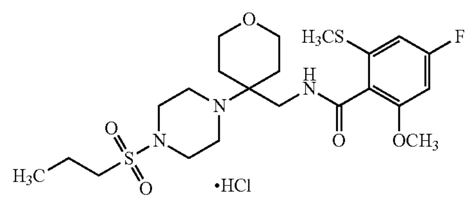 | GSP-1<br>$^1$H NMR (300 MHz, DMSO-d$_6$) δ 10.8 (bs, 1H), 8.73 (s, 1H), 6.80-6.86 (m, 2H), 3.86 (bs, 4H), 3.80 (s, 4H), 3.61-3.68 (m, 8H), 3.08-3.13 (m, 2H), 2.44 (s, 3H), 2.13-2.17 (m, 2H), 1.96-2.0 (m, 2H), 1.67-1.75 (m, 3H), 0.98 (t, J = 15 Hz, 3H); MS (ESI+) m/z 503 (M + H). |
| 123 | 2-Fluoro-6-methoxy-N-((4-(4-(propylsulfonyl)piperazin-1-yl)tetrahydro-2H-pyran-4-yl)methyl)benzamide Hydrochloride | 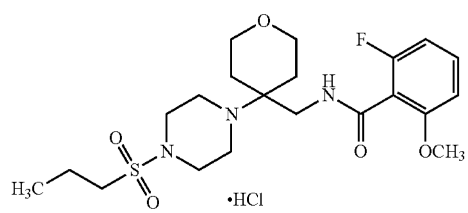 | GSP-1<br>$^1$H NMR (300 MHz, DMSO-d$_6$) δ 10.6 (bs, 1H), 8.93 (bs, 1H), 7.39-7.44 (m, 1H), 6.84-6.96 (m, 2H), 3.89-3.90 (m, 4H), 3.80-3.85 (m, 3H), 3.50-3.74 (m, 8H), 3.09-3.14 (m, 2H), 2.74-2.81 (m, 2H) 2.02-2.12 (m, 2H), 1.94-1.98 (m, 2H), 1.67-1.74 (m, 2 H), 0.98 (t, J = 6.6 Hz, 3H); MS (ESI+) m/z 502 (M + H). |
| 124 | 2,6-Difluoro-N-((4-(4-(1-methyl-1H-imidazol-4-ylsulfonyl)piperazin-1-yl)tetrahydro-2H-pyran-4-yl)methyl)benzamide Hydrochloride | 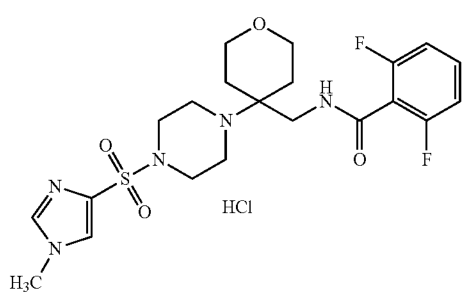 [SMILES: Cn1cnc(S(=O)(=O)N2CCN(C3(CNC(=O)c4c(F)cccc4F)CCOCC3)CC2)c1 ; Cl] | GSP-1<br>$^1$H NMR (300 MHz, DMSO-d$_6$) δ 10.58 (bs, 1H), 9.12-9.27 (m, 1H), 7.90 (d, J = 7.5 Hz, 2H), 7.50-7.68 (m, 1H), 7.23 (t, J = 8.1 Hz, 2H), 3.84 (s, 4H), 3.72 (s, 3H), 3.50-3.78 (m, 6H), 3.11-3.45 (m, 5H), 2.05-2.17 (m, 2H), 1.82-1.95 (m, 2H);MS (ESI+) m/z 483 (M + H). |
| 125 | 2,4-Dichloro-N-((3-(4-(propylsulfonyl)piperazin-1-yl)tetrahydro-2H-pyran-3-yl)methyl)benzamide Hydrochloride | 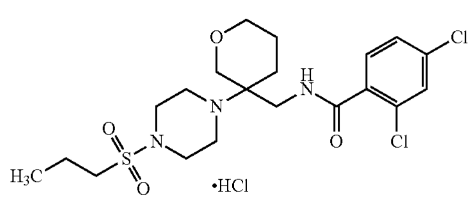 [SMILES: CCCS(=O)(=O)N1CCN(C2(CNC(=O)c3ccc(Cl)cc3Cl)CCCOC2)CC1 ; Cl] | GSP-1<br>$^1$H NMR (400 MHz, CD$_3$OD) δ 11.21 (bs, 1H), 8.92 (bs, 1H), 7.72 (d, J = 1.8 Hz, 1H), 7.56 (d, J = 8.2 Hz, 1H), 7.52 (dd, J = 1.9 Hz, 8.3 Hz, 1H), 4.053.90 (m, 2H), 3.90-3.72 (m, 4H), 3.72-3.60 (m, 4H), 3.43-3.25 (m, 4H), 3.15-3.08 (m, 2H), 2.23-2.10 (m, 2H), 1.95-1.85 (m, 1H), 1.78-1.63 (m, 3H), 1.02-0.95 (t, J = 7.4 Hz, 3H); MS (ESI+) m/z 478 (M + H). |
| 126 | N-((3-(4-(Cyclopropylmethyl-sulfonyl)piperazin-1-yl)tetrahydro-2H-pyran-3-yl)methyl)-2,6-difluorobenzamide Hydrochloride | 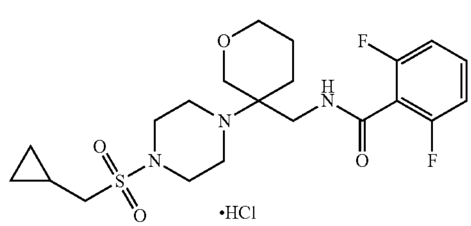 [SMILES: O=C(NCC1(N2CCN(S(=O)(=O)CC3CC3)CC2)CCCOC1)c1c(F)cccc1F ; Cl] | GSP-1<br>$^1$H NMR (300 MHz, DMSO-d$_6$) δ 11.10 (bs, 1H), 9.17 (bs, 1H), 7.60-7.50 (m, 1H), 7.26-7.18 (m, 2H), 4.01-3.50 (m, 9H), 3.50-3.3.20 (m, 3H), 3.15-3.05 (m, 4H), 2.20-2.03 (m, 2H), 1.98-1.80 (m, 1H), 1.70-1.60 (m, 1H), 1.08-0.95 (m, 1H), 0.62-0.56 (m, 2H), 0.45-0.35 (m, 2H); MS (ESI+) m/z 458 (M + H). |

TABLE 1-continued

Examples, General Synthetic Procedures (GSP) and Spectral Data

| Cpd | Name | Structure | General Synthetic Procedure and Spectral Data |
|---|---|---|---|
| 127 | 2,6-Difluoro-N-((3-(4-(1-methyl-1H-imidazol-4-ylsulfonyl)piperazin-1-yl)tetrahydro-2H-pyran-3-yl)methyl)benzamide Hydrochloride | 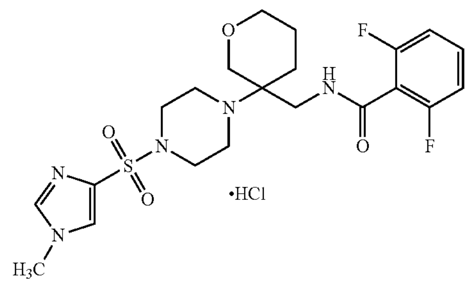 | GSP-1<br>$^1$H NMR (300 MHz, DMSO-d$_6$)<br>δ 10.34 (bs, 1H), 9.12 (bs, 1H), 7.90 (d, J = 4.7 Hz, 2H), 7.62-7.50 (m, 1H), 7.28-7.18 (m, 2H) 3.95-3.80 (m, 2H) 3.80-3.70 (m, 6H), 3.70-3.50 (m, 4H), 3.48-3.31 (m, 5 H) 2.10-1.98 (m, 2H), 1.93-1.72 (m, 1H), 1.70-1.60 (m, 1H); MS (ESI+) m/z 484 (M + H). |
| 128 | 2,6-Difluoro-N-((4-(4-(1-methyl-1H-1,2,3-triazol-4-ylsulfonyl)piperazin-1-yl)tetrahydro-2H-pyran-4-yl)methyl)benzamide Hydrochloride | 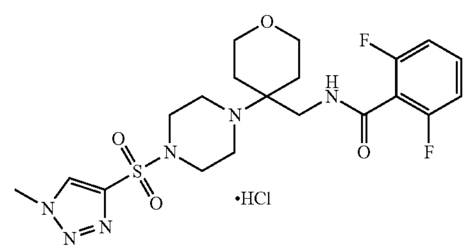 [SMILES: Cn1cc(S(=O)(=O)N2CCN(C3(CNC(=O)c4c(F)cccc4F)CCOCC3)CC2)nn1 ; Cl] | GSP-1<br>$^1$H NMR (300 MHz, DMSO-d$_6$): δ 11.07 (bs, 1H), 9.25 (bs, 1H), 8.88 (s, 1H), 7.60-7.55 (m, 1H), 7.25-7.20 (m, 2H), 4.13 (s, 3H), 3.97-3.80 (m, 4H), 3.78-3.48 (m, 6H), 3.44-3.17 (m, 4H), 2.25-2.06 (m, 2H), 1.97-1.79 (m, 2H); MS (APCI$^+$) m/z 485 (M + H). |
| 129 | 2,4-Dichloro-N-((4-(4-(1-methyl-1H-1,2,3-triazol-4-ylsulfonyl)piperazin-1-yl)tetrahydro-2H-pyran-4-yl)methyl)benzamide Hydrochloride | 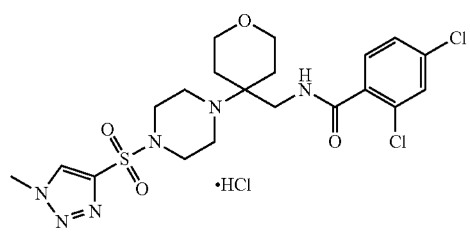 [SMILES: Cn1cc(S(=O)(=O)N2CCN(C3(CNC(=O)c4ccc(Cl)cc4Cl)CCOCC3)CC2)nn1 ; Cl] | GSP-1<br>$^1$H NMR (300 MHz, DMSO-d$_6$): δ 8.62 (bs, 1H), 7.95 (bs, 1H), 7.55 (bs, 1H), 7.44 (bs, 2H), 4.11 (bs, 2H), 3.42-3.51 (m, 4H), 3.12-3.22 (m, 4H), 1.62-1.88 (m, 8H); MS (ESI+) m/z 517 (M + H); MS (APCI$^+$) m/z 518 (M + H). |
| 130 | N-((4,4-Difluoro-1-(4-(propylsulfonyl)piperazin-1-yl)cyclohexyl)methyl)-2,6-difluorobenzamide Hydrochloride | 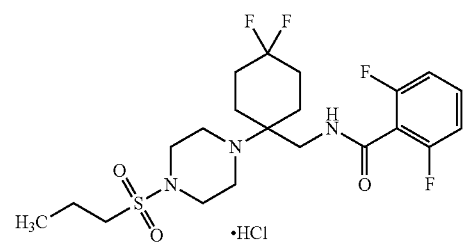 [SMILES: CCCS(=O)(=O)N1CCN(C2(CNC(=O)c3c(F)cccc3F)CCC(F)(F)CC2)CC1 ; Cl] | GSP-1<br>$^1$H NMR (300 MHz, 380 K, DMSO-d$_6$) 8.23 (bs, 1H), 7.45-7.42 (m, 1H), 7.08-7.03 (t, J = 7.8 Hz, 2H), 3.38-3.36 (m, 4H), 3.19 (s, 4H), 2.99-2.94 (m, 2H), 2.79 (s, 4H), 1.95-1.64 (m, 8H), 0.99 (t, J = 4.8 Hz, 3H); MS (APCI$^+$) m/z 480 (M + H). |
| 131 | N-((4,4-Difluoro-1-(4-(propylsulfonyl)piperazin-1-yl)cyclohexyl)methyl)-2-fluorobenzamide Hydrochloride | 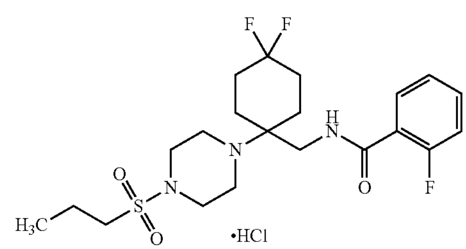 [SMILES: CCCS(=O)(=O)N1CCN(C2(CNC(=O)c3ccccc3F)CCC(F)(F)CC2)CC1 ; Cl] | GSP-1<br>$^1$H NMR (300 MHz, DMSO-d$_6$): δ 10.65 (bs, 1H), 8.81 (bs, 1H), 8.32 (bs, 2H), 7.51-7.77 (m, 2H), 7.21-7.44 (m, 2H), 3.62-3.81 (m, 4H), 3.42-3.58 (m, 2H), 3.24-3.40 (m, 2H), 3.02-3.21 (m, 2H), 2.76-2.88 (m, 2H), 2.02-2.22 (m, 6H), 1.99-2.00 (m, 2H), 0.98 (t, J = 7.5 Hz, 3H); MS (ESI+) m/z 462 (M + H). |
| 132 | N-((4,4-Difluoro-1-(4-(propylsulfonyl)piperazin-1-yl)cyclohexyl)methyl)-2-(trifluoromethyl)benzamide Hydrochloride | 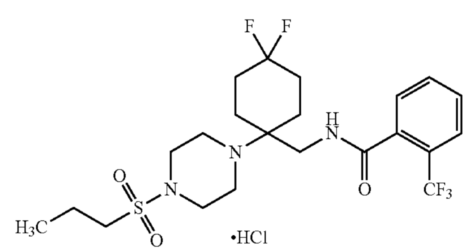 [SMILES: CCCS(=O)(=O)N1CCN(C2(CNC(=O)c3ccccc3C(F)(F)F)CCC(F)(F)CC2)CC1 ; Cl] | GSP-1<br>$^1$H NMR (300 MHz, DMSO-d$_6$): δ 10.73 (bs, 1H), 8.99 (bs, 1H), 7.62-7.91 (m, 3H), 7.45-7.52 (m, 1H), 3.52-3.91 (m, 4H), 3.23-3.45 (m, 2H), 3.05-3.20 (m, 2H), 2.95-3.08 (m, 2H), 2.68-2.82 (m, 2H), 2.02-2.41 (m, 6H), 1.81-2.00 (m, 2H), 1.67-1.82 (m, 2H), 0.97 (t, J = 7.2 Hz, 3H); MS (ESI+) m/z 512 (M + H). |

TABLE 1-continued

Examples, General Synthetic Procedures (GSP) and Spectral Data

| Cpd | Name | Structure | General Synthetic Procedure and Spectral Data |
|---|---|---|---|
| 133 | N-((4,4-Difluoro-1-(4-(propylsulfonyl)piperazin-1-yl)cyclohexyl)methyl)-2-methoxybenzamide Hydrochloride | 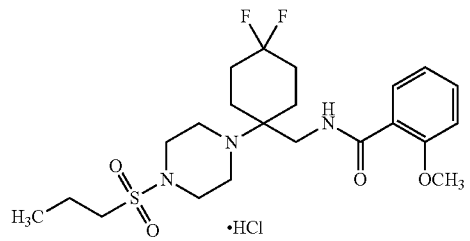 [SMILES: CCCS(=O)(=O)N1CCN(C2(CNC(=O)c3ccccc3OC)CCC(F)(F)CC2)CC1 ; Cl] | GSP-1<br>$^1$H NMR (300 MHz, DMSO-d$_6$) δ 10.61 (bs, 1H), 8.65 (bs, 1H), 7.42-7.71 (m, 2H), 6.98-7.20 (m, 2H), 3.85 (s, 3H), 3.75-3.85 (m, 4H), 3.41-3.75 (m, 2H), 3.11-3.21 (m, 4H), 2.65-2.82 (m, 4H), 2.04-2.34 (m, 6H), 1.95-2.02 (m, 2H), 0.98 (t, J = 7.5 Hz, 3H); MS (ESI+) m/z 474 (M + H). |
| 134 | N-((4,4-Difluoro-1-(4-(propylsulfonyl)piperazin-1-yl)cyclohexyl)methyl)-2-methylbenzamide Hydrochloride | 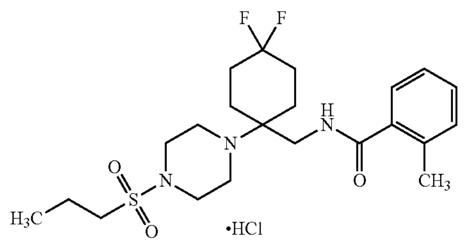 [SMILES: CCCS(=O)(=O)N1CCN(C2(CNC(=O)c3ccccc3C)CCC(F)(F)CC2)CC1 ; Cl] | GSP-1<br>$^1$H NMR (300 MHz, DMSO-d$_6$) δ 10.75 (bs, 1H), 8.74 (bs, 1H), 7.21-7.48 (m, 4H), 3.72-3.81 (m, 3H), 3.48-3.72 (m, 4H), 3.22-3.44 (m, 2H), 3.12-3.22 (m, 2H), 2.72-2.84 (m, 2H), 2.34 (s, 4H), 2.12-2.34 (m, 6H), 1.95-2.02 (m, 2H), 0.98 (t, J = 7.5 Hz, 3H); MS (ESI+) m/z 458 (M + H). |
| 135 | 2,6-Dichloro-N-((4,4-difluoro-1-(4-(propylsulfonyl)piperazin-1-yl)cyclohexyl)methyl)benzamide Hydrochloride | 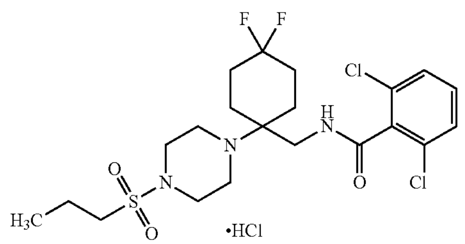 [SMILES: CCCS(=O)(=O)N1CCN(C2(CNC(=O)c3c(Cl)cccc3Cl)CCC(F)(F)CC2)CC1 ; Cl] | GSP-1<br>$^1$H NMR (300 MHz, DMSO-d$_6$) δ 10.48 (bs, 1H), 9.12 (bs, 0.3H), 8.63 (bs, 0.7H), 7.60-7.38 (m, 3H), 3.28 (d, J = 6.3 Hz, 2H), 3.20-3.17 (m, 4H), 3.00 (t, J = 7.5 Hz, 2H), 2.80-2.68 (m, 4H), 2.30-1.58 (m, 10H), 0.99 (t, J = 7.5 Hz, 3H); MS (APCI$^+$) m/z 512 (M + H). |
| 136 | 2,4-Dichloro-N-((4,4-difluoro-1-(4-(propylsulfonyl)piperazin-1-yl)cyclohexyl)methyl)benzamide Hydrochloride | 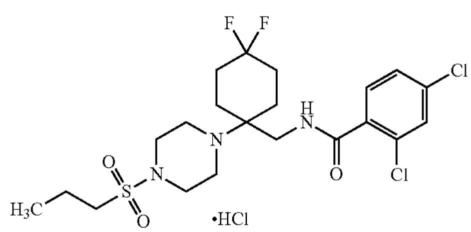 [SMILES: CCCS(=O)(=O)N1CCN(C2(CNC(=O)c3ccc(Cl)cc3Cl)CCC(F)(F)CC2)CC1 ; Cl] | GSP-1<br>$^1$H NMR (300 MHz, DMSO-d$_6$) δ 10.66 (bs, 1H), 8.96 (bs, 0.5H), 8.47 (bs, 0.5H), 7.80-7.35 (m, 3H), 3.85-3.65 (m, 2H), 3.54 (t, J = 11.7 Hz, 2H), 3.40-2.95 (m, 6H), 2.82-2.65 (m, 2H), 2.30-1.50 (m, 10H), 0.99 (t, J = 7.5 Hz, 3H); MS (ESI$^+$) m/z 512 (M + H). |
| 137 | N-((4,4-Difluoro-1-(4-(propylsulfonyl)piperazin-1-yl)cyclohexyl)methyl)-4-fluoro-2-methoxy-6-methylbenzamide Hydrochloride | 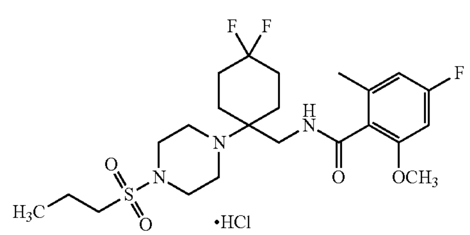 [SMILES: CCCS(=O)(=O)N1CCN(C2(CNC(=O)c3c(C)cc(F)cc3OC)CCC(F)(F)CC2)CC1 ; Cl] | GSP-1<br>$^1$H NMR (300 MHz, DMSO-d$_6$) δ 10.63 (bs, 1H), 8.71 (bs, 0.6H), 8.15 (bs, 0.4H), 6.90-6.58 (m, 2H), 3.76 (s, 3H), 3.74-3.35 (m, 5H), 3.25-2.60 (m, 7H), 2.19 (s, 3H), 2.05-1.52 (m, 10H), 0.98 (t, J = 7.5 Hz, 3H); MS (APCI$^+$) m/z 506 (M + H). |
| 138 | N-((4,4-Difluoro-1-(4-(propylsulfonyl)piperazin-1-yl)cyclohexyl)methyl)-4-fluoro-2-methoxy-6-(methylthio)benzamide Hydrochloride | 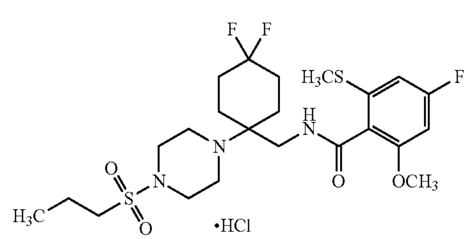 | GSP-1<br>$^1$H NMR (300 MHz, DMSO-d$_6$) δ 10.79 (bs, 1H), 8.76 (bs, 0.5H), 7.82 (bs, 0.5H), 6.92-6.72 (m, 2H), 3.77 (s, 3H), 3.76-3.35 (m, 4H), 3.25-2.60 (m, 8H), 2.45 (s, 3H), 2.32-1.52 (m, 10H), 0.98 (t, J = 7.5 Hz, 3H); MS (APCI$^+$) m/z 538 (M + H). |

TABLE 1-continued

Examples, General Synthetic Procedures (GSP) and Spectral Data

| Cpd | Name | Structure | General Synthetic Procedure and Spectral Data |
|---|---|---|---|
| 139 | 2-Chloro-N-((4,4-difluoro-1-(4-(propylsulfonyl)piperazin-1-yl)cyclohexyl)methyl)benzamide Hydrochloride | 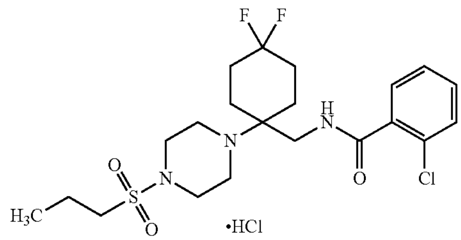 [SMILES: CCCS(=O)(=O)N1CCN(C2(CNC(=O)c3ccccc3Cl)CCC(F)(F)CC2)CC1 ; Cl] | GSP-1<br>$^1$H NMR (300 MHz, DMSO-d$_6$) δ 10.71 (bs, 1H), 8.93 (bs, 0.6H), 8.43 (bs, 0.4H), 7.60-7.32 (m, 4H), 3.73 (t, J = 9.6 Hz, 2H), 3.55 (t, J = 10.8 Hz, 2H), 3.45-2.95 (m, 6H), 2.82-2.65 (m, 2H). 2.35-1.52 (m, 10H), 0.98 (t, J = 7.5 Hz, 3H); MS (ESI$^+$) m/z 478 (M + H). |
| 140 | N-((4,4-Difluoro-1-(4-(propylsulfonyl)piperazin-1-yl)cyclohexyl)methyl)-2,4-difluorobenzamide Hydrochloride | 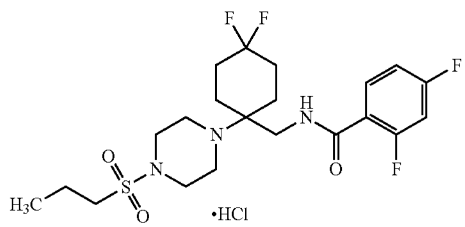 [SMILES: CCCS(=O)(=O)N1CCN(C2(CNC(=O)c3ccc(F)cc3F)CCC(F)(F)CC2)CC1 ; Cl] | GSP-1<br>$^1$H NMR (300 MHz, DMSO-d$_6$) δ 10.68 (bs, 1H), 8.81 (bs, 0.6H), 8.31 (bs, 0.4H), 7.80-7.55 (m, 1H), 7.48-7.12 (m, 2H), 3.90-3.63 (m, 4H), 3.42-3.25 (m, 2H), 3.20-2.94 (m, 4H), 2.80-2.65 (m, 2H), 2.30-1.45 (m, 10H), 0.98 (t, J = 7.5 Hz, 3H); MS (ESI$^+$) m/z 480 (M + H). |
| 141 | N-((4,4-Difluoro-1-(4-(propylsulfonyl)piperazin-1-yl)cyclohexyl)methyl)-2-(trifluoromethoxy)benzamide Hydrochloride | 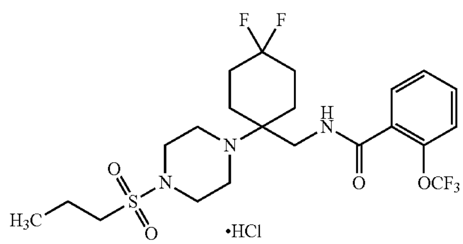 [SMILES: CCCS(=O)(=O)N1CCN(C2(CNC(=O)c3ccccc3OC(F)(F)F)CCC(F)(F)CC2)CC1 ; Cl] | GSP-1<br>$^1$H NMR (300 MHz, DMSO-d$_6$) δ 10.77 (bs, 1H), 8.93 (bs, 0.6H), 8.42 (bs, 0.4H), 7.85-7.40 (m, 4H), 3.90-3.52 (m, 5H), 3.45-2.96 (m, 6H), 2.80-2.55 (m, 2H), 2.31-1.45 (m, 9H), 0.98 (t, J = 7.2 Hz, 3H); MS (APCI$^+$) m/z 528 (M + H). |
| 142 | N-((4,4-Difluoro-1-(4-(propylsulfonyl)piperazin-1-yl)cyclohexyl)methyl)-2-(difluoromethoxy)benzamide Hydrochloride | 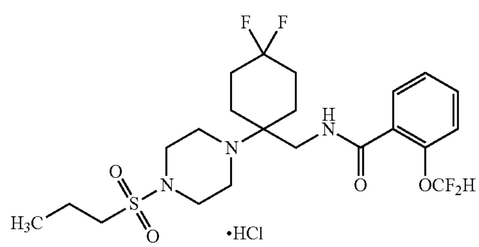 | GSP-1<br>$^1$H NMR (300 MHz, DMSO-d$_6$):<br>δ 10.77 (bs, 1H), 8.93 (bs, 0.6H), 8.42 (bs, 0.4H), 7.85-7.40 (m, 4H), 3.90-3.52 (m, 5H), 3.45-2.96 (m, 6H), 2.80-2.55 (m, 2H), 2.31-1.45 (m, 9H), 0.98 (t, J = 7.2 Hz, 3H); MS (APCI$^+$) m/z 510 (M + H). |
| 143 | 4-Chloro-N-((4,4-difluoro-1-(4-(propylsulfonyl)piperazin-1-yl)cyclohexyl)methyl)-2-fluorobenzamide Hydrochloride | 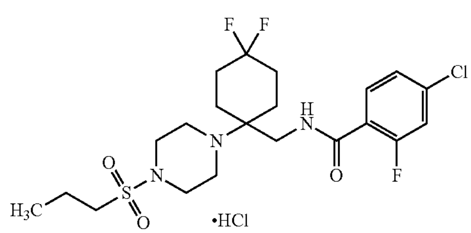 [SMILES: CCCS(=O)(=O)N1CCN(C2(CNC(=O)c3ccc(Cl)cc3F)CCC(F)(F)CC2)CC1 ; Cl] | GSP-1<br>$^1$H NMR (300 MHz, DMSO-d$_6$): δ 10.97 (s, 1H), 8.99 (s, 1H), 7.50-7.72 (m, 2H), 7.32-7.44 (m, 1H), 3.91-3.96 (m, 2H), 3.70-3.81 (m, 4H), 3.39-3.57 (m, 2H), 3.11-3.24 (m, 2H), 2.78-2.89 (m, 2H), 1.81-2.32 (m, 8H), 1.68-1.70 (m, 2H), 0.98 (t, J = 7.2 Hz, 3H); MS (ESI+) m/z 496 (M + H). |
| 144 | N-((4,4-Difluoro-1-(4-(propylsulfonyl)piperazin-1-yl)cyclohexyl)methyl)-2,4,6-trifluorobenzamide Hydrochloride | 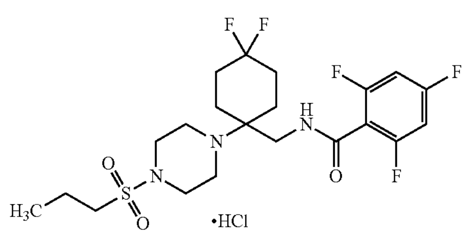 [SMILES: CCCS(=O)(=O)N1CCN(C2(CNC(=O)c3c(F)cc(F)cc3F)CCC(F)(F)CC2)CC1 ; Cl] | GSP-1<br>$^1$H NMR (300 MHz, DMSO-d$_6$): δ 11.02 (s, 1H), 9.23 (s, 1H), 7.22-7.45 (m, 2H), 3.91-3.96 (m, 2H), 3.70-3.81 (m, 4H), 3.39-3.57 (m, 2H), 3.11-3.24 (m, 2H), 2.78-2.89 (m, 2H), 1.81-2.32 (m, 8H), 1.68-1.70 (m, 2H), 0.98 (t, J = 7.2 Hz, 3H); MS (ESI+) m/z 498 (M + H). |

TABLE 1-continued

Examples, General Synthetic Procedures (GSP) and Spectral Data

| Cpd | Name | Structure | General Synthetic Procedure and Spectral Data |
|---|---|---|---|
| 145 | N-((4,4-Difluoro-1-(4-(propylsulfonyl)piperazin-1-yl)cyclohexyl)methyl)-4-fluoro-2-methylbenzamide Hydrochloride | 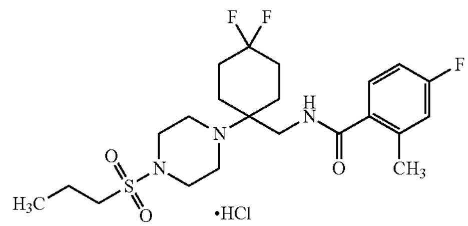 | GSP-1<br>$^1$H NMR (300 MHz, DMSO-d$_6$): δ 10.63 (bs, 1H), 8.71 (bs, 0.6H), 8.15 (bs, 0.4H), 6.90-6.58 (m, 2H), 3.76 (s, 3H), 3.74-3.35 (m, 5H), 3.25-2.60 (m, 7H), 2.19 (s, 3H), 2.05-1.52 (m, 10H), 0.98 (t, J = 7.5 Hz, 3H); MS (APCI$^+$) m/z 476 (M + H). |
| 146 | N-((4,4-Difluoro-1-(4-(propylsulfonyl)piperazin-1-yl)cyclohexyl)methyl)-2,6-dimethylbenzamide Hydrochloride | 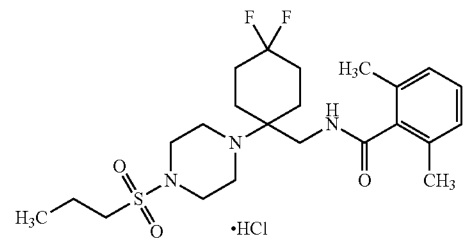 [SMILES: CCCS(=O)(=O)N1CCN(C2(CNC(=O)c3c(C)cccc3C)CCC(F)(F)CC2)CC1 ; Cl] | GSP-1<br>$^1$H NMR (300 MHz, DMSO-d$_6$): δ 11.05 (s, 1H), 8.68 (s, 1H), 7.11-7.22 (m, 1H), 7.06-7.08 (m, 1H), 3.85-3.92 (m, 2H), 3.68-3.70 (m, 4H), 3.22-3.41 (m, 2H), 3.11-3.21 (m, 4H), 2.26 (s, 6H), 1.81-2.32 (m, 8H), 1.68-1.70 (m, 2H), 0.98 (t, J = 7.2 Hz, 3H); MS (ESI+) m/z 472 (M + H). |
| 147 | N-((4,4-Difluoro-1-(4-(propylsulfonyl)piperazin-1-yl)cyclohexyl)methyl)-2-fluoro-6-methyl-benzamide Hydrochloride | 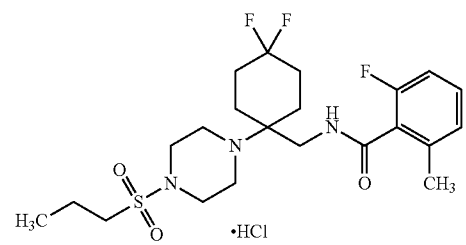 [SMILES: CCCS(=O)(=O)N1CCN(C2(CNC(=O)c3c(C)cccc3F)CCC(F)(F)CC2)CC1 ; Cl] | GSP-1<br>$^1$H NMR (300 MHz, CDCl$_3$): δ 7.26-7.31 (m, 1H), 7.01-7.04 (m, 1H), 6.93-6.97 (m, 1H), 6.02 (bs, 1H), 3.56 (d, J = 6.3 Hz, 2H), 3.19-3.27 (m, 4H), 2.84-2.89 (m, 2H), 2.74-2.78 (m, 4H), 2.40 (s, 3H), 1.55-2.04 (m, 8H), 1.06 (t, J = 7.5 Hz, 3H); MS (ESI+) m/z 476 (M + H). |
| 148 | N-((4,4-Difluoro-1-(4-(propylsulfonyl)piperazin-1-yl)cyclohexyl)methyl)-4-fluoro-2-(trifluoromethyl)benzamide Hydrochloride | 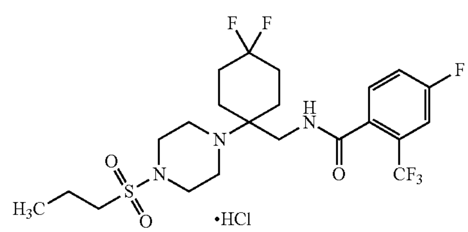 [SMILES: CCCS(=O)(=O)N1CCN(C2(CNC(=O)c3ccc(F)cc3C(F)(F)F)CCC(F)(F)CC2)CC1 ; Cl] | GSP-1<br>$^1$H NMR (300 MHz, DMSO-d$_6$): δ 11.1 (bs, 1H), 9.01 (bs, 1H), 7.62-7.81 (m, 3H), 3.68-3.89 (m, 6H), 3.21-3.33 (m, 2H), 3.11-3.18 (m, 3H), 2.75-2.78 (m, 1H), 2.07-2.19 (m, 8H), 1.66-1.75 (m, 2H), 0.98 (t, J = 12 Hz, 3H); MS (ESI+) m/z 530 (M + H). |
| 149 | N-((4,4-Difluoro-1-(4-(propylsulfonyl)piperazin-1-yl)cyclohexyl)methyl)-2-fluoro-6-(trifluoromethyl)benzamide Hydrochloride | 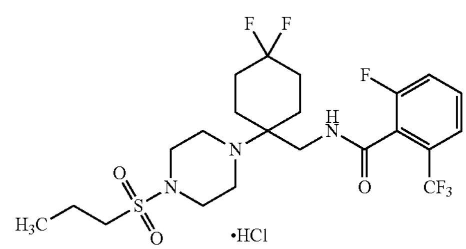 | GSP-1<br>$^1$H NMR (300 MHz, DMSO-d$_6$): δ 10.91 (s, 1H), 9.21 (s, 1H), 7.61-7.82 (m, 3H), 3.55-3.92 (m, 4H), 3.28-3.40 (m, 2H), 2.92-3.21 (m, 4H), 2.62-2.81 (m, 2H), 1.81-2.32 (m, 8H), 1.68-1.70 (m, 2H), 0.98 (t, J = 12 Hz, 3H); MS (ESI+) m/z 530 (M + H). |
| 150 | N-((4,4-Difluoro-1-(4-(propylsulfonyl)piperazin-1-yl)cyclohexyl)methyl)-2-fluoro-4-(trifluoromethyl)benzamide Hydrochloride | 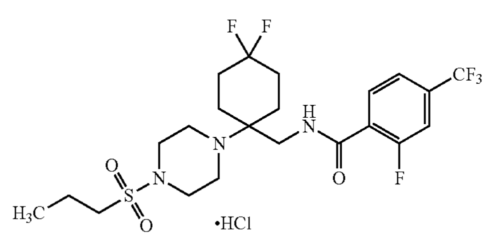 [SMILES: CCCS(=O)(=O)N1CCN(C2(CNC(=O)c3ccc(C(F)(F)F)cc3F)CCC(F)(F)CC2)CC1 ; Cl] | GSP-1<br>$^1$H NMR (300 MHz, DMSO-d$_6$): δ 10.8 (s, 1H), 9.02 (s, 1H), 7.65-7.93 (m, 3H), 3.85-3.92 (m, 2H), 3.68-3.70 (m, 4H), 3.22-3.41 (m, 2H), 3.11-3.21 (m, 4H), 1.81-2.32 (m, 8H), 1.68-1.70 (m, 2H), 0.98 (t, J = 7.2 Hz, 3H); MS (ESI+) m/z 530 (M + H). |

TABLE 1-continued

Examples, General Synthetic Procedures (GSP) and Spectral Data

| Cpd | Name | Structure | General Synthetic Procedure and Spectral Data |
|---|---|---|---|
| 151 | N-((4,4-Difluoro-1-(4-(propylsulfonyl)piperazin-1-yl)cyclohexyl)methyl)-2-chloro-4-(trifluoromethyl)benzamide Hydrochloride | 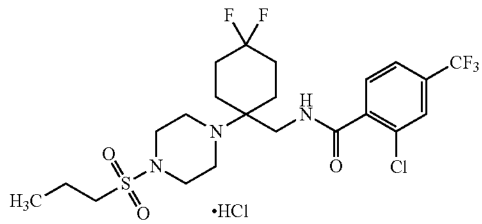 [SMILES: CCCS(=O)(=O)N1CCN(C2(CNC(=O)c3ccc(C(F)(F)F)cc3Cl)CCC(F)(F)CC2)CC1 ; Cl] | GSP-1<br>$^1$H NMR (300 MHz, DMSO-d$_6$): δ 9.31 (bs, 1H), 7.79 (m, 1H), 7.69 (s, 1H), 7.62-7.59 (m, 1H), 4.05 (m, 2H), 3.60 (m, 2H), 3.34 (m, 2H), 3.10-2.78 (m, 6H), 2.31-1.72 (m, 10H), 1.05 (t, J = 7.3 Hz, 3H); MS (APCI$^+$) m/z 546 (M + H). |
| 152 | 2-Chloro-N-((4,4-difluoro-1-(4-(propylsulfonyl)piperazin-1-yl)cyclohexyl)methyl)-6-methoxybenzamide Hydrochloride | 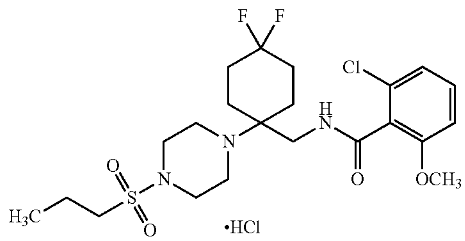 [SMILES: CCCS(=O)(=O)N1CCN(C2(CNC(=O)c3c(Cl)cccc3OC)CCC(F)(F)CC2)CC1 ; Cl] | GSP-1<br>$^1$H NMR (300 MHz, DMSO-d$_6$): δ 10.9 (s, 1H), 8.98 (s, 1H), 7.23-7.51 (m, 1H), 6.99-7.12 (m, 2H), 3.72-3.81 (m, 3H), 3.51-3.71 (m, 4H), 3.35-3.48 (m, 2H), 2.99-3.33 (m, 4H), 2.70-2.88 (m, 2H), 1.90-2.21 (m, 8H), 1.66-1.75 (m, 2H), 0.98 (t, J = 7.5 Hz, 3H); MS (ESI+) m/z 508 (M + H). |
| 153 | 4-Chloro-N-((4,4-difluoro-1-(4-(propylsulfonyl)piperazin-1-yl)cyclohexyl)methyl)-2-methylbenzamide Hydrochloride | 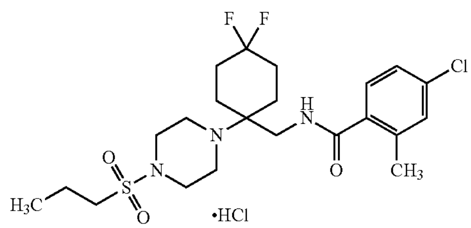 [SMILES: CCCS(=O)(=O)N1CCN(C2(CNC(=O)c3ccc(Cl)cc3C)CCC(F)(F)CC2)CC1 ; Cl] | GSP-1<br>$^1$H NMR (300 MHz, DMSO-d$_6$): δ 10.91 (s, 1H), 8.88 (s, 1H), 7.33-7.49 (m, 3H), 3.59-3.82 (m, 6H), 3.22-3.31 (m, 2H), 3.01-3.26 (m, 3H), 3.75 (bs, 1H), 2.34 (s, 3H), 1.90-2.21 (m, 8H), 1.66-1.75 (m, 2H), 0.98 (t, J = 7.5 Hz, 3H); MS (ESI+) m/z 492 (M + H). |
| 154 | 2-Chloro-N-((4,4-difluoro-1-(4-(propylsulfonyl)piperazin-1-yl)cyclohexyl)methyl)-4-fluorobenzamide Hydrochloride | 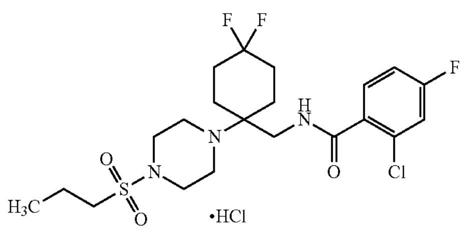 [SMILES: CCCS(=O)(=O)N1CCN(C2(CNC(=O)c3ccc(F)cc3Cl)CCC(F)(F)CC2)CC1 ; Cl] | GSP-1<br>$^1$H NMR (300 MHz, DMSO-d$_6$): δ 10.91 (s, 1H), 8.96 (s, 1H), 7.43-7.61 (m, 2H), 7.21-7.42 (m, 1H), 3.59-3.82 (m, 6H), 3.22-3.31 (m, 2H), 3.01-3.26 (m, 3H), 3.75 (bs, 1H), 2.34 (s, 3H), 1.90-2.21 (m, 8H), 1.66-1.75 (m, 2H), 0.98 (t, J = 7.5 Hz, 3H); MS (ESI+) m/z 495 (M + H). |
| 155 | 2-Chloro-N-((4,4-difluoro-1-(4-(propylsulfonyl)piperazin-1-yl)cyclohexyl)methyl)-6-methylbenzamide Hydrochloride | 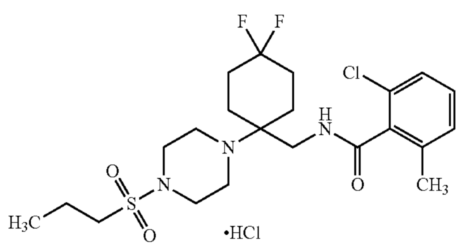 | GSP-1<br>$^1$H NMR (300 MHz, DMSO-d$_6$): δ 10.91 (s, 1H), 8.96 (s, 1H), 7.19-7.32 (m, 3H), 3.56-3.82 (m, 4H), 3.24-3.54 (m, 2H), 2.95-3.21 (m, 3H), 2.73-2.91 (m, 4H), 1.82-2.33 (m, 10H), 1.68-1.70 (m, 2H), 0.98 (t, J = 7.2 Hz, 3H); MS (ESI+) m/z 492 (M + H). |
| 156 | 2-Chloro-N-((4,4-difluoro-1-(4-(propylsulfonyl)piperazin-1-yl)cyclohexyl)methyl)-6-fluorobenzamide Hydrochloride | 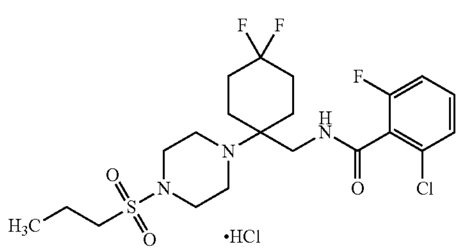 [SMILES: CCCS(=O)(=O)N1CCN(C2(CNC(=O)c3c(F)cccc3Cl)CCC(F)(F)CC2)CC1 ; Cl] | GSP-1<br>$^1$H NMR (300 MHz, DMSO-d$_6$): δ 10.8 (s, 1H), 9.22 (s, 1H), 7.21-7.62 (m, 3H), 3.51-3.98 (m, 4H), 3.22-3.48 (m, 2H), 2.98-3.20 (m, 4H), 2.75-2.90 (m, 2H), 1.80-2.31 (m, 8H), 1.68-1.78 (m, 2H), 0.98 (t, J = 7.2 Hz, 3H); MS (ESI+) m/z 495 (M + H). |

TABLE 1-continued

Examples, General Synthetic Procedures (GSP) and Spectral Data

| Cpd | Name | Structure | General Synthetic Procedure and Spectral Data |
|---|---|---|---|
| 157 | 2-Chloro-N-((4,4-difluoro-1-(4-(propylsulfonyl)piperazin-1-yl)cyclohexyl)methyl)-6-(trifluoromethyl)benzamide Hydrochloride | 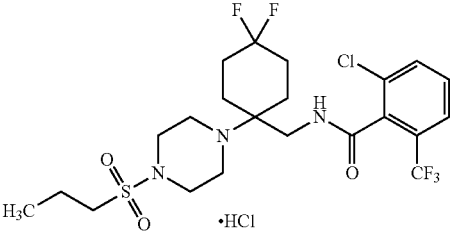 [SMILES: CCCS(=O)(=O)N1CCN(C2(CNC(=O)c3c(Cl)cccc3C(F)(F)F)CCC(F)(F)CC2)CC1 ; Cl] | GSP-1<br>$^1$H NMR (300 MHz, DMSO-d$_6$): δ 8.61 (bs, 1H), 7.81-7.83 (m, 1H), 7.73-7.80 (m, 1H), 7.59-7.64 (m, 1H), 3.31-3.41 (m, 2H), 3.08-3.28 (m, 4H), 2.95-3.05 (m, 2H), 2.61-2.80 (m, 4H), 1.90-2.21 (m, 8H), 1.66-1.75 (m, 2H), 0.98 (t, J = 7.5 Hz, 3H); MS (ESI+) m/z 545 (M + H). |
| 158 | N-((4,4-Difluoro-1-(4-(propylsulfonyl)piperazin-1-yl)cyclohexyl)methyl)-2-fluoro-6-(trifluoromethoxy)benzamide Hydrochloride | 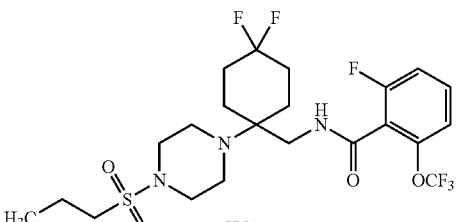 | GSP-1<br>$^1$H NMR (300 MHz, DMSO-d$_6$): δ 10.72 (bs, 1H), 8.76 (bs, 1H), 7.57-7.73 (m, 1H), 7.28-7.41 (m, 2H), 3.71-3.98 (m, 2H), 3.35-3.69 (m, 4H), 2.95-3.21 (m, 4H), 2.78-2.89 (m, 2H), 1.81-2.32 (m, 8H), 1.68-1.70 (m, 2H), 0.98 (t, J = 7.2 Hz, 3H); MS (ESI+) m/z 546 (M + H). |
| 159 | 2-Chloro-N-((4,4-difluoro-1-(4-(propylsulfonyl)piperazin-1-yl)cyclohexyl)methyl)-6-(trifluoromethoxy)benzamide Hydrochloride | 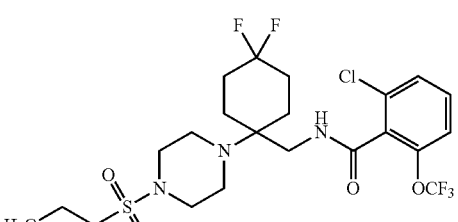 | GSP-1<br>$^1$H NMR (300 MHz, DMSO-d$_6$): δ 10.55 (bs, 1H), 8.68 (bs, 1H), 7.31-7.62 (m, 3H), 3.65-3.82 (m, 2H), 3.22-3.63 (m, 4H), 2.95-3.12 (m, 4H), 2.75-2.82 (m, 2H), 1.81-2.32 (m, 8H), 1.68-1.70 (m, 2H), 0.98 (t, J = 7.2 Hz, 3H); MS (ESI+) m/z 562 (M + H). |
| 160 | 2-Chloro-N-((4,4-difluoro-1-(4-(1-methyl-1H-imidazol-4-ylsulfonyl)piperazin-1-yl)cyclohexyl)methyl)benzamide Hydrochloride | 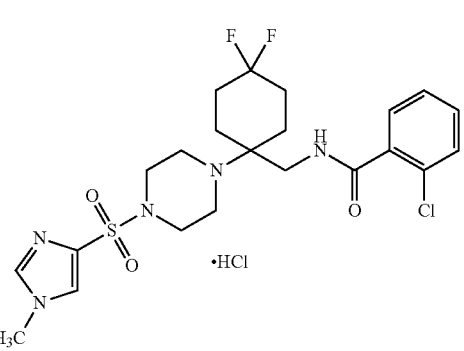 | GSP-1<br>$^1$H NMR (300 MHz, DMSO-d$_6$) δ 10.45 (bs, 1H), 8.92 (bs, 1H), 7.89 (d, J = 8.4 Hz, 2H), 7.60-7.40 (m, 4H), 4.00-3.60 (m, 9H), 3.50-3.10 (m, 4H), 2.30-2.0 (m, 8H); MS (ESI+) m/z 516 (M + H). |
| 161 | N-((4,4-difluoro-1-(4-(1-methyl-1H-imidazol-4-ylsulfonyl)piperazin-1-yl)cyclohexyl)methyl)-2-(trifluoromethoxy)benzamide Hydrochloride | 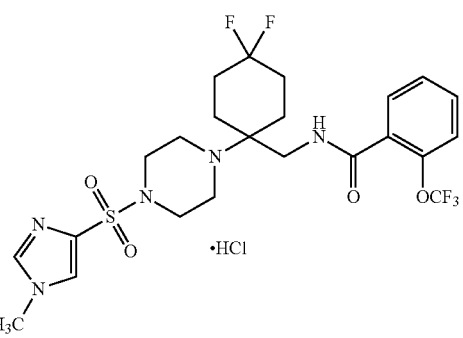 | GSP-1<br>$^1$H NMR (300 MHz, DMSO-d$_6$) δ 10.33 (bs, 1H), 8.91 (bs, 1H), 7.89 (d, J = 10.0 Hz, 2H), 7.70-7.40 (m, 4H), 4.00-3.60 (m, 9H), 3.50-3.10 (m, 4H), 2.30-2.0 (m, 8H); MS (ESI+) m/z 566 (M + H). |

TABLE 1-continued

Examples, General Synthetic Procedures (GSP) and Spectral Data

| Cpd | Name | Structure | General Synthetic Procedure and Spectral Data |
|---|---|---|---|
| 162 | N-((4,4-difluoro-1-(4-(1-methyl-1H-imidazol-4-ylsulfonyl)piperazin-1-yl)cyclohexyl)methyl)-2,4-difluorobenzamide Hydrochloride | 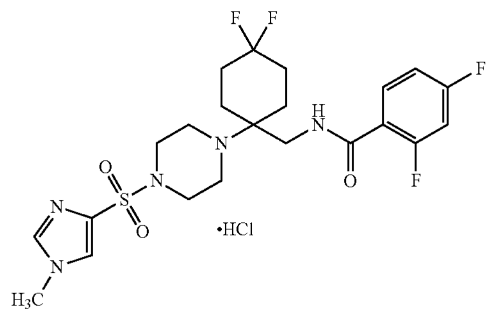 [SMILES: Cn1cnc(S(=O)(=O)N2CCN(C3(CNC(=O)c4ccc(F)cc4F)CCC(F)(F)CC3)CC2)c1 ; Cl] | GSP-1<br>$^1$H NMR (300 MHz, DMSO-$d_6$): δ9.83 (bs, 1H). 8.7 (bs, 1H), 7.95-7.50 (m, 3H), 7.50-7.10 (m, 2H), 4.00-3.60 (m, 9H), 3.50-3.20 (m, 2H), 3.20-2.90 (m, 2H), 2.40-1.90 (m, 8H; MS (ESI+) m/z 518 (M + H). |
| 163 | N-((4,4-Difluoro-1-(4-(1-methyl-1H-imidazol-4-ylsulfonyl)piperazin-1-yl)cyclohexyl)methyl)-2,6-difluorobenzamide Hydrochloride | 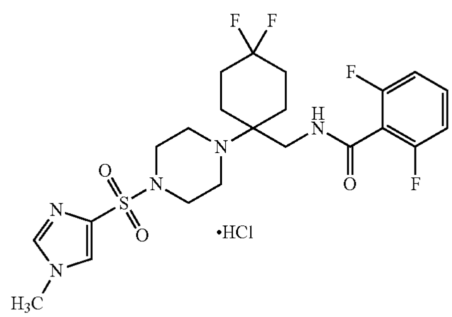 [SMILES: Cn1cnc(S(=O)(=O)N2CCN(C3(CNC(=O)c4c(F)cccc4F)CCC(F)(F)CC3)CC2)c1 ; Cl] | GSP-1<br>$^1$H NMR (300 MHz, CD$_3$OD): δ 8.87-8.57 (m, 1H), 8.22-8.10 (m, 1H), 7.63-7.45 (m, 1H), 7.21-6.99 (m, 2H), 4.20-3.71 (m, 9H), 3.68-3.34 (m, 4H), 2.35-2.03 (m, 8H); MS (APCI$^+$) m/z 519 (M + H). |
| 164 | N-((4,4-Difluoro-1-(4-(1-methyl-1H-imidazol-4-ylsulfonyl)piperazin-1-yl)cyclohexyl)methyl)-2,6-dimethylbenzamide Hydrochloride | 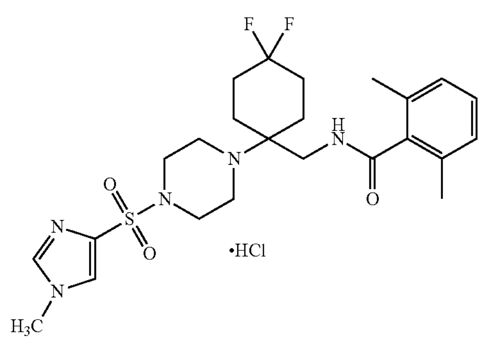 | GSP-1<br>$^1$H NMR (300 MHz, DMSO-$d_6$): δ 10.08 (s, 1H), 8.63 (s, 1H), 7.88 (m, 2H), 7.19 (m, 1H), 7.07 (m, 2H), 3.73 (s, 3H), 3.62 (m, 2H), 3.41 (m, 4H), 3.25 (m, 4H), 2.22 (s, 6H), 2.40-2.00 (m, 8H); MS (APCI$^+$) m/z 519 (M + H). |
| 165 | 4-Chloro-N-((4,4-difluoro-1-(4-(1-methyl-1H-imidazol-4-ylsulfonyl)piperazin-1-yl)cyclohexyl)methyl)-2-fluorobenzamide Hydrochloride | 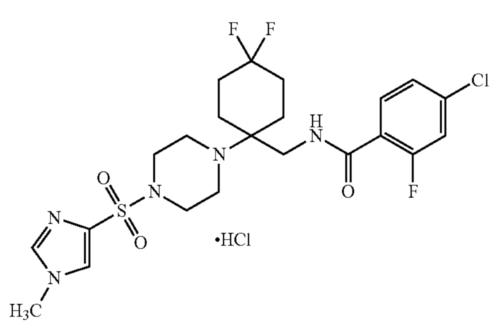 [SMILES: Cn1cnc(S(=O)(=O)N2CCN(C3(CNC(=O)c4ccc(Cl)cc4F)CCC(F)(F)CC3)CC2)c1 ; Cl] | GSP-1<br>$^1$H NMR (300 MHz, DMSO-$d_6$) δ 10.02 (s, 1H), 8.84 (s, 1H), 7.90 (m, 2H), 7.67 (m, 2H), 7.39 (m, 2H), 3.73 (s, 3H), 3.62 (m, 2H), 3.41 (m, 4H), 3.25 (m, 4H), 2.40-2.00 (m, 8H); MS (APCI+) m/z 534 (M + H). |

TABLE 1-continued

Examples, General Synthetic Procedures (GSP) and Spectral Data

| Cpd | Name | Structure | General Synthetic Procedure and Spectral Data |
|---|---|---|---|
| 166 | 2-Chloro-N-((4,4-difluoro-1-(4-(1-methyl-1H-imidazol-4-ylsulfonyl)piperazin-1-yl)cyclohexyl)methyl)-4-fluorobenzamide Hydrochloride | 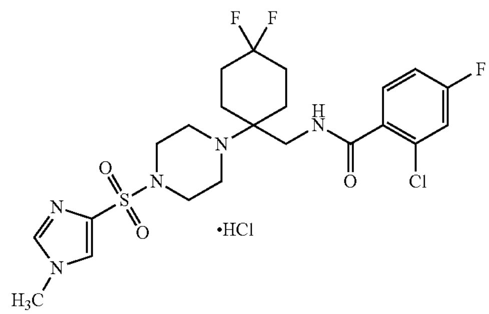 | GSP-1<br>$^1$H NMR (300 MHz, DMSO-d$_6$) δ 10.15 (s, 1H), 8.91 (s, 1H),7.86 (m, 2H), 7.80-7.34 (m, 3H), 3.73 (s, 3H), 3.62 (m, 2H), 3.41 (m, 4H), 3.25 (m, 4H), 2.40-2.00 (m, 8H); MS (APCI+) m/z 534 (M + H). |
| 167 | N-((4,4-Difluoro-1-(4-(1-methyl-1H-imidazol-4-ylsulfonyl)piperazin-1-yl)cyclohexyl)methyl)-2,4,6-trifluorobenzamide Hydrochloride | 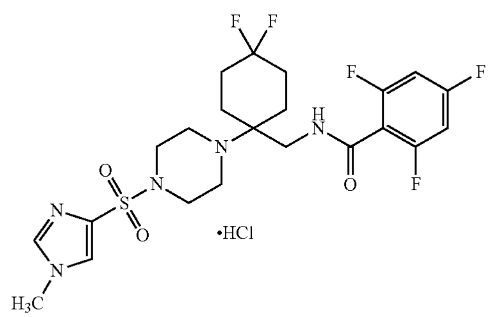 [SMILES: Cn1cnc(S(=O)(=O)N2CCN(C3(CNC(=O)c4c(F)cc(F)cc4F)CCC(F)(F)CC3)CC2)c1 ; Cl] | GSP-1<br>$^1$H NMR (300 MHz, DMSO-d$_6$) δ 10.24 (s, 1H), 9.22 (s, 1H), 7.86 (m, 1H), 7.33 (m, 2H), 3.73 (s, 3H), 3.62 (m, 2H), 3.41 (m, 4H), 3.25 (m, 4H), 2.40-2.00 (m, 8H); MS (APCI+) m/z 536 (M + H). |
| 168 | 4-Chloro-N-((4,4-difluoro-1-(4-(1-methyl-1H-imidazol-4-ylsulfonyl)piperazin-1-yl)cyclohexyl)methyl)-2-methylbenzamide Hydrochloride | 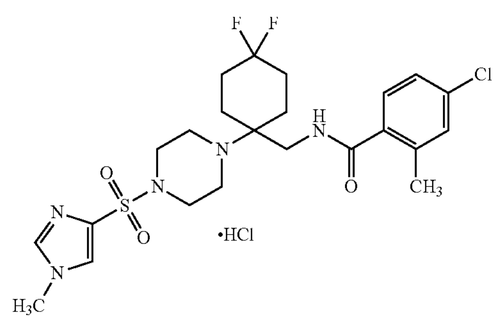 | GSP-1<br>$^1$H NMR (300 MHz, DMSO-d$_6$) δ 10.575 (s, 1H), 8.99 (s, 1H), 7.89 (m, 1H), 7.77 (m, 1H) 7.67 (m, 1H), 3.73 (s, 3H), 3.62 (m, 2H), 3.30 (m, 4H), 3.08 (m, 4H), 2.34 (s, 3H), 2.40-2.00 (m, 8H); MS (APCI+) m/z 550 (M + H). |
| 169 | N-((4,4-Difluoro-1-(4-(1-methyl-1H-imidazol-4-ylsulfonyl)piperazin-1-yl)cyclohexyl)methyl)-4-fluoro-2-(trifluoromethyl)benzamide Hydrochloride | 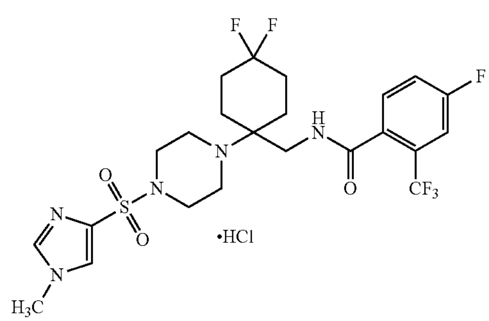 [SMILES: Cn1cnc(S(=O)(=O)N2CCN(C3(CNC(=O)c4ccc(F)cc4C(F)(F)F)CCC(F)(F)CC3)CC2)c1 ; Cl] | GSP-1<br>$^1$H NMR (300 MHz, DMSO-d$_6$) δ 10.57 (s, 1H), 8.99 (s, 1H), 7.90 (m, 2H), 7.77 (m, 2H), 7.65 (m, 1H), 3.73 (s, 3H), 3.62 (m, 2H), 3.41 (m, 4H), 3.25 (m, 4H), 2.40-2.00 (m, 8H); MS (APCI+) m/z 550 (M + H). |

TABLE 1-continued

Examples, General Synthetic Procedures (GSP) and Spectral Data

| Cpd | Name | Structure | General Synthetic Procedure and Spectral Data |
|---|---|---|---|
| 170 | N-((4,4-Difluoro-1-(4-(1-methyl-1H-imidazol-4-ylsulfonyl)piperazin-1-yl)cyclohexyl)methyl)-2-fluoro-4-(trifluoromethyl)benzamide Hydrochloride | 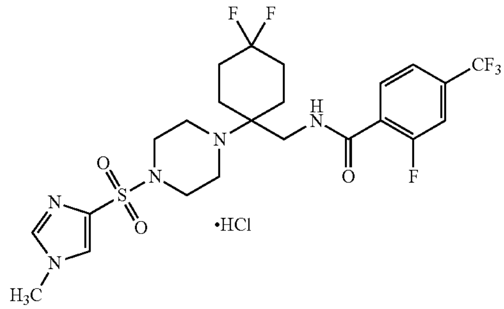 [SMILES: Cn1cnc(S(=O)(=O)N2CCN(C3(CNC(=O)c4ccc(C(F)(F)F)cc4F)CCC(F)(F)CC3)CC2)c1 ; Cl] | GSP-1 $^1$H NMR (300 MHz, DMSO-$d_6$) δ 10.78 (s, 1H), 9.07 (s, 1H), 7.89 (m, 4H), 7.71 (m, 1H), 3.73 (s, 3H), 3.62 (m, 2H), 3.41 (m, 4H), 3.25 (m, 4H), 2.40-2.00 (m, 8H); MS (APCI+) m/z 568 (M + H). |
| 171 | N-((4,4-Difluoro-1-(4-(1-methyl-1H-imidazol-4-ylsulfonyl)piperazin-1-yl)cyclohexyl)methyl)-2-chloro-4-(trifluoromethyl)benzamide Hydrochloride | 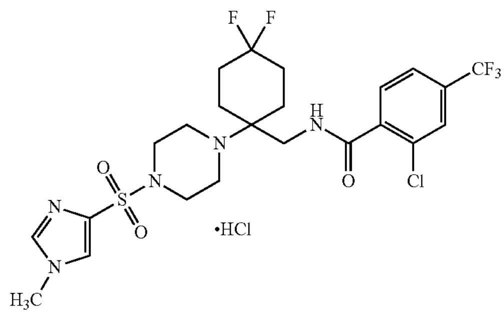 [SMILES: Cn1cnc(S(=O)(=O)N2CCN(C3(CNC(=O)c4ccc(C(F)(F)F)cc4Cl)CCC(F)(F)CC3)CC2)c1 ; Cl] | GSP-1 $^1$H NMR (300 MHz, DMSO-$d_6$) δ 10.78 (s, 1H), 9.07 (s, 1H), 7.89 (m, 4H), 7.71 (m, 1H), 3.73 (s, 3H), 3.62 (m, 2H), 3.41 (m, 4H), 3.25 (m, 4H), 2.40-2.00 (m, 8H); MS (APCI+) m/z 584 (M + H). |
| 172 | N-((4,4-Difluoro-1-(4-(1-methyl-1H-imidazol-4-ylsulfonyl)piperazin-1-yl)cyclohexyl)methyl)-2-fluoro-6-(trifluoromethyl)benzamide Hydrochloride | 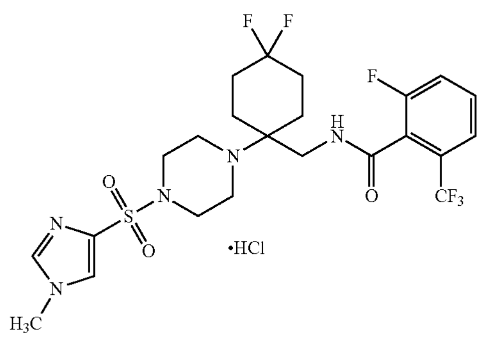 | GSP-1 $^1$H NMR (300 MHz, DMSO-$d_6$) δ 10.26 (s, 1H), 9.20 (s, 1H), 7.89 (m, 2H), 7.71 (m, 3H), 3.72 (s, 3H), 3.62 (m, 2H), 3.41 (m, 4H), 3.25 (m, 4H), 2.40-1.55 (m, 8H); MS (APCI+) m/z 568 (M + H). |
| 173 | 2-Chloro-N-((4,4-Difluoro-1-(4-(1-methyl-1H-imidazol-4-ylsulfonyl)piperazin-1-yl)cyclohexyl)methyl)-6-methoxybenzamide Hydrochloride | 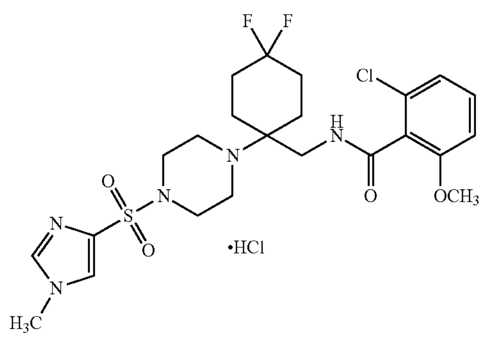 [SMILES: COc1cccc(Cl)c1C(=O)NCC1(N2CCN(S(=O)(=O)c3cn(C)cn3)CC2)CCC(F)(F)CC1 ; Cl] | GSP-1 $^1$H NMR (300 MHz, DMSO-$d_6$) δ 9.93 (s, 1H), 8.90 (s, 1H), 7.91 (m, 2H), 7.40 (m, 1H), 7.11 (m, 2H), 3.81 (s, 3H), 3.73 (s, 3H), 3.62 (m, 2H), 3.41 (m, 4H), 3.25 (m, 4H), 2.40-2.00 (m, 8H); MS (APCI+) m/z 546 (M + H). |

TABLE 1-continued

Examples, General Synthetic Procedures (GSP) and Spectral Data

| Cpd | Name | Structure | General Synthetic Procedure and Spectral Data |
|---|---|---|---|
| 174 | 2,6-Dichloro-N-((4,4-difluoro-1-(4-(1-methyl-1H-imidazol-4-ylsulfonyl)piperazin-1-yl)cyclohexyl)methyl)benzamide Hydrochloride | 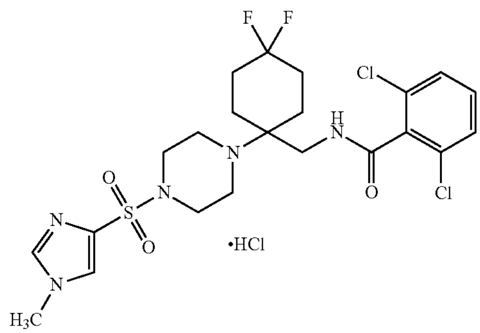 [SMILES: Cn1cnc(S(=O)(=O)N2CCN(C3(CNC(=O)c4c(Cl)cccc4Cl)CCC(F)(F)CC3)CC2)c1 ; Cl] | GSP-1<br>$^1$H NMR (300 MHz, DMSO-d$_6$): δ (10.95, s, 1H), 9.16 (s, 1H), 7.89 (m, 2H), 7.58-7.46 (m, 3H), 3.73 (s, 3H), 3.62 (m, 2H), 3.41 (m, 4H), 3.25 (m, 4H), 2.40-2.00 (m, 8H); MS (APCI+) m/z 550 (M + H). |
| 175 | N-((4,4-Difluoro-1-(4-(1-methyl-1H-imidazol-4-ylsulfonyl)piperazin-1-yl)cyclohexyl)methyl)-2-fluorobenzamide Hydrochloride | 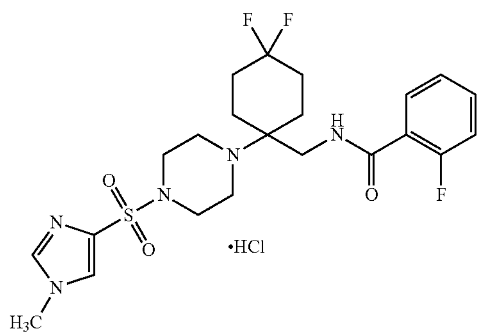 | GSP-1<br>$^1$H NMR (300 MHz, DMSO-d$_6$): δ (10.95, s, 1H), 9.16 (s, 1H), 7.89 (m, 2H), 7.58-7.46 (m, 3H), 3.73 (s, 3H), 3.62 (m, 2H), 3.41 (m, 4H), 3.25 (m, 4H), 2.40-2.00 (m, 8H); MS (APCI+) m/z 550 (M + H). |
| 176 | N-((4,4-Difluoro-1-(4-(1-methyl-1H-imidazol-4-ylsulfonyl)piperazin-1-yl)cyclohexyl)methyl)-2-(trifluoromethyl)benzamide Hydrochloride | 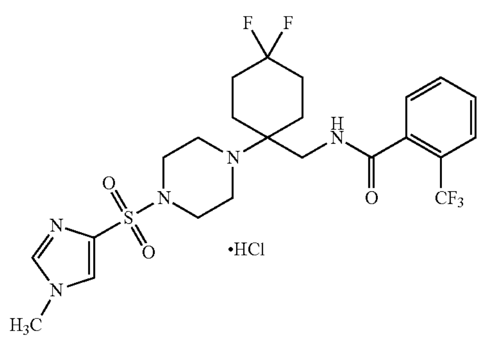 | GSP-1<br>$^1$H NMR (300 MHz, CDCl$_3$): δ 7.71 (m, 1H), 7.62-7.45 (m, 3H), 7.49 (d, J = 1.2 Hz, 1H), 7.43 (d, J = 1.2 Hz, 1H), 5.87 (m, 1H), 3.77 (s, 3H), 3.55 (d, J = 5.9 Hz, 2H), 3.20 (m, 4H), 2.78 (m, 4H), 2.04-1.82 (m, 6H), 1.81-1.68 (m, 2H); MS (APCI+) m/z 550 (M + H). |
| 177 | N-((4,4-Difluoro-1-(4-(1-methyl-1H-imidazol-4-ylsulfonyl)piperazin-1-yl)cyclohexyl)methyl)-2-methoxybenzamide Hydrochloride | 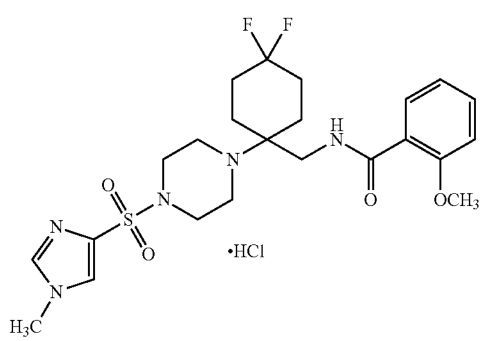 [SMILES: COc1ccccc1C(=O)NCC1(N2CCN(S(=O)(=O)c3cn(C)cn3)CC2)CCC(F)(F)CC1 ; Cl] | GSP-1<br>$^1$H NMR (300 MHz, DMSO-d$_6$) δ 10.77 (s, 1H), 8.59 (s, 1H), 7.90 (d, J = 7.5, 2H), 7.58 (d, J = 7.2 Hz, 2H), 7.50 (t, J = 8.4 Hz, 1H), 7.16 (d, J = 8.4 Hz, 1H). 7.05 (d, J = 7.5 Hz, 2H), 3.87 (s, 3H), 3.72 (s, 3H), 3.62 (m, 2H), 3.49 (m, 4H), 3.24 (m, 4H), 2.40-2.00 (m, 8H); MS (APCI+) m/z 512 (M + H). |

TABLE 1-continued

Examples, General Synthetic Procedures (GSP) and Spectral Data

| Cpd | Name | Structure | General Synthetic Procedure and Spectral Data |
|---|---|---|---|
| 178 | 2,4-Dichloro-N-((4,4-difluoro-1-(4-(1-methyl-1H-imidazol-4-ylsulfonyl)piperazin-1-yl)cyclohexyl)methyl)benzamide Hydrochloride | 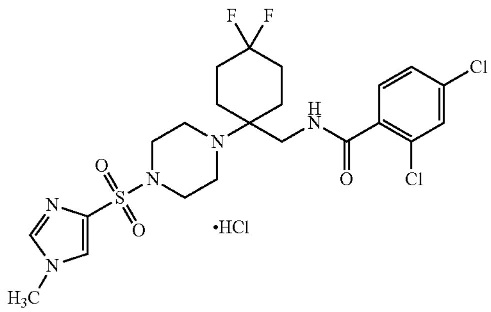 | GSP-1<br>$^1$H NMR (300 MHz, DMSO-$d_6$) δ (10.58, s, 1H), 8.97 (s, 1H), 7.89 (m, 2H), 7.74 (m, 1H), 7.55 (m, 2H), 7.58-7.46 (m, 3H), 3.73 (s, 3H), 3.62 (m, 2H), 3.41 (m, 4H), 3.25 (m, 4H), 2.40-2.00 (m, 8H); MS (APCI+) m/z 550 (M + H). |
| 179 | N-((4,4-difluoro-1-(4-(1-methyl-1H-imidazol-4-ylsulfonyl)piperazin-1-yl)cyclohexyl)methyl)-2-methylbenzamide Hydrochloride | 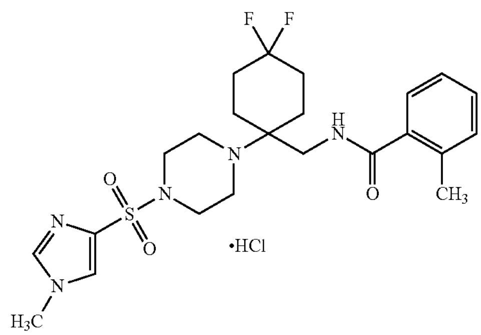 | GSP-1<br>$^1$H NMR (300 MHz, DMSO-$d_6$) δ 10.65 (s, 1H), 8.71 (s, 1H), 7.89 (m, 2H), 7.44-7.25 (m, 4H), 3.73 (s, 3H), 3.62 (m, 2H), 3.41 (m, 4H), 3.25 (m, 4H), 2.43 (s, 3H), 2.40-2.00 (m, 8H); MS (APCI+) m/z 496 (M + H). |
| 180 | 2-Chloro-N-((4,4-difluoro-1-(4-(1-methyl-1H-imidazol-4-ylsulfonyl)piperazin-1-yl)cyclohexyl)methyl)-6-fluorobenzamide Hydrochloride | 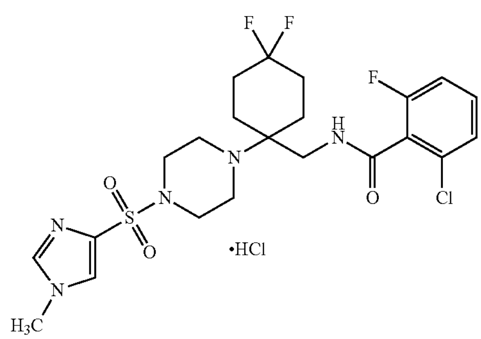 | GSP-1<br>$^1$H NMR (300 MHz, DMSO-$d_6$) δ 10.68 (s, 1H), 9.21 (s, 1H), 7.89 (m, 2H), 7.55-7.50 (m, 1H), 7.44-7.33 (m, 2H), 3.73 (s, 3H), 3.62 (m, 2H), 3.37 (m, 4H), 3.25 (m, 4H), 2.40-2.00 (m, 8H); MS (APCI+) m/z 534 (M + H). |
| 181 | 2-Chloro-N-((4,4-difluoro-1-(4-(1-methyl-1H-imidazol-4-ylsulfonyl)piperazin-1-yl)cyclohexyl)methyl)-6-methylbenzamide Hydrochloride | 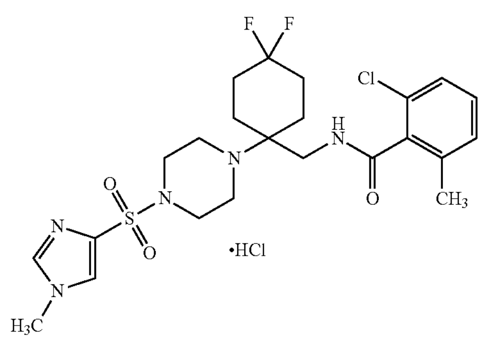 | GSP-1<br>$^1$H NMR (300 MHz, DMSO-$d_6$) δ 10.61 (s, 1H), 8.92 (s, 1H), 7.89 (m, 2H), 7.34 (m, 2H), 7.26 (m, 1H), 3.73 (s, 3H), 3.62 (m, 2H), 3.41 (m, 4H), 3.25 (m, 4H), 2.27 (s, 3H), 2.40-2.00 (m, 8H); MS (APCI+) m/z 530 (M + H). |

TABLE 1-continued

Examples, General Synthetic Procedures (GSP) and Spectral Data

| Cpd | Name | Structure | General Synthetic Procedure and Spectral Data |
|---|---|---|---|
| 182 | N-((4,4-Difluoro-1-(4-(1-methyl-1H-imidazol-4-ylsulfonyl)piperazin-1-yl)cyclohexyl)methyl)-2-fluoro-6-methylbenzamide Hydrochloride | 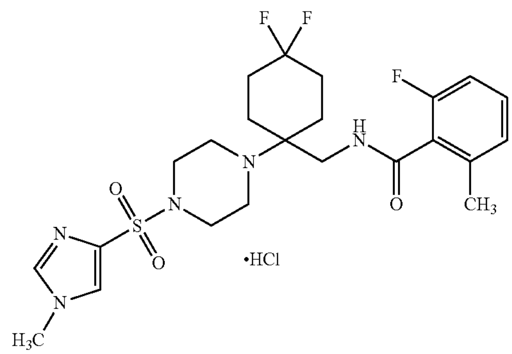 [SMILES: Cc1cccc(F)c1C(=O)NCC1(N2CCN(S(=O)(=O)c3cn(C)cn3)CC2)CCC(F)(F)CC1 ; Cl] | GSP-1<br>$^1$H NMR (300 MHz, DMSO-$d_6$) δ 10.38 (s, 1H), 8.97 (s, 1H), 7.89 (m, 2H), 7.36 (m, 1H), 7.12 (m, 2H), 3.73 (s, 3H), 3.62 (m, 2H), 3.41 (m, 4H), 3.25 (m, 4H), 2.28 (s, 3H) 2.40-2.00 (m, 8H); MS (APCI+) m/z 514 (M + H). |
| 183 | N-((4,4-Difluoro-1-(4-(1-methyl-1H-imidazol-4-ylsulfonyl)piperazin-1-yl)cyclohexyl)methyl)-2-(difluoromethoxy)benzamide Hydrochloride | 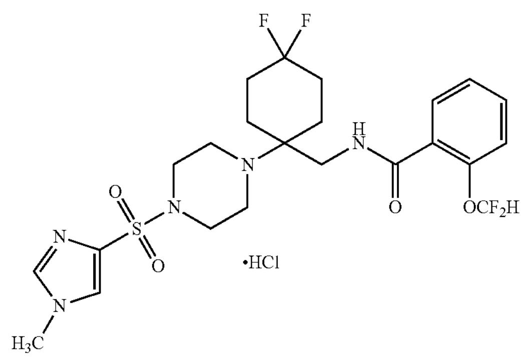 | GSP-1<br>$^1$H NMR (300 MHz, DMSO-$d_6$): δ 10.44 (bs, 1H), 8.9 (bs, 1H), 7.95-7.85 (m, 2H), 7.7-7.4 (m, 4H), 3.90-3.60 (m, 7H) 3.40-2.70 (m, 6H), 2.4-2.0 (m, 8H ); MS (APCI$^+$) m/z 548 (M + H). |
| 184 | N-((4,4-Difluoro-1-(4-(1-methyl-1H-imidazol-4-ylsulfonyl)piperazin-1-yl)cyclohexyl)methyl)-4-fluoro-2-methylbenzamide Hydrochloride | 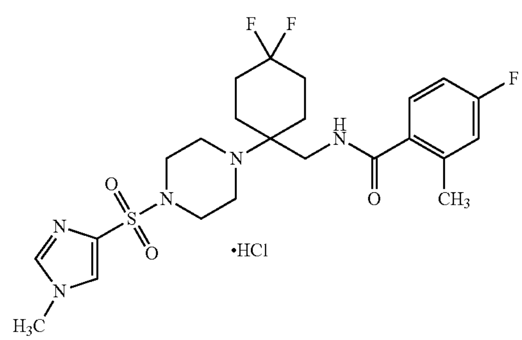 [SMILES: Cc1cc(F)ccc1C(=O)NCC1(N2CCN(S(=O)(=O)c3cn(C)cn3)CC2)CCC(F)(F)CC1 ; Cl] | GSP-1<br>$^1$H NMR (300 MHz, DMSO-$d_6$) δ 10.56 (s, 1H), 8.72 (s, 1H), 7.89 (m, 2H), 7.52 (m, 1H), 7.14 (m, 2H), 3.68 (s, 3H), 3.62 (m, 2H), 3.41 (m, 4H), 3.25 (m, 4H), 2.36 (s, 3H), 2.40-2.00 (m, 8H); MS (APCI+) m/z 514 (M + H). |
| 185 | 2-Chloro-N-((4,4-difluoro-1-(4-(1-methyl-1H-imidazol-4-ylsulfonyl)piperazin-1-yl)cyclohexyl)methyl)-6-(trifluoromethyl)benzamide Hydrochloride | 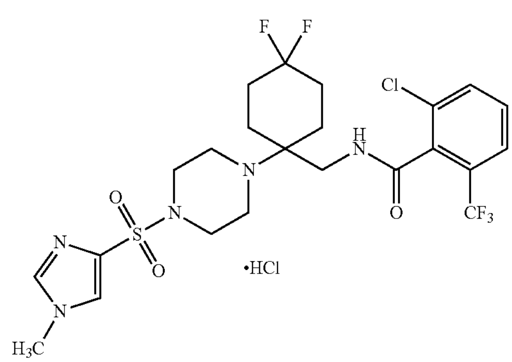 [SMILES: Cn1cnc(S(=O)(=O)N2CCN(C3(CNC(=O)c4c(Cl)cccc4C(F)(F)F)CCC(F)(F)CC3)CC2)c1 ; Cl] | GSP-1<br>$^1$H NMR (300 MHz, DMSO-$d_6$) δ 9.79 (s, 1H), 9.09 (s, 1H), 7.91-7.62 (m, 3H), 3.73 (s, 3H), 3.62 (m, 2H), 3.41 (m, 4H), 3.25 (m, 4H), 2.40-2.00 (m, 8H); MS (APCI+) m/z 584 (M + H). |

TABLE 1-continued

Examples, General Synthetic Procedures (GSP) and Spectral Data

| Cpd | Name | Structure | General Synthetic Procedure and Spectral Data |
|---|---|---|---|
| 186 | N-((4,4-Difluoro-1-(4-(1-methyl-1H-imidazol-4-ylsulfonyl)piperazin-1-yl)cyclohexyl)methyl)-2-fluoro-6-(trifluoromethoxy)benzamide Hydrochloride | 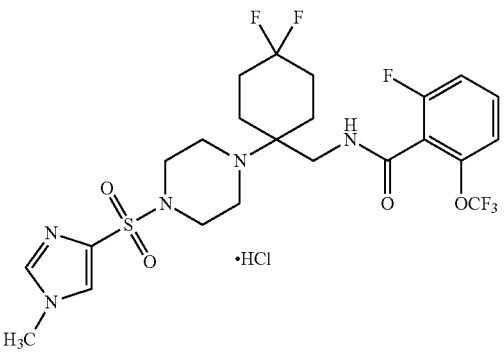 [SMILES: Cn1cnc(S(=O)(=O)N2CCN(C3(CNC(=O)c4c(F)cccc4OC(F)(F)F)CCC(F)(F)CC3)CC2)c1 ; Cl] | GSP-1<br>$^1$H NMR (300 MHz, DMSO-$d_6$) δ 9.98 (s, 1H), 9.92 (s, 1H), 7.89 (m, 2H), 7.64 (m, 1H), 7.36 (m, 2H), 3.73 (s, 3H), 3.62 (m, 2H), 3.41 (m, 4H), 3.25 (m, 4H), 2.40-2.00 (m, 8H); MS (APCI+) m/z 584 (M + H). |
| 187 | 2-Chloro-N-((4,4-difluoro-1-(4-(1-methyl-1H-imidazol-4-ylsulfonyl)piperazin-1-yl)cyclohexyl)methyl)-6-(trifluoromethoxy)benzamide Hydrochloride | 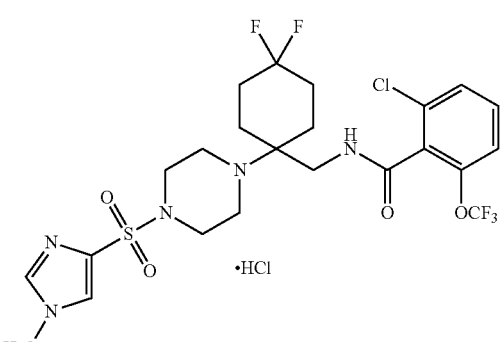 | GSP-1<br>$^1$H NMR (300 MHz, DMSO-$d_6$) δ 10.09 (s, 1H), 9.14 (s, 1H), 7.89 (m, 2H), 7.55 (m, 3H), 3.73 (s, 3H), 3.62 (m, 2H), 3.41 (m, 4H), 3.25 (m, 4H), 2.40-2.00 (m, 8H); MS (APCI+) m/z 600 (M + H). |
| 188 | N-((4,4-Difluoro-1-(4-(1-methyl-1H-imidazol-4-ylsulfonyl)piperazin-1-yl)cyclohexyl)methyl)-2-(difluoromethoxy)-6-fluorobenzamide Hydrochloride | 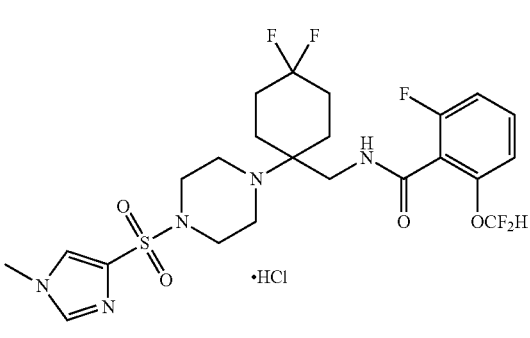 | GSP-1<br>$^1$H NMR (300 MHz, DMSO-$d_6$) δ 10.39 (s, 1H), 9.14 (s, 1H), 7.90 (m, 2H), 7.57 (m, 1H), 7.21 (m, 2H), 3.73 (s, 3H), 3.62 (m, 2H), 3.41 (m, 4H), 3.25 (m, 4H), 2.40-2.00 (m, 8H); MS (APCI+) m/z 566 (M + H). |
| 189 | N-((4,4-Difluoro-1-(4-(1-melhyl-1H-1,2,3-triazol-4-ylsulfonyl)piperazin-1-yl)cyclohexyl)methyl)-2,6-difluorobenzamide Hydrochloride | 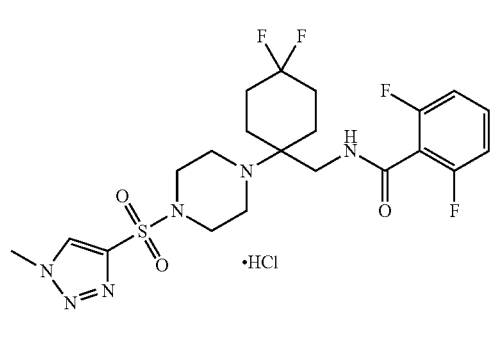 [SMILES: Cn1cc(S(=O)(=O)N2CCN(C3(CNC(=O)c4c(F)cccc4F)CCC(F)(F)CC3)CC2)nn1 ; Cl] | GSP-1<br>$^1$H NMR (300 MHz, DMSO-$d_6$): δ 9.24 (m, 1H), 8.71 (m, 1H), 7.53 (m, 1H), 7.20 (m, 2H), 4.14 (s, 3H), 3.86 (m, 2H), 3.39 (m, 2H), 3.12 (m, 2H), 2.73 (m, 2H), 2.11 (m, 2H), 1.91 (m, 2H), 1.78 (m, 2H), 1.53 (m, 2H); MS (APCI+) 519 (M + H). |

TABLE 1-continued

Examples, General Synthetic Procedures (GSP) and Spectral Data

| Cpd | Name | Structure | General Synthetic Procedure and Spectral Data |
|---|---|---|---|
| 190 | 2,6-Dichloro-N-((4,4-difluoro-1-(4-(1-methyl-1H-1,2,3-triazol-4-ylsulfonyl)piperazin-1-yl)cyclohexyl)methyl)benzamide Hydrochloride | 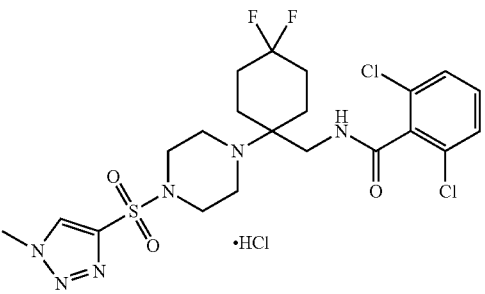 [SMILES: Cn1cc(S(=O)(=O)N2CCN(C3(CNC(=O)c4c(Cl)cccc4Cl)CCC(F)(F)CC3)CC2)nn1 ; Cl] | GSP-1<br>$^1$H NMR (300 MHz, DMSO-d$_6$): δ 10.3 (bs, 1H). 8.70 (bs, 1H), 8.55-8.95 (m, 1H), 7.32-7.67 (m, 3H), 4.13 (s, 3H), 3.75-3.80 (m, 2H), 3.33-3.73 (m, 2H), 2.89-3.33 (m, 4H), 2.78-2.89 (m, 2H), 1.51-2.44 (m, 8H); MS (ESI+) m/z 550 (M + H). |
| 191 | 2-Chloro-N-((4,4-difluoro-1-(4-(1-methyl-1H-1,2,3-triazol-4-ylsulfonyl)piperazin-1-yl)cyclohexyl)methyl)-6-(trifluoromethoxy)benzamide Hydrochloride | 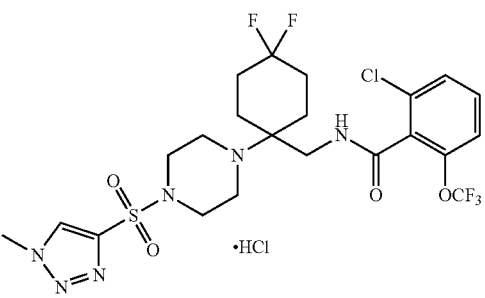 [SMILES: Cn1cc(S(=O)(=O)N2CCN(C3(CNC(=O)c4c(Cl)cccc4OC(F)(F)F)CCC(F)(F)CC3)CC2)nn1 ; Cl] | GSP-1<br>$^1$H NMR (300 MHz, DMSO-d$_6$): δ 10.3 (bs, 1H), 9.15 (bs, 1H), 8.55-8.95 (m, 1H), 7.32-7.77 (m, 3H), 4.13 (s, 3H), 3.75-3.80 (m, 2H), 3.33-3.73 (m, 2H), 2.89-3.33 (m, 4H), 2.78-2.89 (m, 2H), 1.51-2.44 (m, 8H); MS (ESI+) m/z 601 (M + H). |
| 192 | 2-Chloro-N-((4,4-difluoro-1-(4-(1-methyl-1H-1,2,3-triazol-4-ylsulfonyl)piperazin-1-yl)cyclohexyl)methyl)-4-fluorobenzamide Hydrochloride | 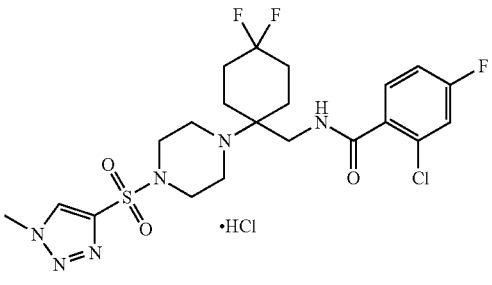 [SMILES: Cn1cc(S(=O)(=O)N2CCN(C3(CNC(=O)c4ccc(F)cc4Cl)CCC(F)(F)CC3)CC2)nn1 ; Cl] | GSP-1<br>$^1$H NMR (300 MHz, DMSO-d$_6$): δ 9.95 (bs, 1H), 8.72-8.90 (bs, 1H), 8.35-8.51 (m, 1H), 7.21-7.67 (m, 3H), 4.13 (s, 3H), 3.75-3.80 (m, 2H), 3.33-3.73 (m, 2H), 2.89-3.33 (m, 4H), 2.78-2.89 (m, 2H), 1.51-2.44 (m, 8H); MS (ESI+) m/z 535 (M + H). |
| 193 | 2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide Hydrochloride | 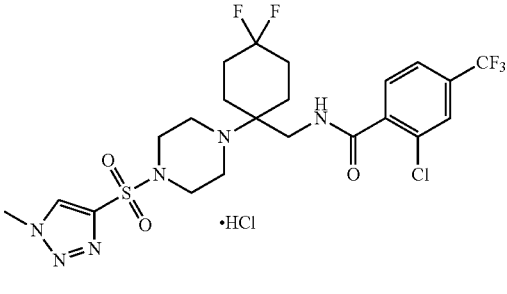 [SMILES: Cn1cc(S(=O)(=O)N2CCN(C3(CNC(=O)c4ccc(C(F)(F)F)cc4Cl)CCC(F)(F)CC3)CC2)nn1 ; Cl] | GSP-1<br>$^1$H NMR (300 MHz, DMSO-d$_6$): δ 10.3 (bs, 1H), 9.15 (bs, 1H), 8.55-8.95 (m, 1H), 7.52-8.05 (m, 3H), 4.13 (s, 3H), 3.75-3.80 (m, 2H), 3.33-3.73 (m, 2H), 2.89-3.33 (m, 4H), 2.78-2.89 (m, 2H), 1.51-2.44 (m, 8H); MS (ESI+) m/z 585 (M + H). |
| 194 | N-(1-(4,4-Difluoro-1-(4-(1-methyl-1H-imidazol-4-ylsulfonyl)piperazin-1-yl)cyclohexyl)ethyl)-2,6-difluorobenzamide Hydrochloride | 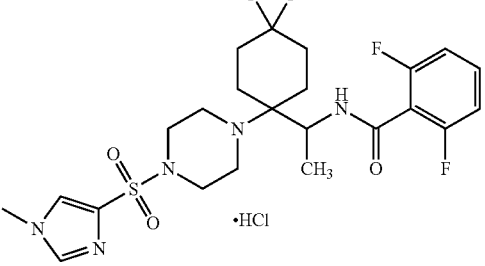 | GSP-4<br>$^1$H NMR (500 MHz, CD$_3$OD) δ 8.06 (bs, 1H), 7.81 (s, 1H), 7.45 (bs, 1H), 7.08-7.05 (m, 2H), 4.42-4.40 (m, 1H), 3.82 (s, 3H), 3.35-2.80 (m, 8H), 2.08-1.50 (m, 8H), 1.17 (bs, 3H); MS (ESI+) m/z 532 (M + H). |

TABLE 1-continued

Examples, General Synthetic Procedures (GSP) and Spectral Data

| Cpd | Name | Structure | General Synthetic Procedure and Spectral Data |
|---|---|---|---|
| 195 | N-(1-(4,4-Difluoro-1-(4-(1-methyl-1H-imidazol-4-yl)sulfonyl)piperazin-1-yl)cyclohexyl)ethyl)-2,6-difluorobenzamide Hydrochloride | 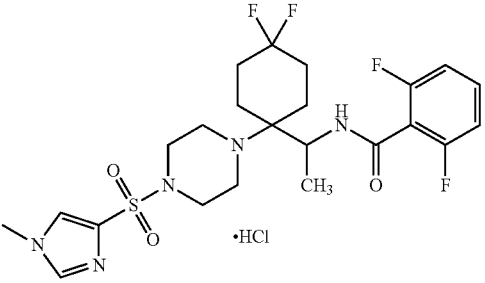 [SMILES: CC(NC(=O)c1c(F)cccc1F)C1(N2CCN(S(=O)(=O)c3cn(C)cn3)CC2)CCC(F)(F)CC1 ; Cl] | GSP-4<br>$^1$H NMR (500 MHz, CD$_3$OD) δ 8.06 (bs, 1H), 7.81 (s, 1H), 7.45 (bs, 1H), 7.08-7.05 (m, 2H), 4.42-4.40 (m, 1H), 3.82 (s, 3H), 3.35-2.80 (m, 8H), 2.08-1.50 (m, 8H), 1.17 (bs, 3H); MS (ESI+) m/z 532 (M + H). |
| 196 | N-(1-(4,4-Difluoro-1-(4-(propylsulfonyl)piperazin-1-yl)cyclohexyl)ethyl)-2,6-difluorobenzamide Hydrochloride | 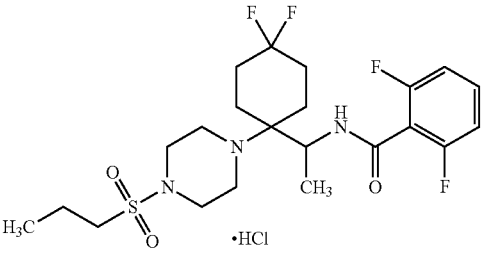 [SMILES: CCCS(=O)(=O)N1CCN(C2(C(C)NC(=O)c3c(F)cccc3F)CCC(F)(F)CC2)CC1 ; Cl] | GSP-4<br>$^1$H NMR (500 MHz, CD$_3$OD) δ 7.49-7.45 (m, 1H), 7.05 (t, J = 8.0 Hz, 2H), 4.43 (q, J = 6.5 Hz, 1H), 3.30-3.06 (m, 4H), 3.04-2.80 (m, 6H), 2.07-1.94 (m, 4H), 1.89-1.62 (m, 6H), 1.18 (d, J = 7.0 Hz, 3H), 1.06 (t, J = 7.0 Hz, 3H); MS (ESI+) m/z 494 (M + H). |
| 197 | N-(1-(4,4-Difluoro-1-(4-(propylsulfonyl)piperazin-1-yl)cyclohexyl)ethyl)-2,6-difluorobenzamide Hydrochloride | 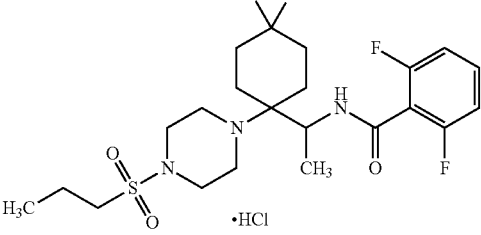 | GSP-4<br>$^1$H NMR (500 MHz, CD$_3$OD) δ 7.49-7.45 (m, 1H), 7.05 (t, J = 8.0 Hz, 2H), 4.43 (q, J = 6.5 Hz, 1H), 3.30-3.06 (m, 4H), 3.04-2.80 (m, 6H), 2.07-1.94 (m, 4H), 1.89-1.62 (m, 6H), 1.18 (d, J = 7.0 Hz, 3H), 1.06 (t, J = 7.0 Hz, 3H); MS (ESI+) m/z 494 (M + H). |
| 198 | 2,6-Difluoro-N-((6-(4-(propylsulfonyl)piperazin-1-yl)spiro[2.5]octan-6-yl)methyl)benzamide Hydrochloride | 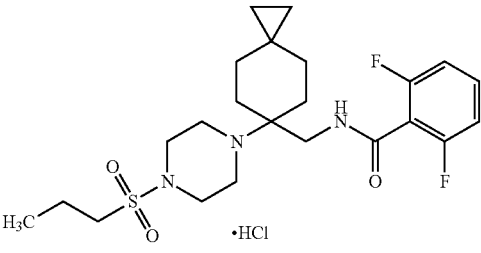 [SMILES: CCCS(=O)(=O)N1CCN(C2(CNC(=O)c3c(F)cccc3F)CCC3(CC3)CC2)CC1 ; Cl] | GSP-1<br>$^1$H NMR (400 MHz, CDCl$_3$) δ 7.56-7.40 (m, 1H), 7.20-6.99 (m, 2H), 4.00-3.95 (m, 2H), 3.95-3.87 (m, 2H), 3.50-3.43 (m, 2H), 3.33-3.20 (m, 2H), 3.10-2.84 (m, 4H), 2.22-1.55 (m, 8H), 1.20-0.82 (m, 2H), 1.05 (t, J = 7.5 Hz, 3H), 0.45-0.20 (m, 4H); MS (ESI+) m/z 470 (M + H). |
| 199 | 2,6-Difluoro-N-((3-(4-(propylsulfonyl)piperazin-1-yl)bicyclo[3.1.0]hexan-3-yl)methyl)benzamide Hydrochloride | 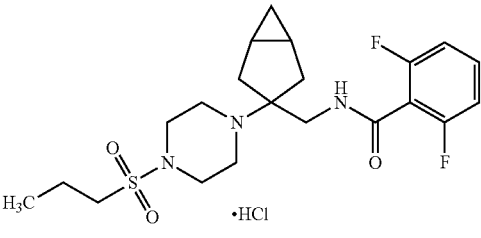 [SMILES: CCCS(=O)(=O)N1CCN(C2(CNC(=O)c3c(F)cccc3F)CC3CC3C2)CC1 ; Cl] | GSP-1<br>$^1$H NMR (500 MHz, CD$_3$OD) δ 7.55-7.51 (m, 1H), 7.10 (t, J = 8.5 Hz, 2H), 4.04-3.70 (m, 6H), 3.48-3.40 (m, 2H), 3.12-3.08 (m, 4H), 2.44 (d, J = 12.0 Hz, 2H), 2.09-2.02 (m, 2H), 1.86-1.82 (m, 2H), 1.60 (bs, 2H), 1.07 (t, J = 7.5 Hz, 3H), 0.85-0.83 (m, 1H), 0.49 (bs, 1H); MS (ESI+) m/z 442 (M + H). |
| 200 | 2,4-Dichloro-N-((1-(4-(cyclopropylmethyl-sulfonyl)piperidin-1-yl)cyclohexyl)methyl)benzamide Hydrochloride | 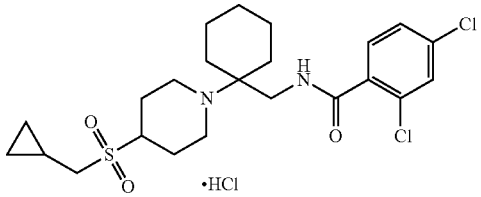 [SMILES: O=C(NCC1(N2CCC(S(=O)(=O)CC3CC3)CC2)CCCCC1)c1ccc(Cl)cc1Cl ; Cl] | GSP-1<br>$^1$H NMR (300 MHz, CDCl$_3$): δ 7.70 (d, J = 8.4 Hz, 1H), 7.43 (d, J = 1.8 Hz, 1H), 7.34-7.30 (m, 1H), 6.88 (bs, 1H), 3.57 (d, J = 4.8 Hz, 2H), 3.25-3.20 (m, 2H), 2.99-2.88 (m, 1H), 2.86 (d, J = 7.2 Hz, 2H), 2.40-2.35 (m, 2H), 2.20-2.00 (m, 2H), 1.90-1.41 (m, 12H), 1.15-1.05 (m, 1H) 0.75-0.65 (m, 2H), 0.40-0.30 (m, 2H); MS (ESI$^+$) m/z 487 (M + H). |

TABLE 1-continued

Examples, General Synthetic Procedures (GSP) and Spectral Data

| Cpd | Name | Structure | General Synthetic Procedure and Spectral Data |
|---|---|---|---|
| 201 | N-((4,4-difluoro-1-(4-(propylsulfonyl)piperidin-1-yl)cyclohexyl)methyl)-2,6-difluorobenzamide Hydrochloride | 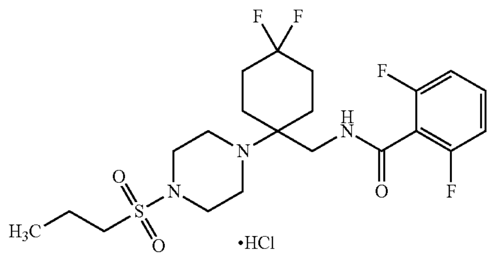 [SMILES: CCCS(=O)(=O)N1CCN(C2(CNC(=O)c3c(F)cccc3F)CCC(F)(F)CC2)CC1 ; Cl] | GSP-1<br>$^1$H NMR (300 MHz, DMSO-d$_6$) δ 9.73 (bs, 1H), 9.27 (bs, 1H), 7.63-7.52 (m, 1H) 7.27-7.16 (m, 2H), 3.8 (d, J = 6.0 Hz, 2H), 3.82-3.73 (m, 3H) 3.40-3.24 (m, 3H), 3.18-3.10 (m, 2H), 2.30-2.03 (m, 10 H), 1.78-1.63 (m, 2H), 1.02 (t, J = 7.5 Hz, 3H); MS (ESI+) m/z 479 (M + H). |
| 202 | 4-Chloro-N-((1-(4-(propylsulfonyl)piperazin-1-yl)cyclohexyl)methyl)benzamide Hydrochloride | 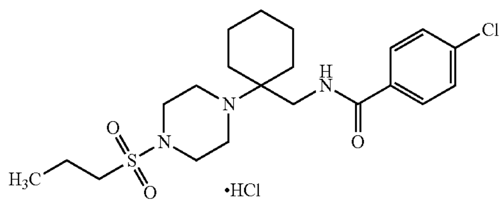 | GSP-1<br>$^1$H NMR (300 MHz, CDCl$_3$) δ 7.80-7.72 (m, 2H), 7.50-7.42 (m, 1H), 6.61 (bs, 1H), 3.58-3.56 (d, J = 5.2 Hz, 2H), 3.23-3.20 (m, 4H), 2.87-2.82 (m, 2H), 2.79-2.71 (m, 4H), 1.89-1.80 (m, 2H), 1.79-1.42 (m, 10H), 1.08-1.01 (t, J = 7.4 Hz, 3H); MS (ESI+) m/z 433 (M + H). |
| 203 | 2-Chloro-N-((1-(4-(ethylsulfonyl)piperazin-1-yl)-4,4-difluorocyclohexyl)methyl)-4-(trifluoromethyl)benzamide Hydrochloride | 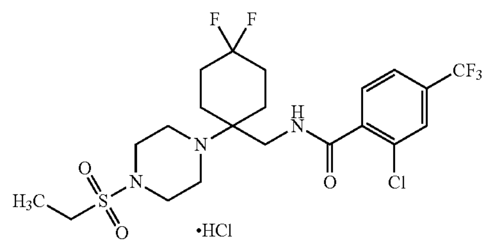 [SMILES: CCS(=O)(=O)N1CCN(C2(CNC(=O)c3ccc(C(F)(F)F)cc3Cl)CCC(F)(F)CC2)CC1 ; Cl] | GSP-1<br>$^1$H NMR (400 MHz, DMSO-d$_6$): δ 10.64 (bs, 1H), 9.08 (bs, 1H), 8.63 (bs, 1H), 8.0 (d, J 19.2 Hz, 1H ), 7.90-7.70 (m, 2H), 7.59 (d, J = 7.8 Hz, 1H), 3.7 (m, 2H), 3.60-2.44 (m, 8H), 2.30-1.50 (m, 10H), 1.22 (t, J = 6.0 Hz, 3H).<br>MS (ESI+) m/z 532 (M + H). |
| 204 | N-((1-(4-(Ethylsulfonyl)piperazin-1-yl)-4,4-difluorocyclohexyl)methyl)-2,4-bis(trifluoromethyl)benzamide Hydrochloride | 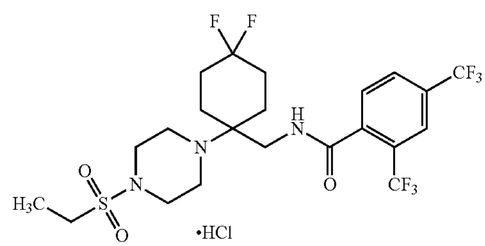 [SMILES: CCS(=O)(=O)N1CCN(C2(CNC(=O)c3ccc(C(F)(F)F)cc3C(F)(F)F)CCC(F)(F)CC2)CC1 ; Cl] | GSP-1<br>$^1$H NMR (300 MHz, DMSO-d$_6$) δ 8.62 (s, 1H), 8.13 (s, 2H), 7.74 (s, 1H), 3.90-3.00 (m, 10H), 2.89 (s, 2H), 2.30-1.80 (m, 8H), 1.25 (t, J = 7.2 Hz, 3H); MS (DUIS$^+$) m/z 566 (M + H). |
| 205 | 2-Chloro-4-(1,1-difluoroethyl)-N-((1-(4-(ethylsulfonyl)piperazin-1-yl)-4,4-difluorocyclohexyl)methyl)benzamide Hydrochloride | 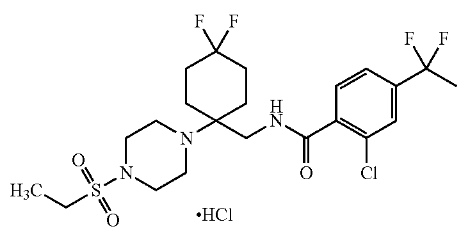 [SMILES: CCS(=O)(=O)N1CCN(C2(CNC(=O)c3ccc(C(C)(F)F)cc3Cl)CCC(F)(F)CC2)CC1 ; Cl] | GSP-1<br>$^1$H NMR (300 MHz, DMSO-d$_6$): δ 10.82 (bs, 1H), 8.99 (bs, 1H ), 7.8-7.4 (m, 3H), 3.9-3.5 (m, 5H), 3.50-3.0 (m, 5H), 2.7 (m, 2H), 2.5-1.5 (m, 8H), 1.99 (t, J = ,18.9 Hz, 3H ) 1.22 (t, J = 7.2 Hz, 3H); MS (ESI+) m/z 529 (M + H). |
| 206 | 2-Chloro-N-((1-(4-(ethylsulfonyl)piperazin-1-yl)-4,4-difluorocyclohexyl)methyl)-4,6-bis(trifluoromethyl)benzamide Hydrochloride | 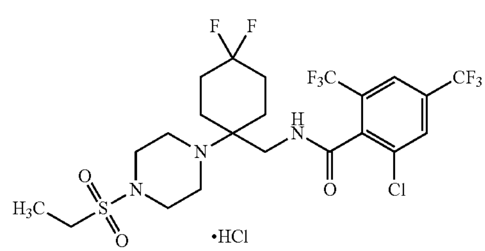 [SMILES: CCS(=O)(=O)N1CCN(C2(CNC(=O)c3c(Cl)cc(C(F)(F)F)cc3C(F)(F)F)CCC(F)(F)CC2)CC1 ; Cl] | GSP-1<br>$^1$H NMR (300 MHz, DMSO-d$_6$) δ 8.70 (s, 1H), 8.40 (s, 1H), 8.14 (s, 1H), 3.40-2.68 (m, 10H), 2.30-1.60 (m, 10H), 1.22 (t, J = 7.2 Hz, 3H); MS (DUIS$^+$) m/z 600 (M + H). |

TABLE 1-continued

Examples, General Synthetic Procedures (GSP) and Spectral Data

| Cpd | Name | Structure | General Synthetic Procedure and Spectral Data |
|---|---|---|---|
| 207 | 2,6-Dichloro-N-((1-(4-(ethylsulfonyl)piperazin-1-yl)-4,4-difluoro-cyclohexyl)methyl)-4-(trifluoromethyl) benzamide Hydrochloride | 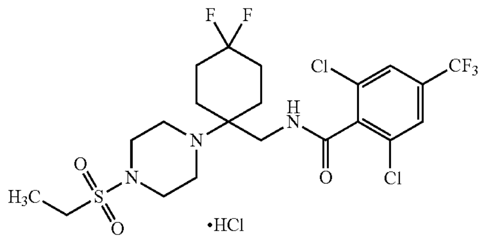 [SMILES: CCS(=O)(=O)N1CCN(C2(CNC(=O)c3c(Cl)cc(C(F)(F)F)cc3Cl)CCC(F)(F)CC2)CC1 ; Cl] | GSP-1<br>$^1$H NMR (300 MHz, DMSO-$d_6$) δ 8.03 (s, 2H), 3.90-3.80 (m, 2H), 3.70-3.00 (m, 8H), 2.80-2.70 (m, 2H), 2.40-1.60 (m, 9H), 1.22 (t, J = 7.2 Hz, 3H); MS (DUIS$^+$) m/z 566 (M + H). |
| 208 | 4-Chloro-N-((1-(4-(ethylsulfonyl)piperazin-1-yl)-4,4-difluoro-cyclohexyl)methyl)-2,6-difluorobenzamide Hydrochloride | 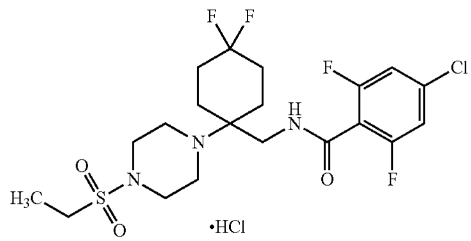 [SMILES: CCS(=O)(=O)N1CCN(C2(CNC(=O)c3c(F)cc(Cl)cc3F)CCC(F)(F)CC2)CC1 ; Cl] | GSP-1<br>$^1$H NMR (300 MHz, DMSO-$d_6$) δ 7.49 (s, 2H), 3.80-3.00 (m, 10H), 2.71 (s, 2H), 2.30-1.40 (m, 9H), 1.22 (t, J = 7.2 Hz, 3H); MS (DUIS$^+$) m/z 500 (M + H). |
| 209 | 2,4,6-Trichloro-N-((1-(4-(ethylsulfonyl)piperazin-1-yl)-4,4-difluorocyclohexyl)methyl) benzamide Hydrochloride | 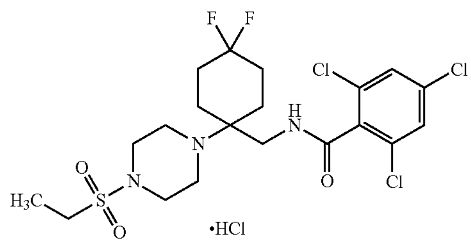 [SMILES: CCS(=O)(=O)N1CCN(C2(CNC(=O)c3c(Cl)cc(Cl)cc3Cl)CCC(F)(F)CC2)CC1 ; Cl] | GSP-1<br>$^1$H NMR (300 MHz, DMSO-$d_6$) δ 7.79 (d, J = 16.8 Hz, 2H), 3.80-3.00 (m, 11H), 2.73 (s, 2H), 2.30-1.60 (m, 8H), 1.22 (t, J = 7.5 Hz, 3H); MS (DUIS$^+$) m/z 532 (M + H). |
| 210 | 2,4-Dichloro-N-((1-(4-(ethylsulfonyl)piperazin-1-yl)-4,4-difluorocyclohexyl)methyl)-6-fluorobenzamide Hydrochloride | 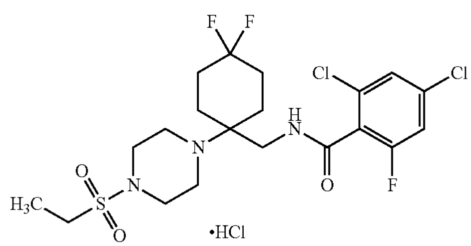 [SMILES: CCS(=O)(=O)N1CCN(C2(CNC(=O)c3c(F)cc(Cl)cc3Cl)CCC(F)(F)CC2)CC1 ; Cl] | GSP-1<br>$^1$H NMR (300 MHz, DMSO-$d_6$):<br>δ 10.93-10.78 (m, 1H), 9.30-8.62 (m, 1H), 7.72-7.57 (m, 2H), 3.92-3.52 (m, 4H), 3.47-3.25 (m, 2H), 3.19-3.02 (m, 4H), 2.78-2.58 (m, 2H), 2.24-2.08 (m, 5H), 1.97-1.72 (m, 2H), 1.68-1.54 (m, 1H); MS (ESI+) m/z 517 (M + H). |
| 211 | N-((1-(4-(Ethylsulfonyl)piperazin-1-yl)-4,4-difluorocyclohexyl)methyl)-2,6-difluoro-3-(trifluoromethyl) benzamide Hydrochloride | 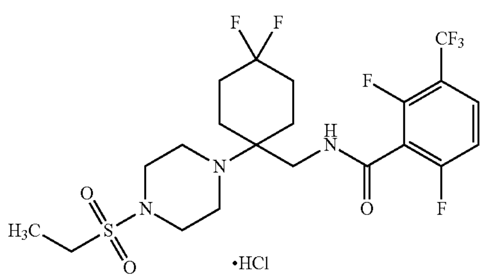 [SMILES: CCS(=O)(=O)N1CCN(C2(CNC(=O)c3c(F)ccc(C(F)(F)F)c3F)CCC(F)(F)CC2)CC1 ; Cl] | GSP-1<br>$^1$H NMR (300 MHz, DMSO-$d_6$) δ 8.00 (s, 1H), 7.46 (s, 1H), 3.80-3.50 (m, 4H), 3.40-3.25 (m, 2H), 3.20-2.90 (m, 5H), 2.73 (s, 2H), 2.30-1.50 (m, 8H), 1.22 (t, J = 7.5 Hz, 3H); MS (DUIS$^+$) m/z 534 (M + H). |
| 212 | 2,4-Dichloro-N-((1-(4-(ethylsulfonyl)piperazin-1-yl)-4,4-difluorocyclohexyl)methyl)-5-fluorobenzamide Hydrochloride | 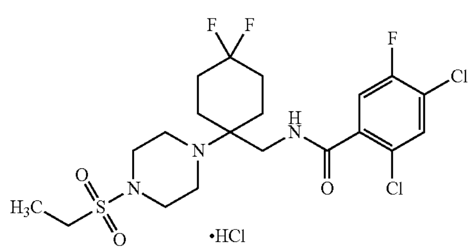 [SMILES: CCS(=O)(=O)N1CCN(C2(CNC(=O)c3cc(F)c(Cl)cc3Cl)CCC(F)(F)CC2)CC1 ; Cl] | GSP-1<br>$^1$H NMR (300 MHz, DMSO-$d_6$)<br>δ 11.08-10.92 (m, 1H), 9.49-8.72 (m, 1H), 7.89-7.69 (m, 1H), 7.39-7.29 (m, 1H), 4.16 (br s, 3H), 3.89 (br s, 1H), 3.78-3.61 (m, 4H), 3.2 5H), 3.49-3.02 (m, 5H), 2.53-2.52 (m, 1H), 2.04-2.01 (m, 5H), 1.90-1.50 (m, 3H), 1.22 (t, J = 9.6 Hz, 3H); MS (ESI+) m/z 517 (M + H). |

TABLE 1-continued

Examples, General Synthetic Procedures (GSP) and Spectral Data

| Cpd | Name | Structure | General Synthetic Procedure and Spectral Data |
|---|---|---|---|
| 213 | 3-Chloro-N-((1-(4-(ethylsulfonyl)piperazin-1-yl)-4,4-difluorocyclohexyl)methyl)-2,6-difluorobenzamide Hydrochloride | 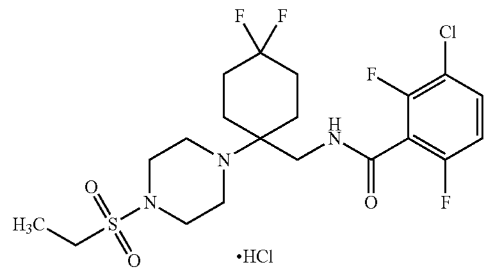 [SMILES: CCS(=O)(=O)N1CCN(C2(CNC(=O)c3c(F)ccc(Cl)c3F)CCC(F)(F)CC2)CC1 ; Cl] | GSP-1<br>$^1$H NMR (300 MHz, DMSO-d$_6$) δ 11.08-10.92 (m, 1H), 9.49-8.72 (m, 1H), 7.89-7.69 (m, 1H), 7.39-7.29 (m, 1H), 4.16 (br s, 3H), 3.89 (br s, 1H), 3.78-3.61 (m, 4H), 3.2 5H), 3.49-3.02 (m, 5H), 2.53-2.52 (m, 1H), 2.04-2.01 (m, 5H), 1.90-1.50 (m, 3H), 1.22 (t, J = 9.6 Hz, 3H); MS (ESI+) m/z 500 (M + H). |
| 214 | 2-Chloro-N-((1-(4-(ethylsulfonyl)piperazin-1-yl)-4,4-difluorocyclohexyl)methyl)-4,5-difluorobenzamide Hydrochloride | 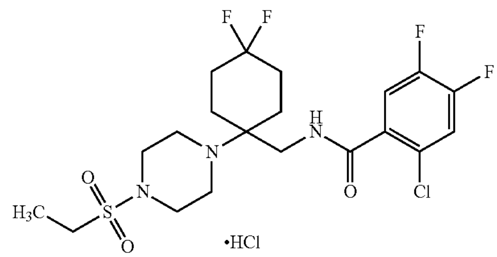 [SMILES: CCS(=O)(=O)N1CCN(C2(CNC(=O)c3cc(F)c(F)cc3Cl)CCC(F)(F)CC2)CC1 ; Cl] | GSP-1<br>$^1$H NMR (300 MHz, DMSO-d$_6$): δ 11.08-10.92 (m, 1H), 9.08-8.51 (m, 1H), 7.98-7.52 (m, 2H), 4.49-4.33 (m, 3H), 3.85-3.54 (m, 5H), 3.34-3.02 (m, 3H), 2.74-2.62 (m, 1H), 2.25-2.13 (m, 6H), 1.98-1.52 (m, 1H), 1.22 (t, J = 7.2 Hz, 3H); MS (ESI+) m/z 500 (M + H). |
| 215 | 2,6-Dichloro-N-((1-(4-(ethylsulfonyl)piperazin-1-yl)-4,4-difluorocyclohexyl)methyl)-3-(trifluoromethyl)benzamide Hydrochloride | 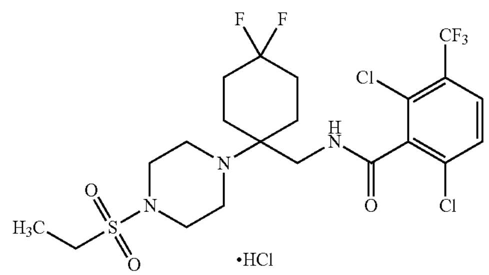 [SMILES: CCS(=O)(=O)N1CCN(C2(CNC(=O)c3c(Cl)ccc(C(F)(F)F)c3Cl)CCC(F)(F)CC2)CC1 ; Cl] | GSP-1<br>$^1$H NMR (300 MHz, DMSO-d$_6$) δ 11.08-10.92 (m, 1H), 9.28-8.75 (m, 1H), 8.05-7.94 (m, 1H), 7.85-7.74 (m, 1H), 3.92-3.24 (m, 5H), 3.38-3.05 (m, 7H), 2.73 (br s, 1H), 2.38-1.63 (m, 7H), 1.22 (t, J = 7.2 Hz, 3H); MS (ESI+) m/z 567 (M + H). |
| 216 | N-((1-(4-(Ethylsulfonyl)piperazin-1-yl)-4,4-difluorocyclohexyl)methyl)-2,6-difluoro-4-methoxybenzamide Hydrochloride | 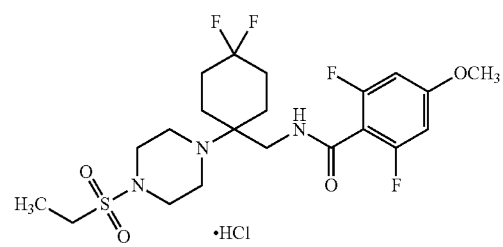 [SMILES: CCS(=O)(=O)N1CCN(C2(CNC(=O)c3c(F)cc(OC)cc3F)CCC(F)(F)CC2)CC1 ; Cl] | GSP-1<br>$^1$H NMR (300 MHz, DMSO-d$_6$) δ 10.99 (br s, 1H), 9.18-8.54 (m, 1H), 6.98-6.73 (m, 2H), 3.98-3.78 (m, 7H), 3.72-3.53 (m, 5H), 3.43-3.24 (m, 2H), 3.18-3.04 (m, 1H), 2.42-2.02 (m, 6H), 1.97-1.48 (m, 2H), 1.22 (t, J = 7.5 Hz, 3H).<br>MS (ESI+) m/z 496 (M + H). |
| 217 | N-((1-(4-(Ethylsulfonyl)piperazin-1-yl)-4,4-difluorocyclohexyl)methyl)-2,4,6-trimethylbenzamide Hydrochloride | 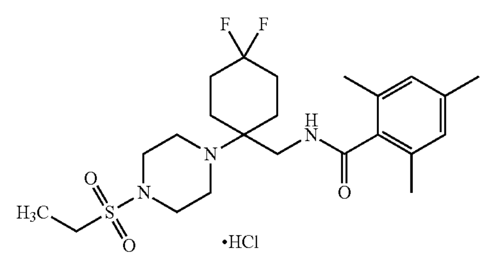 [SMILES: CCS(=O)(=O)N1CCN(C2(CNC(=O)c3c(C)cc(C)cc3C)CCC(F)(F)CC2)CC1 ; Cl] | GSP-1<br>$^1$H NMR (300 MHz, DMSO-d$_6$) δ 10.92-10.54 (m, 1H), 8.62-8.14 (m, 1H), 6.92-6.85 (m, 2H), 3.74-3.67 (m, 6H), 3.55-3.25 (m, 3H), 3.21-3.04 (m, 3H), 2.75-2.69 (m, 1H), 2.42-2.32 (m, 1H), 2.23 (br s, 3H), 2.18 (s, 9H), 2.03-1.74 (m, 2H), 1.64-1.52 (m, 1H), 1.22 (t, J = 1.2 Hz, 3H).<br>MS (ESI+) m/z 472 (M + H). |
| 218 | (±)-N-((1-(4-(Ethylsulfonyl)-2-methylpiperazin-1-yl)-4,4-difluorocyclohexyl)methyl)-2,4-bis(trifluoromethyl)benzamide Hydrochloride | 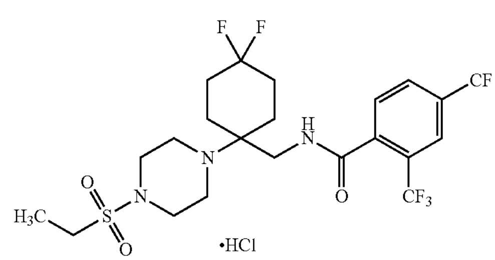 | GSP-1<br>$^1$H NMR (300 MHz, DMSO-d$_6$):<br>δ 10.48 (bs, 0.2H), 9.26 (bs, 0.2H), δ 8.57 (bs, 0.6H), 8.17 (d, J = 7.2 Hz, 1H), 8.11 (s, 1H), 7.71 (d, J = 7.8 Hz, 1H), 3.78-2.69 (m, 10H), 2.29-1.49 (m, 9H), 1.23-1.18 (m, 6H).<br>MS (ESI+) m/z 580 (M + H). |

TABLE 1-continued

Examples, General Synthetic Procedures (GSP) and Spectral Data

| Cpd | Name | Structure | General Synthetic Procedure and Spectral Data |
|---|---|---|---|
| 219 | 2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide Hydrochloride | 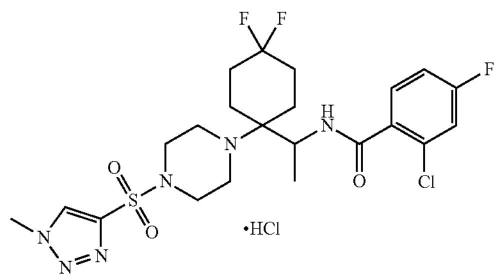 [SMILES: CC(NC(=O)c1ccc(F)cc1Cl)C1(N2CCN(S(=O)(=O)c3cn(C)nn3)CC2)CCC(F)(F)CC1 ; Cl] | GSP-4<br>$^1$H NMR (300 MHz, DMSO-$d_6$): δ 8.76 (s, 1H), 8.38 (d, J = 9.6 Hz, 1H ), 7.50 (dd, J = 2.4 Hz, 9.0 Hz, 1H), 7.4 (dt, J = 6.3 Hz, 8.7 Hz, 1H ), 7.30 (dt, J = 2.4 Hz, 8.4 Hz, 1H ), 4.27 (m, 1H), 4.12 (s, 3H), 3.30-2.7 (m, 8H), 2.0-1.4 (m, 8H), 1.0 (d, J = 6.6 Hz, 3H).<br>MS (ESI+) m/z 550 (M + H). |
| 220 | 2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide Hydrochloride | 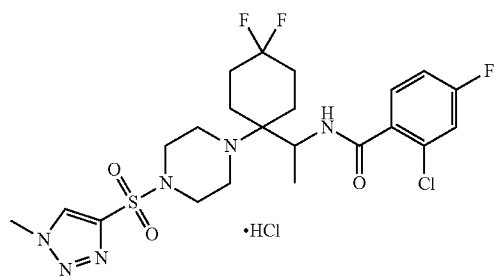 [SMILES: CC(NC(=O)c1ccc(F)cc1Cl)C1(N2CCN(S(=O)(=O)c3cn(C)nn3)CC2)CCC(F)(F)CC1 ; Cl] | GSP-4<br>$^1$H NMR (300 MHz, DMSO-$d_6$): δ 8.76 (s, 1H), 8.38 (d, J = 9.6 Hz, 1H ), 7.50 (dd, J = 2.4 Hz, 9.0 Hz, 1H), 7.4 (dt, J = 6.3 Hz, 8.7 Hz, 1H ), 7.30 (dt, J = 2.4 Hz, 8.4 Hz, 1H), 4.27 (m, 1H), 4.12 (s, 3H), 3.30-2.7 (m, 8H), 2.0-1.4 (m, 8H), 1.0 (d, J = 6.6 Hz, 3H).<br>MS (ESI+) m/z 550 (M + H). |
| 221 | N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide Hydrochloride | 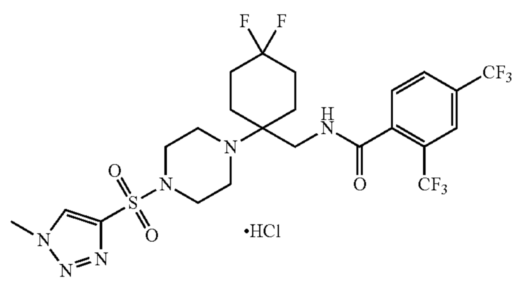 [SMILES: Cn1cc(S(=O)(=O)N2CCN(C3(CNC(=O)c4ccc(C(F)(F)F)cc4C(F)(F)F)CCC(F)(F)CC3)CC2)nn1 ; Cl] | GSP-1<br>$^1$H NMR (300 MHz, DMSO-$d_6$) δ 8.75 (s, 1H), 8.62 (s, 1H), 8.18-8.12 (m, 2H), 7.74-7.71 (m, 1H), 4.15 (s, 3H), 3.31-3.30 (m, 2H), 3.10-2.90 (m, 4H), 2.85-2.70 (m, 4H), 2.00-1.40 (m, 8H); MS (DUIS$^+$) m/z 619 (M + H). |
| 222 | (±)-2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide Hydrochloride | 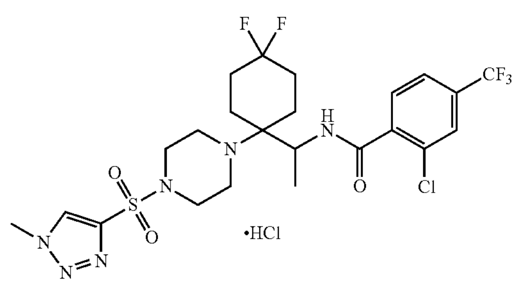 [SMILES: CC(NC(=O)c1ccc(C(F)(F)F)cc1Cl)C1(N2CCN(S(=O)(=O)c3cn(C)nn3)CC2)CCC(F)(F)CC1 ; Cl] | GSP-4<br>$^1$H NMR (300 MHz, DMSO-$d_6$): δ 8.74 (s, 1H), 8.47 (d, J = 9.6 Hz, 1H), 7.94 (s, 1H), 7.79 (d, J = 7.8 Hz, 1H), 7.55 (d, J = 7.8 Hz, 1H ), 4.27 (q, J = 6.9 Hz, 14.1 Hz, 1H), 4.12 (s, 3H), 3.30-2.7 (m, 8H), 2.0-1.4 (m, 8H), 1.0 (d, J = 6.9 Hz, 3H); MS (ESI+) m/z 600 (M + H). |
| 223 | 2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide Hydrochloride | 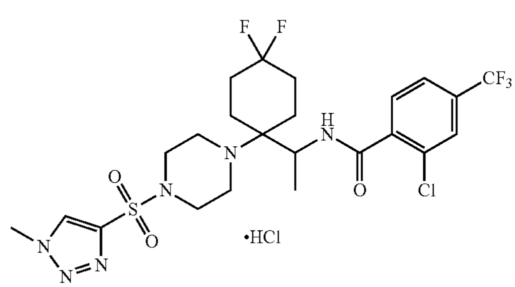 [SMILES: CC(NC(=O)c1ccc(C(F)(F)F)cc1Cl)C1(N2CCN(S(=O)(=O)c3cn(C)nn3)CC2)CCC(F)(F)CC1 ; Cl] | GSP-4<br>$^1$H NMR (300 MHz, DMSO-$d_6$): δ 8.74 (s, 1H), 8.47 (d, J = 9.6 Hz, 1H), 7.94 (s, 1H), 7.79 (d, J = 7.8 Hz, 1H), 7.55 (d, J = 7.8 Hz, 1H), 4.27 (q, J = 6.9 Hz, 14.1 Hz, 1H), 4.12 (s, 3H), 3.30-2.7 (m, 8H), 2.0-1.4 (m, 8H), 1.0 (d, J = 6.9 Hz, 3H); MS (ESI+) m/z 600 (M + H). |

TABLE 1-continued

Examples, General Synthetic Procedures (GSP) and Spectral Data

| Cpd | Name | Structure | General Synthetic Procedure and Spectral Data |
|---|---|---|---|
| 224 | 2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide Hydrochloride | 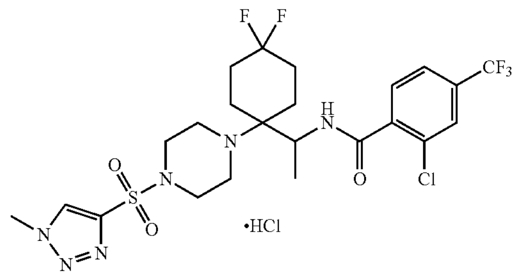 [SMILES: CC(NC(=O)c1ccc(C(F)(F)F)cc1Cl)C1(N2CCN(S(=O)(=O)c3cn(C)nn3)CC2)CCC(F)(F)CC1 ; Cl] | GSP-4<br>$^1$H NMR (300 MHz, DMSO-d$_6$): δ 8.74 (s, 1H), 8.47 (d, J = 9.6 Hz, 1H ), 7.94 (s, 1H), 7.79 (d, J = 7.8 Hz, 1H), 7.55 (d, J = 7.8 Hz, 1H), 4.27 (q, J = 6.9 Hz, 14.1 Hz, 1H), 4.12 (s, 3H), 3.30-2.7 (m, 8H), 2.0-1.4 (m, 8H), 1.0 (d, J = 6.9 Hz, 3H); MS (ESI+) m/z 600 (M + H). |
| 225 | N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide Hydrochloride | 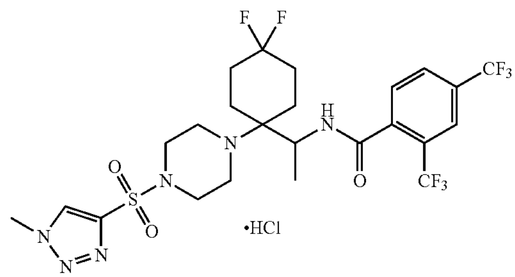 [SMILES: CC(NC(=O)c1ccc(C(F)(F)F)cc1C(F)(F)F)C1(N2CCN(S(=O)(=O)c3cn(C)nn3)CC2)CCC(F)(F)CC1 ; Cl] | GSP-4<br>$^1$H NMR (300 MHz, DMSO-d$_6$): δ 8.74 (s, 1H), 8.52 (d, J = 9.3 Hz, 1H ), 8.20-8.10 (m, 2H), 7.67 (d, J = 8.1 Hz, 1H ), 4.22 (q, J = 9.3 Hz, 16.8 Hz, 1H), 4.12 (s, 3H), 3.30-2.7 (m, 8H), 2.0-1.4 (m, 8H), 1.0 (d, J = 6.9 Hz, 3H); MS (ESI+) m/z 633 (M + H). |
| 226 | N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide Hydrochloride | 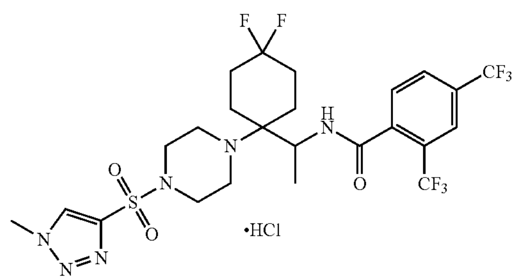 | GSP-4<br>$^1$H NMR (300 MHz, DMSO-d$_6$): δ 8.74 (s, 1H), 8.52 (d, J = 9.3 Hz, 1H ), 8.20-8.10 (m, 2H), 7.67 (d, J = 8.1 Hz, 1H ), 4.22 (q, J = 9.3 Hz, 16.8 Hz, 1H), 4.12 (s, 3H), 3.30-2.7 (m, 8H), 2.0-1.4 (m, 8H), 1.0 (d, J = 6.9 Hz, 3H); MS (ESI+) m/z 633 (M + H). |
| 227 | (±)-2-Chloro-N-((4,4-difluoro-1-(3-methyl-4-(1-methyl-1H-1,2,3-triazol-4-ylsulfonyl)piperazin-1-yl)cyclohexyl)methyl)-4-(trifluoromethyl)benzamide Hydrochloride | 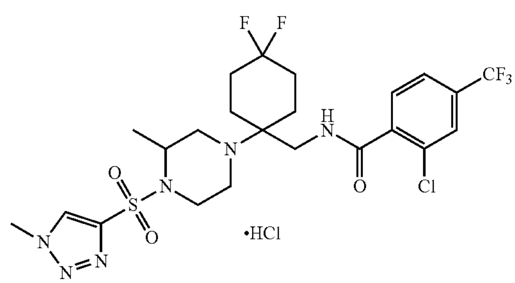 [SMILES: CC1CN(C2(CNC(=O)c3ccc(C(F)(F)F)cc3Cl)CCC(F)(F)CC2)CCN1S(=O)(=O)c1cn(C)nn1 ; Cl] | GSP-1<br>$^1$H NMR (300 MHz, DMSO-d$_6$): δ .69 (s, 1H), 8.55 (bs, 1H), 7.947 (s, 1H), 7.77 (d, J = 7.8 Hz, 1H), 7.57 (d, J = 8.4 Hz, 1H), 4.09 (s, 3H), 4.01 (m, 1H), 3.5 (m, 1H), 3.30-2.7 (m, 7H), 2.1-1.5 (m, 8H), 1.13 (d J = 6.6 Hz, 3H).; MS (ESI+) m/z 600 (M + H). |
| 228 | 2,4-Dichloro-N-((4,4-difluoro-1-(4-(1-methyl-1H-1,2,3-triazol-4-ylsulfonyl)piperazin-1-yl)cyclohexyl)methyl)benzamide Hydrochloride | 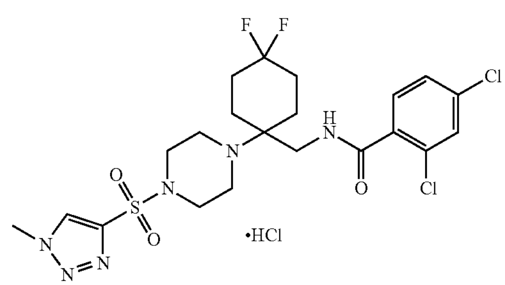 [SMILES: Cn1cc(S(=O)(=O)N2CCN(C3(CNC(=O)c4ccc(Cl)cc4Cl)CCC(F)(F)CC3)CC2)nn1 ; Cl] | GSP-1<br>$^1$H NMR (300 MHz, DMSO-d$_6$): δ 10.31 (bs, 1H), 8.70-8.92 (m, 1H), 8.33-8.45 (m, 1H), 7.62-7.71 (m, 1H), 7.32-7.57 (m, 2H), 4.13 (s, 3H), 3.75-3.80 (m, 2H), 3.33-3.73 (m, 2H), 2.89-3.33 (m, 4H), 2.78-2.89 (m, 2H), 1.51-2.44 (m, 8H); MS (ESI+) m/z 550 (M + H). |

TABLE 1-continued

Examples, General Synthetic Procedures (GSP) and Spectral Data

| Cpd | Name | Structure | General Synthetic Procedure and Spectral Data |
|---|---|---|---|
| 229 | N-((4,4-Difluoro-1-(4-(1-methyl-1H-1,2,3-triazol-4-ylsulfonyl)piperazin-1-yl)cyclohexyl)methyl)-2,4-difluorobenzamide Hydrochloride | 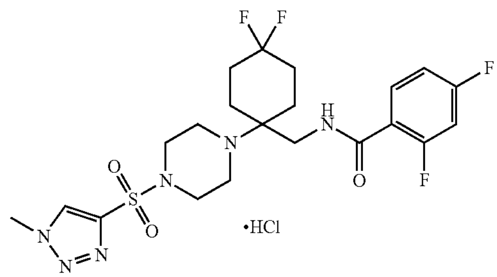 [SMILES: Cn1cc(S(=O)(=O)N2CCN(C3(CNC(=O)c4ccc(F)cc4F)CCC(F)(F)CC3)CC2)nn1 ; Cl] | GSP-1<br>$^1$H NMR (300 MHz, DMSO-d$_6$): δ 10.21 (bs, 1H), 8.72-8.90 (m, 1H), 8.35-8.51 (m, 1H), 7.51-7.82 (m, 1H), 7.25-7.42 (m, 1H), 7.07-7.22 (m, 1H), 4.14 (s, 3H), 3.75-3.80 (m, 2H), 3.33-3.73 (m, 2H), 2.89-3.33 (m, 4H), 2.78-2.89 (m, 2H), 1.51-2.44 (m, 8H); MS (ESI+) m/z 518 (M + H). |
| 230 | 4-Chloro-N-((4,4-difluoro-1-(4-(1-methyl-1H-1,2,3-triazol-4-ylsulfonyl)piperazin-1-yl)cyclohexyl)methyl)-2,6-difluorobenzamide Hydrochloride | 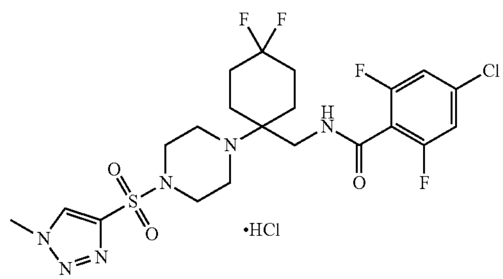 [SMILES: Cn1cc(S(=O)(=O)N2CCN(C3(CNC(=O)c4c(F)cc(Cl)cc4F)CCC(F)(F)CC3)CC2)nn1 ; Cl] | GSP-1<br>$^1$H NMR (300 MHz, DMS)-d$_6$): δ 10.19 (bs, 1H), 9.25 (bs, 0.4H), 8.82 (bs, 0.6H), 8.75 (s, 1H), 7.49 (s, 2H), 4.13 (s, 3H), 3.92-3.70 (m, 2H), 3.50-2.92 (m, 6H), 2.85-2.65 (m, 2H), 2.26-1.63 (m, 7H), 1.63-1.41 (m, 1H); MS (ESI+) m/z 553 (M + H). |
| 231 | 2,4-Dichloro-N-((4,4-difluoro-1-(4-(1-methyl-1H-1,2,3-triazol-4-ylsulfonyl)piperazin-1-yl)cyclohexyl)methyl)-5-fluorobenzamide Hydrochloride | 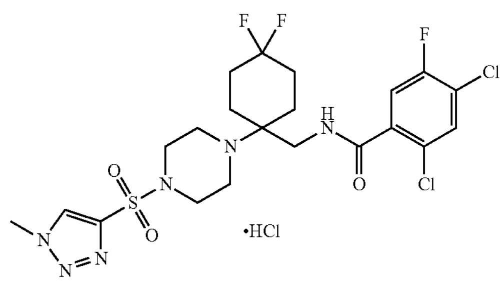 | GSP-1<br>$^1$H NMR (300 MHz, DMSO-d$_6$): δ 10.21 (bs, 1H), 8.98 (bs, 0.2H), 8.89 (bs, 0.3H), 8.75 (s, 1H), 8.52 (bs, 0.5H), 7.98-7.90 (m, 1H), 7.80-7.51 (m, 1H), 4.13 (s, 3H), 3.90-3.71 (m, 2H), 3.48-2.96 (m, 6H), 2.84-2.68 (m, 2H), 2.32-1.67 (m, 7H), 1.62-1.45 (m, 1H); MS (ESI+) m/z 570 (M + H). |
| 232 | N-((4,4-Difluoro-1-(4-(1-methyl-1H-1,2,3-triazol-4-ylsulfonyl)piperazin-1-yl)cyclohexyl)methyl)-2-fluoro-4-(trifluoromethyl)benzamide Hydrochloride | 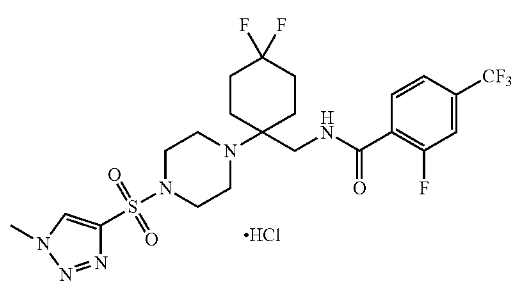 [SMILES: Cn1cc(S(=O)(=O)N2CCN(C3(CNC(=O)c4ccc(C(F)(F)F)cc4F)CCC(F)(F)CC3)CC2)nn1 ; Cl] | GSP-1<br>$^1$H NMR (300 MHz, DMSO-d$_6$): δ 10.08 (bs, 1H), 9.01 (bs, 0.2H), 8.88 (bs, 0.3H), 8.75 (s, 1H), 8.54 (bs, 0.5H), 7.90-7.62 (m, 3H), 4.13 (s, 3H), 3.92-3.70 (m, 2H), 3.50-2.94 (m, 6H), 2.86-2.68 (m, 2H), 2.30-1.67 (m, 7H), 1.62-1.40 (m, 1H); MS (ESI+) m/z 569 (M + H). |
| 233 | N-((4,4-Difluoro-1-(4-(1-methyl-1H-1,2,3-triazol-4-ylsulfonyl)piperazin-1-yl)cyclohexyl)methyl)-4-fluoro-2-(trifluoromethyl)benzamide Hydrochloride | 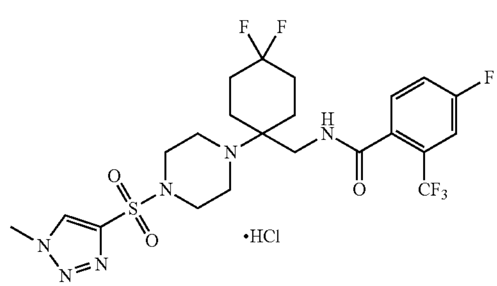 | GSP-1<br>$^1$H NMR (300 MHz, DMSO-d$_6$): δ 10.18 (bs, 1H), 8.96 (bs, 0.2H), 8.87 (bs, 0.3H), 8.75 (s, 1H), 8.49 (bs, 0.5H), 7.82-7.51 (m, 3H), 4.13 (s, 3H), 3.92-3.71 (m, 2H), 3.48-2.94 (m, 6H), 2.85-2.68 (m, 2H), 2.30-1.65 (m, 7H), 1.60-1.41 (m, 1H); MS (ESI+) m/z 569 (M + H). |

TABLE 1-continued

Examples, General Synthetic Procedures (GSP) and Spectral Data

| Cpd | Name | Structure | General Synthetic Procedure and Spectral Data |
|---|---|---|---|
| 234 | N-((4,4-Difluoro-1-(4-(1-methyl-1H-1,2,3-triazol-4-ylsulfonyl)piperazin-1-yl)cyclohexyl)methyl)-2,4,6-trifluorobenzamide Hydrochloride | 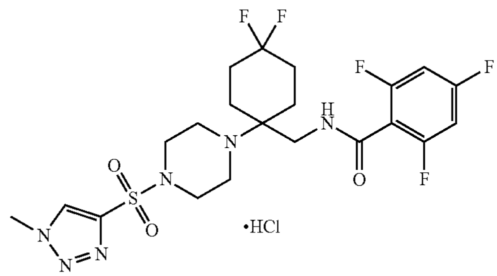 [SMILES: Cn1cc(S(=O)(=O)N2CCN(C3(CNC(=O)c4c(F)cc(F)cc4F)CCC(F)(F)CC3)CC2)nn1 ; Cl] | GSP-1<br>$^1$H NMR (300 MHz, DMSO-$d_6$): δ 10.45 (bs, 1H), 9.23 (bs, 0.2H), 8.87 (bs, 0.3H), 8.75 (s, 1H), 8.68 (bs, 0.5H), 7.32 (bs, 2H), 4.13 (s, 3H), 3.95-3.70 (m, 3H), 3.50-2.95 (m, 5H), 2.84-2.68 (m, 2H), 2.30-1.67 (m, 7H), 1.65-1.45 (m, 1H); MS (ESI+) m/z 537 (M + H). |
| 235 | 2-Chloro-N-((4,4-difluoro-1-(4-(1-methyl-1H-1,2,3-triazol-4-ylsulfonyl)piperazin-1-yl)cyclohexyl)methyl)-4,5-difluorobenzamide Hydrochloride | 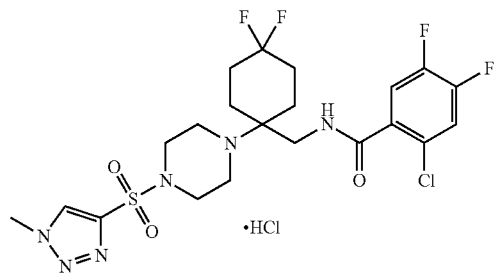 | GSP-1<br>$^1$H NMR (300 MHz, DMSO-$d_6$): δ 10.38 (bs, 1H), 8.97 (bs, 0.2H), 8.87 (bs, 0.3H), 8.75 (s, 1H), 8.47 (bs, 0.5H), 7.95-7.46 (m, 2H), 4.13 (s, 3H), 3.90-3.70 (m, 3H), 3.50-2.98 (m, 5H), 2.84-2.68 (m, 2H), 2.32-1.65 (m, 7H), 1.63-1.48 (m, 1H); MS (ESI+) m/z 553 (M + H). |
| 236 | 2-Chloro-N-((1-(4-(1-(difluoromethyl)-1H-1,2,3-triazol-4-ylsulfonyl)piperazin-1-yl)-4,4-difluorocyclohexyl)methyl)-4-(trifluoromethyl) benzamide Hydrochloride | 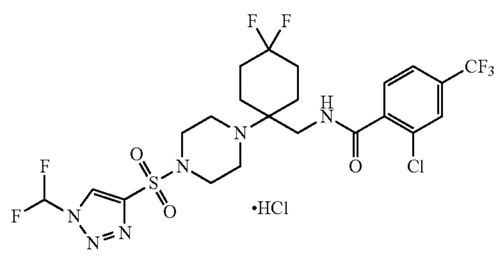 [SMILES: O=C(NCC1(N2CCN(S(=O)(=O)c3cn(C(F)F)nn3)CC2)CCC(F)(F)CC1)c1ccc(C(F)(F)F)cc1Cl ; Cl] | GSP-1<br>$^1$H NMR (300 MHz, DMSO-$d_6$, $^{19}$F-decoupled): δ 9.48 (s, 1H), 8.57 (bs, 1H ), 8.28 (s, 1H), 7.94 (s, 1H), 7.79 (d, J = 7.5 Hz, 1H) 7.59 (d, J = 8.1 Hz, 1H), 3.31 (d, J = 5.4 Hz, 2H), 3.2-3.0 (m, 4H), 2.90-2.70 (m, 4H), 2.0-1.7 (m, 6H), 1.70-1.50 (m, 2H); MS (ESI+) m/z 621 (M + H). |
| 237 | N-((1-(2,5-Dimethyl-4-(1-methyl-1H-1,2,3-triazol-4-ylsulfonyl)piperazin-1-yl)-4,4-difluorocyclohexyl)methyl)-2,4-bis(trifluoromethyl) benzamide Hydrochloride | 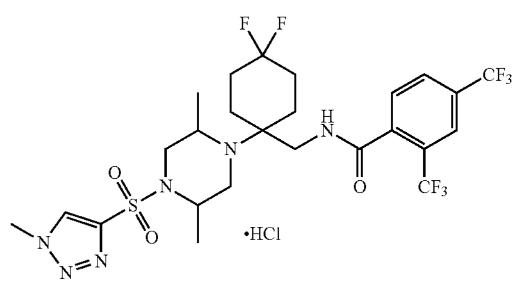 [SMILES: CC1CN(S(=O)(=O)c2cn(C)nn2)C(C)CN1C1(CNC(=O)c2ccc(C(F)(F)F)cc2C(F)(F)F)CCC(F)(F)CC1 ; Cl] | GSP-1<br>$^1$H NMR (400 MHz, DMSO-$d_6$): δ 8.68 (s, 1H), 8.54 (s, 1H), 8.16 (d, J = 8.4 Hz, 1H), 8.11 (s, 1H), 7.69 (d, J = 8.4 Hz, 1H) 4.10 (s, 1H), 3.50-3.20 (m, 6H ), 3.10-3.00 (m, 1H), 2.75-2.60 (m, 1H), 2.00-1.4 (m, 8 H), 1.01 (d, J = 6.3 Hz, 3H), 1.0 (d, J = 5.1 Hz, 3H); MS (ESI+) m/z 647 (M + H). |
| 238 | 4-Chloro-N-((4,4-difluoro-1-(4-(1-methyl-1H-1,2,3-triazol-4-ylsulfonyl)piperazin-1-yl)cyclohexyl)methyl)-2,5-difluorobenzamide Hydrochloride | 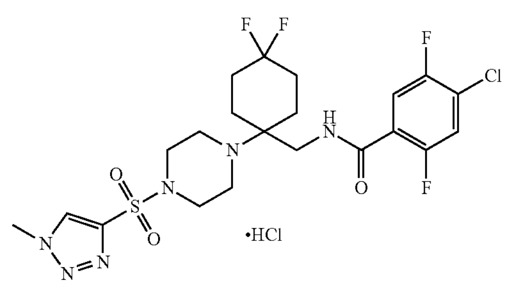 [SMILES: Cn1cc(S(=O)(=O)N2CCN(C3(CNC(=O)c4cc(F)c(Cl)cc4F)CCC(F)(F)CC3)CC2)nn1 ; Cl] | GSP-1<br>$^1$H NMR (300 MHz, DMSO-$d_6$): δ 8.75-8.92 (m, 1H), 8.45 (m, 1H), 7.55-7.85 (m, 2H), 4.45 (m, 2H), 4.13 (s, 3H), 3.86-3.89 (m, 2H), 3.26 (m, 2H), 3.05 (m, 3H), 2.75 (m, 2H), 2.15 (m, 2H), 1.75-1.95 (m, 4H), 1.5 (m, 1H), 1.25 (m, 1H); MS (ESI+) 553 (M + H). |

TABLE 1-continued

Examples, General Synthetic Procedures (GSP) and Spectral Data

| Cpd | Name | Structure | General Synthetic Procedure and Spectral Data |
|---|---|---|---|
| 239 | N-((4,4-Difluoro-1-(4-(1-methyl-1H-1,2,3-triazol-4-ylsulfonyl)piperazin-1-yl)cyclohexyl)methyl)-2,5-difluoro-4-methylbenzamide Hydrochloride | 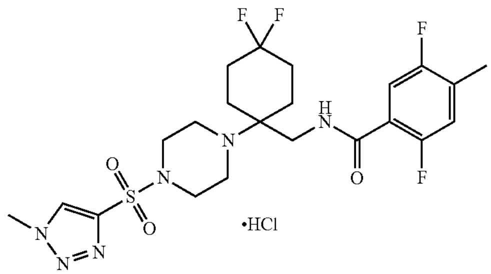 | GSP-1<br>$^1$H NMR (300 MHz, DMSO-d$_6$): δ 8.85 (m, 1H), 7.35 (m, 2H), 4.34 (m, 4H), 4.13 (s, 3H), 3.86-3.89 (m, 3H), 3.45 (m, 1H), 3.0-3.35 (m, 4H), 2.75 (m, 2H), 2.34 (m, 3H), 1.75-2.15 (m, 6H), 1.5 (m, 1H); MS (ESI+) 533 (M + H). |
| 240 | 2-Chloro-N-((4,4-difluoro-1-(4-(1-(tris-deutero)methyl-1H-1,2,3-triazol-4-ylsulfonyl)piperazin-1-yl)cyclohexyl)methyl)-4-(trifluoromethyl)benzamide Hydrochloride | 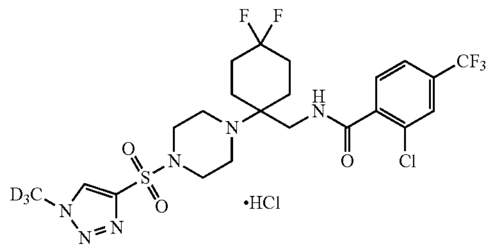 [SMILES: [2H]C([2H])([2H])n1cc(S(=O)(=O)N2CCN(C3(CNC(=O)c4ccc(C(F)(F)F)cc4Cl)CCC(F)(F)CC3)CC2)nn1 ; Cl] | GSP-1<br>$^1$H NMR (300 MHz, DMSO-d$_6$): δ 10.55 (bs, 1H), 9.2-8.5 (m, 2H), 8.0-7.5 (m, 3H), 3.9-3.80 (m, 4H) 3.60-2.70 (m, 6H), 2.40-1.50 (m, 8H); MS (ESI+) m/z 589 (M + H). |
| 241 | 2,4-Dichloro-N-((4,4-difluoro-1-(4-(1-methyl-1H-1,2,3-triazol-4-ylsulfonyl)piperazin-1-yl)cyclohexyl)methyl)-6-fluorobenzamide Hydrochloride | 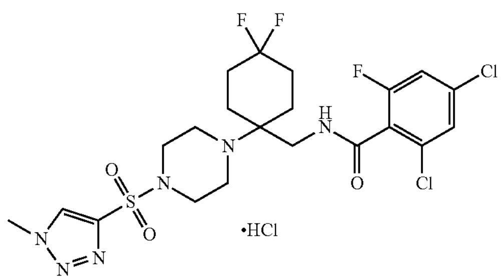 [SMILES: Cn1cc(S(=O)(=O)N2CCN(C3(CNC(=O)c4c(F)cc(Cl)cc4Cl)CCC(F)(F)CC3)CC2)nn1 ; Cl] | GSP-1<br>$^1$H NMR (300 MHz, DMSO-d$_6$): δ 8.75 (m, 1H), 7.61 (m, 2H), 4.54-4.62 (m, 4H), 4.13 (s, 3H), 3.86-3.89 (m, 1H), 3.28 (m, 1H), 3.0 (m, 3H), 2.75 (m, 3H), 1.98 (m, 4H), 1.55 (m, 1H); MS (DUIS+) 569 (M + H). |
| 242 | 2-Chloro-N-((4,4-difluoro-1-(4-(1-methyl-1H-1,2,3-triazol-4-ylsulfonyl)piperazin-1-yl)cyclohexyl)methyl)-3-fluoro-4-methylbenzamide Hydrochloride | 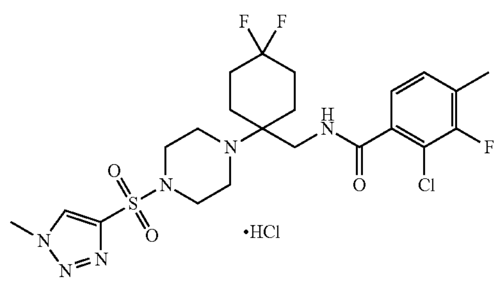 [SMILES: Cc1ccc(C(=O)NCC2(N3CCN(S(=O)(=O)c4cn(C)nn4)CC3)CCC(F)(F)CC2)c(Cl)c1F ; Cl] | GSP-1<br>$^1$H NMR (300 MHz, DMSO-d$_6$): δ 9.04 (bs, 1H), 8.54 (d, J = 1.2 Hz, 1H), 7.34-7.23 (m, 2H), 4.21 (d, J = 1.5 Hz, 3H), 4.15-4.05 (m, 2H), 3.94-3.70 (m, 5H), 3.61-3.40 (m, 2H), 2.90-2.75 (m, 1H), 2.50-2.10 (m, 11H); MS (ESI+) m/z 550 (M + H). |
| 243 | 2,5-Dichloro-N-((4,4-difluoro-1-(4-(propylsulfonyl)piperazin-1-yl)cyclohexyl)methyl) benzamide Hydrochloride | 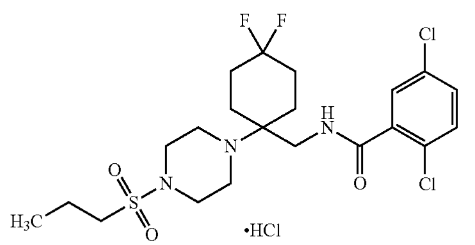 [SMILES: CCCS(=O)(=O)N1CCN(C2(CNC(=O)c3cc(Cl)ccc3Cl)CCC(F)(F)CC2)CC1 ; Cl] | GSP-1<br>$^1$H NMR (300 MHz, DMSO-d$_6$): δ 10.7 (bs, 0.4H), 8.98 (bs, 0.4H), 8.52 (bs, 0.2H), 7.64-7.57 (m, 1H), 7.57-7.54 (m, 1H), 7.44 (s, 1H), 3.82-3.74 (m, 2H), 3.70-3.51 (m, 2H), 3.34-3.28 (m, 2H), 3.16-3.12 (m, 4H), 2.89 (m, 2H), 2.24-2.07 (m, 4H), 1.96-1.90 (m, 2H), 1.85-1.57 (m, 4H), 0.98 (t, J = 7.5 Hz, 3H). |

TABLE 1-continued

Examples, General Synthetic Procedures (GSP) and Spectral Data

| Cpd | Name | Structure | General Synthetic Procedure and Spectral Data |
|---|---|---|---|
| 244 | 2-Chloro-N-((4,4-difluoro-1-(4-(1-fluoropropylsulfonyl)piperazin-1-yl)cyclohexyl)methyl)-4-(trifluoromethyl)benzamide Hydrochloride | 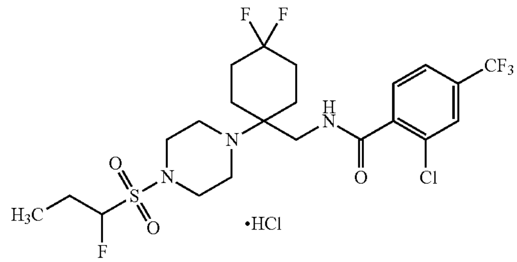 [SMILES: CCC(F)S(=O)(=O)N1CCN(C2(CNC(=O)c3ccc(C(F)(F)F)cc3Cl)CCC(F)(F)CC2)CC1 ; Cl] | GSP-1<br>$^1$H NMR (300 MHz, DMSO-$d_6$): δ 10.80 (s, 1H), 9.01 (m, 1H), 8.61 (s, 1H), 8.01 (s, 1H), 7.86-7.84 (s, 2H), 7.60 (s, 1H), 5.68 (t, J = 41.1 Hz, 1H), 3.45-3.30 (m, 4H), 2.85-2.75 (m, 4H), 1.60-2.55 (m, 8H), 0.67-0.57 (m, 2H), 0.98 (t, J = 7.5 Hz, 3H) ppm. |
| 245 | 4-Chloro-N-((4,4-difluoro-1-(4-(propylsulfonyl)piperazin-1-yl)cyclohexyl)methyl)-2-(trifluoromethyl)benzamide Hydrochloride | 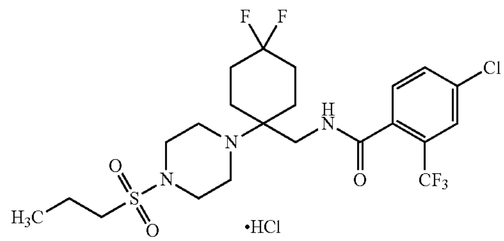 [SMILES: CCCS(=O)(=O)N1CCN(C2(CNC(=O)c3ccc(Cl)cc3C(F)(F)F)CCC(F)(F)CC2)CC1 ; Cl] | GSP-1<br>$^1$H NMR (300 MHz, DMSO-$d_6$):<br>δ 10.85 (bs, 0.4H), 9.01 (bs, 0.4H), 8.53 (bs, 0.2H), 7.94-7.87 (m, 2H), 7.76-7.52 (m, 1H), 3.84-3.58 (m, 4H), 3.38-3.00 (m, 6H), 2.79-2.64 (m, 2H), 2.27-1.45 (m, 10H), 0.97 (t, J = 7.3 Hz, 3H). |
| 246 | N-((4,4-Difluoro-1-(4-(propylsulfonyl)piperazin-1-yl)cyclohexyl)methyl)-2,4-bis(trifluoromethyl)benzamide Hydrochloride | 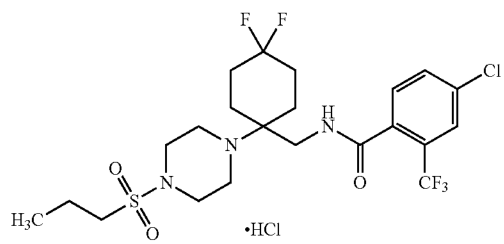 [SMILES: CCCS(=O)(=O)N1CCN(C2(CNC(=O)c3ccc(Cl)cc3C(F)(F)F)CCC(F)(F)CC2)CC1 ; Cl] | GSP-1<br>$^1$H NMR (300 MHz, DMSO-$_6$):<br>δ 10.95 (bs, 0.5H), 9.12 (bs, 0.4H), 8.64 (bs, 0.1H), 8.20-8.17 (m, 2H), 7.98-7.73 (m, 1H), 3.86-3.64 (m, 5H), 3.30-3.02 (m, 6H), 2.73-2.50 (m, 1H), 2.20-1.53 (m, 10H), 0.97 (t, J = 7.3 Hz, 3H). |
| 247 | 2-Chloro-4-cyclopropyl-N-((4,4-difluoro-1-(4-(propylsulfonyl)piperazin-1-yl)cyclohexyl)methyl)benzamide Hydrochloride | 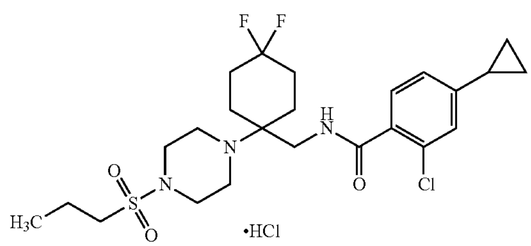 [SMILES: CCCS(=O)(=O)N1CCN(C2(CNC(=O)c3ccc(C4CC4)cc3Cl)CCC(F)(F)CC2)CC1 ; Cl] | GSP-1<br>$^1$H NMR (300 MHz, DMSO-$d_6$) δ 7.38-7.10 (m, 3H), 3.6-2.70 (m, 13H), 2.3-1.90 (m, 8H), 1.80-1.60 (m, 2H), 1.10-0.90 (m, 6H), 0.80-0.70 (m, 2H); MS (DUIS$^+$) m/z 518 (M + H). |
| 248 | N-((4,4-Difluoro-1-(4-(propylsulfonyl)piperazin-1-yl)cyclohexyl)methyl)-2,5-bis(trifluoromethyl)benzamide Hydrochloride | 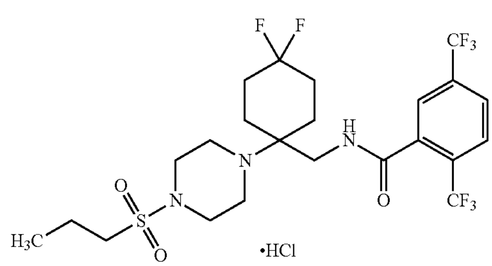 [SMILES: CCCS(=O)(=O)N1CCN(C2(CNC(=O)c3cc(C(F)(F)F)ccc3C(F)(F)F)CCC(F)(F)CC2)CC1 ; Cl] | GSP-1<br>$^1$H NMR (300 MHz, DMSO-$d_6$):<br>δ 10.91 (bs, 0.4H), 9.08 (bs, 0.4H), 8.63 (bs, 0.2H), 8.09-7.83 (m, 3H), 3.91-3.79 (m, 2H), 3.40-3.20 (m, 2H), 3.19-3.02 (m, 4H), 2.84-2.65 (m, 2H), 2.35-2.07 (m, 4H), 2.03-1.98 (m, 2H), 1.97-1.89 (m, 2H), 1.80-1.54 (m, 4H), 0.98 (t, J = 7.3 Hz, 3H). |
| 249 | 4-Chloro-N-((4,4-difluoro-1-(4-(propylsulfonyl)piperazin-1-yl)cyclohexyl)methyl)-2-(difluoromethoxy)benzamide Hydrochloride | 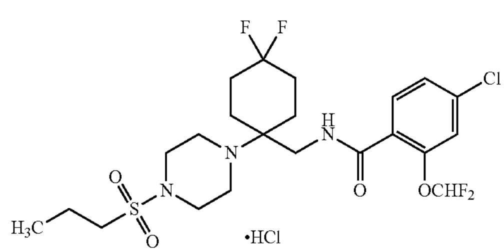 [SMILES: CCCS(=O)(=O)N1CCN(C2(CNC(=O)c3ccc(Cl)cc3OC(F)F)CCC(F)(F)CC2)CC1 ; Cl] | GSP-1<br>$^1$H NMR (300 MHz, DMSO-$d_6$): δ 10.82 (s, 1H), 8.21 (s, 1H), 7.21-7.62 (m, 3H), 7.11-7.22 (m, 1H), 3.55-3.92 (m, 4H), 3.28-3.40 (m, 2H), 2.92-3.21 (m, 4H), 2.62-2.81 (m, 2H), 1.81-2.32 (m, 8H), 1.66-1.73 (m, 2H), 0.98 (t, J = 7.2 Hz, 3H); MS (ESI+) m/z 543 (M + H). |

TABLE 1-continued

Examples, General Synthetic Procedures (GSP) and Spectral Data

| Cpd | Name | Structure | General Synthetic Procedure and Spectral Data |
|---|---|---|---|
| 250 | N-((4,4-Difluoro-1-(4-(propylsulfonyl)piperazin-1-yl)cyclohexyl)methyl)-2-(difluoromethoxy)-6-fluorobenzamide Hydrochloride | 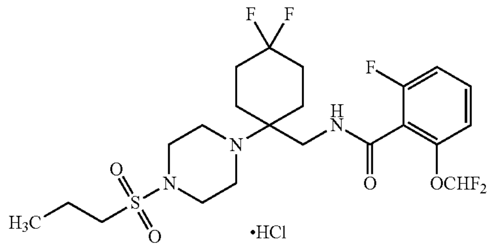 [SMILES: CCCS(=O)(=O)N1CCN(C2(CNC(=O)c3c(F)cccc3OC(F)F)CCC(F)(F)CC2)CC1 ; Cl] | GSP-1<br>$^1$H NMR (300 MHz, DMSO-d$_6$): δ 10.91 (s, 1H), 9.21 (s, 1H), 7.11-7.32 (m, 3H), 7.41-7.62 (m, 1H), 3.55-3.92 (m, 4H), 3.28-3.40 (m, 2H), 2.92-3.21 (m, 4H), 2.62-2.81 (m, 2H), 1.81-2.32 (m, 8H), 1.66-1.73 (m, 2H), 0.98 (t, J = 7.2 Hz, 3H); MS (ESI+) m/z 527 (M + H). |
| 251 | 2-Chloro-N-((1-(4-(1,1-difluoropropylsulfonyl)piperazin-1-yl)-4,4-difluorocyclohexyl)methyl)-4-(trifluoromethyl)benzamide Hydrochloride | 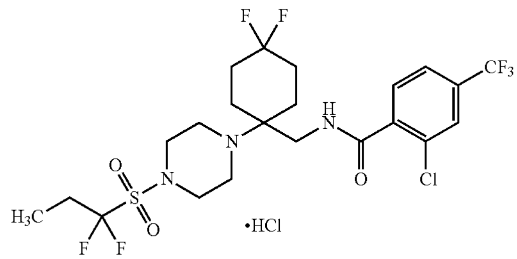 [SMILES: CCC(F)(F)S(=O)(=O)N1CCN(C2(CNC(=O)c3ccc(C(F)(F)F)cc3Cl)CCC(F)(F)CC2)CC1 ; Cl] | GSP-1<br>$^1$H NMR (300 MHz, DMSO-d$_6$): δ 9.10 (s, 1H), 8.56 (m, 1H), 7.98 (s, 1H), 7.88 (s, 1H), 7.68 (s, 1H), 3.98 (m, 4H), 3.45-3.65 (m, 4H), 2.88-2.78 (m, 4H), 2.40-1.55 (m, 10H), 1.50-1.54 (m, 2H), 0.95 (t, J = 9.0 Hz, 3H) ppm;<br>MS (ESI+) m/z 582 (M + H). |
| 252 | 2-Chloro-N-((4,4-difluoro-1-(4-(2-hydroxypropylsulfonyl)piperazin-1-yl)cyclohexyl)methyl)-4-(trifluoromethyl)benzamide Hydrochloride | 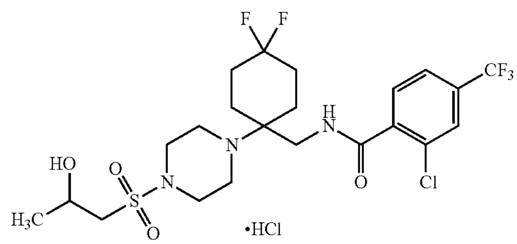 [SMILES: CC(O)CS(=O)(=O)N1CCN(C2(CNC(=O)c3ccc(C(F)(F)F)cc3Cl)CCC(F)(F)CC2)CC1 ; Cl] | GSP-1<br>$^1$H NMR (400 MHz, DMSO-d$_6$): δ 7.81 (d, J = 8.1 Hz 1H), 7.70 (s, 1H), 7.62 (d, J = 8.4 Hz, 1H), 6.42 (s, 1H), 4.42-4.36 (m, 1H), 3.59 (d, J = 6.3 Hz, 2H), 3.28 (m, 4H), 3.11 (d, J = 2.1 Hz, 1H), 3.0 (m, 2H), 2.88 (m, 4H), 2.10-1.9 (m, 6 H), 1.75-1.60 (m, 2H), 1.31 (d, J = 6.3 Hz, 3H); MS (ESI+) m/z 562 (M + H). |
| 253 | 4-Chloro-2-cyclopropyl-N-((4,4-difluoro-1-(4-(propylsulfonyl)piperazin-1-yl)cyclohexyl)methyl)benzamide Hydrochloride | 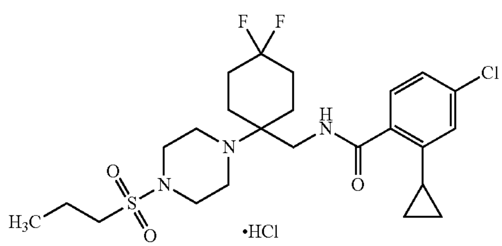 [SMILES: CCCS(=O)(=O)N1CCN(C2(CNC(=O)c3ccc(Cl)cc3C3CC3)CCC(F)(F)CC2)CC1 ; Cl] | GSP-1<br>$^1$H NMR (300 MHz, DMSO-d$_6$) δ 7.42-7.24 (m, 2H), 6.98 (d, J = 17.1 Hz, 1H), 3.82-2.99 (m, 12H), 2.74 (s, 2H), 2.27-1.50 (m, 10H), 1.01-0.90 (m, 5H), 0.72 (s, 2H); MS (DUIS$^+$) m/z 518 (M + H). |
| 254 | 2-Chloro-N-((4,4-difluoro-1-(4-(propylsulfonyl)piperazin-1-yl)cyclohexyl)methyl)-4,6-bis(trifluoromethyl)benzamide Hydrochloride | 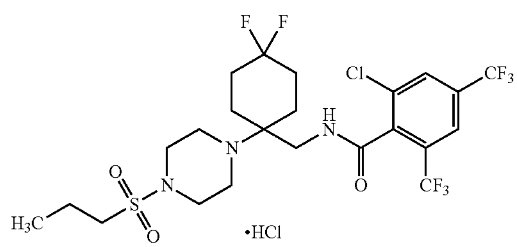 [SMILES: CCCS(=O)(=O)N1CCN(C2(CNC(=O)c3c(Cl)cc(C(F)(F)F)cc3C(F)(F)F)CCC(F)(F)CC2)CC1 ; Cl] | GSP-1<br>$^1$H NMR (300 MHz, DMSO-d$_6$) δ 8.70 (s, 1H), 8.40 (s, 1H), 8.14 (s, 1H), 3.50-2.72 (m, 10H), 2.48-1.57 (m, 12H), 0.99 (t, J = 7.2 Hz, 3H); MS (DUIS$^+$) m/z 614 (M + H). |
| 255 | 2,4-Dichloro-N-((4,4-difluoro-1-(4-(propylsulfonyl)piperazin-1-yl)cyclohexyl)methyl)-6-Fluorobenzamide Hydrochloride | 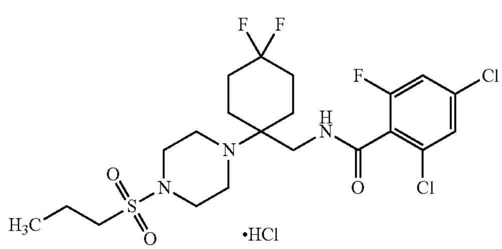 | GSP-1<br>$^1$H NMR (300 MHz, DMSO-d$_6$):<br>δ 10.48-10.35 (m, 1H), 9.20-8.62 (m, 1H), 7.72-7.57 (m, 2H), 3.82-3.62 (m, 2H), 3.33-3.25 (m, 2H), 3.19-2.95 (m, 5H), 2.78-2.58 (m, 3H), 2.24-2.08 (m, 2H), 1.97-1.72 (m, 5H), 1.74-1.54 (m, 3H), 0.98 (t, J = 7.5 Hz, 3H);<br>MS (ESI+) m/z 531 (M + H). |

TABLE 1-continued

Examples, General Synthetic Procedures (GSP) and Spectral Data

| Cpd | Name | Structure | General Synthetic Procedure and Spectral Data |
|---|---|---|---|
| 256 | 2-Chloro-N-((4,4-difluoro-1-(3-methyl-4-(propylsulfonyl)piperazin-1-yl)cyclohexyl)methyl)-4-(trifluoromethyl)benzamide Hydrochloride | 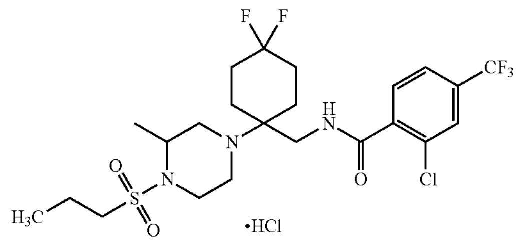 [SMILES: CCCS(=O)(=O)N1CCN(C2(CNC(=O)c3ccc(C(F)(F)F)cc3Cl)CCC(F)(F)CC2)CC1C ; Cl] | GSP-1<br>$^1$H NMR (300 MHz, DMSO-$d_6$): δ 8.58 (bs, 1H), 7.95 (s, 1H), 7.79 (d, J = 7.8 Hz, 1H), 7.58 (d, J = 7.8 Hz, 1H), 3.90-3.88 (m, 1H), 3.28-3.26 (m, 2H), 3.19-2.54 (m, 8H), 2.08-1.52 (m, 10H), 1.27 (d, J = 6.9 Hz, 3H), 0.98 (t, J = 7.3 Hz, 3H); MS (ESI+) m/z 561 (M + H). |
| 257 | 2-Chloro-N-((4,4-difluoro-1-(2-methyl-4-(propylsulfonyl)piperazin-1-yl)cyclohexyl)methyl)-4-(trifluoromethyl)benzamide Hydrochloride | 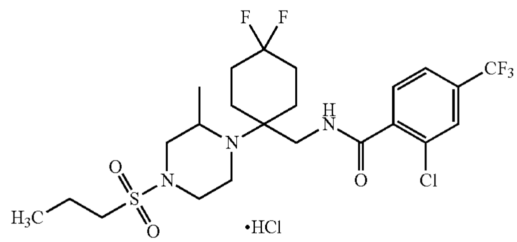 [SMILES: CCCS(=O)(=O)N1CCN(C2(CNC(=O)c3ccc(C(F)(F)F)cc3Cl)CCC(F)(F)CC2)C(C)C1 ; Cl] | GSP-1<br>$^1$H NMR (300 MHz, DMSO-$d_6$): δ 10.41(bs, 0.2H), 9.20 (bs, 0.2H), 8.54 (bs, 0.6H), 7.95 (s, 1H), 7.81-7.78 (m, 1H), 7.60-7.57 (m, 1H), 3.96-3.86 (m, 1H), 3.78-2.69 (m, 9H), 2.27-1.45 (m, 11H), 1.18 (d, J = 6.0 Hz, 3H), 0.99 (t, J = 7.3 Hz, 3H). |
| 258 | 2,6-Dichloro-N-((4,4-difluoro-1-(4-(propylsulfonyl)piperazin-1-yl)cyclohexyl)methyl)-4-(trifluoromethyl)benzamide Hydrochloride | 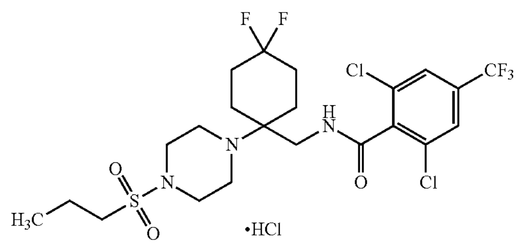 [SMILES: CCCS(=O)(=O)N1CCN(C2(CNC(=O)c3c(Cl)cc(C(F)(F)F)cc3Cl)CCC(F)(F)CC2)CC1 ; Cl] | GSP-1<br>$^1$H NMR (300 MHz, DMSO-$d_6$) δ 8.07 (s, 1H), 8.01 (s, 1H), 3.95-3.85 (m, 3H), 3.40-2.95 (m, 8H), 2.80-2.70 (m, 2H), 2.30-1.80 (m, 6H), 1.75-1.60 (m, 4H), 0.99 (t, J = 7.5 Hz, 3H); MS (DUIS$^+$) m/z 580 (M + H). |
| 259 | 4-Chloro-N-((4,4-difluoro-1-(4-(propylsulfonyl)piperazin-1-yl)cyclohexyl)methyl)-2,6-difluorobenzamide Hydrochloride | 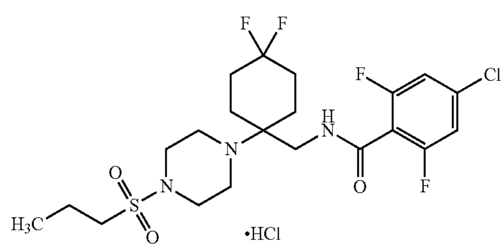 | GSP-1<br>$^1$H NMR (300 MHz, DMSO-$d_6$) δ 7.51-7.49 (m, 2H), 3.90-3.40 (m, 4H), 3.40-3.20 (m, 2H), 3.20-2.85 (m, 4H), 2.80-2.60 (m, 3H), 2.30-1.80 (m, 8H), 1.75-1.60 (m, 2H), 0.98 (t, J = 7.5 Hz, 3H); MS (DUIS$^+$) m/z 514 (M + H). |
| 260 | 2,4,6-Trichloro-N-((4,4-difluoro-1-(4-(propylsulfonyl)piperazin-1-yl)cyclohexyl)methyl)benzamide Hydrochloride | 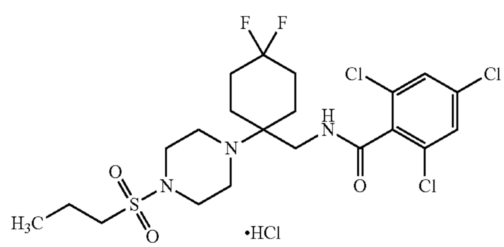 | GSP-1<br>$^1$H NMR (300 MHz, DMSO-$d_6$) δ 7.81 (s, 1H), 7.75 (s, 1H), 3.90-3.80 (m, 2H), 3.60-2.95 (m, 8H), 2.73 (s, 2H), 2.25-1.85 (m, 8H), 1.75-1.60 (m, 3H), 0.99 (t, J = 7.5 Hz, 3H); MS (DUIS$^+$) m/z 546 (M + H). |
| 261 | 2-Chloro-N-((4,4-difluoro-1-(3-(propylsulfonyl)-3,8-diazabicyclo[3.2.1]octan-8-yl)cyclohexyl)methyl)-4-(trifluoromethyl)benzamide Hydrochloride | 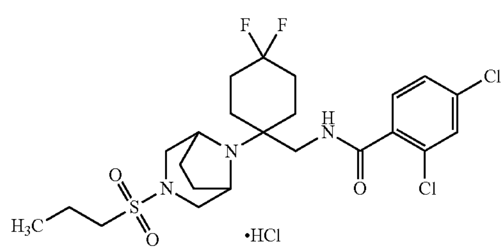 | GSP-1<br>$^1$H NMR (300 MHz, DMSO-$d_6$): δ 10.10 (s, 1H), 8.55 (m, 1H), 7.88 (s, 1H), 7.87 (d, J = 9.0 Hz, 1H), 7.56 (d, J = 9.0 Hz, 1H), 3.65 (s, 2H), 3.30 (d, J = 8.1 Hz, 2H), 3.14 (d, J = 8.1 Hz, 2H), 2.85 (m, 4H), 2.20-2.22 (m, 4H), 1.60-1.80 (m, 2H), 0.95 (t, J = 7.2 Hz, 3H) ppm; MS (ESI+) m/z 573 (M + H). |

183
184

TABLE 1-continued

Examples, General Synthetic Procedures (GSP) and Spectral Data

| Cpd | Name | Structure | General Synthetic Procedure and Spectral Data |
|---|---|---|---|
| 262 | N-((4,4-Difluoro-1-(4-(propylsulfonyl)piperazin-1-yl)cyclohexyl)methyl)-2,6-difluoro-3-(trifluoromethyl)benzamide Hydrochloride | 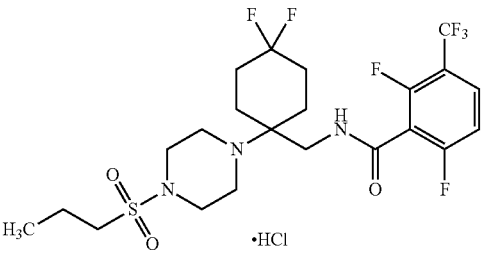 [SMILES: CCCS(=O)(=O)N1CCN(C2(CNC(=O)c3c(F)ccc(C(F)(F)F)c3F)CCC(F)(F)CC2)CC1 ; Cl] | GSP-1<br>$^1$H NMR (300 MHz, DMSO-$d_6$):<br>δ 11.18-10.86 (m, 1H), 9.46-8.82 (m, 1H), 7.98 (br s, 1H), 7.47 (br s, 1H), 3.92-3.81 (m, 4H), 3.35-2.92 (m, 6H), 2.81-2.64 (m, 2H), 2.23-1.48 (m, 10H), 0.98 (t, J = 7.5 Hz, 3H);<br>MS (ESI+) m/z 548 (M + H). |
| 263 | 2,4-Dichloro-N-((4,4-difluoro-1-(4-(propylsulfonyl)piperazin-1-yl)cyclohexyl)methyl)-5-fluorobenzamide Hydrochloride | 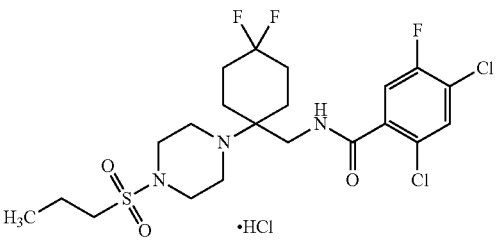 [SMILES: CCCS(=O)(=O)N1CCN(C2(CNC(=O)c3cc(F)c(Cl)cc3Cl)CCC(F)(F)CC2)CC1 ; Cl] | GSP-1<br>$^1$H NMR (300 MHz, DMSO-$d_6$)<br>δ 11.18-11.08 (m, 1H), 9.1-8.55 (m, 1H), 7.95-7.84 (m, 1H), 7.82-7.72 (m, 1H), 4.32 (br s, 2H), 3.88-3.58 (m, 6H), 3.38-2.97 (m, 5H), 2.78-2.71 (m, 1H), 2.27-2.05 (m, 6H), 1.74-1.63 (m, 2H), 0.98 (t, J = 7.5 Hz, 3H);<br>MS (ESI+) m/z 531 (M + H). |
| 264 | 2-Chloro-N-((4,4-difluoro-1-(4-(propylsulfonyl)piperazin-1-yl)cyclohexyl)methyl)-4,5-difluorobenzamide Hydrochloride | 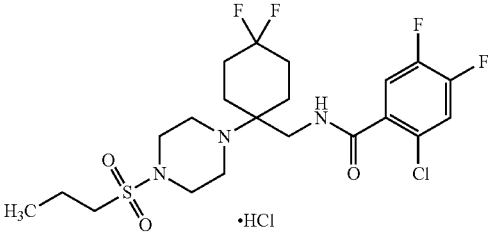 [SMILES: CCCS(=O)(=O)N1CCN(C2(CNC(=O)c3cc(F)c(F)cc3Cl)CCC(F)(F)CC2)CC1 ; Cl] | GSP-1<br>$^1$H NMR (300 MHz, DMSO-$d_6$):<br>δ 10.82-11.52 (m, 1H), 9.01-8.43 (m, 1H), 7.91-7.57 (m, 2H), 3.88-3.43 (m, 6H), 3.38-2.94 (m, 6H), 2.78-2.68 (m, 2H), 2.25-1.91 (m, 6H), 1.74-1.57 (m, 4H), 0.98 (t, J = 7.5 Hz, 3H); MS (ESI+) m/z 514 (M + H). |
| 265 | 2,6-Dichloro-N-((4,4-difluoro-1-(4-(propylsulfonyl)piperazin-1-yl)cyclohexyl)methyl)-3-(trifluoromethyl)benzamide Hydrochloride | 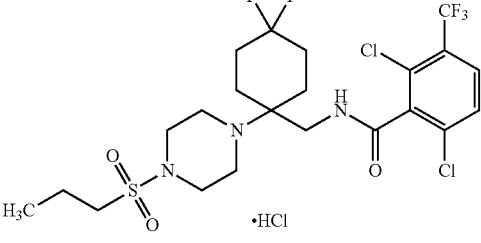 | GSP-1<br>$^1$H NMR (300 MHz, DMSO-$d_6$):<br>δ 10.82-10.52 (m, 1H), 9.18-8.78 (m, 1H), 8.01-7.82 (m, 1H), 7.83-7.72 (m, 1H), 3.94-3.64 (m, 2H), 3.34-2.95 (m, 7H), 2.23-1.57 (m, 11H), 1.31-1.22 (m, 2H), 0.98 (t, J = 7.5 Hz, 3H); MS (ESI+) m/z 581 (M + H). |
| 266 | 4-Chloro-N-((4,4-difluoro-1-(4-(propylsulfonyl)piperazin-1-yl)cyclohexyl)methyl)-2,6-dimethylbenzamide Hydrochloride | 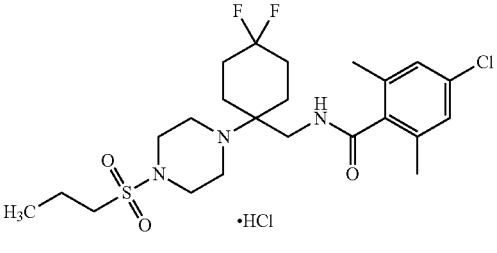 [SMILES: CCCS(=O)(=O)N1CCN(C2(CNC(=O)c3c(C)cc(Cl)cc3C)CCC(F)(F)CC2)CC1 ; Cl] | GSP-1<br>$^1$H NMR (300 MHz, DMSO-$d_6$):<br>δ 11.18-10.86 ( m, 1H), 9.46-8.82 (m, 1H), 7.98 (br s, 1H), 7.47 (br s, 1H), 3.92-3.81 (m, 4H), 3.35-2.92 (m, 6H), 2.81-2.64 (m, 2H), 2.23-1.48 (m, 10H), 0.98 (t, J = 7.5 Hz, 3H);<br>MS (ESI+) m/z 507 (M + H). |
| 267 | N-((4-(4-(propylsulfonyl)piperazin-1-yl)tetrahydro-2H-pyran-4-yl)methyl)-2,4-bis(trifluoromethyl)benzamide Hydrochloride | 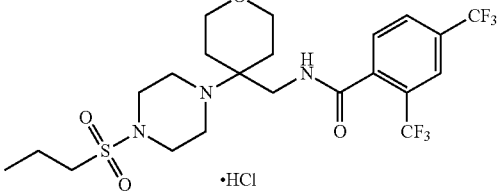 | GSP-1<br>$^1$H NMR (400 MHz, DMSO-$d_6$): δ 10.55 (bs, 1H), 8.934 (s, 1H), 7.74 (s, 1H), 7.55 (m, 2H), 3.95-3.80 (m, 4H) 3.80-3.40 (m, 8H), 3.42-3.25 (m, 2H ), 3.25-3.15 (m, 2H), 225-2.00 (m, 2H), 2.00-1.8 (m, 2 H), 1.70 (m, 2H), 0.9 (t, J = 7.2 Hz, 3H); MS (ESI+) m/z 546 (M + H). |

TABLE 1-continued

Examples, General Synthetic Procedures (GSP) and Spectral Data

| Cpd | Name | Structure | General Synthetic Procedure and Spectral Data |
|---|---|---|---|
| 268 | 2,6-Difluoro-N-((4-(4-(propylsulfonyl)piperazin-1-yl)oxepan-4-yl)methyl)benzamide Hydrochloride | 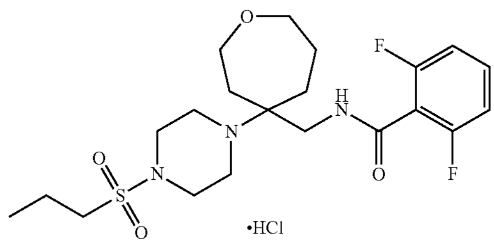 [SMILES: CCCS(=O)(=O)N1CCN(C2(CNC(=O)c3c(F)cccc3F)CCCOCC2)CC1 ; Cl] | GSP-1<br>$^1$H NMR (500 MHz, DMSO-d$_6$): δ 10.15 (bs, 1H), 9.23 (bs, 1H), 7.55 (bs, 1H), 7.20 (t, J = 7.5 Hz, 2H), 4.00-3.52 (m, 14H), 3.35-2.95 (m, 4H), 2.33-2.02 (m, 2H), 1.90-1.65 (m, 4H), 0.98 (t, J = 7.5 Hz, 3H); MS (ESI+) m/z 460 (M + H). |
| 269 | N-((4,4-Difluoro-1-(4-(pyridin-3-ylsulfonyl)piperazin-1-yl)cyclohexyl)methyl)-2,6-difluorobenzamide Hydrochloride | 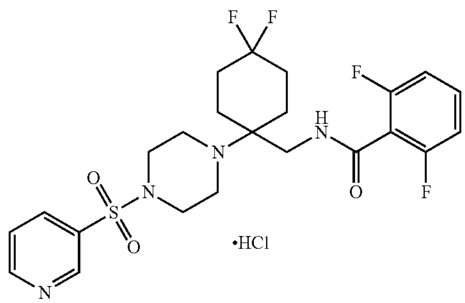 [SMILES: O=C(NCC1(N2CCN(S(=O)(=O)c3cccnc3)CC2)CCC(F)(F)CC1)c1c(F)cccc1F ; Cl] | GSP-1<br>$^1$H NMR (300 MHz, DMSO-d$_6$): δ 10.03 (bs, 0.5H), 9.18 (bs, 0.5H), 8.91 (s, 2H), 8.80 (s, 1H), 8.20-8.11 (m, 1H), 7.85-7.80 (m, 1H), 7.62-7.58 (m, 1H), 7.21-7.05 (m, 2H), 3.98-3.20 (m, 6H), 3.10-2.75 (m, 6H), 1.98-1.35 (m, 6H); MS (ESI+) m/z 515 (M + H). |
| 270 | 2-Chloro-N-((4,4-difluoro-1-(4-(pyrrolidin-1-ylsulfonyl)piperazin-1-yl)cyclohexyl)methyl)-4-(trifluoromethyl)benzamide Hydrochloride | 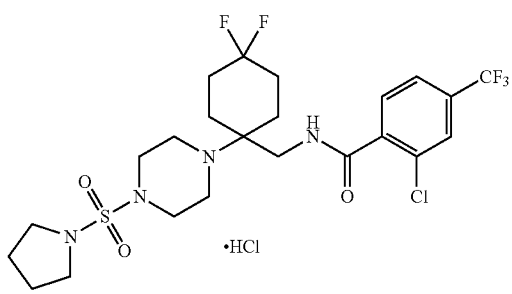 [SMILES: O=C(NCC1(N2CCN(S(=O)(=O)N3CCCC3)CC2)CCC(F)(F)CC1)c1ccc(C(F)(F)F)cc1Cl ; Cl] | GSP-1<br>$^1$H NMR (300 MHz, DMSO-d$_6$): δ 10.67 (bs, 1H), 9.05 (bs, 0.5H), 8.57 (bs, 0.5H), 8.01-7.60 (m, 3H), 4.01-3.05 (m, 12H), 2.72 (s, 1H), 2.21-1.50 (m, 13H); MS (ESI+) m/z 574 (M + H). |
| 271 | N-((1-(4-(azetidin-1-ylsulfonyl)piperazin-1-yl)-4,4difluorocyclohexyl)methyl)-2-chloro-4-(trifluoromethyl)benzamide Hydrochloride | 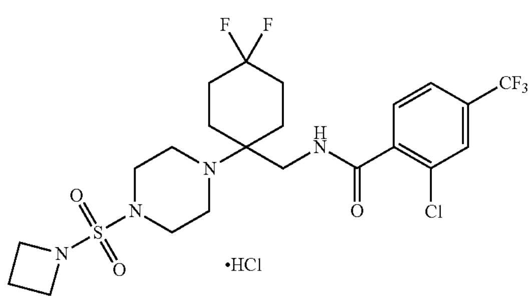 [SMILES: O=C(NCC1(N2CCN(S(=O)(=O)N3CCC3)CC2)CCC(F)(F)CC1)c1ccc(C(F)(F)F)cc1Cl ; Cl] | GSP-1<br>$^1$H NMR (300 MHz, DMSO-d$_6$): δ 8.45 (bs, 1H), 7.41-7.62 (m, 2H), 7.25 (m, 1H), 3.82 (m, 2H), 3.31 (m, 2H), 3.09 (m, 4H), 2.77 (m, 4H), 2.23 (m, 2H), 1.50-2.01 (m, 8H); MS (ESI+) m/z 559 (M + H). |
| 272 | 2-Chloro-N-((1-(4-(3,3-difluoropyrrolidin-1-ylsulfonyl)piperazin-1-yl)-4,4-difluorocyclohexyl)methyl)-4-(trifluoromethyl) benzamide Hydrochloride | 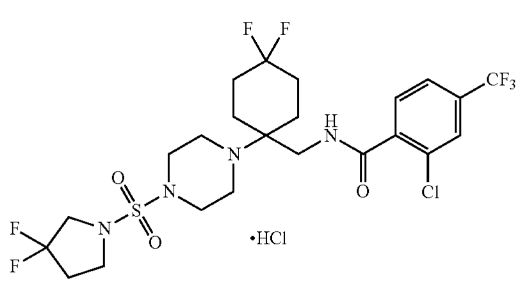 [SMILES: O=C(NCC1(N2CCN(S(=O)(=O)N3CCC(F)(F)C3)CC2)CCC(F)(F)CC1)c1ccc(C(F)(F)F)cc1Cl ; Cl] | GSP-1<br>$^1$H NMR (300 MHz, DMSO-d$_6$): δ 8.55 (bs, 1H), 7.99 (s, 1H), 7.87 (m, 1H), 7.55 (m, 1H), 3.67 (m, 2H), 3.50 (m, 2H), 3.17 (m, 4H), 2.80 (m, 4H), 2.44 (m, 3H), 1.55-2.01 (m, 8H); MS (ESI+) m/z 610 (M + H). |

TABLE 1-continued

Examples, General Synthetic Procedures (GSP) and Spectral Data

| Cpd | Name | Structure | General Synthetic Procedure and Spectral Data |
|---|---|---|---|
| 273 | 2-Chloro-N-((1-(4-(N,N-dimethylsulfamoyl)piperazin-1-yl)-4,4-difluorocyclohexyl)methyl)-4-(trifluoromethyl)benzamide Hydrochloride | 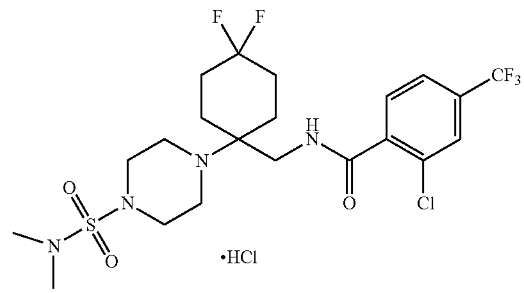 [SMILES: CN(C)S(=O)(=O)N1CCN(C2(CNC(=O)c3ccc(C(F)(F)F)cc3Cl)CCC(F)(F)CC2)CC1 ; Cl] | GSP-1<br>$^1$H NMR (300 MHz, DMSO-d$_6$): δ 8.45 (bs, 1H), 7.41-7.62 (m, 2H), 7.25 (m, 1H), 3.82 (m, 4H), 2.77 (m, 4H), 2.66 (m, 6H), 1.50-2.01 (m, 8H); MS (ESI+) m/z 547 (M + H). |
| 274 | N-((4,4-Difluoro-1-(1-(1-methyl-1H-1,2,3-triazol-4-ylsulfonyl)piperidin-4-yl)cyclohexyl)methyl)-2,4-bis(trifluoromethyl)benzamide | 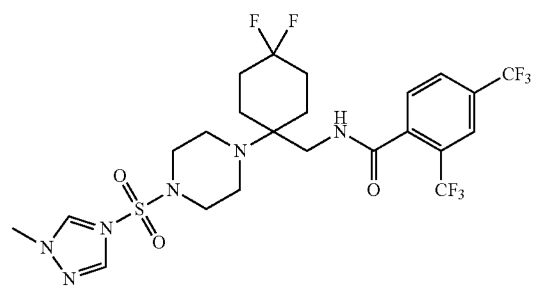 | GSP-7<br>$^1$H NMR (300 MHz, DMSO-d$_6$): δ 7.95 (s, 1H), 7.87 (m, 1H), 7.70 (s, 1H), 7.61 (m, 1H), 6.05 (m, 1H), 4.46 (s, 3H), 4.02 (m, 2H), 3.55 (m, 2H), 2.67 (m, 2H), 181-2.01 (m, 4H), 1.79 (m, 2H), 1.66 (m, 2H), 1.51-1.60 (m, 12H), 1.39 (m, 1H); (MS (ESI+) m/z 584 (M + H). |
| 275 | N-((1-(4-(1-Methyl-1H-1,2,3-triazol-4-ylsulfonyl)piperazin-1-yl)cyclopentyl)methyl)-2,4-bis(trifluoromethyl)benzamide Hydrochloride | 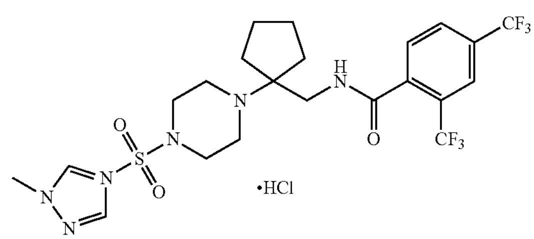 | GSP-1<br>$^1$H NMR (300 MHz, DMSO-d$_6$): δ 10.65 (bs, 1H), 9.09 (m, 1H), 8.88 (s, 1H), 8.17 (m, 2H), 7.89 (m, 1H), 4.14 (s, 3H), 3.61 (m, 2H), 3.37 (m, 4H), 3.15 (m, 2H), 2.00 (m, 4H), 1.74 (m, 4H); (MS (ESI+) m/z 569 (M + H). |
| 276 | N-((4-(4-(1-Methyl-1H-1,2,3-triazol-4-ylsulfonyl)piperazin-1-yl)tetrahydro-2H-pyran-4-yl)methyl)-2,4-bis(trifluoromethyl)benzamide Hydrochloride | 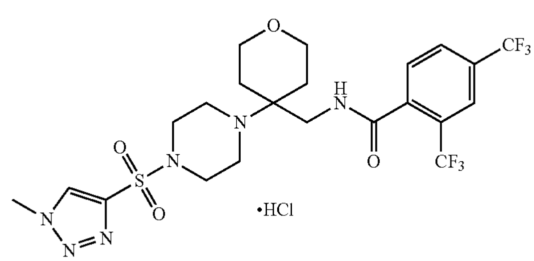 | GSP-1<br>MS (ESI+) m/z 586 (M + H); mp = 145° C. |
| 277 | 2-Chloro-N-((4-(4-(1-methyl-1H-1,2,3-triazol-4-ylsulfonyl)piperazin-1-yl)tetrahydro-2H-pyran-4-yl)methyl)-4-(trifluoromethyl)benzamide Hydrochloride | 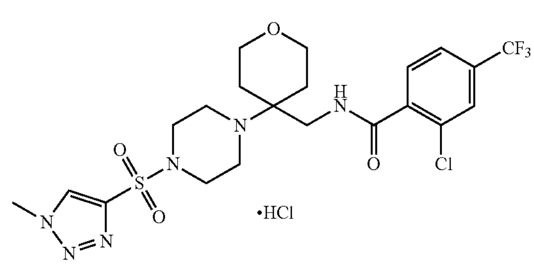 [SMILES: Cn1cc(S(=O)(=O)N2CCN(C3(CNC(=O)c4ccc(C(F)(F)F)cc4Cl)CCOCC3)CC2)nn1 ; Cl] | GSP-1<br>MS (ESI+) m/z 551 (M + H); mp = 147° C. |

TABLE 1-continued

Examples, General Synthetic Procedures (GSP) and Spectral Data

| Cpd | Name | Structure | General Synthetic Procedure and Spectral Data |
|---|---|---|---|
| 278 | (Enantiomer A)-2-Chloro-N-((4,4-difluoro-1-(4-(2-hydroxypropylsulfonyl)piperazin-1-yl)cyclohexyl)methyl)-4-(trifluoromethyl)benzamide Hydrochloride | 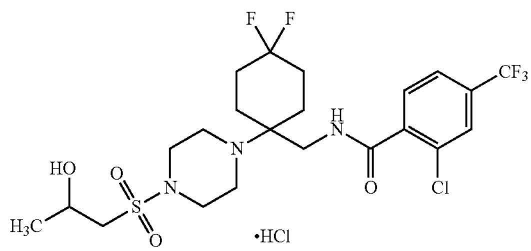 [SMILES: CC(O)CS(=O)(=O)N1CCN(C2(CNC(=O)c3ccc(C(F)(F)F)cc3Cl)CCC(F)(F)CC2)CC1 ; Cl] | GSP-1<br>$^1$H NMR (400 MHz, DMSO-$d_6$): δ 7.81 (d, J = 8.1 Hz 1H), 7.70 (s, 1H), 7.62 (d, J = 8.4 Hz, 1H), 6.42 (s, 1H), 4.42-4.36 (m, 1H), 3.59 (d, J = 6.3 Hz, 2H), 3.28 (m, 4H), 3.11 (d, J = 2.1 Hz, 1H), 3.0 (m, 2H), 2.88 (m, 4H), 2.10-1.9 (m, 6 H), 1.75-1.60 (m, 2H), 1.31 (d, J= 6.3 Hz, 3H); MS (ESI+) m/z 562 (M + H);<br>mp = 80-82° C. |
| 279 | (Enantiomer B)-2-Chloro-N-((4,4-difluoro-1-(4-(2-hydroxypropylsulfonyl)piperazin-1-yl)cyclohexyl)methyl)-4-(trifluoromethyl)benzamide Hydrochloride | 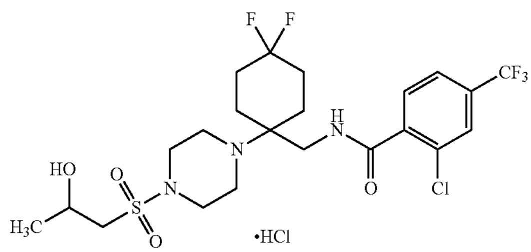 [SMILES: CC(O)CS(=O)(=O)N1CCN(C2(CNC(=O)c3ccc(C(F)(F)F)cc3Cl)CCC(F)(F)CC2)CC1 ; Cl] | GSP-1<br>$^1$H NMR (400 MHz, DMSO-$d_6$): δ 7.81 (d, J = 8.1 Hz 1H), 7.70 (s, 1H), 7.62 (d, J = 8.4 Hz, 1H), 6.42 (s, 1H), 4.42-4.36 (m, 1H), 3.59 (d, J = 6.3 Hz, 2H), 3.28 (m, 4H), 3.11 (d, J = 2.1 Hz, 1H), 3.0 (m, 2H), 2.88 (m, 4H), 2.10-1.9 (m, 6 H), 1.75-1.60 (m, 2H), 1.31 (d, J = 6.3 Hz, 3H); MS (ESI+) m/z 562 (M + H);<br>mp = 80-82° C. |
| 280 | 2-Chloro-N-((4,4-difluoro-1-(4-(2-oxopropylsulfonyl)piperazin-1-yl)cyclohexyl)methyl)-4-(trifluoromethyl)benzamide Hydrochloride | 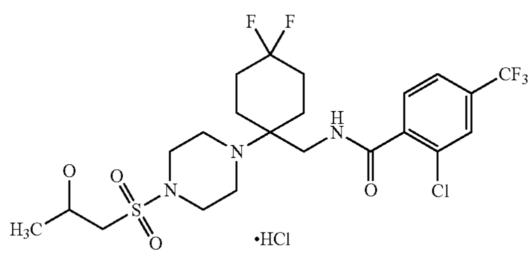 [SMILES: CC(O)CS(=O)(=O)N1CCN(C2(CNC(=O)c3ccc(C(F)(F)F)cc3Cl)CCC(F)(F)CC2)CC1 ; Cl] | GSP-1<br>$^1$H NMR (400 MHz, DMSO-$d_6$): δ 7.82 (m, 1H), 7.72 (s, 1H), 7.65 (m, 1H), 6.50 (m, 1H), 3.99 (s, 2H), 3.58 (m, 2H), 3.29 (m, 4H), 2.79 (m, 4H), 2.40 (s, 3H), 1.89-2.09 (m, 6H), 1.67 (m, 2H); MS (ESI+) m/z 560 (M + H);<br>mp = 65-67° C. |
| 281 | 2-Chloro-N-((4,4-difluoro-1-(4-(1-methyl-1H-1,2,4-triazol-3-ylsulfonyl)piperazin-1-yl)cyclohexyl)methyl)-4-(trifluoromethyl)benzamide Hydrochloride | 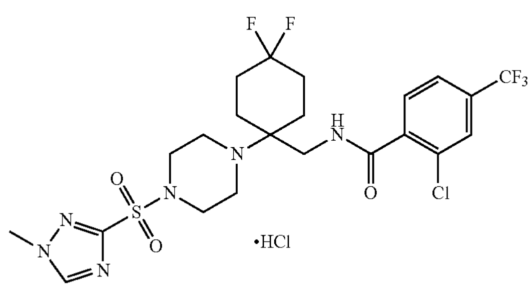 [SMILES: Cn1cnc(S(=O)(=O)N2CCN(C3(CNC(=O)c4ccc(C(F)(F)F)cc4Cl)CCC(F)(F)CC3)CC2)n1 ; Cl] | GSP-1<br>$^1$H NMR (400 MHz, DMSO-$d_6$): δ 9.05 (m, 0.5H), 8.81 (m, 1H), 8.59 (m, 0.5H), 8.00 (m, 1H), 7.81 (m, 2H), 4.01 (m, 4H), 3.79 (m, 2H), 3.33-3.45 (m, 3H), .12 (m, 2H), 2.78 (m, 2H), 1.51-2.32 (m, 9H); MS (ESI+) m/z 585 (M + H);<br>mp = 180-185° C. |
| 282 | 2-Chloro-N-(1-(1-(4-(1-methyl-1H-1,2,3-triazol-4-ylsulfonyl)piperazin-1-yl)cyclopentyl)ethyl)-4-(trifluoromethyl)benzamide Hydrochloride | 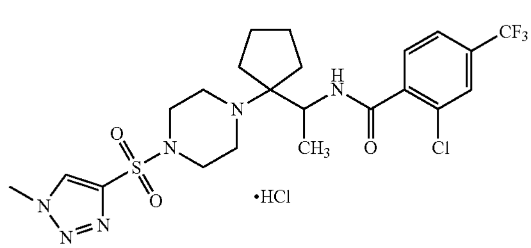 [SMILES: CC(NC(=O)c1ccc(C(F)(F)F)cc1Cl)C1(N2CCN(S(=O)(=O)c3cn(C)nn3)CC2)CCCC1 ; Cl] | GSP-1<br>$^1$H NMR (400 MHz, DMSO-$d_6$): δ 9.79 (bs 1H), 8.90 (s, 1H), 8.72 (m, 1H), 7.97 (m, s, 1H), 7.81 (m, 1H), 7.70 (m, 1H), 4.63 (m, 1H), 4.15 (s, 3H), 3.80-3.66 (m, 4H), 3.17 (m, 2H), 2.06-1.71 (m, 4H), 1.69-1.59 (,5H), 1.26 (m, 3H); MS (ESI+) m/z 549 (M + H); |

TABLE 1-continued

Examples, General Synthetic Procedures (GSP) and Spectral Data

| Cpd | Name | Structure | General Synthetic Procedure and Spectral Data |
|---|---|---|---|
| 283 | 2-Chloro-N-((4,4-difluoro-1-(4-(1-methyl-1H-pyrazol-3-ylsulfonyl)piperazin-1-yl)cyclohexyl)methyl)-4-(trifluoromethyl)benzamide Hydrochloride | 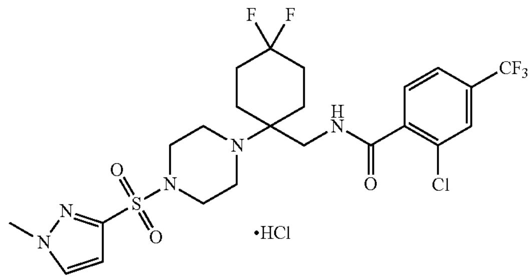 [SMILES: Cn1ccc(S(=O)(=O)N2CCN(C3(CNC(=O)c4ccc(C(F)(F)F)cc4Cl)CCC(F)(F)CC3)CC2)n1 ; Cl] | GSP-1<br>$^1$H NMR (400 MHz, DMSO-$d_6$): δ 10.56 (bs, 1H), 9.09 (bs, 1H), 7.99 (m 2H), 7.63-7.90 (m, 2H), 6.70 (m, 1H), 4.00 (m, 5H), 3.74-3.95 (m, 4H), 2.72-3.55 (m, 2H), 2.40-2.10 (m, 4H), 1.72-2.00 (m, 4H), 1.56 (m, 1H); MS (ESI+) m/z 584 (M + H); |
| 284 | 2-Chloro-N-((1-(4-(1-methyl-1H-1,2,3-triazol-4-ylsulfonyl)piperazin-1-yl)cyclopentyl)methyl)-4-(trifluoromethyl)benzamide Hydrochloride | 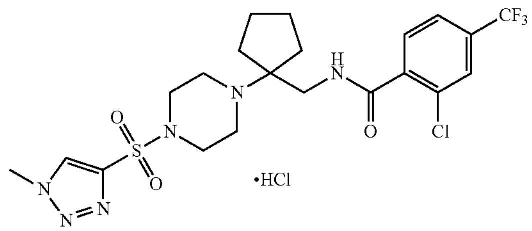 [SMILES: Cn1cc(S(=O)(=O)N2CCN(C3(CNC(=O)c4ccc(C(F)(F)F)cc4Cl)CCCC3)CC2)nn1 ; Cl] | GSP-1<br>$^1$H NMR (400 MHz, DMSO-$d_6$): δ 10.41 (bs, 1H), 8.98 (bs, 1H), 8.00 (s, 1H), 7.89 (m, 1H), 7.76 (m, 1H), 4.14 (s, 3H), 3.62 (m, 2H), 3.40-3.60 (m, 6H), 3.23 (m, 2H), 2.00 (m, 4H), 1.75 (m, 4H); MS (ESI+) m/z 535 (M + H); |
| 285 | 2-Chloro-4-fluoro-I-((1-(4-(1-methyl-1H-1,2,3-triazol-4-ylsulfonyl)piperazin-1-yl)cyclopentyl)methyl)benzamide Hydrochloride | 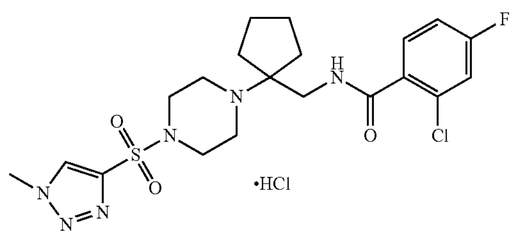 [SMILES: Cn1cc(S(=O)(=O)N2CCN(C3(CNC(=O)c4ccc(F)cc4Cl)CCCC3)CC2)nn1 ; Cl] | GSP-1<br>$^1$H NMR (400 MHz, DMSO-$d_6$): δ 110.62 (bs (1H), 8.89 (bs, 1H), 7.57 (m, 2H), 7.32 (m, 1H), 4.14 (s, 3H), 3.48-3.62 (m, 10H), 3.21 (m, 2H), 1.96-2.02 (m, 4H), 1.60-1.74 (m, 4H); MS (ESI+) m/z 485 (M + H); |

Example 63

In Vitro [$^3$H]Glycine Uptake Assay

The inhibitory activity of compounds of the invention against the glycine transporter-1 (GlyT-1) can be determined by the following scintillation proximity assay. The potency of each compound was assessed in inhibiting the uptake of radiolabeled glycine ([$^{14}$C]glycine) using the human choriocarcinoma cell line, JAR cells (ATCC#HTB-144), which endogenously express GlyT-1. In brief, 50,000 JARS cells were plated per well of tissue culture treated 96-well Cytostar-T plate (PerkinElmer) in RPMI media supplemented with 10% heat inactivated FBS and allowed to attach overnight at 37° C. and 5% $CO_2$. Compounds were serially diluted 3-fold in DMSO generating a nine (9) data point response curve for each compound. Two replicates were performed per determination. The compounds were then diluted into Uptake Buffer (10 mM Hepes, 120 mM NaCl, 2 mM KCl, 1 mM $CaCl_2$ and 1 mM $MgCl_2$, 5 mM Alanine, pH 7.4) with a final DMSO concentration of 0.75% (v/v). Following the overnight incubation, the media was replaced with Uptake Buffer in the presence or absence of diluted compound and pre-incubated at room temperature for 10 minutes prior to the addition of [$^{14}$C]glycine at a final concentration of 5 µM. Following a 3 hour incubation period at 37° C. and 5% $CO_2$, the plates were sealed and placed at room temperature in the dark for 15 minutes prior to quantification of incorporated radioactivity using a MicroBeta Trilux scintillation plate reader (PerkinElmer). Data were fit into a four-parameter model to determine the inhibitor concentration at half-maximal response ($IC_{50}$). The assay window was established by control wells incubated with [$^{14}$C]glycine in the presence or absence of 10 mM non-labeled glycine. A dose response curve for a synthesized reference standard was generated on every plate as a positive control.

Selectivity for GlyT-1 versus glycine transporter-2 (GlyT-2) was established using a GlyT-2 transfected cell model. The cDNA for the human gene of GlyT-2 (SLC6A5—solute carrier family 6, member 5; Accession #NM_004211 was synthesized (Enzymax LLC) and sub-cloned into mammalian expression vector, pcDNA3.1 (Invitrogen Corp.) using standard molecular biology techniques. HEK293 cells (ATCC #CRL-1573) transfected with pcDNA3.1 (Invitrogen Corp.) were selected for stable incorporation of the construct by resistance to the selective pressure of Geneticin (450 µg/mL; Invitrogen Corp.). A polyclonal HEK-GlyT2 cell population was used in the [$^{14}$C]glycine uptake assay previously described to evaluate the activity of the compounds of the invention with the following protocol modifications. The HEK-GlyT-2 cells were plated in Poly-L-Lysine coated Cytostar-T plates in DMEM media supplemented with 10% heat inactivated FBS. After an overnight incubation at 37° C. and 5% $CO_2$, the media was removed and the assay was conducted as described above. Compounds of the invention were diluted in Uptake Buffer and tested against JAR or HEK-GlyT-2 cells in parallel to evaluate relative potency and selectivity for GlyT-1 versus GlyT-2. The inhibitory activity and selectivity results for the compounds in Table 1 are shown in Table 2, below:

TABLE 2

| Compound | GlyT-1 IC$_{50}$ (nM) | GlyT-2 IC$_{50}$ (nM) |
|---|---|---|
| 1 | 15 | >75,000 |
| 2 | 22 | 22,687 |
| 3 | 541 | 45,000 |
| 4 | 22 | 39,067 |
| 5 | 43 | 75,000 |
| 6 | 118 | 28,623 |
| 7 | 126 | >30,000 |
| 8 | 36 | >75,000 |
| 9 | 22 | >75,000 |
| 10 | 28 | >75,000 |
| 11 | 222 | >75,000 |
| 12 | 63 | >75,000 |
| 13 | 1,269 | >75,000 |
| 14 | 157 | 50,000 |
| 15 | 786 | >75,000 |
| 16 | 23 | >75,000 |
| 17 | 647 | >75,000 |
| 18 | 28 | >75,000 |
| 19 | 15 | 39,000 |
| 20 | 6 | >75,000 |
| 21 | 4 | 39,000 |
| 22 | 77 | 41,250 |
| 23 | 1,140 | 61,884 |
| 24 | 782 | >75,000 |
| 25 | 767 | >75,000 |
| 26 | 245 | >75,000 |
| 27 | 549 | 635 |
| 28 | 523 | >75,000 |
| 29 | 766 | >75,000 |
| 30 | 79 | >75,000 |
| 31 | 590 | n.a. |
| 32 | 71 | >75,000 |
| 33 | 488 | n.a. |
| 34 | 646 | n.a. |
| 35 | 1,071 | n.a. |
| 36 | 39 | >75,000 |
| 37 | 1,136 | n.a. |
| 38 | 172 | 1,398 |
| 39 | 132 | 75,000 |
| 40 | 629 | n.a. |
| 41 | 71 | >75,000 |
| 42 | 118 | >35,000 |
| 43 | 12 | >75,000 |
| 44 | 17 | >75,000 |
| 45 | 322 | >75,000 |
| 46 | 357 | >75,000 |
| 47 | 12 | >75,000 |
| 48 | 16 | >75,000 |
| 49 | 16 | >75,000 |
| 50 | 48 | >75,000 |
| 51 | 13 | >75,000 |
| 52 | 404 | >75,000 |
| 53 | 373 | >75,000 |
| 54 | 20 | >75,000 |
| 55 | 14 | >75,000 |
| 56 | 6 | 39,000 |
| 57 | 887 | n.a. |
| 58 | 265 | 52,954 |
| 59 | 128 | >75,000 |
| 60 | 11 | >75,000 |
| 61 | 105 | 27,973 |
| 62 | 81 | 3,642 |
| 63 | 99 | >75,000 |
| 64 | 11 | >75,000 |
| 65 | 204 | >75,000 |
| 66 | 29 | >45,000 |
| 67 | 863 | n.a. |
| 68 | 174 | 3,150 |
| 69 | 4 | >75,000 |
| 70 | 9 | >75,000 |
| 71 | 22 | >75,000 |
| 72 | 171 | >75,000 |
| 73 | 1,987 | n.a. |
| 74 | 131 | >75,000 |
| 75 | 268 | >75,000 |
| 76 | 1,816 | n.a. |
| 77 | 183 | >30,000 |
| 78 | 2,445 | n.a. |
| 79 | 29 | >75,000 |
| 80 | 29 | >75,000 |
| 81 | 61 | >75,000 |
| 82 | 50 | >75,000 |
| 83 | 57 | >75,000 |
| 84 | 56 | >75,000 |
| 85 | 182 | >75,000 |
| 86 | 99 | >75,000 |
| 87 | 155 | >75,000 |
| 88 | 195 | >75,000 |
| 89 | 2,294 | >75,000 |
| 90 | 339 | >75,000 |
| 91 | 73 | 41,250 |
| 92 | 952 | 54,833 |
| 93 | 319 | >75,000 |
| 94 | 13 | >75,000 |
| 95 | 1 | >75,000 |
| 96 | 2 | >75,000 |
| 97 | 2 | >75,000 |
| 98 | 4 | >75,000 |
| 99 | 2 | >75,000 |
| 100 | 30 | >75,000 |
| 101 | 2 | >75,000 |
| 102 | 10 | >75,000 |
| 103 | 45 | >75,000 |
| 104 | 346 | >75,000 |
| 105 | 102 | >75,000 |
| 106 | 5 | >75,000 |
| 107 | 9 | >75,000 |
| 108 | 55 | >75,000 |
| 109 | 31 | >75,000 |
| 110 | 27 | >75,000 |
| 111 | 242 | >75,000 |
| 112 | 14 | >75,000 |
| 113 | 3 | >75,000 |
| 114 | 2 | >75,000 |
| 115 | 661 | >75,000 |
| 116 | 500 | >75,000 |
| 117 | 1,072 | >75,000 |
| 118 | 78 | >75,000 |
| 119 | 276 | >45,000 |
| 120 | 175 | 41,250 |
| 121 | 191 | >45,000 |
| 122 | 95 | >75,000 |
| 123 | 418 | >75,000 |
| 124 | 337 | >75,000 |
| 125 | 177 | >75,000 |
| 126 | 724 | >75,000 |
| 127 | 369 | >75,000 |
| 128 | 83 | >75,000 |
| 129 | 11 | >75,000 |
| 130 | 67 | >75,000 |
| 131 | 291 | n.a. |
| 132 | 64 | >75,000 |
| 133 | 48 | >75,000 |
| 134 | 70 | n.a. |
| 135 | 42 | >75,000 |
| 136 | 36 | >75,000 |
| 137 | 28 | >75,000 |
| 138 | 25 | >75,000 |
| 139 | 54 | >75,000 |
| 140 | 195 | n.a. |
| 141 | 48 | >75,000 |
| 142 | 158 | n.a. |
| 143 | 137 | n.a. |
| 144 | 46 | n.a. |
| 145 | 52 | n.a. |
| 146 | 30 | n.a. |
| 147 | 31 | n.a. |
| 148 | 30 | n.a. |
| 149 | 69 | n.a. |
| 150 | 61 | n.a. |

TABLE 2-continued

IC$_{50}$ Values (nM)

| Compound | GlyT-1 IC$_{50}$ (nM) | GlyT-2 IC$_{50}$ (nM) |
|---|---|---|
| 151 | 17 | >75,000 |
| 152 | 34 | n.a. |
| 153 | 69 | n.a. |
| 154 | 38 | n.a. |
| 155 | 26 | n.a. |
| 156 | 43 | n.a. |
| 157 | 59 | n.a. |
| 158 | 35 | n.a. |
| 159 | 29 | n.a. |
| 160 | 9 | >75,000 |
| 161 | 1 | >75,000 |
| 162 | 46 | >135,000 |
| 163 | 18 | 74,923 |
| 164 | 4 | n.a. |
| 165 | 29 | n.a. |
| 166 | 5 | >75,000 |
| 167 | 11 | >75,000 |
| 168 | 15 | n.a. |
| 169 | 2 | n.a. |
| 170 | 14 | n.a. |
| 171 | 2 | n.a. |
| 172 | 3 | n.a. |
| 173 | 2 | n.a. |
| 174 | 5 | n.a. |
| 175 | 57 | n.a. |
| 176 | 3 | 69,200 |
| 177 | 34 | n.a. |
| 178 | 5 | n.a. |
| 179 | 25 | n.a. |
| 180 | 8 | n.a. |
| 181 | 2 | n.a. |
| 182 | 6 | n.a. |
| 183 | 5 | n.a. |
| 184 | 13 | n.a. |
| 185 | 6 | >75,000 |
| 186 | 1 | n.a. |
| 187 | 1 | n.a. |
| 188 | 1 | n.a. |
| 189 | 5 | >75,000 |
| 190 | 1 | n.a. |
| 191 | 1 | n.a. |
| 192 | 1 | >75,000 |
| 193 | 1 | >75,000 |
| 194 | 784 | n.a. |
| 195 | 19 | >75,000 |
| 196 | 3,780 | n.a. |
| 197 | 304 | n.a. |
| 198 | 162 | n.a. |
| 199 | 621 | n.a. |
| 200 | 1,078 | >75,000 |
| 201 | 3,060 | >75,000 |
| 202 | 175 | >75,000 |
| 203 | 94 | >75,000 |
| 204 | 95 | n.a. |
| 205 | 187 | n.a. |
| 206 | 83 | n.a. |
| 207 | 64 | >75,000 |
| 208 | 137 | n.a. |
| 209 | 83 | n.a. |
| 210 | 72 | n.a. |
| 211 | 2780 | n.a. |
| 212 | 209 | n.a. |
| 213 | 875 | n.a. |
| 214 | 329 | n.a. |
| 215 | 2460 | n.a. |
| 216 | 1290 | n.a. |
| 217 | 216 | n.a. |
| 218 | 86 | n.a. |
| 219 | 3 | >75,000 |
| 220 | 83 | >75,000 |
| 221 | 1 | >75,000 |
| 222 | 1 | >75,000 |
| 223 | 33 | >75,000 |
| 224 | 1 | >75,000 |
| 225 | 28 | >75,000 |
| 226 | 1 | >75,000 |
| 227 | 7 | >75,000 |
| 228 | 1 | >75,000 |
| 229 | 10 | n.a. |
| 230 | 3 | >75,000 |
| 231 | 1 | >75,000 |
| 232 | 6 | >75,000 |
| 233 | 1 | >75,000 |
| 234 | 4 | >75,000 |
| 235 | 3 | >75,000 |
| 236 | 41 | >75,000 |
| 237 | 2 | n.a. |
| 238 | 12 | n.a. |
| 239 | 20 | n.a. |
| 240 | 49 | n.a. |
| 241 | 1 | n.a. |
| 242 | 1 | n.a. |
| 243 | 57 | n.a. |
| 244 | 51 | n.a. |
| 245 | 18 | >75,000 |
| 246 | 7 | >75,000 |
| 247 | 37 | n.a. |
| 248 | 159 | n.a. |
| 249 | 37 | n.a. |
| 250 | 24 | n.a. |
| 251 | 987 | n.a. |
| 252 | 33 | >75,000 |
| 253 | 21 | >75,000 |
| 254 | 7 | >75,000 |
| 255 | 14 | n.a. |
| 256 | 133 | >75,000 |
| 257 | 18 | >75,000 |
| 258 | 9 | >75,000 |
| 259 | 25 | >75,000 |
| 260 | 17 | >75,000 |
| 261 | 311 | >75,000 |
| 262 | 223 | n.a. |
| 263 | 23 | >75,000 |
| 264 | 48 | >75,000 |
| 265 | 228 | n.a. |
| 266 | 11 | >75,000 |
| 267 | 46 | n.a. |
| 268 | 238 | n.a. |
| 269 | 817 | n.a. |
| 270 | 47 | >75,000 |
| 271 | 350 | n.a. |
| 272 | 1,100 | n.a. |
| 273 | 350 | n.a. |
| 274 | 3 | n.a. |
| 275 | 7 | n.a. |
| 276 | 7 | n.a. |
| 277 | 8 | n.a. |
| 278 | 24 | n.a. |
| 279 | 68 | n.a. |
| 280 | 61 | n.a. |
| 281 | 284 | n.a. |
| 282 | 29 | n.a. |
| 283 | 2410 | n.a. | n.a. = data not available

Example 64

CSF-Glycine Assay

This study measured cerebrospinal fluid (CSF) glycine levels after oral administration of test compound. Drug naïve rats were administered vehicle or a dose of the test compound orally and sacrificed after 30 or 120 minutes. After the specified pretreatment time, the rats were euthanized by $CO_2$ asphyxiation and a hypodermic needle was inserted into the cisterna magna to withdraw 50-100 µl of CSF. The CSF was diluted with deuterated-glycine as an internal standard glycine was quantified by LC/MS/MS. The results for particular compounds in Table 1 are shown below:

TABLE 3

CSF-glycine Assay Values

| Compound | Dose (mg/kg) | Pretreatment (mins) | % CSF Glycine Increase versus Vehicle Control |
|---|---|---|---|
| 130 | 10 | 30 | 148 |
| 130 | 30 | 30 | 185 |
| 130 | 75 | 30 | 201 |
| 130 | 10 | 120 | 123 |
| 130 | 30 | 120 | 125 |
| 130 | 75 | 120 | 201 |
| 162 | 10 | 30 | 154 |
| 162 | 30 | 30 | 178 |
| 162 | 100 | 30 | 207 |
| 162 | 10 | 120 | 130 |
| 162 | 30 | 120 | 156 |
| 162 | 100 | 120 | 156 |
| 163 | 10 | 30 | 123 |
| 163 | 30 | 30 | 202 |
| 163 | 100 | 30 | 280 |
| 163 | 10 | 120 | 132 |
| 163 | 30 | 120 | 215 |
| 163 | 100 | 120 | 221 |
| 189 | 10 | 30 | 158 |
| 189 | 30 | 30 | 219 |
| 189 | 100 | 30 | 281 |
| 189 | 10 | 120 | 203 |
| 189 | 30 | 120 | 270 |
| 189 | 100 | 120 | 288 |
| 151 | 10 | 30 | 209 |
| 151 | 30 | 30 | 221 |
| 151 | 100 | 30 | 204 |
| 151 | 10 | 120 | 169 |
| 151 | 30 | 120 | 249 |
| 151 | 100 | 120 | 238 |
| 192 | 3 | 30 | 173 |
| 192 | 10 | 30 | 195 |
| 192 | 30 | 120 | 219 |
| 192 | 3 | 120 | 199 |
| 192 | 10 | 120 | 311 |
| 192 | 30 | 120 | 363 |
| 246 | 10 | 120 | 191 |
| 246 | 30 | 120 | 205 |
| 246 | 10 | 360 | 166 |
| 246 | 30 | 360 | 244 |
| 193 | 10 | 120 | 282 |
| 193 | 30 | 120 | 279 |
| 193 | 10 | 360 | 303 |
| 193 | 30 | 360 | 355 |
| 221 | 10 | 120 | 226 |
| 221 | 10 | 360 | 241 |
| 219 | 3 | 120 | 181 |
| 219 | 10 | 120 | 310 |
| 224 | 3 | 120 | 186 |
| 224 | 10 | 120 | 347 |
| 226 | 3 | 120 | 243 |
| 226 | 10 | 120 | 344 |
| 226 | 3 | 360 | 227 |
| 226 | 10 | 360 | 339 |
| 267 | 10 | 120 | 138 |
| 267 | 30 | 120 | 229 |
| 267 | 10 | 360 | 129 |
| 267 | 30 | 360 | 190 |
| 252 | 30 | 120 | 207 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of the formula (I):

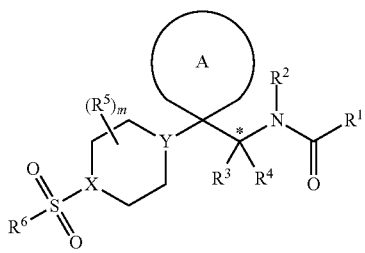

wherein:

$R^1$ is phenyl independently substituted from 1 to 5 times with halogen, $C_1$-$C_3$ alkyl, $C_3$-$C_6$ cycloalkyl, $OR^9$, or $SR^{10}$, wherein $C_1$-$C_3$ alkyl and $C_3$-$C_6$ cycloalkyl are optionally substituted with 1 to 10 times with $R^7$;

$R^2$ is H;

$R^3$ and $R^4$ are each individually H or $CH_3$;

$R^5$ is selected from the group consisting of:
(1) hydrogen,
(2) $C_1$-$C_6$ alkyl which is optionally substituted from 1 to 11 times with $R^7$,
(3) gem-dialkyl, and
(4) gem-dihalo; or two $R^5$ substituents on the same carbon, together with the carbon atom to which they are attached, may form a 3-, 4-, or 5-membered cycloalkyl optionally substituted from 1 to 10 times with $R^7$; or two $R^5$ substituents on adjacent carbons of the ring to which they are attached, together may form a 3-, 4-, 5- or 6-membered cycloalkyl optionally substituted from 1 to 10 times with $R^7$;

$R^6$ is

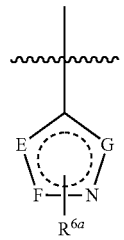

wherein E, F, and G are each independently nitrogen or carbon and $R^{6a}$ is $C_1$-$C_2$ alkyl, which is optionally substituted 1 to 5 times with halogen or deuterium;

$R^7$ is selected from the group consisting of:
(1) hydrogen,
(2) halogen,
(3) deuterium,
(4) gem-dialkyl,
(5) gem-dihalo,
(6) —$OR^9$, —$NR^{11}R^{12}$, —$NR^{11}C(O)_pR^{10}$, —$S(O)_pR^{10}$, —CN, —$NO_2$, —$C(O)_pR^{10}$, —$C(O)NR^{11}R^{12}$, or —$NR^{11}C(S)R^{10}$, and
(7) oxo or thio;

R⁸ is selected from the group consisting of:
 (1) hydrogen,
 (2) halogen,
 (3) $C_1$-$C_6$ alkyl, $C_2$-$C_6$ alkenyl, $C_2$-$C_6$ alkynyl, $C_3$-$C_7$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_7$ cycloalkyl, and $C_4$-$C_7$ cycloalkylalkyl is independently and optionally substituted from 1 to 11 times with R⁷, or
 (4) —OR⁹, —NR¹¹R¹², —NR¹¹C(O)$_p$R¹⁰, —S(O)$_p$R¹⁰, —CN, —NO₂, —C(O)$_p$R¹⁰, —C(O)NR¹¹R¹², or —NR¹¹C(S)R¹⁰;

R⁹ is selected from the group consisting of hydrogen, $C_1$-$C_4$ alkyl, $C_3$-$C_7$ cycloalkyl, $C_4$-$C_7$ cycloalkylalkyl, —C(O)NR¹¹R¹², and —C(O)$_p$R¹⁰, wherein each of $C_1$-$C_4$ alkyl, $C_3$-$C_7$ cycloalkyl, and $C_4$-$C_7$ cycloalkylalkyl is optionally substituted from 1 to 11 times with R⁷;

R¹⁰ is selected from the group consisting of hydrogen, $C_1$-$C_4$ alkyl, $C_3$-$C_7$ cycloalkyl $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in R⁷ and aryl or heteroaryl is optionally substituted from 1 to 10 times with R⁸;

R¹¹ and R¹² are each independently selected from the group consisting hydrogen, $C_1$-$C_4$ alkyl, $C_3$-$C_7$ cycloalkyl, $C_4$-$C_7$ cycloalkylalkyl, aryl, and heteroaryl, wherein each of $C_1$-$C_4$ alkyl, $C_3$-$C_7$ cycloalkyl, and $C_4$-$C_7$ cycloalkylalkyl is optionally substituted from 1 to 11 times with substituents as defined in R⁷ and aryl or heteroaryl is optionally substituted from 1 to 10 times with R⁸, or R¹¹ and R¹² are taken together with the nitrogen to which they are attached to form a saturated or partially saturated monocyclic or fused bicyclic heterocycle optionally substituted from 1 to 11 times with R⁷;

A is

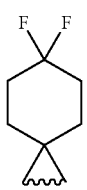

X is N;
Y is N;
p is 1, or 2; and
m is 0;
with the following provisos that: R⁶ cannot be (a) 1H-1,2,3-triazol-4-yl, or (b) 5-methylisoxazol-4-yl;
or an oxide thereof, a pharmaceutically acceptable salt thereof, or an individual enantiomer or diastereomer thereof.

2. The compound according to claim 1, wherein:
R¹ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, $CH_3$, $CF_3$, $OCH_3$, $CF_2H$, $SCH_3$, $NH_2$, $OCF_3$, or $OCF_2H$.

3. The compound according to claim 1, wherein:
R¹ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, $CH_3$, $CF_3$, $OCH_3$, $CF_2H$, $SCH_3$, $NH_2$, $OCF_3$, or $OCF_2H$; and R⁶ is

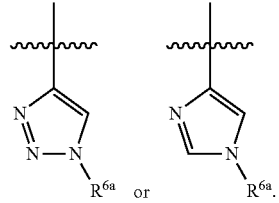

4. The compound according to claim 1, wherein
R¹ is phenyl, independently substituted at the 2-, 2,4-, 2,6-, 2,4,6-, 2,3-, 2,5-, 2,3,4-, 2,3,5-, 2,3,6-, or 2,5,6-positions with F, Cl, Br, $CH_3$, $CF_3$, $OCH_3$, $CF_2H$, $SCH_3$, $NH_2$, $OCF_3$, or $OCF_2H$; and
A is

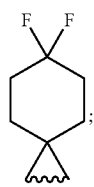

and
R⁶ is

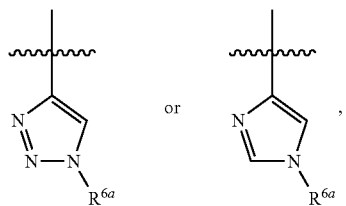

wherein $R^{6a}$ is $CH_3$, $CF_2H$, or $CD_3$.

5. The compound according to claim 1, wherein the compound is selected from the group consisting of:
2-Chloro-N-((4,4-difluoro-1-(4-(1-methyl-1H-imidazol-4-ylsulfonyl)piperazin-1-yl)cyclohexyl)methyl)benzamide;
N-((4,4-difluoro-1-(4-(1-methyl-1H-imidazol-4-ylsulfonyl)piperazin-1-yl)cyclohexyl)methyl)-2-(trifluoromethoxy)benzamide;
N-((4,4-difluoro-1-(4-(1-methyl-1H-imidazol-4-ylsulfonyl)piperazin-1-yl)cyclohexyl)methyl)-2,4-difluorobenzamide;
N-((4,4-Difluoro-1-(4-(1-methyl-1H-imidazol-4-ylsulfonyl)piperazin-1-yl)cyclohexyl)methyl)-2,6-difluorobenzamide;
N-((4,4-Difluoro-1-(4-(1-methyl-1H-imidazol-4-ylsulfonyl)piperazin-1-yl)cyclohexyl)methyl)-2,6-dimethylbenzamide;
4-Chloro-N-((4,4-difluoro-1-(4-(1-methyl-1H-imidazol-4-ylsulfonyl)piperazin-1-yl)cyclohexyl)methyl)-2-fluorobenzamide;
2-Chloro-N-((4,4-difluoro-1-(4-(1-methyl-1H-imidazol-4-ylsulfonyl)piperazin-1-yl)cyclohexyl)methyl)-4-fluorobenzamide;
N-((4,4-Difluoro-1-(4-(1-methyl-1H-imidazol-4-ylsulfonyl)piperazin-1-yl)cyclohexyl)methyl)-2,4,6-trifluorobenzamide;

4-Chloro-N-((4,4-difluoro-1-(4-(1-methyl-1H-imidazol-4-ylsulfonyl)piperazin-1-yl)cyclohexyl)methyl)-2-methylbenzamide;

N-((4,4-Difluoro-1-(4-(1-methyl-1H-imidazol-4-ylsulfonyl)piperazin-1-yl)cyclohexyl)methyl)-4-fluoro-2-(trifluoromethyl)benzamide;

N-((4,4-Difluoro-1-(4-(1-methyl-1H-imidazol-4-ylsulfonyl)piperazin-1-yl)cyclohexyl)methyl)-2-fluoro-4-(trifluoromethyl)benzamide;

N-((4,4-Difluoro-1-(4-(1-methyl-1H-imidazol-4-ylsulfonyl)piperazin-1-yl)cyclohexyl)methyl)-2-chloro-4-(trifluoromethyl)benzamide;

N-((4,4-Difluoro-1-(4-(1-methyl-1H-imidazol-4-ylsulfonyl)piperazin-1-yl)cyclohexyl)methyl)-2-fluoro-6-(trifluoromethyl)benzamide;

2-Chloro-N-((4,4-Difluoro-1-(4-(1-methyl-1H-imidazol-4-ylsulfonyl)piperazin-1-yl)cyclohexyl)methyl)-6-methoxybenzamide;

2,6-Dichloro-N-((4,4-difluoro-1-(4-(1-methyl-1H-imidazol-4-ylsulfonyl)piperazin-1-yl)cyclohexyl)methyl)benzamide;

N-((4,4-Difluoro-1-(4-(1-methyl-1H-imidazol-4-ylsulfonyl)piperazin-1-yl)cyclohexyl)methyl)-2-fluorobenzamide;

N-((4,4-Difluoro-1-(4-(1-methyl-1H-imidazol-4-ylsulfonyl)piperazin-1-yl)cyclohexyl)methyl)-2-(trifluoromethyl)benzamide;

N-((4,4-Difluoro-1-(4-(1-methyl-1H-imidazol-4-ylsulfonyl)piperazin-1-yl)cyclohexyl)methyl)-2-methoxybenzamide;

2,4-Dichloro-N-((4,4-difluoro-1-(4-(1-methyl-1H-imidazol-4-ylsulfonyl)piperazin-1-yl)cyclohexyl)methyl)benzamide;

N-((4,4-difluoro-1-(4-(1-methyl-1H-imidazol-4-ylsulfonyl)piperazin-1-yl)cyclohexyl)methyl)-2-methylbenzamide;

2-Chloro-N-((4,4-difluoro-1-(4-(1-methyl-1H-imidazol-4-ylsulfonyl)piperazin-1-yl)cyclohexyl)methyl)-6-fluorobenzamide;

2-Chloro-N-((4,4-difluoro-1-(4-(1-methyl-1H-imidazol-4-ylsulfonyl)piperazin-1-yl)cyclohexyl)methyl)-6-methylbenzamide;

N-((4,4-Difluoro-1-(4-(1-methyl-1H-imidazol-4-ylsulfonyl)piperazin-1-yl)cyclohexyl)methyl)-2-fluoro-6-methylbenzamide;

N-((4,4-Difluoro-1-(4-(1-methyl-1H-imidazol-4-ylsulfonyl)piperazin-1-yl)cyclohexyl)methyl)-2-(difluoromethoxy)benzamide;

N-((4,4-Difluoro-1-(4-(1-methyl-1H-imidazol-4-ylsulfonyl)piperazin-1-yl)cyclohexyl)methyl)-4-fluoro-2-methylbenzamide;

2-Chloro-N-((4,4-difluoro-1-(4-(1-methyl-1H-imidazol-4-ylsulfonyl)piperazin-1-yl)cyclohexyl)methyl)-6-(trifluoromethyl)benzamide;

N-((4,4-Difluoro-1-(4-(1-methyl-1H-imidazol-4-ylsulfonyl)piperazin-1-yl)cyclohexyl)methyl)-2-fluoro-6-(trifluoromethoxy)benzamide;

2-Chloro-N-((4,4-difluoro-1-(4-(1-methyl-1H-imidazol-4-ylsulfonyl)piperazin-1-yl)cyclohexyl)methyl)-6-(trifluoromethoxy)benzamide;

N-((4,4-Difluoro-1-(4-(1-methyl-1H-imidazol-4-ylsulfonyl)piperazin-1-yl)cyclohexyl)methyl)-2-(difluoromethoxy)-6-fluorobenzamide;

N-((4,4-Difluoro-1-(4-(1-methyl-1H-1,2,3-triazol-4-ylsulfonyl)piperazin-1-yl)cyclohexyl)methyl)-2,6-difluorobenzamide;

2,6-Dichloro-N-((4,4-difluoro-1-(4-(1-methyl-1H-1,2,3-triazol-4-ylsulfonyl)piperazin-1-yl)cyclohexyl)methyl)benzamide;

2-Chloro-N-((4,4-difluoro-1-(4-(1-methyl-1H-1,2,3-triazol-4-ylsulfonyl)piperazin-1-yl)cyclohexyl)methyl)-6-(trifluoromethoxy)benzamide;

2-Chloro-N-((4,4-difluoro-1-(4-(1-methyl-1H-1,2,3-triazol-4-ylsulfonyl)piperazin-1-yl)cyclohexyl)methyl)-4-fluorobenzamide;

2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide;

N-(1-(4,4-Difluoro-1-(4-(1-methyl-1H-imidazol-4-ylsulfonyl)piperazin-1-yl)cyclohexyl)ethyl)-2,6-difluorobenzamide;

2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;

N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;

2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;

N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide;

2,4-Dichloro-N-((4,4-difluoro-1-(4-(1-methyl-1H-1,2,3-triazol-4-ylsulfonyl)piperazin-1-yl)cyclohexyl)methyl)benzamide;

N-((4,4-Difluoro-1-(4-(1-methyl-1H-1,2,3-triazol-4-ylsulfonyl)piperazin-1-yl)cyclohexyl)methyl)-2,4-difluorobenzamide;

4-Chloro-N-((4,4-difluoro-1-(4-(1-methyl-1H-1,2,3-triazol-4-ylsulfonyl)piperazin-1-yl)cyclohexyl)methyl)-2,6-difluorobenzamide;

2,4-Dichloro-N-((4,4-difluoro-1-(4-(1-methyl-1H-1,2,3-triazol-4-ylsulfonyl)piperazin-1-yl)cyclohexyl)methyl)-5-fluorobenzamide;

N-((4,4-Difluoro-1-(4-(1-methyl-1H-1,2,3-triazol-4-ylsulfonyl)piperazin-1-yl)cyclohexyl)methyl)-2-fluoro-4-(trifluoromethyl)benzamide;

N-((4,4-Difluoro-1-(4-(1-methyl-1H-1,2,3-triazol-4-ylsulfonyl)piperazin-1-yl)cyclohexyl)methyl)-4-fluoro-2-(trifluoromethyl)benzamide;

N-((4,4-Difluoro-1-(4-(1-methyl-1H-1,2,3-triazol-4-ylsulfonyl)piperazin-1-yl)cyclohexyl)methyl)-2,4,6-trifluorobenzamide;

2-Chloro-N-((4,4-difluoro-1-(4-(1-methyl-1H-1,2,3-triazol-4-ylsulfonyl)piperazin-1-yl)cyclohexyl)methyl)-4,5-difluorobenzamide;

2-Chloro-N-((1-(4-(1-(difluoromethyl)-1H-1,2,3-triazol-4-ylsulfonyl)piperazin-1-yl)-4,4-difluorocyclohexyl)methyl)-4-(trifluoromethyl)benzamide;

4-Chloro-N-((4,4-difluoro-1-(4-(1-methyl-1H-1,2,3-triazol-4-ylsulfonyl)piperazin-1-yl)cyclohexyl)methyl)-2,5-difluorobenzamide;

N-((4,4-Difluoro-1-(4-(1-methyl-1H-1,2,3-triazol-4-ylsulfonyl)piperazin-1-yl)cyclohexyl)methyl)-2,5-difluoro-4-methylbenzamide;

2-Chloro-N-((4,4-difluoro-1-(4-(1-(tris-deutero)methyl-1H-1,2,3-triazol-4-ylsulfonyl)piperazin-1-yl)cyclohexyl)methyl)-4-(trifluoromethyl)benzamide;

2,4-Dichloro-N-((4,4-difluoro-1-(4-(1-methyl-1H-1,2,3-triazol-4-ylsulfonyl)piperazin-1-yl)cyclohexyl)methyl)-6-fluorobenzamide;

2-Chloro-N-((4,4-difluoro-1-(4-(1-methyl-1H-1,2,3-triazol-4-ylsulfonyl)piperazin-1-yl)cyclohexyl)methyl)-3-fluoro-4-methylbenzamide;

N-((4,4-Difluoro-1-(1-(1-methyl-1H-1,2,3-triazol-4-ylsulfonyl)piperidin-4-yl)cyclohexyl)methyl)-2,4-bis(trifluoromethyl)benzamide; and 2-Chloro-N-((4,4-difluoro-1-(4-(1-methyl-1H-1,2,4-triazol-3-ylsulfonyl)piperazin-1-yl)cyclohexyl)methyl)-4-(trifluoromethyl)benzamide.

6. The compound according to claim 1, wherein the compound is selected from the group consisting of:

2-Chloro-N-((4,4-difluoro-1-(4-(1-methyl-1H-imidazol-4-ylsulfonyl)piperazin-1-yl)cyclohexyl)methyl)benzamide;

N-((4,4-difluoro-1-(4-(1-methyl-1H-imidazol-4-ylsulfonyl)piperazin-1-yl)cyclohexyl)methyl)-2-(trifluoromethoxy)benzamide;

N-((4,4-difluoro-1-(4-(1-methyl-1H-imidazol-4-ylsulfonyl)piperazin-1-yl)cyclohexyl)methyl)-2,4-difluorobenzamide;

N-((4,4-Difluoro-1-(4-(1-methyl-1H-imidazol-4-ylsulfonyl)piperazin-1-yl)cyclohexyl)methyl)-2,6-difluorobenzamide;

N-((4,4-Difluoro-1-(4-(1-methyl-1H-imidazol-4-ylsulfonyl)piperazin-1-yl)cyclohexyl)methyl)-2,6-dimethylbenzamide;

4-Chloro-N-((4,4-difluoro-1-(4-(1-methyl-1H-imidazol-4-ylsulfonyl)piperazin-1-yl)cyclohexyl)methyl)-2-fluorobenzamide;

2-Chloro-N-((4,4-difluoro-1-(4-(1-methyl-1H-imidazol-4-ylsulfonyl)piperazin-1-yl)cyclohexyl)methyl)-4-fluorobenzamide;

N-((4,4-Difluoro-1-(4-(1-methyl-1H-imidazol-4-ylsulfonyl)piperazin-1-yl)cyclohexyl)methyl)-2,4,6-trifluorobenzamide;

4-Chloro-N-((4,4-difluoro-1-(4-(1-methyl-1H-imidazol-4-ylsulfonyl)piperazin-1-yl)cyclohexyl)methyl)-2-methylbenzamide;

N-((4,4-Difluoro-1-(4-(1-methyl-1H-imidazol-4-ylsulfonyl)piperazin-1-yl)cyclohexyl)methyl)-4-fluoro-2-(trifluoromethyl)benzamide;

N-((4,4-difluoro-1-(4-(1-methyl-1H-imidazol-4-ylsulfonyl)piperazin-1-yl)cyclohexyl)methyl)-2-fluoro-4-(trifluoromethyl)benzamide;

N-((4,4-Difluoro-1-(4-(1-methyl-1H-imidazol-4-ylsulfonyl)piperazin-1-yl)cyclohexyl)methyl)-2-chloro-4-(trifluoromethyl)benzamide;

N-((4,4-Difluoro-1-(4-(1-methyl-1H-imidazol-4-ylsulfonyl)piperazin-1-yl)cyclohexyl)methyl)-2-fluoro-6-(trifluoromethyl)benzamide;

2-Chloro-N-((4,4-Difluoro-1-(4-(1-methyl-1H-imidazol-4-ylsulfonyl)piperazin-1-yl)cyclohexyl)methyl)-6-methoxybenzamide;

2,6-Dichloro-N-((4,4-difluoro-1-(4-(1-methyl-1H-imidazol-4-ylsulfonyl)piperazin-1-yl)cyclohexyl)methyl)benzamide;

N-((4,4-Difluoro-1-(4-(1-methyl-1H-imidazol-4-ylsulfonyl)piperazin-1-yl)cyclohexyl)methyl)-2-fluorobenzamide;

N-((4,4-Difluoro-1-(4-(1-methyl-1H-imidazol-4-ylsulfonyl)piperazin-1-yl)cyclohexyl)methyl)-2-(trifluoromethyl)benzamide;

N-((4,4-Difluoro-1-(4-(1-methyl-1H-imidazol-4-ylsulfonyl)piperazin-1-yl)cyclohexyl)methyl)-2-methoxybenzamide;

2,4-Dichloro-N-((4,4-difluoro-1-(4-(1-methyl-1H-imidazol-4-ylsulfonyl)piperazin-1-yl)cyclohexyl)methyl)benzamide;

N-((4,4-difluoro-1-(4-(1-methyl-1H-imidazol-4-ylsulfonyl)piperazin-1-yl)cyclohexyl)methyl)-2-methylbenzamide;

2-Chloro-N-((4,4-difluoro-1-(4-(1-methyl-1H-imidazol-4-ylsulfonyl)piperazin-1-yl)cyclohexyl)methyl)-6-fluorobenzamide;

2-Chloro-N-((4,4-difluoro-1-(4-(1-methyl-1H-imidazol-4-ylsulfonyl)piperazin-1-yl)cyclohexyl)methyl)-6-methylbenzamide;

N-((4,4-Difluoro-1-(4-(1-methyl-1H-imidazol-4-ylsulfonyl)piperazin-1-yl)cyclohexyl)methyl)-2-fluoro-6-methylbenzamide;

N-((4,4-Difluoro-1-(4-(1-methyl-1H-imidazol-4-ylsulfonyl)piperazin-1-yl)cyclohexyl)methyl)-2-(difluoromethoxy)benzamide;

N-((4,4-Difluoro-1-(4-(1-methyl-1H-imidazol-4-ylsulfonyl)piperazin-1-yl)cyclohexyl)methyl)-4-fluoro-2-methylbenzamide;

2-Chloro-N-((4,4-difluoro-1-(4-(1-methyl-1H-imidazol-4-ylsulfonyl)piperazin-1-yl)cyclohexyl)methyl)-6-(trifluoromethyl)benzamide;

N-((4,4-Difluoro-1-(4-(1-methyl-1H-imidazol-4-ylsulfonyl)piperazin-1-yl)cyclohexyl)methyl)-2-fluoro-6-(trifluoromethoxy)benzamide;

2-Chloro-N-((4,4-difluoro-1-(4-(1-methyl-1H-imidazol-4-ylsulfonyl)piperazin-1-yl)cyclohexyl)methyl)-6-(trifluoromethoxy)benzamide;

N-((4,4-Difluoro-1-(4-(1-methyl-1H-imidazol-4-ylsulfonyl)piperazin-1-yl)cyclohexyl)methyl)-2-(difluoromethoxy)-6-fluorobenzamide;

N-((4,4-Difluoro-1-(4-(1-methyl-1H-1,2,3-triazol-4-ylsulfonyl)piperazin-1-yl)cyclohexyl)methyl)-2,6-difluorobenzamide;

2,6-Dichloro-N-((4,4-difluoro-1-(4-(1-methyl-1H-1,2,3-triazol-4-ylsulfonyl)piperazin-1-yl)cyclohexyl)methyl)benzamide;

2-Chloro-N-((4,4-difluoro-1-(4-(1-methyl-1H-1,2,3-triazol-4-ylsulfonyl)piperazin-1-yl)cyclohexyl)methyl)-6-(trifluoromethoxy)benzamide;

2-Chloro-N-((4,4-difluoro-1-(4-(1-methyl-1H-1,2,3-triazol-4-ylsulfonyl)piperazin-1-yl)cyclohexyl)methyl)-4-fluorobenzamide;

2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide;

N-(1-(4,4-Difluoro-1-(4-(1-methyl-1H-imidazol-4-ylsulfonyl)piperazin-1-yl)cyclohexyl)ethyl)-2,6-difluorobenzamide;

2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;

N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;

2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;

N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide;

2,4-Dichloro-N-((4,4-difluoro-1-(4-(1-methyl-1H-1,2,3-triazol-4-ylsulfonyl)piperazin-1-yl)cyclohexyl)methyl)benzamide;

N-((4,4-Difluoro-1-(4-(1-methyl-1H-1,2,3-triazol-4-ylsulfonyl)piperazin-1-yl)cyclohexyl)methyl)-2,4-difluorobenzamide;

4-Chloro-N-((4,4-difluoro-1-(4-(1-methyl-1H-1,2,3-triazol-4-ylsulfonyl)piperazin-1-yl)cyclohexyl)methyl)-2,6-difluorobenzamide;

2,4-Dichloro-N-((4,4-difluoro-1-(4-(1-methyl-1H-1,2,3-triazol-4-ylsulfonyl)piperazin-1-yl)cyclohexyl)methyl)-5-fluorobenzamide;

N-((4,4-Difluoro-1-(4-(1-methyl-1H-1,2,3-triazol-4-ylsulfonyl)piperazin-1-yl)cyclohexyl)methyl)-2-fluoro-4-(trifluoromethyl)benzamide;

N-((4,4-Difluoro-1-(4-(1-methyl-1H-1,2,3-triazol-4-ylsulfonyl)piperazin-1-yl)cyclohexyl)methyl)-4-fluoro-2-(trifluoromethyl)benzamide;

N-((4,4-Difluoro-1-(4-(1-methyl-1H-1,2,3-triazol-4-ylsulfonyl)piperazin-1-yl)cyclohexyl)methyl)-2,4,6-trifluorobenzamide;

2-Chloro-N-((4,4-difluoro-1-(4-(1-methyl-1H-1,2,3-triazol-4-ylsulfonyl)piperazin-1-yl)cyclohexyl)methyl)-4,5-difluorobenzamide;

2-Chloro-N-((1-(4-(1-(difluoromethyl)-1H-1,2,3-triazol-4-ylsulfonyl)piperazin-1-yl)-4,4-difluorocyclohexyl)methyl)-4-(trifluoromethyl)benzamide;

4-Chloro-N-((4,4-difluoro-1-(4-(1-methyl-1H-1,2,3-triazol-4-ylsulfonyl)piperazin-1-yl)cyclohexyl)methyl)-2,5-difluorobenzamide;

N-((4,4-Difluoro-1-(4-(1-methyl-1H-1,2,3-triazol-4-ylsulfonyl)piperazin-1-yl)cyclohexyl)methyl)-2,5-difluoro-4-methylbenzamide;

2-Chloro-N-((4,4-difluoro-1-(4-(1-(tris-deutero)methyl-1H-1,2,3-triazol-4-ylsulfonyl)piperazin-1-yl)cyclohexyl)methyl)-4-(trifluoromethyl)benzamide;

2,4-Dichloro-N-((4,4-difluoro-1-(4-(1-methyl-1H-1,2,3-triazol-4-ylsulfonyl)piperazin-1-yl)cyclohexyl)methyl)-6-fluorobenzamide; and 2-Chloro-N-((4,4-difluoro-1-(4-(1-methyl-1H-1,2,3-triazol-4-ylsulfonyl)piperazin-1-yl)cyclohexyl)methyl)-3-fluoro-4-methylbenzamide.

7. The compound according to claim 1, wherein the compound is selected from the group consisting of:

N-((4,4-difluoro-1-(4-(1-methyl-1H-imidazol-4-ylsulfonyl)piperazin-1-yl)cyclohexyl)methyl)-2,4-difluorobenzamide;

N-((4,4-Difluoro-1-(4-(1-methyl-1H-imidazol-4-ylsulfonyl)piperazin-1-yl)cyclohexyl)methyl)-2,6-difluorobenzamide;

N-((4,4-Difluoro-1-(4-(1-methyl-1H-1,2,3-triazol-4-ylsulfonyl)piperazin-1-yl)cyclohexyl)methyl)-2,6-difluorobenzamide;

2-Chloro-N-((4,4-difluoro-1-(4-(1-methyl-1H-1,2,3-triazol-4-ylsulfonyl)piperazin-1-yl)cyclohexyl)methyl)-4-fluorobenzamide;

2-Chloro-N-((4,4-difluoro-1-(4-(1-methyl-1H-1,2,3-triazol-4-ylsulfonyl)piperazin-1-yl)cyclohexyl)methyl)-4-(trifluoromethyl)benzamide;

2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;

N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;

2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;

N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide; and 2-Chloro-N-((4,4-difluoro-1-(4-(1-methyl-1H-imidazol-4-ylsulfonyl)piperazin-1-yl)cyclohexyl)methyl)-4-fluorobenzamide.

8. The compound according to claim 1, wherein the compound is selected from the group consisting of:

2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide;

2-Chloro-N-((4,4-difluoro-1-(4-(1-methyl-1H-1,2,3-triazol-4-ylsulfonyl)piperazin-1-yl)cyclohexyl)methyl)-4-fluorobenzamide;

N-((4,4-Difluoro-1-(4-(1-methyl-1H-1,2,3-triazol-4-ylsulfonyl)piperazin-1-yl)cyclohexyl)methyl)-2,4-bis(trifluoromethyl)benzamide;

2-Chloro-N-(1-(4,4-difluoro-1-(4-(1-methyl-1H-1,2,3-triazol-4-ylsulfonyl)piperazin-1-yl)cyclohexyl)ethyl)-4-fluorobenzamide;

2-Chloro-N-(1-(4,4-difluoro-1-(4-(1-methyl-1H-1,2,3-triazol-4-ylsulfonyl)piperazin-1-yl)cyclohexyl)ethyl)-4-(trifluoromethyl)benzamide; and N-(1-(4,4-Difluoro-1-(4-(1-methyl-1H-1,2,3-triazol-4-ylsulfonyl)piperazin-1-yl)cyclohexyl)ethyl)-2,4-bis(trifluoromethyl)benzamide.

9. A pharmaceutical composition comprising a pharmaceutically acceptable carrier and a therapeutically effective amount of the compound of claim 1.

10. The compound according to claim 1, wherein $R^3$ and $R^4$ are different substituents and the carbon atom designated * is in the R configuration.

11. The compound according to claim 1, wherein $R^3$ and $R^4$ are different substituents and the carbon atom designated * is in the S configuration.

12. The compound according to claim 1, wherein the compound is a (+)-stereoisomer.

13. The compound according to claim 1, wherein the compound is a (−)-stereoisomer.

* * * * *

UNITED STATES PATENT AND TRADEMARK OFFICE
CERTIFICATE OF CORRECTION

PATENT NO. : 9,045,445 B2
APPLICATION NO. : 13/151992
DATED : June 2, 2015
INVENTOR(S) : Christopher L. Cioffi et al.

It is certified that error appears in the above-identified patent and that said Letters Patent is hereby corrected as shown below:

In the specification,

In compound 51, cols. 105 and 106, sixth structure from the top, delete:

" 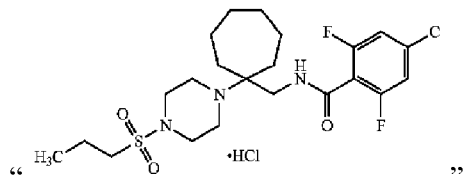 "

and replace with:

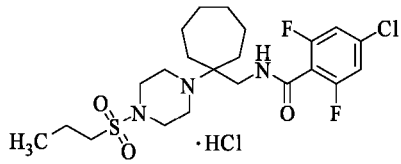

.

In compound 59, cols. 107 and 108, seventh structure from the top, delete:

" 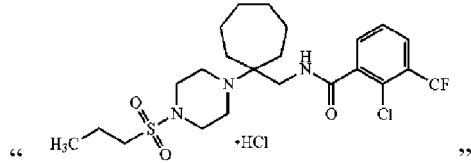 "

and replace with:

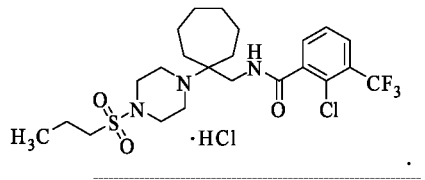

.

Signed and Sealed this
Twenty-ninth Day of December, 2015

Michelle K. Lee
*Director of the United States Patent and Trademark Office*

In compound 218, cols. 165 and 166, sixth structure from the top, delete:
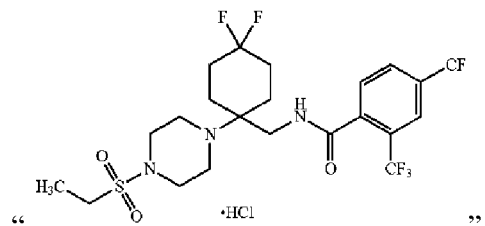
" "
and replace with:
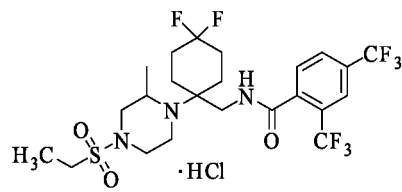
.
In compound 246, cols. 177 and 178, third structure from the top, delete:
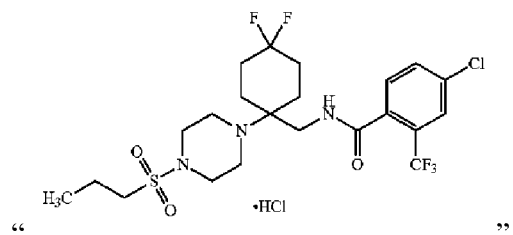
" "
and replace with:
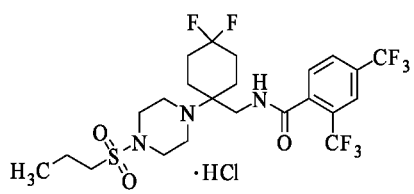
.
In compound 261, cols. 181 and 182, sixth structure from the top, delete:
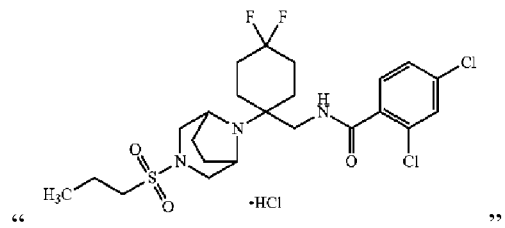
" "
and replace with:
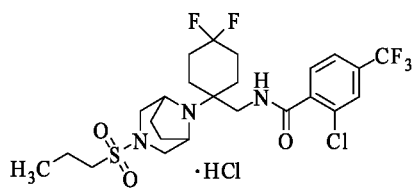
.

CERTIFICATE OF CORRECTION (continued)
U.S. Pat. No. 9,045,445 B2

In the claims,

In claim 1, col. 199, line 20, delete "$C_3$-$C_7$ cycloalkyl $C_4$-$C_7$ cycloalkylalkyl" and insert in its place --$C_3$-$C_7$ cycloalkyl, $C_4$-$C_7$ cycloalkylalkyl--.